(12) United States Patent
Bolin et al.

(10) Patent No.: US 7,067,529 B2
(45) Date of Patent: Jun. 27, 2006

(54) GLUTAMINE FRUCTOSE-Y-PHOSPHATE AMIDOTRANSFERASE (GFAT) INHIBITORS

(75) Inventors: David Robert Bolin, Montclair, NJ (US); Shoaqing Chen, Bridgewater, NJ (US); Steven Gregory Mischke, Florham Park, NJ (US); Yimin Qian, Wayne, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 163 days.

(21) Appl. No.: 10/827,514

(22) Filed: Apr. 19, 2004

(65) Prior Publication Data

US 2004/0259910 A1    Dec. 23, 2004

Related U.S. Application Data

(60) Provisional application No. 60/471,690, filed on May 19, 2003.

(51) Int. Cl.
*C07D 217/00* (2006.01)
*A61K 31/47* (2006.01)

(52) U.S. Cl. ...................... 514/307; 546/146
(58) Field of Classification Search ................ 514/307; 546/146

See application file for complete search history.

(56) References Cited

U.S. PATENT DOCUMENTS 4,042,697 A    8/1977    Garside et al.

FOREIGN PATENT DOCUMENTS

| FR | 2.199.462 | 4/1974 |
| JP | 63-310813 | 12/1988 |
| WO | WO 01/55117 A1 | 8/2001 |

OTHER PUBLICATIONS

Postaire et al, Bulletin de la Societe Chimique de France, vol. 6, p. 982-988, 1988.*
Reen-Yen Kuo et al, Bioorganic & Medicinal Chemistry Letters, vol. 13, No. 16, pp. 2789-2793 (XP-002302935) (2003).
Almudena Bermejo et al, Journal of Medicinal Chemistry, vol. 45, No. 23, pp. 5058-5068 (XP002302936) (2002).
Anselmi, Else, et. al., "Selective inhibition of calcium entry induced by benzylisoquinolines in rat smooth muscle", J. Pharm. Pharmacol. (1992) 44(4), 337-343.
M.A. Badet-Denisot, et. al., Bioorg. Med. Chem. Letters, 5, 815-820 (1995).
S.L. Bearne, J. Biol. Chem., 271, 3052-3057 (1996).
S.L. Bearne, et. al., Biochem., 34, 11515-11520 (1995).
F. Bister-Miel, et. al., Plantes Medicinales et Phytotherapie (1986), Tome XX, N°1, p. 3-7.
Chen Chen, et. al., J. Med. Chem. (2001) 44, 4001-4010.
H. Chmara, J. Gen. Microbiol., 131, 265-271 (1985).
Markwardt, Fritz, et. al., "Influence of 6,7-dimethoxyisoquinoline derivatives on the function of thrombocytes" Acta Biologica et Medica Germanica (1969) 23(2), 295-306.
F. Massiere, et. al., J. Amer. Chem., Soc., 119, 5748-5749 (1997).
S. Milewski, et. al., Biochim. Biophys. Acta, 1115, 225-229 (1992).
E. Postaire, et. al., Ann. Pharmaceutiques Francaises (1985), 43, n°6, pp. 547-556.
D. Walterova, et. al., Collective Czechoslov. Chem. Commun, (1980), 45, pp. 956-965.

* cited by examiner

*Primary Examiner*—Zinna Northington Davis
(74) *Attorney, Agent, or Firm*—George W. Johnston; Dennis P. Tramaloni; Samuel H. Megerditchian

(57) ABSTRACT

Compounds of formula I are provided (I)

$$\text{[chemical structure: isoquinoline with } R^1O\text{-, } R^2O\text{- substituents at 6,7-positions, } R^3 \text{ at 4-position, and a carbonyl-linked phenyl with } R^4, R^5, R^6 \text{ substituents at 1-position]}$$

as well as pharmaceutically acceptable salts and esters thereof, wherein the substituents are as disclosed in the specification. The compounds have utility for the treatment of type 2 diabetes mellitus.

22 Claims, No Drawings

GLUTAMINE FRUCTOSE-Y-PHOSPHATE AMIDOTRANSFERASE (GFAT) INHIBITORS

PRIORITY TO RELATED APPLICATIONS

This application claims the benefit of Provisional Application(s) Ser. No. 60/471,690, filed May 19, 2003.

BACKGROUND OF THE INVENTION

Diabetes is characterized by peripheral insulin resistance, increased glucose production and a decrease in the levels of insulin secretion. In general the levels of glucose in the serum are elevated. Moreover, serum glucose levels are raised for a longer period of time after ingestion of meals, and return to normal at a reduced rate. The consequences of increased glucose levels are well known, although the biochemical and molecular mechanisms underlying these phenomenon have not yet been clearly defined. Free fatty acids, triglycerides and other factors can also directly lead to increased levels of glucose.

The hexosamine pathway has been linked as one of the biochemical pathways that can contribute to insulin resistance, increased glucose production, and decreased insulin secretion. The hexosamine pathway is involved the synthesis of UDP-GlcNAc. Glucose is sequentially converted to fructose-6-phosphate, glucosamine-6-phosphate, and eventually converted to UDP-GlcNAc. Once UDP-GlcNAc is synthesized, it is incorporated into a variety of glyco-containing macromolecules, many of which are key cellular components. In addition, UDP-GlcNAc is a substrate for the enzyme OGT, O-linked GlcNAc transferase, that catalyzes the transfer of GlcNAc residues to various proteins in the cell, including cytoplasmic proteins, nuclear proteins, membrane proteins, and transcription factors. In so doing, the activity of these proteins can be significantly modulated. The rate limiting enzyme in this pathway is glutamine fructose-6-phosphate amidotransferase (GFAT), which catalyzes the amido transfer and isomerization of fructose-6-phosphate to glucosamine-6-phosphate. GFAT has been implicated in the development of diabetic symptoms, as GFAT transgenic mice are insulin resistant. The biochemical pathways that lead to insulin resistance include activation of PKC, alteration of membrane components, altered transcriptional activity, as well as other biochemical mechanisms that remain to be elucidated.

GFAT levels are elevated in type 2 diabetes mellitus (T2DM) and in rodent T2DM models. GFAT transgenic mice (muscle, liver, adipose and pancreas specific) are both insulin resistant and hyperinsulinemic. Glucosamine and products of the hexosamine pathway cause insulin resistance, increased hepatic glucose output and decreased insulin secretion. GFAT may play a role in T2DM kidney complications. GFAT is the rate limiting enzyme in the hexosamine pathway, and decreasing GFAT enzymatic activity should result in glucose lowering and be beneficial in treating diabetes.

Known classes of GFAT inhibitors are substrate-like or non-substrate-like and are believed to inhibit by either reversible or irreversible (covalent) mechanisms. The two subtrates of GFAT are the saccharide, fructose-6-phosphate, and the amino acid, glutamine. Fructose-6-phosphate-like inhibitors include: N-iodoacetylglucosamine-6-phosphate (S. L. Bearne, J. Biol. Chem., 271, 3052–3057 (1996)), and 2-amino-2-deoxyglucitol-6-phosphate (M.-A. Badet-Denisot, C. Leriche, F. Massiere, and B. Badet, Bioorg. Med. Chem. Letters, 5, 815–820 (1995)). Glutamine-like or glutamine-based inhibitors include: glutamate-γ-semialdehyde (S. L. Bearne and R. Wolfenden, Biochem., 34, 11515–11520 (1995)), L-γ-glutamyl-2-[((p-difluoromethyl) phenyl)thio]-glycine (F. Massiere, M.-A. Badet-Denisot, L. Rene, and B. Badet, J. Amer. Chem. Soc., 119, 5748–5749 (1997)), anticapsin (H. Chmara, J. Gen. Microbiol., 131, 265–271 (1985)), 6-diazo-5-oxo-norleucine (DON), azaserine, and N³-haloacetyl-L-2,3-diaminopropanoic acid (where halo=I, Br, and Cl) (S. Milewski, H. Chmara, R. Andruszkiewicz, and E. Borowski, Biochim. Biophys. Acta, 1115, 225–229 (1992)).

Papaveraldine (CA Index Name: Methanone (6,7-dimethoxy-1-isoquinolinyl) (3,4-dimethoxyphenyl)-(9C1)) exhibits properties which implicate potential usefulness in the treatment of heart disease. (Anselmi, Elsa, et al., "Selective inhibition of calcium entry induced by benzylisoquinolines in rat smooth muscle", J. Pharm. Pharmacol. (1992) 44(4), 337–43; Markwardt, Fritz, et al., "Influence of 6,7-dimethoxyisoquinoline derivatives on the function of thrombocytes", Acta Biologica et Medica Germanica (1969) 23(2), 295–306).

SUMMARY OF THE INVENTION

The present invention provides compounds of formula (I)

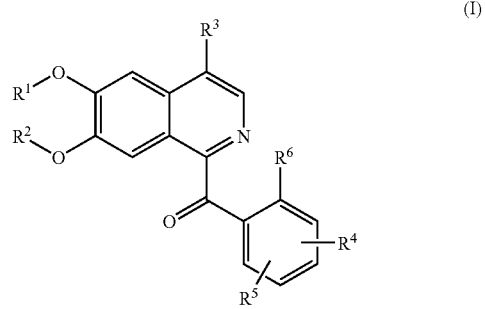

wherein
R¹ is -lower alkyl, —CH₂-aryl, -cycloalkyl, —(CH₂)₃—OC(=O)CH₃, -lower alcohol, -lower alkyl-R¹⁰, —CH₂COOH, or —CH₂CH₂OCH₂CH₃;
R² is -lower alkyl, —CH₂-aryl, -lower alcohol, —CH₂C(=O)NH₂, or -lower alkyl-R¹⁰, wherein at least one of R¹ or R² is —CH₃;
R³ is —COOH, -lower alkyl-COOH, -lower alcohol, —CH₂OCH₃, —CH₂NH₂, —CH₂NHSO₂R¹¹, —C(=O)R¹², —CNHCH₂CH₂—R¹², —C(=NH)—R¹², —(CH₂)ₙNHC(=O)R¹³, —(CH₂)ₘC(=O)N(R¹⁵)(R¹⁶), —C(=NH)—R¹⁷, or —(CH₂)ₙ—R¹⁸;
R⁴ is —H, -lower alkoxy, —O—C(R⁷R⁸)C(=O)R¹⁹, -halo, —SCH₃, —C=CHC(=O)—R¹⁰, —CH₂CH₂C(=O)—R¹⁰, —O-lower alcohol, —OCH₂CH(OH)CH₂N=N³⁰ ⁺N⁻, —OCH₂CH₂OCH₂CH₂Cl, —NHC(=O)CH₂—R¹⁰, —NHC(=O)CH₂-lower alkyl, —O(CH₂)ₙ-cycloalkyl, —O-lower alkene, or a 5 membered unsaturated heterocyclic ring containing one hetero atom which is S or O;
R⁵ and R⁶ are each independently —H, -halo or -lower alkoxy;
R⁷ and R⁸ are each independently —H or —CH₃,
R¹⁰ is a 5 or 6 membered saturated heterocyclyl containing 1 or 2 heteroatoms, wherein each hetero atom is selected from N and O, and the group is bound to the remainder of the molecule at a ring N;

R¹ is —CF₃, -lower alkyl, —CH₂Cl, —CH₂CF₃, or —R¹²;
R¹² is a 5 or 6 membered saturated substituted or unsubstituted heterocyclic ring containing one hetero atom which is selected from N, O, and S wherein the substituted ring is the heterocyclic ring substituted with —OH or -phenyl;
R¹³ is -lower alkyl, -lower alkoxy, or —(CH₂)ₙR¹⁴;
R¹⁴ is a 5 or 6 membered saturated or unsaturated heterocyclic ring containing one or two hetero atoms which are selected from N and O;
R¹⁵ is —H or —CH₃;
R¹⁶ is —H, -lower alkyl, —C≡N, —OH, -lower alkoxy, or —CH₂COOCH₂CH₃;
R¹⁷ is -lower alkoxy —NH₂ or —N-lower alkyl;
R¹⁸ is a saturated or unsaturated 5 membered substituted or unsubstituted heterocyclic ring containing from 1 to 4 hetero atoms wherein the hetero atoms are selected from N, O and S, wherein the substituted ring is the heterocyclic ring which is substituted at one or two ring carbons with =O, or substituted at a ring N with -lower alcohol or -lower alkyl;
R¹⁹ is —OH, —NHCH(CH₃)₂, —N(CH₃)CH₂-aryl, —N(CH₃)-lower alkyl,

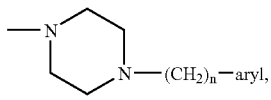

or 5 or 6 membered saturated substituted or an unsubstituted heterocyclyl containing 1 or 2 heteroatoms wherein each heteroatom is independently selected from N, O and S, wherein said substituted heterocyclyl is the heterocyclyl substituted with lower alkyl;
m is 0, 1 or 2;
n is 0 or 1;
and pharmaceutically acceptable salts and esters thereof.
Compounds of the present invention are GFAT inhibitors which may be used to treat type II diabetes.

DETAILED DESCRIPTION OF THE INVENTION

The present invention provides compounds of formula (I)

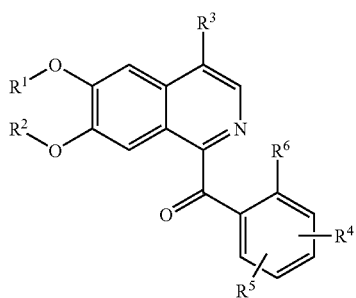

(I)

wherein
R¹ is -lower alkyl, —CH₂-aryl, -cycloalkyl, —(CH₂)₃—OC(=O)CH₃, -lower alcohol, -lower alkyl-R¹¹, —CH₂COOH, or —CH₂CH₂OCH₂CH₃;

R² is -lower alkyl, —CH₂-aryl, -lower alcohol, —CH₂C(=O)NH₂, or -lower alkyl-R¹⁰, wherein at least one of R¹ or R² is —CH₃;
R³ is —COOH, -lower alkyl-COOH, -lower alcohol, —CH₂OCH₃, —CH₂NH₂, —CH₂NHSO₂R¹¹, —C(=O)R¹², —CNHCH₂CH₂—R¹², —C(=NH)—R₁₂, —(CH₂)ₙNHC(=O)R¹³, —(CH₂)ₘC(=O)N(R¹⁵)(R¹⁶), —C(=NH)—R¹⁷, or —(CH₂)ₙ—R¹⁸;
R⁴ is —H, -lower alkoxy, —O—C(R⁷R⁸)C(=O)R¹⁹, -halo, —SCH₃, —C=CHC(=O)—R¹⁰, —CH₂CH₂C(=O)—R¹⁰, —O-lower alcohol, —OCH₂CH(OH)CH₂N=N⁺N⁻, —OCH₂CH₂OCH₂CH₂Cl, —NHC(=O)CH₂—R¹⁰, —NHC(=O)CH₂-lower alkyl, —O(CH₂)ₙ-cycloalkyl, —O-lower alkene, or a 5 membered unsaturated heterocyclic ring containing one hetero atom which is S or O;
R⁵ and R⁶ are each independently —H, -halo or -lower alkoxy;
R⁷ and R⁸ are each independently —H or —CH₃,
R¹⁰ is a 5 or 6 membered saturated heterocyclyl containing 1 or 2 heteroatoms, wherein each hetero atom is selected from N and O, and the group is bound to the remainder of the molecule at a ring N;
R¹¹ is —CF₃, -lower alkyl, —CH₂Cl, —CH₂CF₃, or —R¹²;
R¹² is a 5 or 6 membered saturated substituted or unsubstituted heterocyclic ring containing one hetero atom which is selected from N, O, and S wherein the substituted ring is the heterocyclic ring substituted with —OH or -phenyl;
R¹³ is -lower alkyl, -lower alkoxy, or —(CH₂)ₙR¹⁴;
R¹⁴ is a 5 or 6 membered saturated or unsaturated heterocyclic ring containing one or two hetero atoms which are selected from N and O;
R¹⁵ is —H or —CH₃;
R¹⁶ is —H, -lower alkyl, —C≡N, —OH, -lower alkoxy, or —CH₂COOCH₂CH₃;
R¹⁷ is -lower alkoxy —NH₂ or —N-lower alkyl;
R¹⁸ is a saturated or unsaturated 5 membered substituted or unsubstituted heterocyclic ring containing from 1 to 4 hetero atoms wherein the hetero atoms are selected from N, O and S, wherein the substituted ring is the heterocyclic ring which is substituted at one or two ring carbons with =O, or substituted at a ring N with -lower alcohol or -lower alkyl;
R¹⁹ is —OH, —NHCH(CH₃)₂, —N(CH₃)CH₂-aryl, —N(CH₃)-lower alkyl,

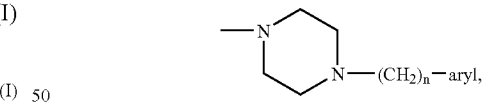

or 5 or 6 membered saturated substituted or an unsubstituted heterocyclyl containing 1 or 2 heteroatoms wherein each heteroatom is independently selected from N, O and S, wherein said substituted heterocyclyl is the heterocyclyl substituted with lower alkyl;
m is 0, 1 or 2;
n is 0 or 1;
and pharmaceutically acceptable salts and esters thereof.
Compounds of the present invention are GFAT inhibitors which may be used to treat type II diabetes.
Preferably, R⁴ is -lower alkoxy, —O—C(R⁷R⁸)C(=O)R¹⁹, -halo, —SCH₃, —C=CHC(=O)—R¹⁰, —CH₂CH₂C(=O)—R¹⁰, —O-lower alcohol, —OCH₂CH(OH)CH₂N=N⁺N⁻, —OCH₂CH₂OCH₂CH₂Cl, —NHC(=O)CH₂—R¹⁰, —NHC(=O)CH₂-lower alkyl, —O(CH₂)ₙ- cycloalkyl, —O-lower alkene, or a 5 membered unsaturated heterocyclic ring containing one hetero atom which is S or O.

When $R^4$, $R^5$ and $R^6$ are each —H, then preferably $R^1$ and $R^2$ are each —$CH_3$. Also when $R^4$, $R^5$ and $R^6$ are each —H, then preferably, $R^3$ is —COOH.

As used herein, the following terms set forth the scope and meaning of the various terms used to describe the invention. The term "lower" is used to mean a group consisting of one to six carbon atoms, preferably one to four carbon atoms.

"Cycloalkyl" means a non-aromatic, partially or completely saturated cyclic hydrocarbon group containing from 3 to 7 carbon atoms. Examples of cycloalkyl groups include cyclopropyl, cyclobutyl, cyclopentyl and cyclohexyl.

The term "halogen" and the term "halo" or "hetero atom", unless otherwise stated, designate all four halogens, i.e., fluorine, chlorine, bromine and iodine.

"Lower alkyl" includes both straight chain and branched chain alkyl groups having from 1 to 7 carbon atoms, preferably from 1 to 4 carbon atoms. Typical lower alkyl groups include methyl, ethyl, propyl, isopropyl, butyl, t-butyl, 2-butyl, pentyl and hexyl.

"Lower alkoxy" means a group of the formula —O-lower alkyl, in which the term "lower alkyl" has the previously given significance. Typical lower alkoxy groups include methoxy, ethoxy, propoxy, isopropoxy, n-butoxy, isobutoxy, sec. butoxy, and tert.butoxy.

"Lower alcohol" means a -lower alkyl where at least one of the hydrogens is replaced by a hydroxy, at any site including the end. Typical lower alcohol groups include ethanol, isopropanol, and n-propanol.

"Lower alkene" means a -lower alkyl having at least 3C atoms, where at least one of the bonds between two carbon atoms starting from at least the second carbon of the -lower alkyl has a double bond and at least one H atom on each of these C's is not present. The lower alkene is thus at least partially unsaturated. Typical lower alkenes include 2-propene, 3-methyl-2-butene, and 2,3-dimethyl-2-butene.

"Aryl" signifies a phenyl group. Where indicated herein, aryl may be substituted in one or more positions with a designated substituent or substituents.

"$IC_{50}$" refers to the concentration of a particular compound of the present invention required to inhibit 50% of in vitro GFAT activity measured as indicated herein.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to whom the particular compound is administered.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. In the present invention, esters may be present, for example, where $R^3$ is —COOH or -lower alkyl-COOH, where $R^1$ is —$CH_2$COOH, or where $R^4$ is —O—C($R^7R^8$)C(=O)$R^{19}$ and $R^{19}$ is —OH. Examples of ester groups which are cleaved (in this case hydrolyzed) in vivo to the corresponding carboxylic acids are those in which the cleaved hydrogen is replaced with -lower alkyl which is optionally substituted with heterocycle, cycloalkyl, etc. Examples of substituted lower alkyl esters are those in which -lower alkyl is substituted with pyrrolidine, piperidine, morpholine, N-methylpiperazine, etc.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

In another embodiment, compounds of formula (I) are provided, wherein
$R^1$ and $R^2$ are each independently -lower alkyl or -lower alkyl-$R^{10}$, wherein at least one of $R^1$ or $R^2$ is —$CH_3$;
$R^3$ is —COOH, -lower alkyl-COOH, —$(CH_2)_n$NHC(=O)$R^3$, —$CH_2$NHSO$_2R^{11}$, or —$(CH_2)_n$—$R^{18}$;
$R^4$ is -lower alkoxy or —OC($R^7R^8$)C(=O)$R^{19}$,
$R^5$ and $R^6$ are each independently —H or -halo;
$R^7$, $R^8$, $R^{10}$, $R^{11}$, $R^{12}$, $R^{13}$, $R^{18}$, $R^{19}$ and n are as above.
Preferably, $R^7$ and $R^8$ are each —$CH_3$.
Preferably, $R^{10}$ is —$CH_2CH_2$-morpholinyl.
Preferably, $R^{11}$ is —$CF_3$.
Preferably, $R^{13}$ is —$CH_3$.
Preferably, $R^{18}$ is an unsaturated 5 membered substituted or unsubstituted heterocyclic ring containing from 2 to 4 hetero atoms which are each N, wherein the substituted ring is the heterocyclic ring which is substituted at a ring N with -lower alkyl or -lower alcohol, and n is 0. More preferably, $R^{18}$ is tetrazole or substituted tetrazole.
Preferably, $R^{19}$ is —NHCH($CH_3$)$_2$ and n is 1.

The present invention also provides pharmaceutical compositions comprising at least one compound of formula I, or a pharmaceutically acceptable salt or ester thereof, and a pharmaceutically acceptable carrier.

The pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, stearic acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. In such case, the pharmaceutically acceptable carrier is deemed to be the soft gelatin capsule. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The compounds of the present invention are useful as medicaments for the treatment of type II diabetes. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 1,000 mg per day should be appropriate, although the upper limit may be exceeded when indicated. The daily dosage can be administered as a single dose or in divided doses, or for parenteral administration, it may be given as continuous infusion.

Synthetic Procedures

Isoquinoline analogs were generally prepared by either of three routes. Classic Bischler-Napieralski (as in Scheme 1a through Scheme 31, Scheme 37 and 45) or a modification of Pomeranz-Fritsch chemistry (as in Scheme 32 through 35) were used to prepare $R^4$/C-ring or $R^1,R^2$/C-ring analogs, respectively. N,N'-Dimethyl-imidazolium catalyzed acylation of 1-bromo-isoquinolines (as in Scheme 36, 38, 39, and 47) was used to prepare a variety of C-ring (aroyl) analogs. Starting materials may be obtained from commercial sources or prepared from information provided.

Scheme 1a

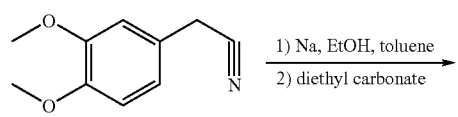
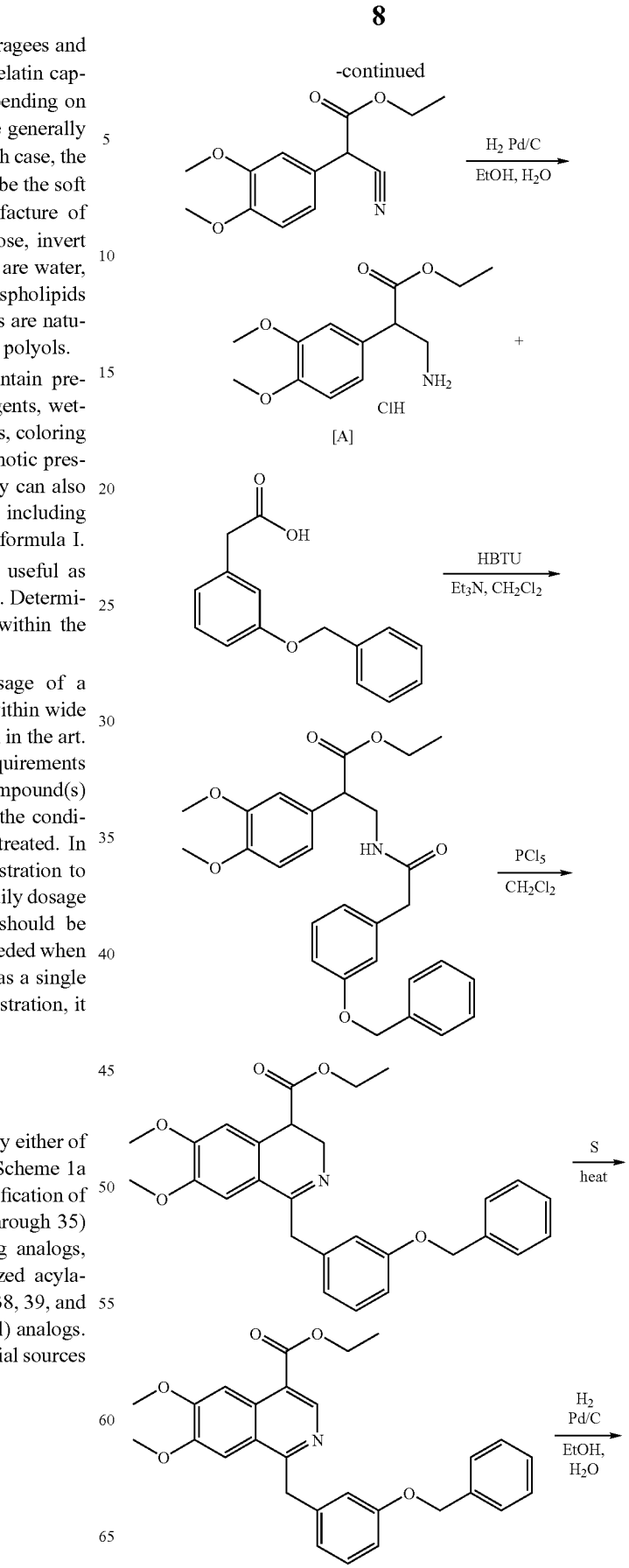

-continued
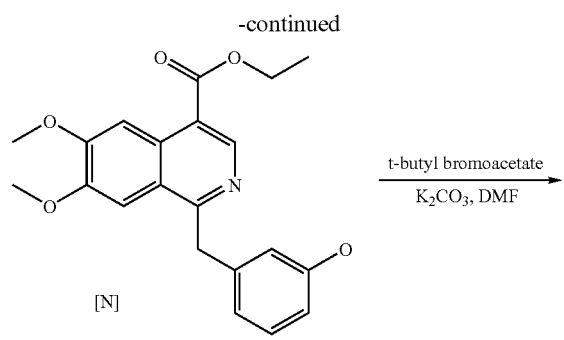
[N]
t-butyl bromoacetate
K₂CO₃, DMF
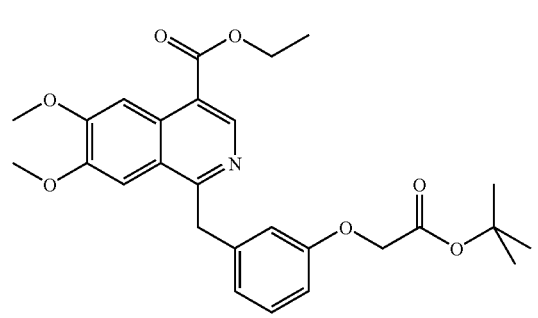
Scheme 1b
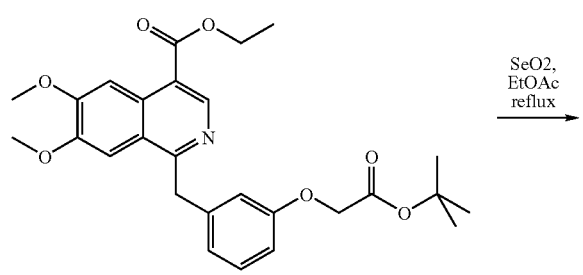
SeO2,
EtOAc
reflux
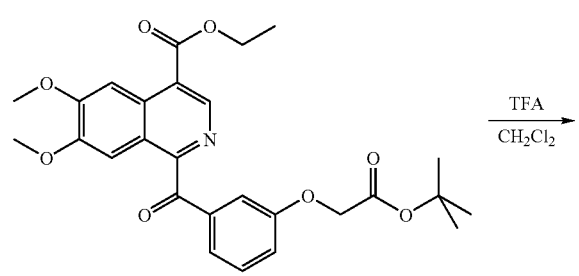
TFA
CH₂Cl₂
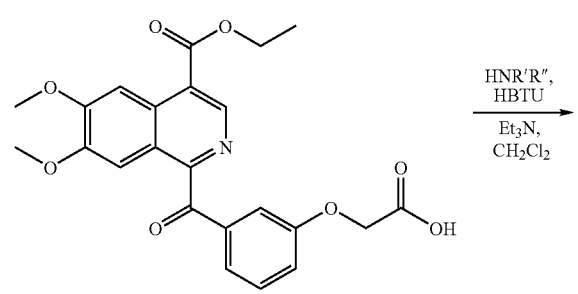
HNR'R",
HBTU
Et₃N,
CH₂Cl₂
-continued
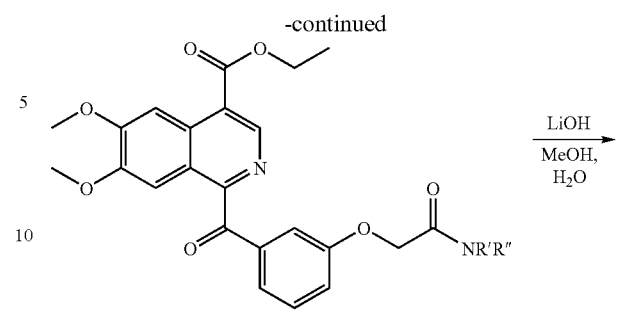
LiOH
MeOH,
H₂O
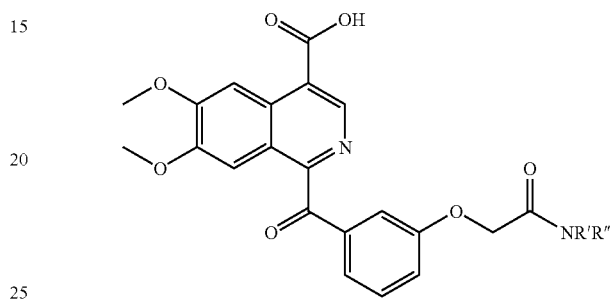
Scheme 2
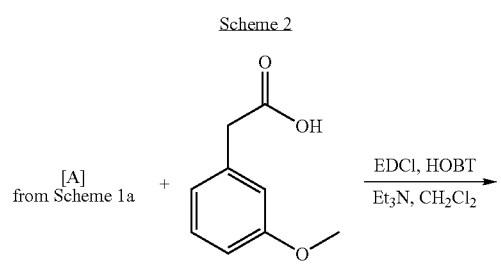
[A] from Scheme 1a
EDCl, HOBT
Et₃N, CH₂Cl₂
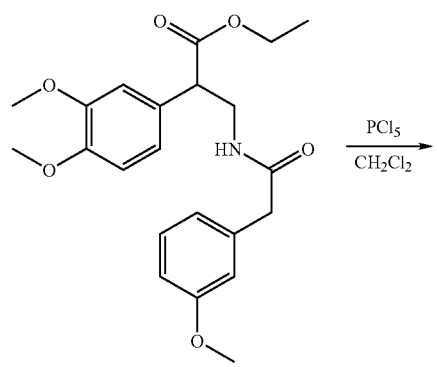
PCl₅
CH₂Cl₂
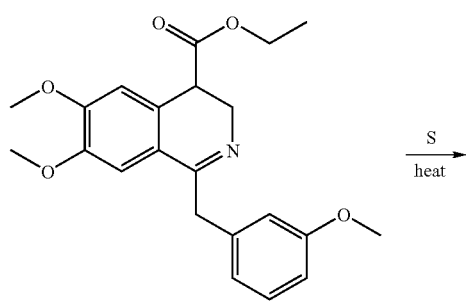
S
heat

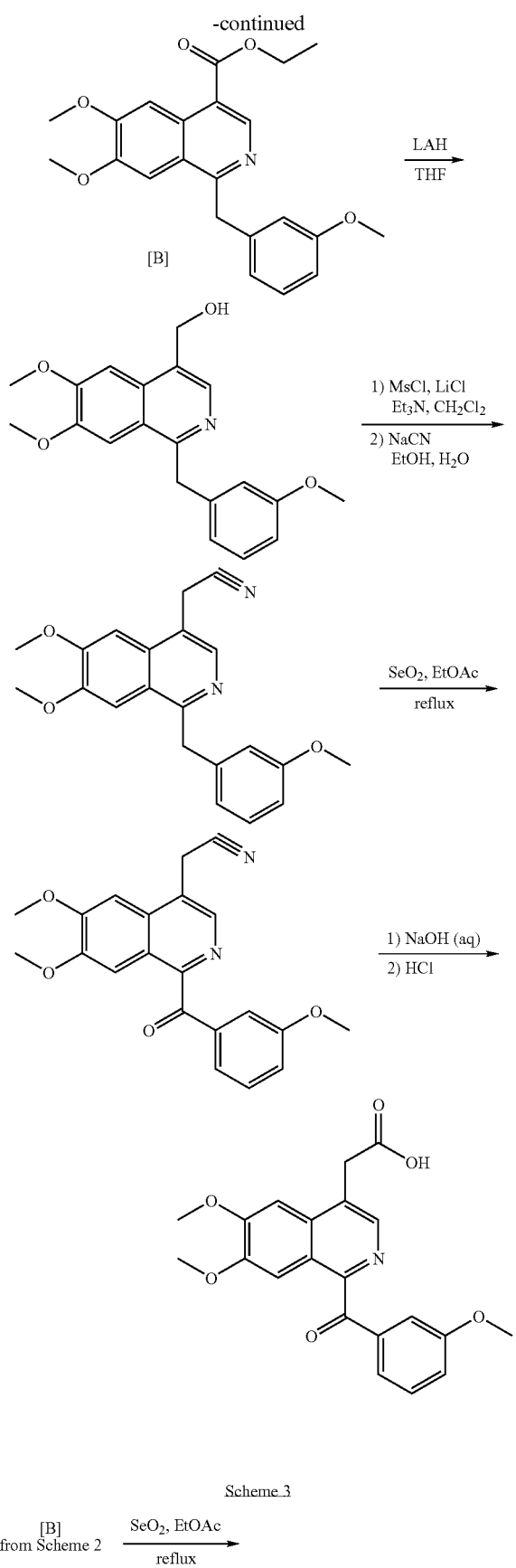
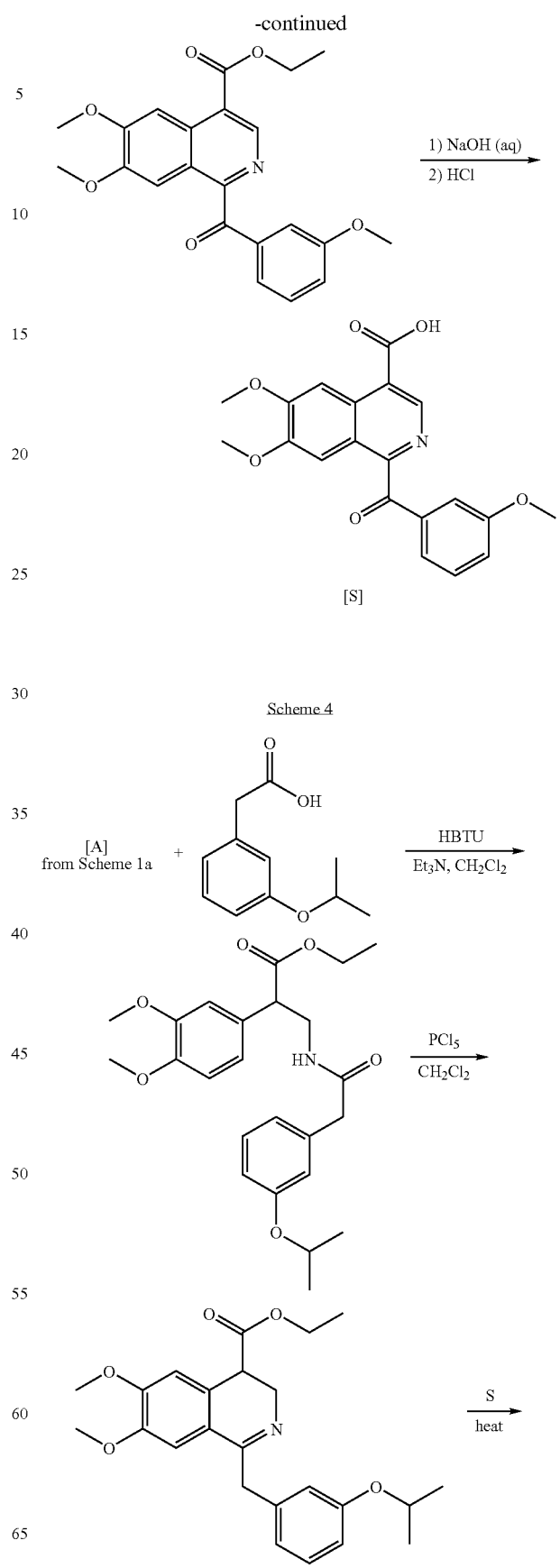
Scheme 3
Scheme 4

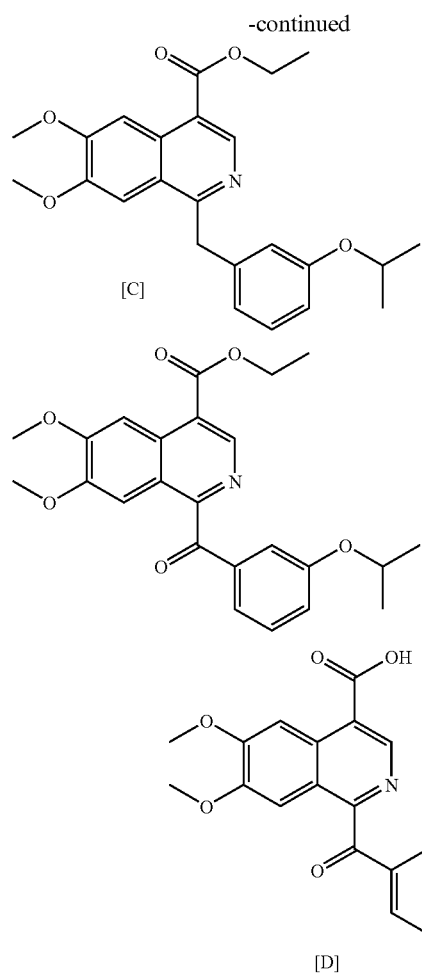
[C]
[D]
Scheme 5
[E]
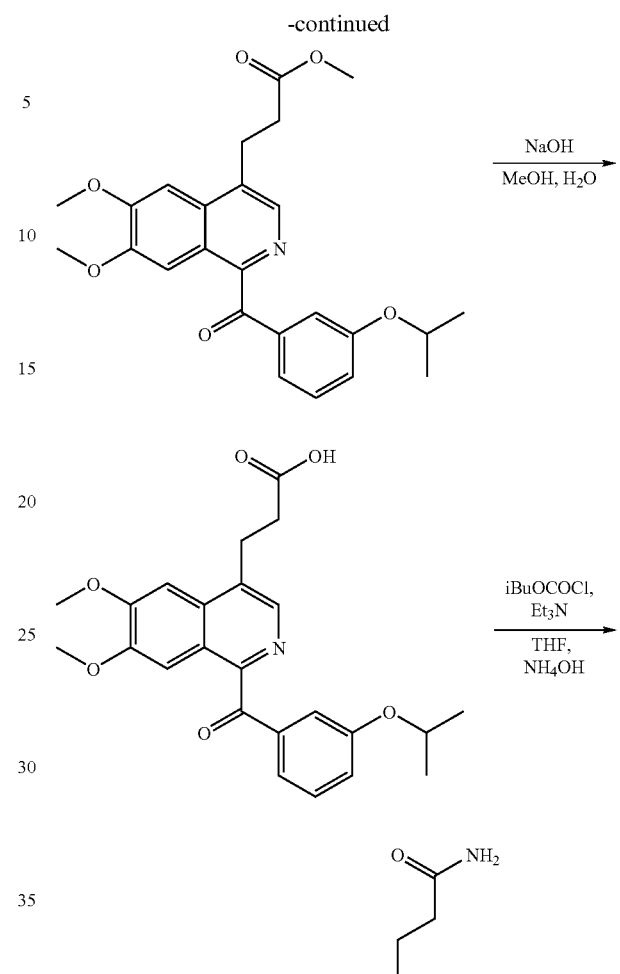
Scheme 6
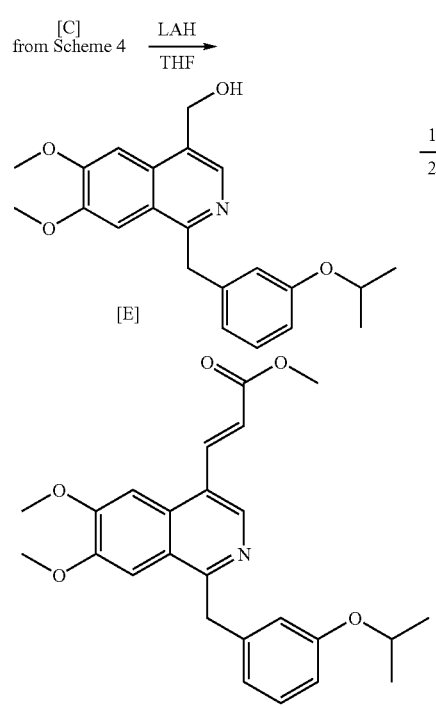
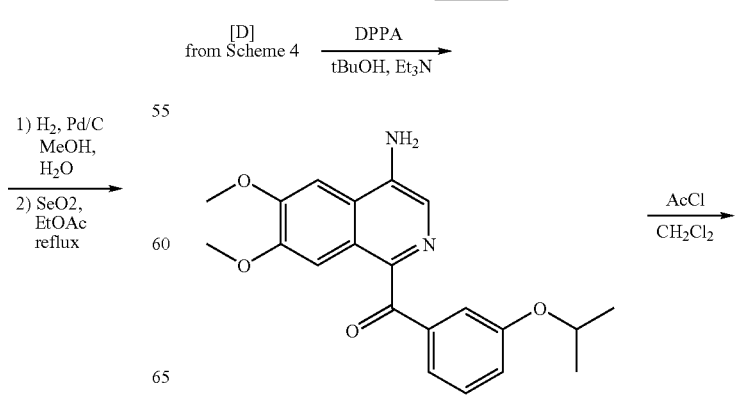

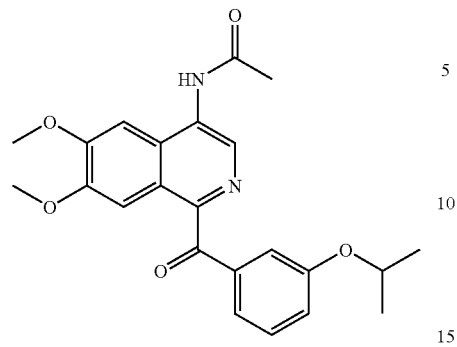
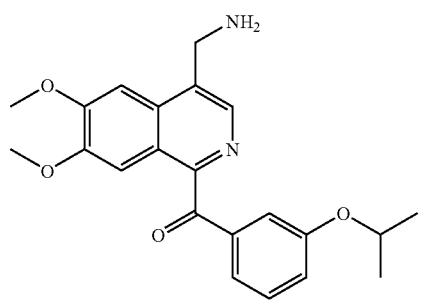
[F]
Scheme 7
[E] from Scheme 5 → MsCl, LiCl / Et₃N, CH₂Cl₂
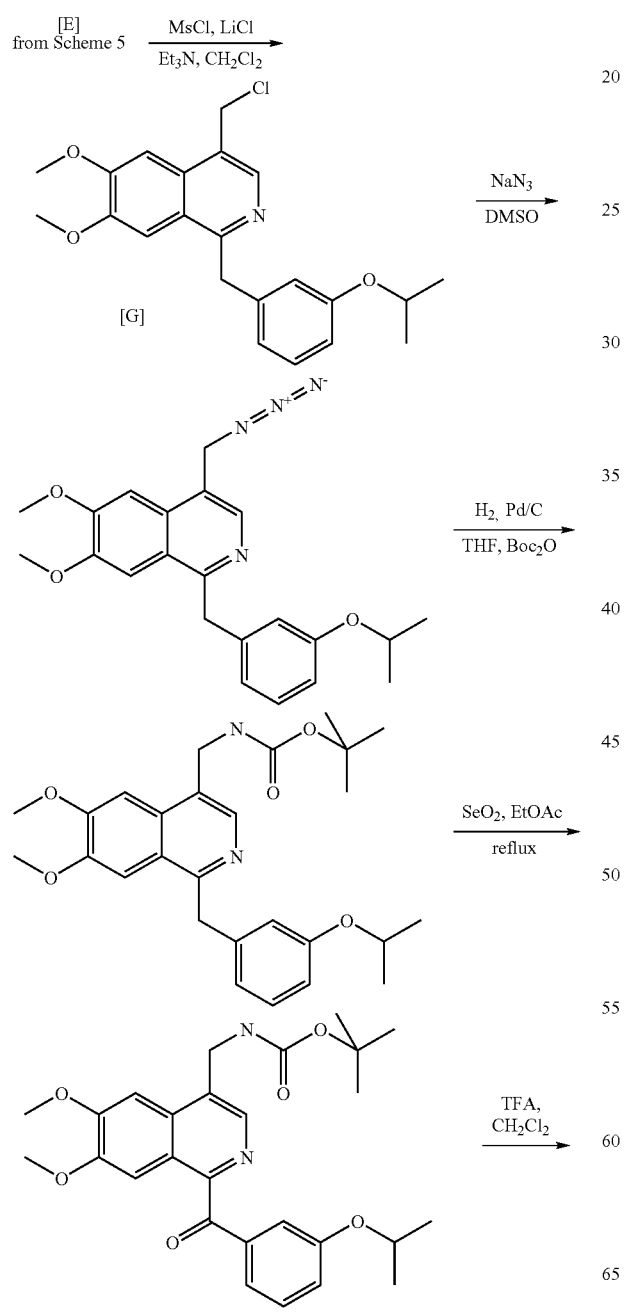
[G]
NaN₃ / DMSO
H₂, Pd/C / THF, Boc₂O
SeO₂, EtOAc / reflux
TFA, CH₂Cl₂
Scheme 8
[F] from Scheme 7 → Et₃N, CH₂Cl₂ / Ac₂O or RCO₂H, EDCl / RCO₂H, CO₂Cl₂, DMF / RCO₂H, HBTU / RCOCl / RSO₂Cl / (RSO₂)₂O
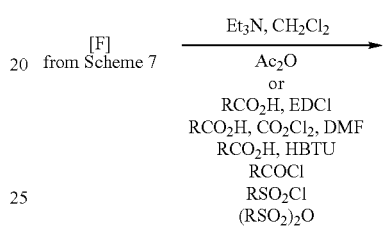
X = —COR, or —SO₂R
Scheme 9
[G] from Scheme 7 → NaCN / DMSO
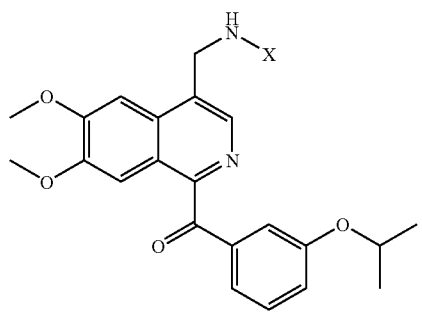
SeO₂, EtOAc / reflux
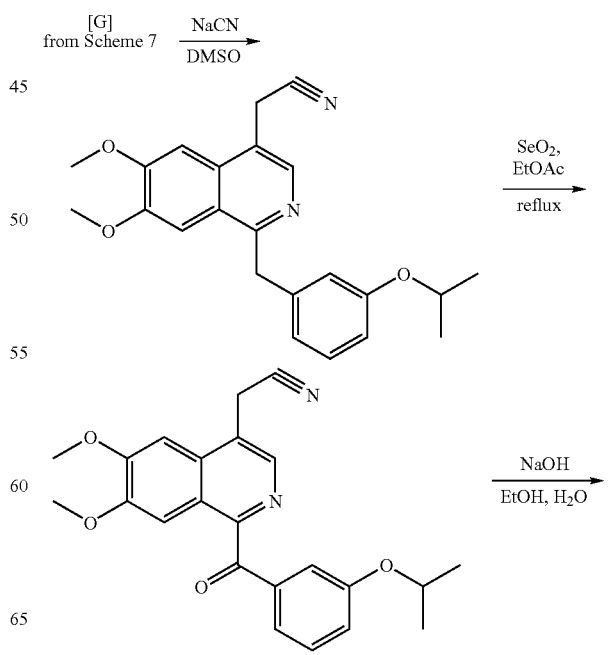
NaOH / EtOH, H₂O

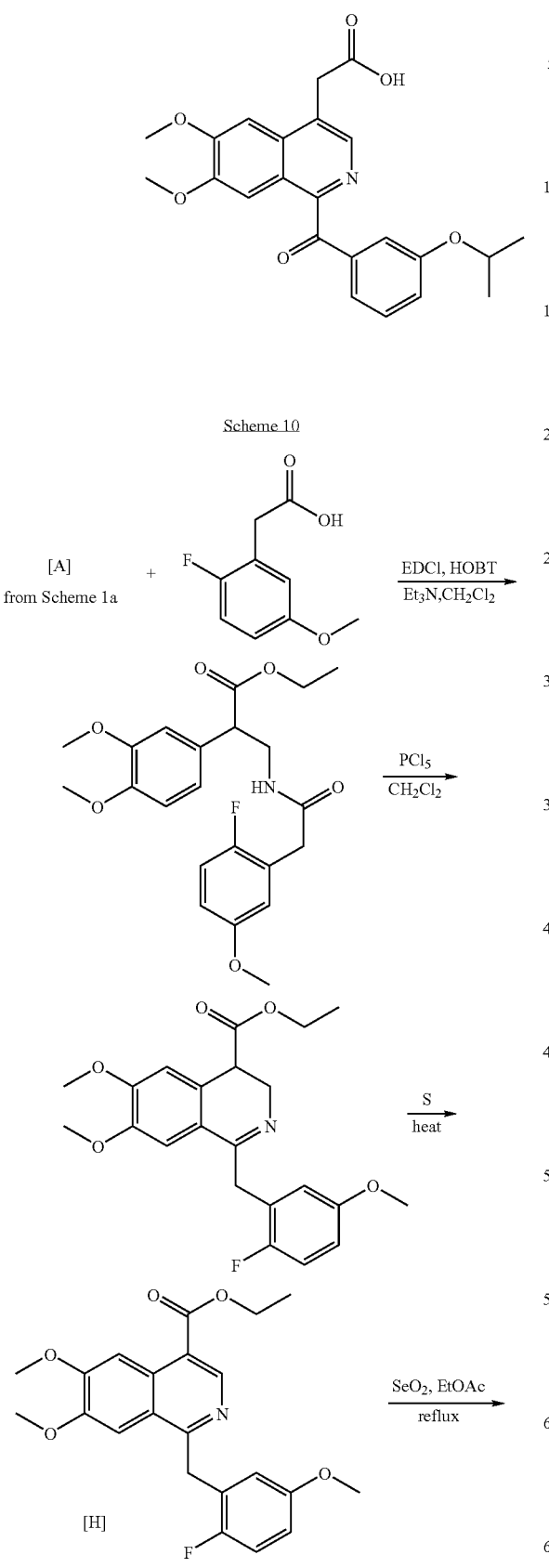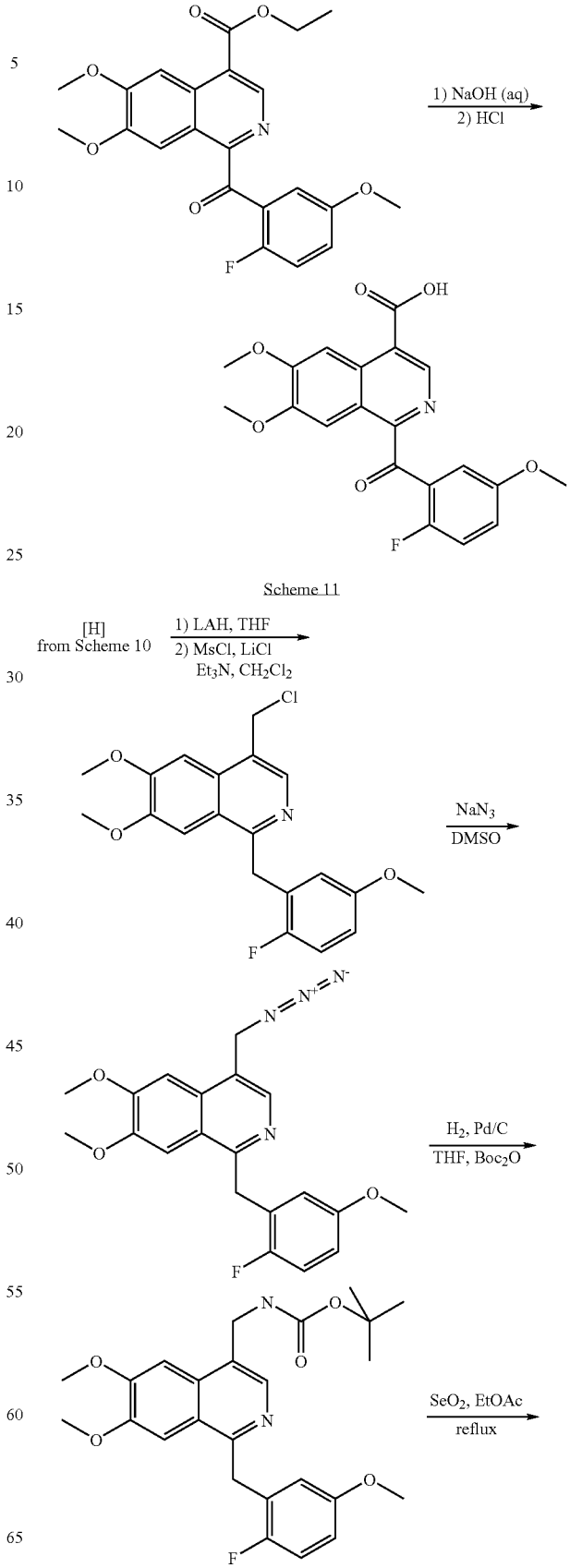

19
-continued
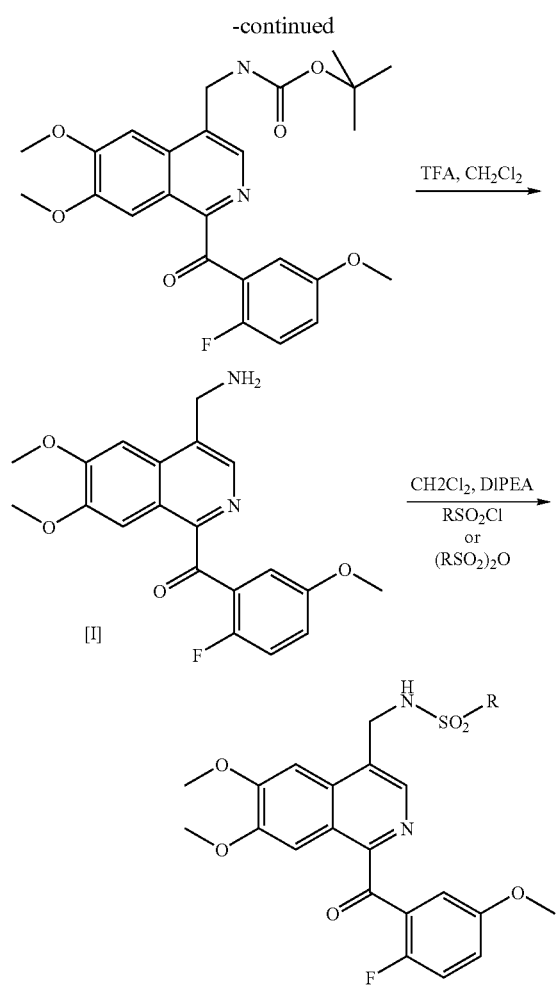
20
-continued
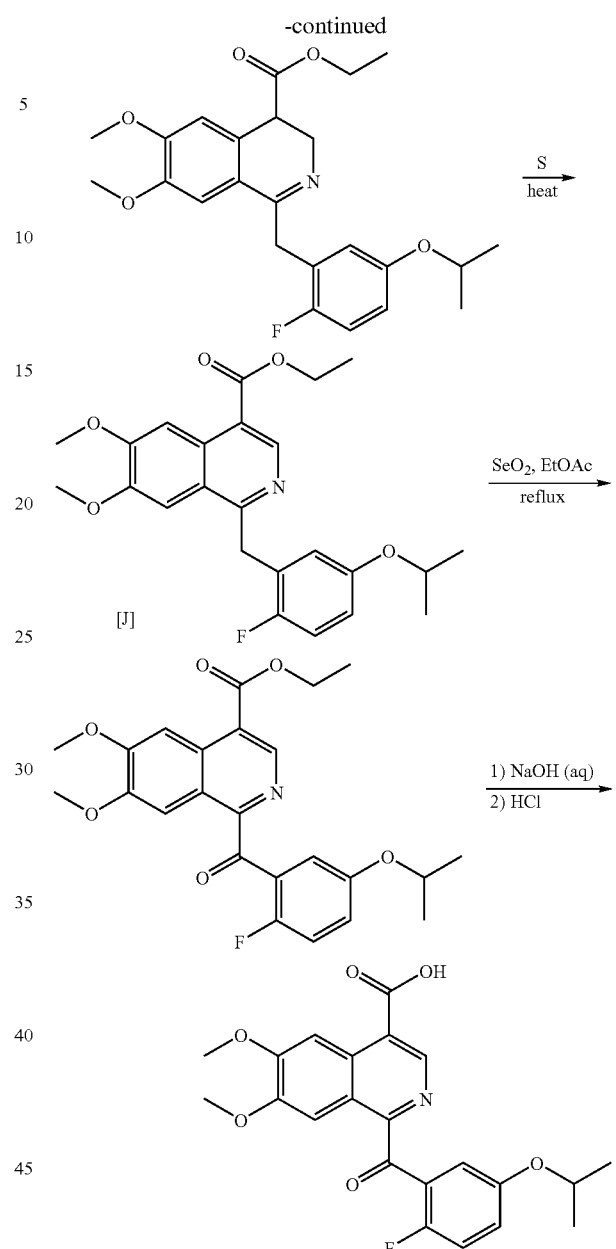
Scheme 12
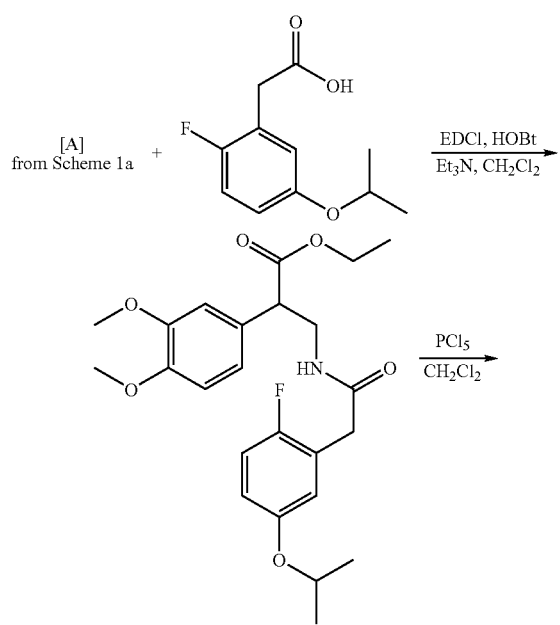
Scheme 13
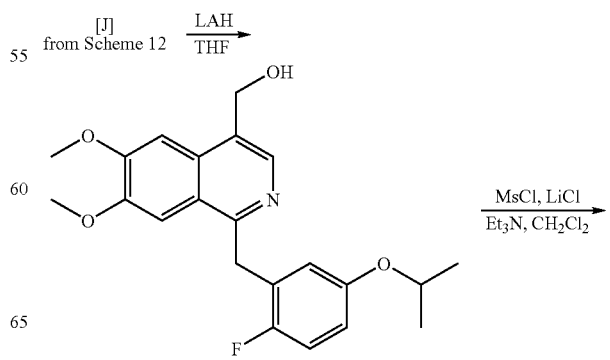

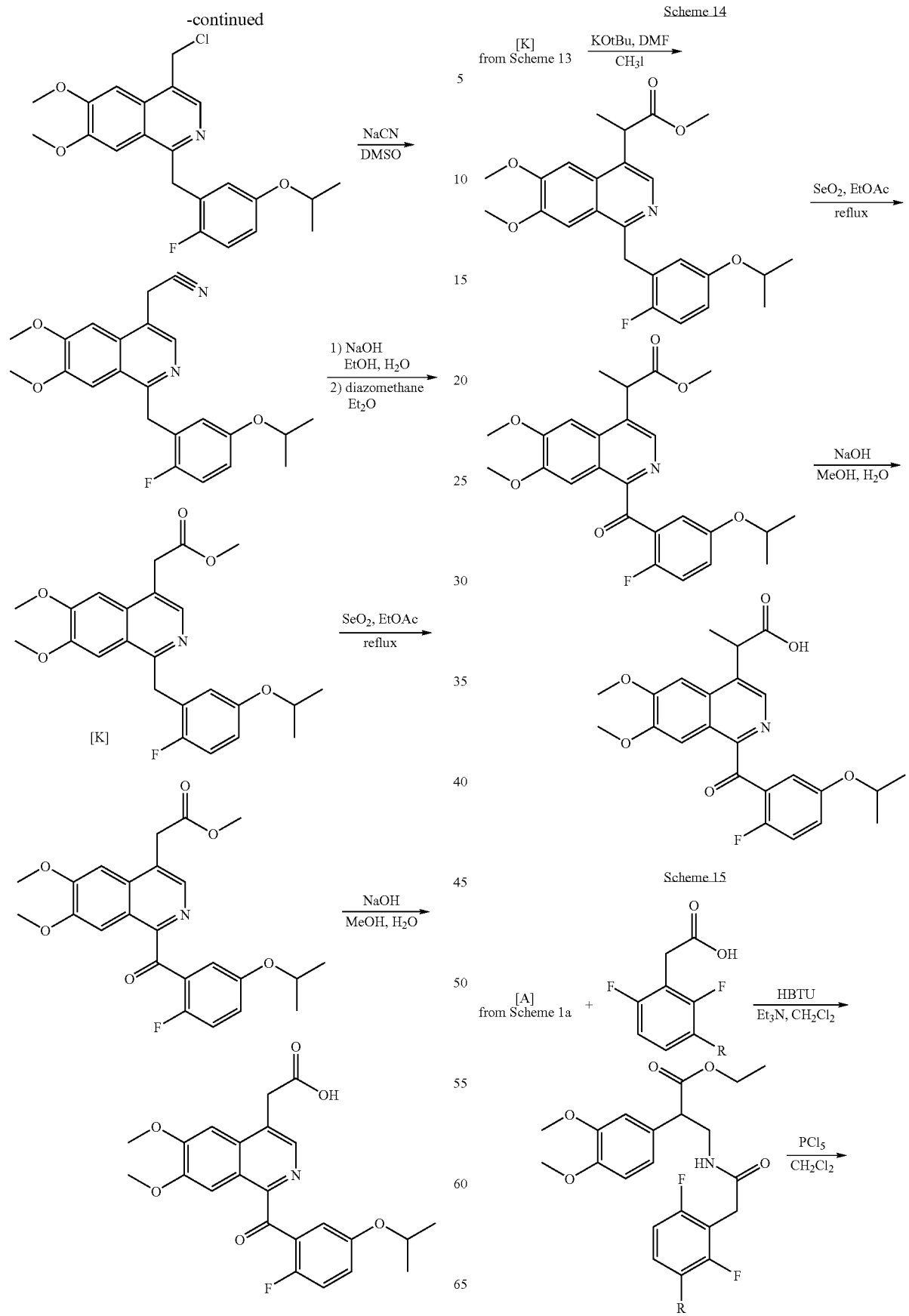

-continued
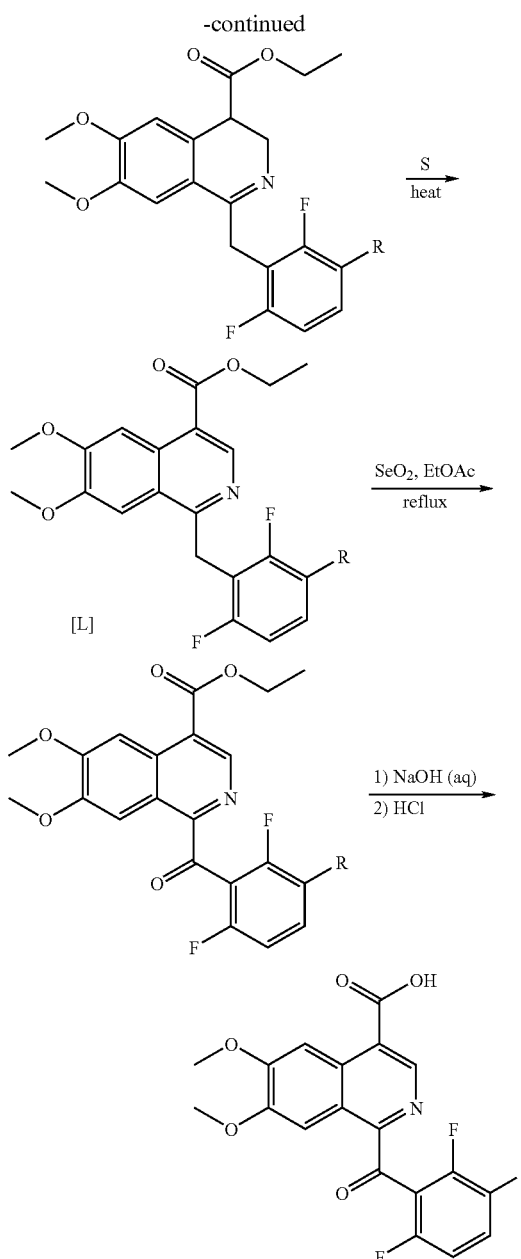
R = H, OCH₃, OCH(CH₃)₂
Scheme 16
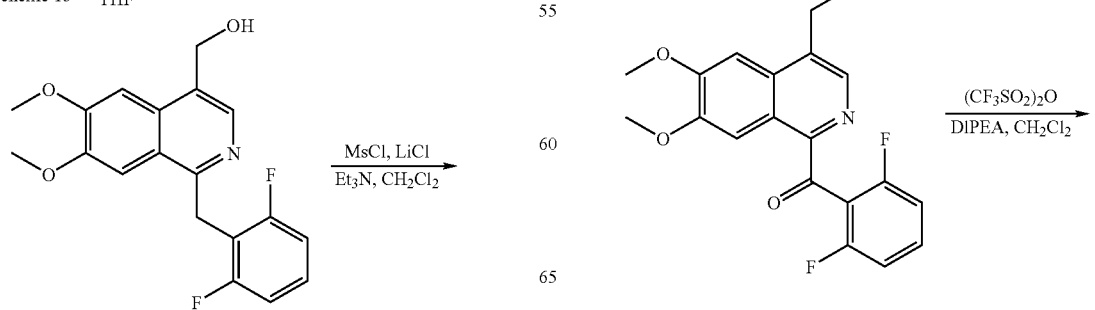
-continued
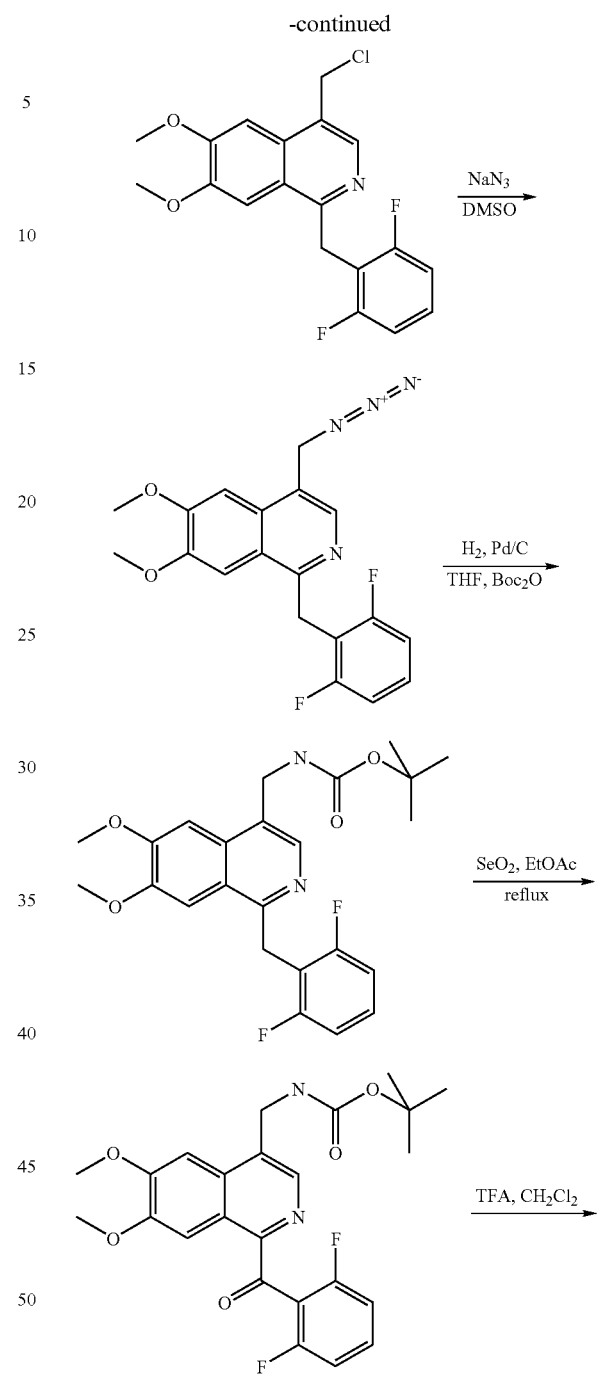

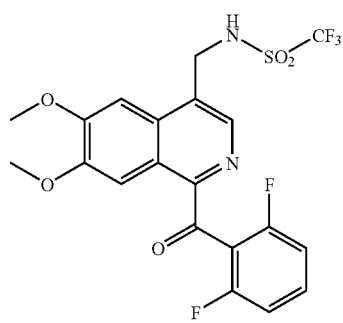
Scheme 17
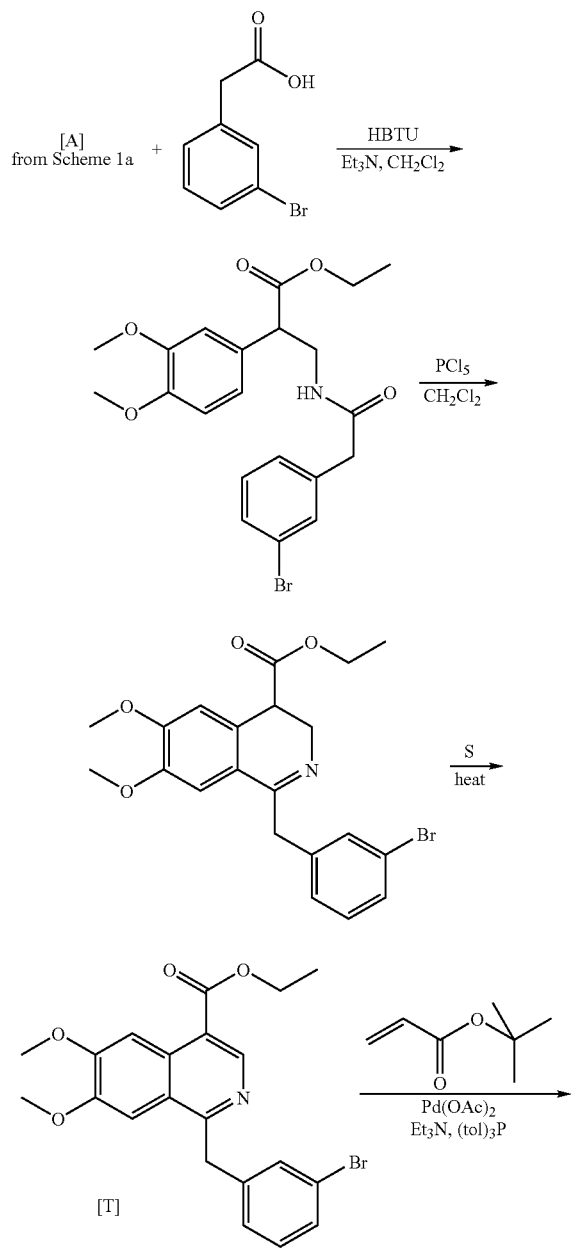
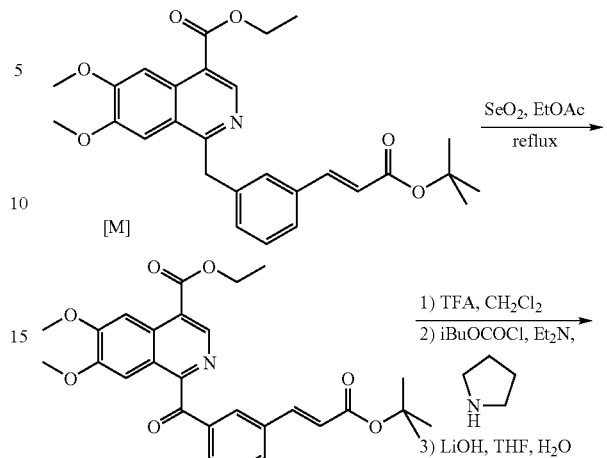
Scheme 18
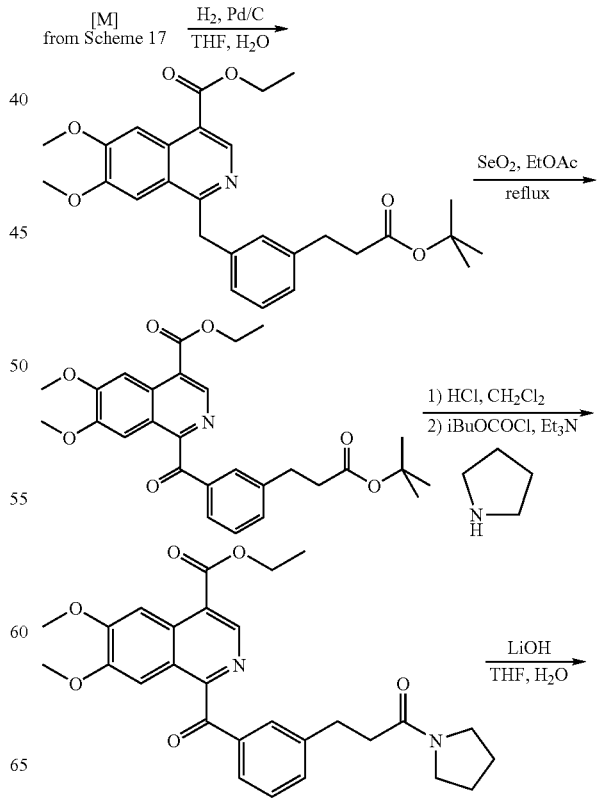

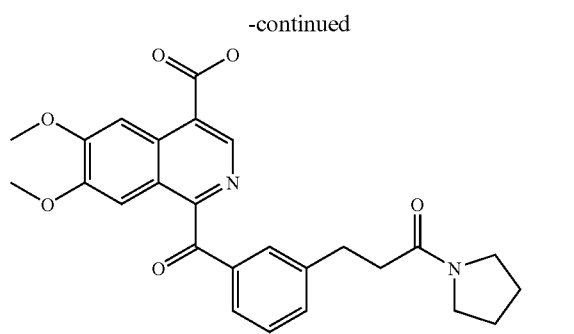
Scheme 19
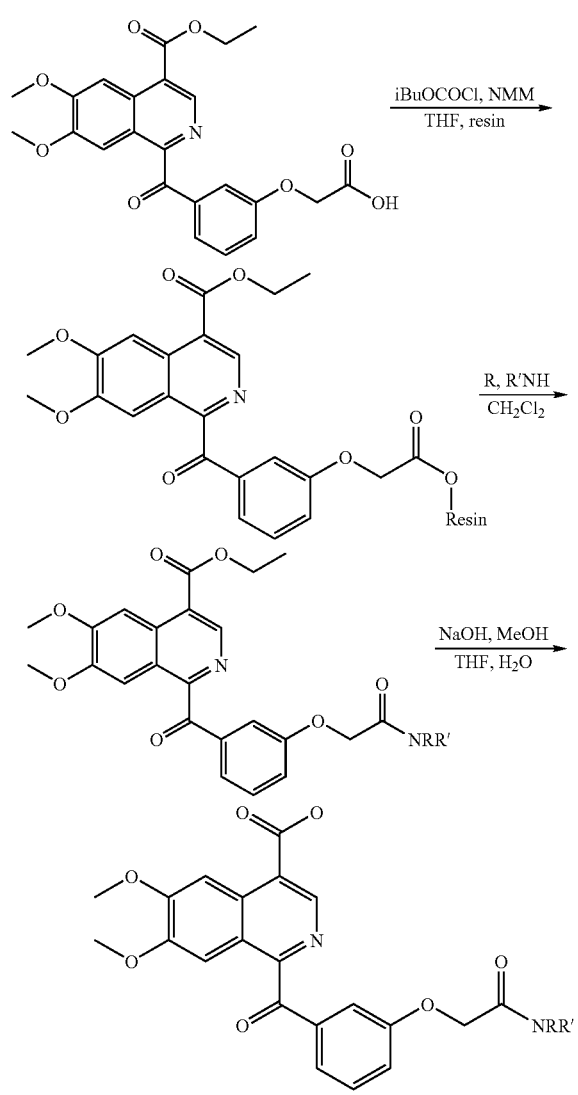
Scheme 20
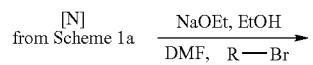
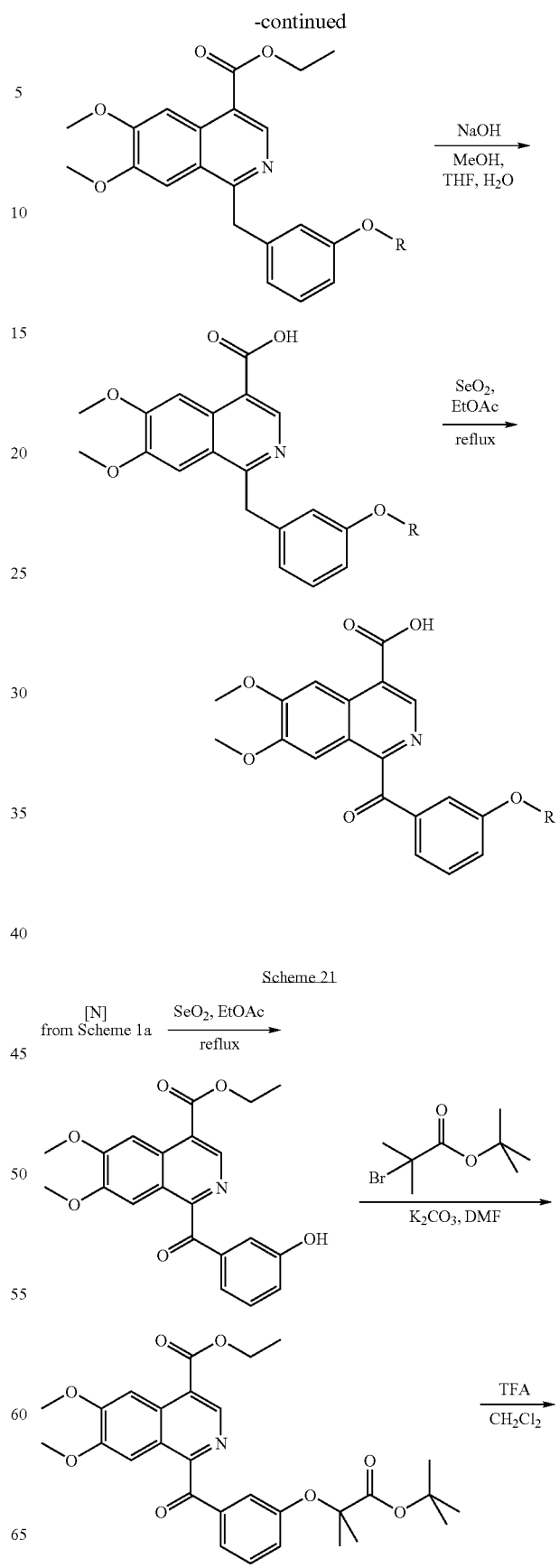
Scheme 21

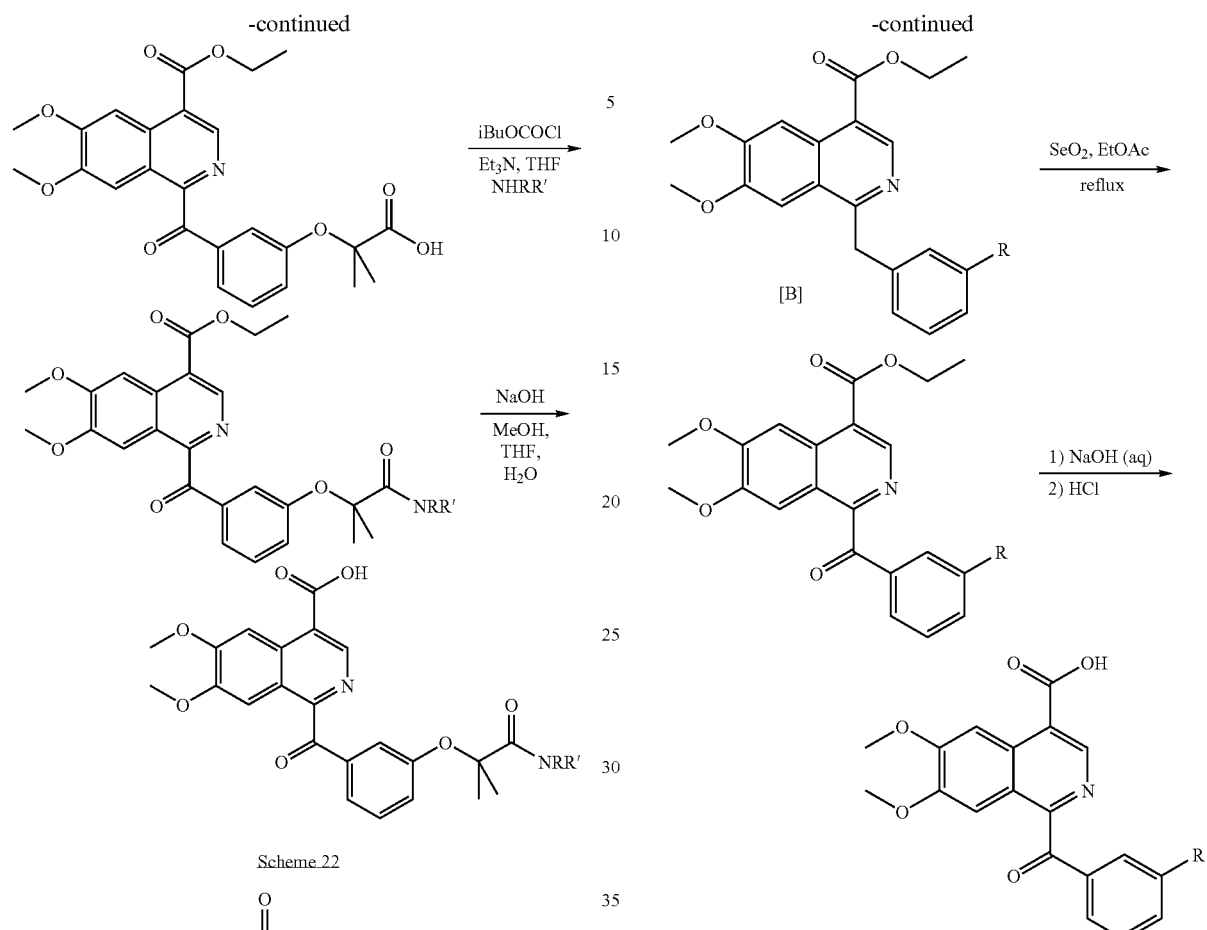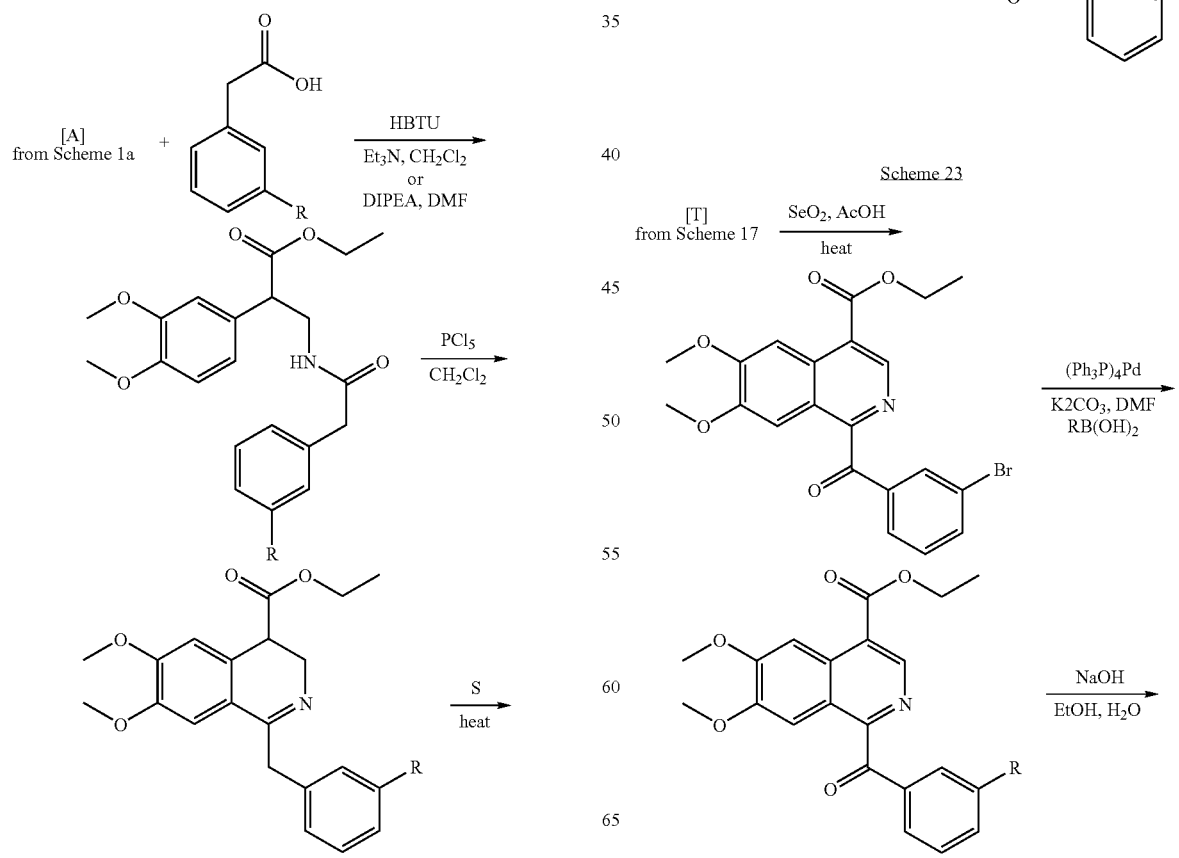

-continued
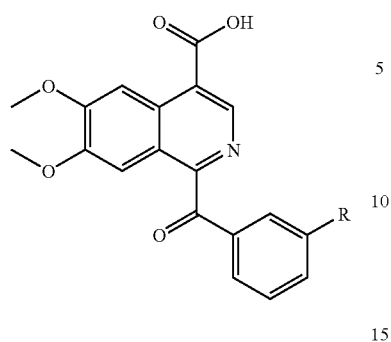
Scheme 24
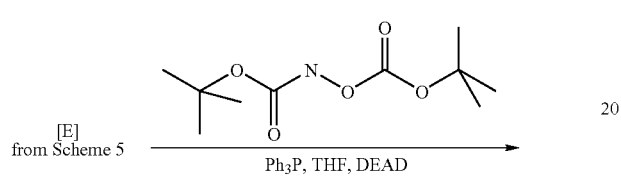
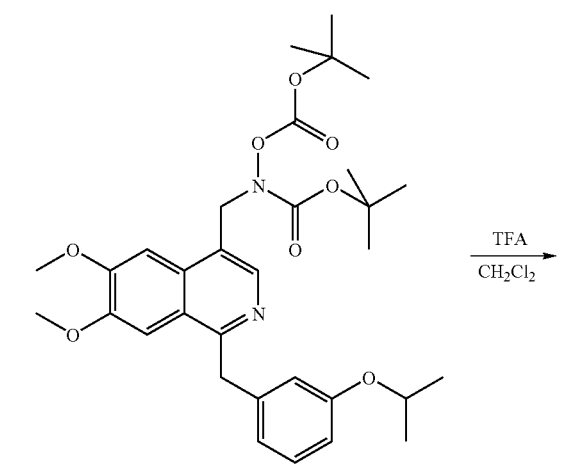
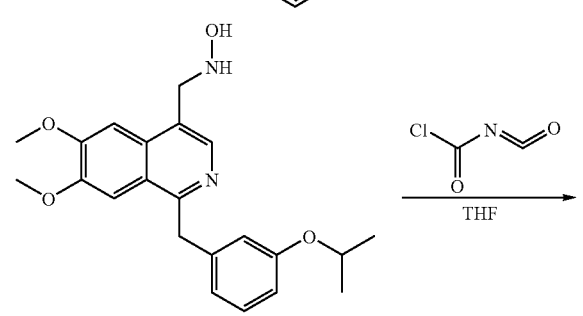
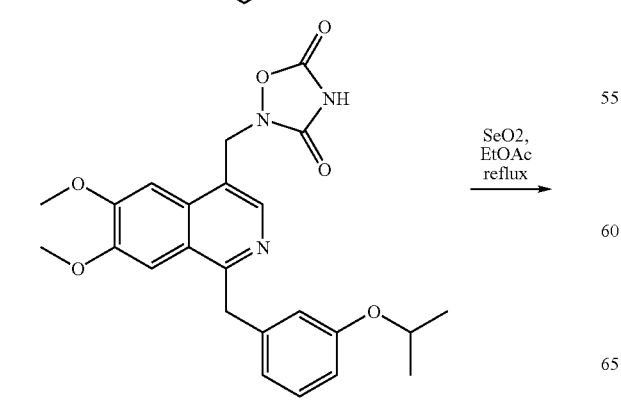
-continued
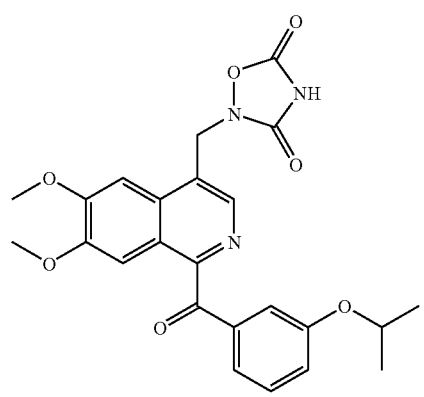
Scheme 25
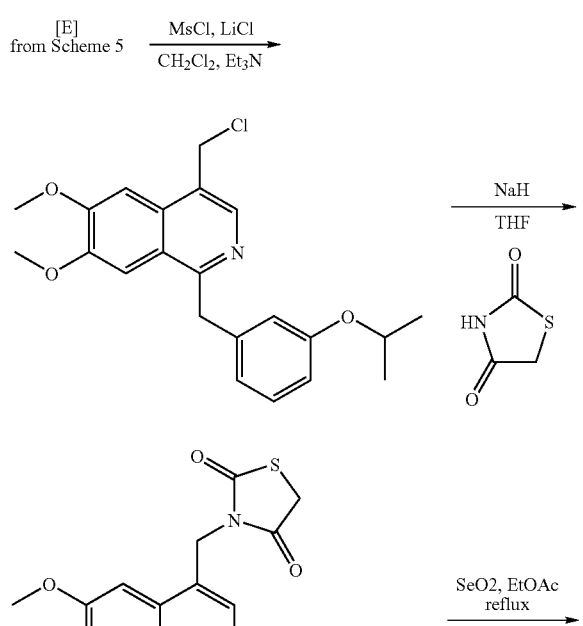
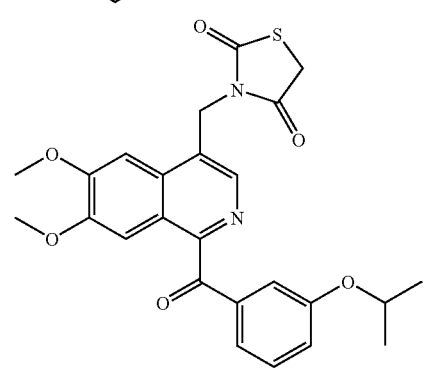

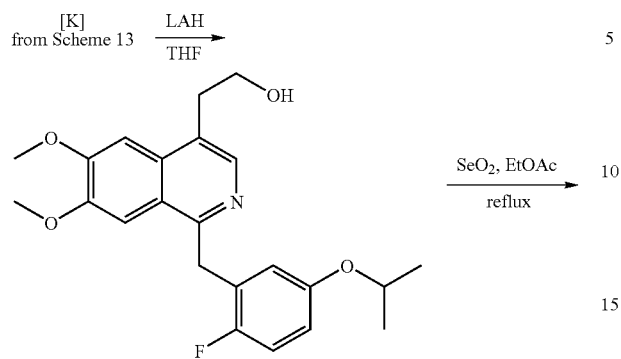
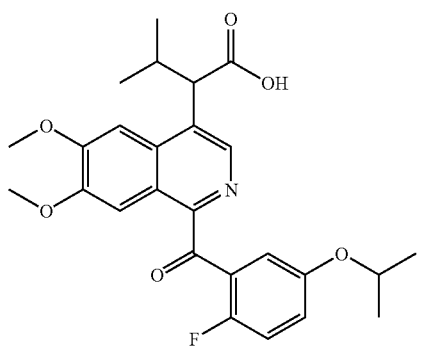
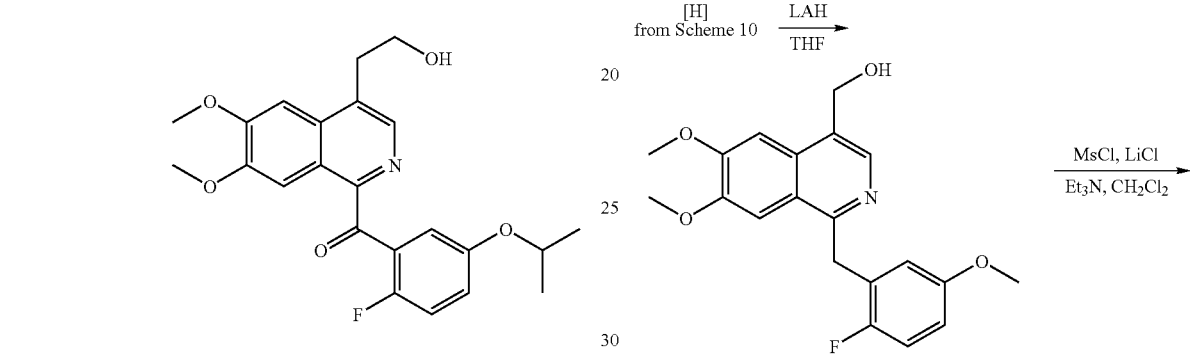
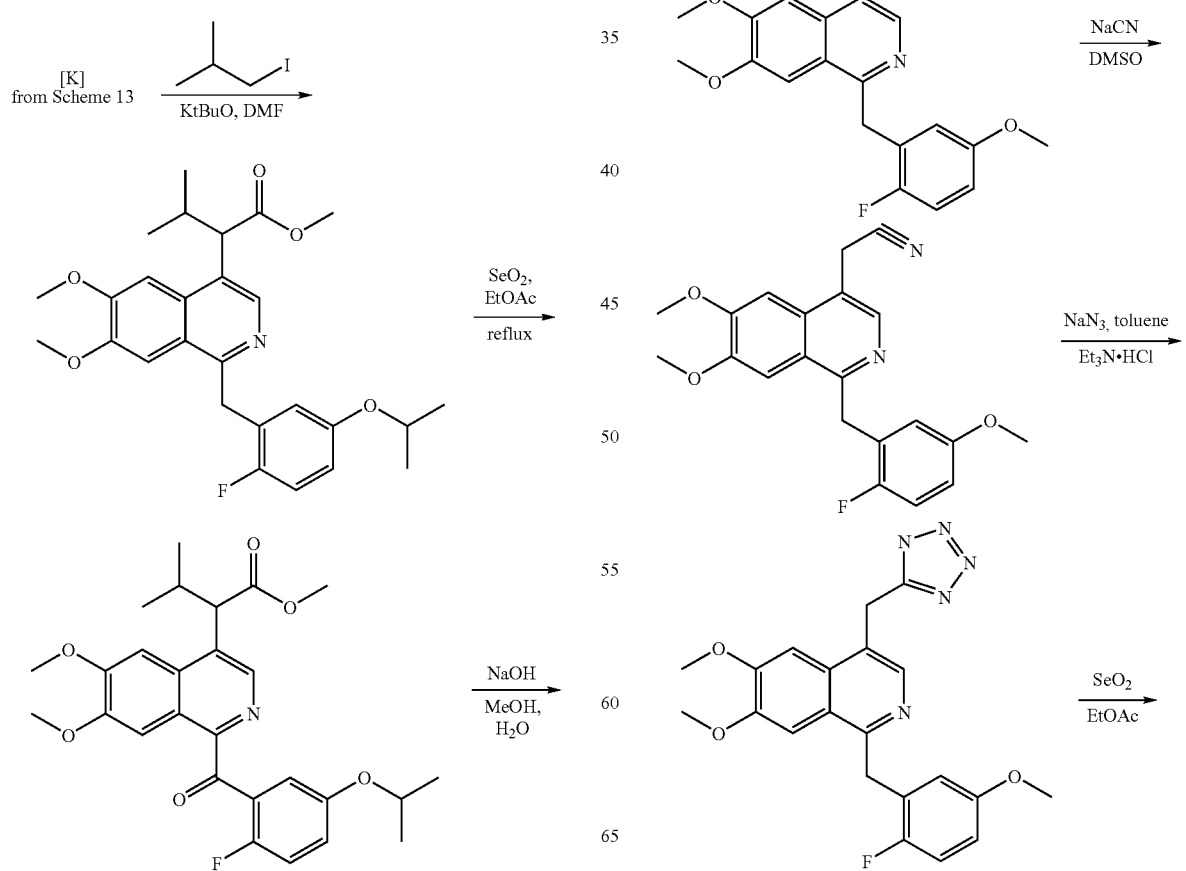

-continued

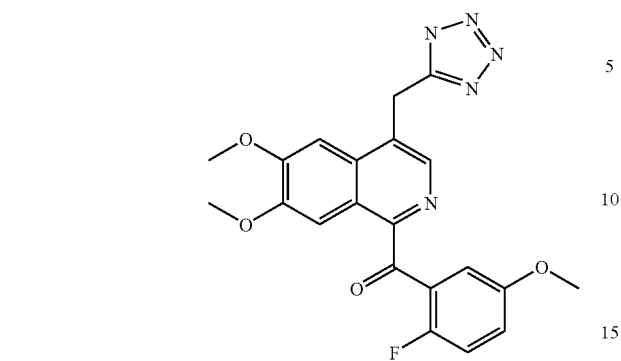

Scheme 29

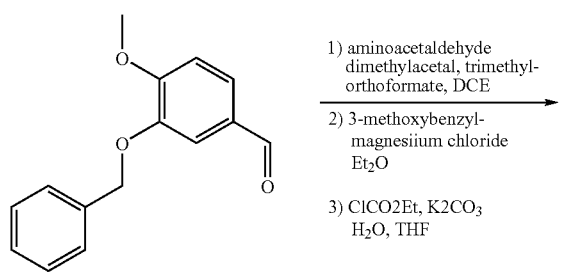

1) aminoacetaldehyde dimethylacetal, trimethyl-orthoformate, DCE
2) 3-methoxybenzyl-magnesium chloride Et₂O
3) ClCO2Et, K2CO3 H₂O, THF

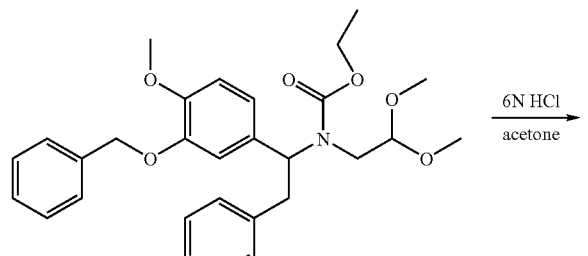

6N HCl acetone

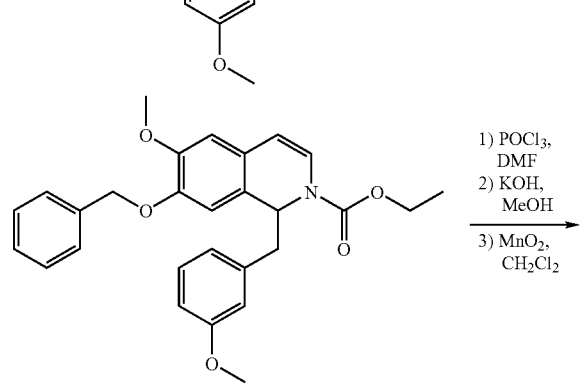

1) POCl₃, DMF
2) KOH, MeOH
3) MnO₂, CH₂Cl₂

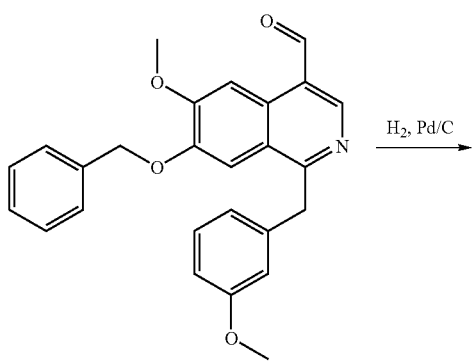

H₂, Pd/C

-continued

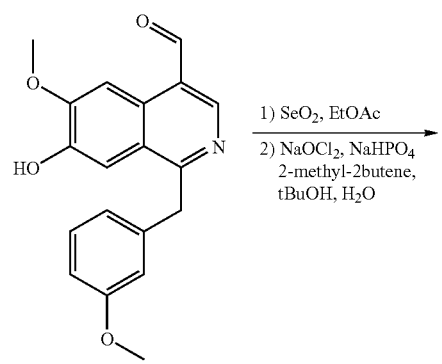

1) SeO₂, EtOAc
2) NaOCl₂, NaHPO₄ 2-methyl-2butene, tBuOH, H₂O

[P]

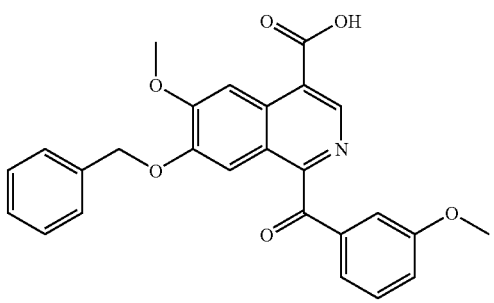

Scheme 30

[P] from Scheme 29 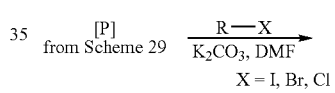 R—X / K₂CO₃, DMF
X = I, Br, Cl

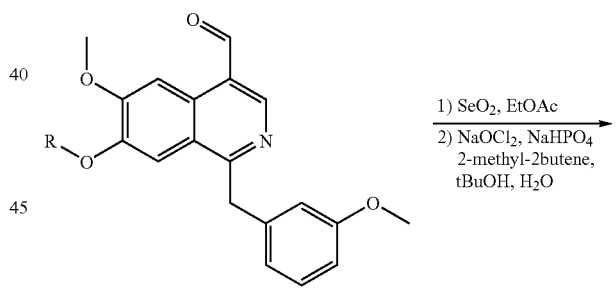

1) SeO₂, EtOAc
2) NaOCl₂, NaHPO₄ 2-methyl-2butene, tBuOH, H₂O

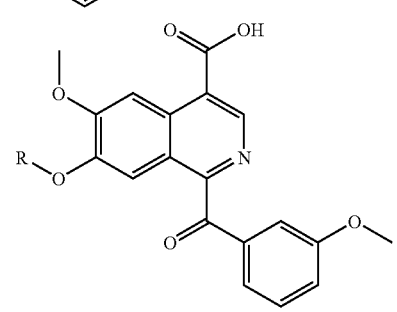

Scheme 31

[P] from Scheme 29 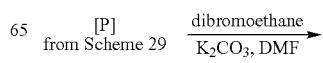 dibromoethane / K₂CO₃, DMF

37
-continued
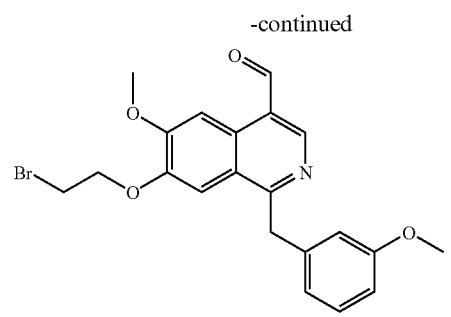
SeO₂, EtOAc →
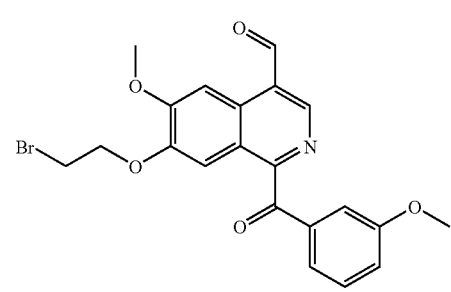
pyrrolidine NH, DMF →
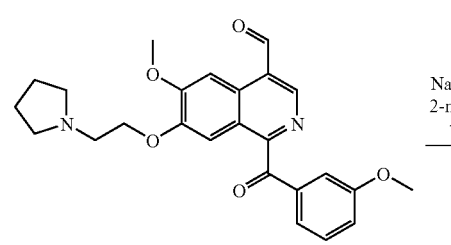
NaOCl₂, NaHPO₄
2-methyl-2butene,
tBuOH, H₂O →
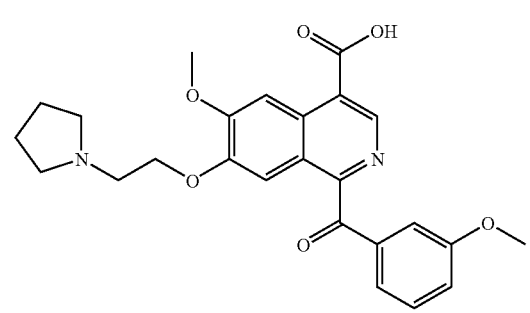
Scheme 32
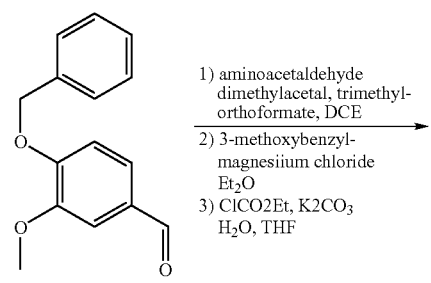
1) aminoacetaldehyde dimethylacetal, trimethyl-orthoformate, DCE
2) 3-methoxybenzyl-magnesiium chloride Et₂O
3) ClCO2Et, K2CO3 H₂O, THF
38
-continued
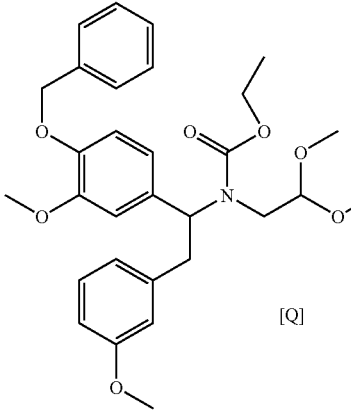
6N HCl
acetone →
[Q]
POCl₃, DMF →
KOH, MeOH →
1) SeO₂, EtOAc
2) NaOCl₂, NaHPO₄
2-methyl-2butene,
tBuOH, H₂O →

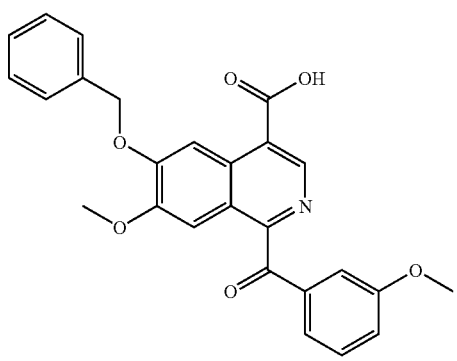
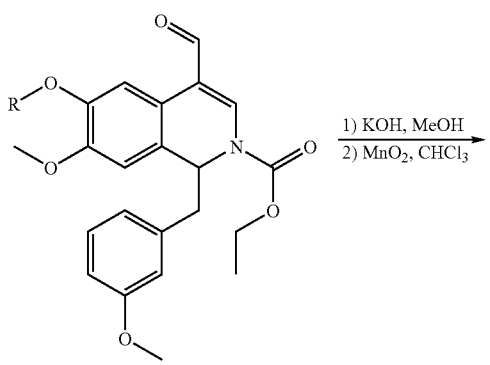
Scheme 33
[Q] from Scheme 32 →(H₂, Pd/C, EtOAc)
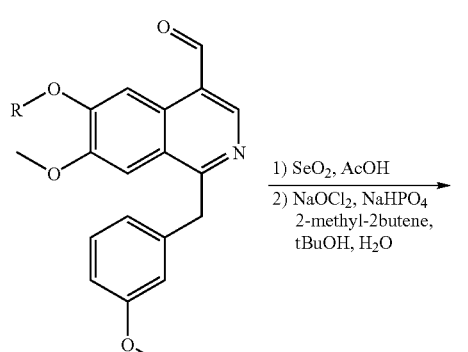
→(6N HCl, acetone)
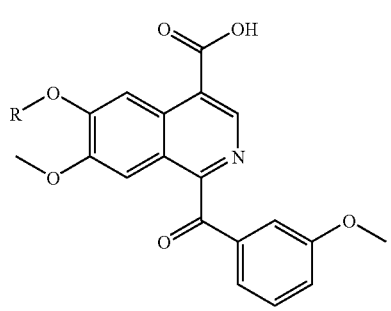
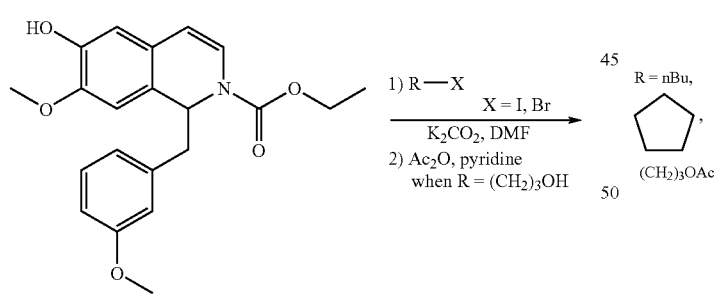
→ 1) R—X  X = I, Br  K₂CO₃, DMF
2) Ac₂O, pyridine when R = (CH₂)₃OH
R = nBu, 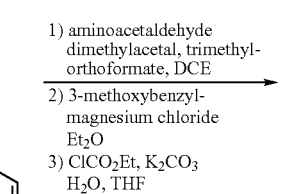, (CH₂)₃OAc
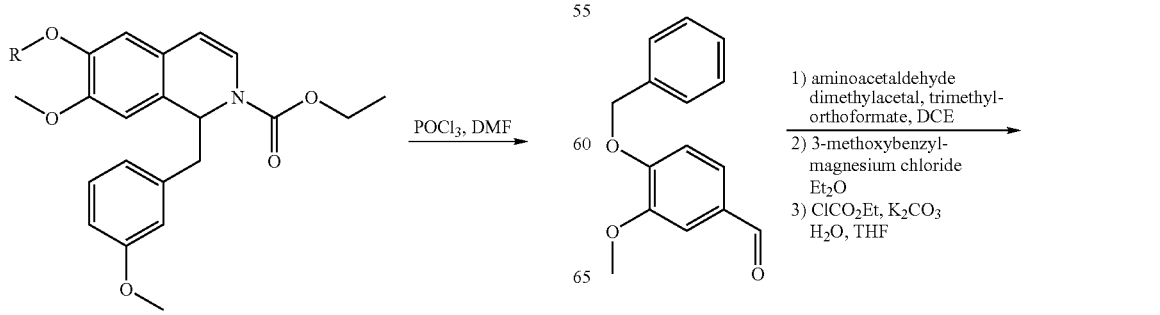
→ POCl₃, DMF
Scheme 34
1) aminoacetaldehyde dimethylacetal, trimethyl-orthoformate, DCE
2) 3-methoxybenzyl-magnesium chloride Et₂O
3) ClCO₂Et, K₂CO₃ H₂O, THF

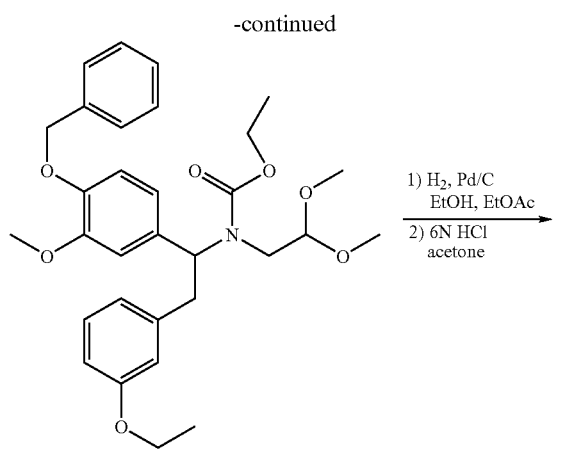
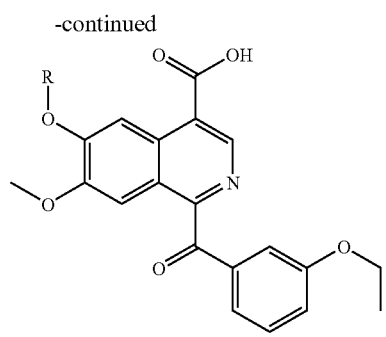
Scheme 35
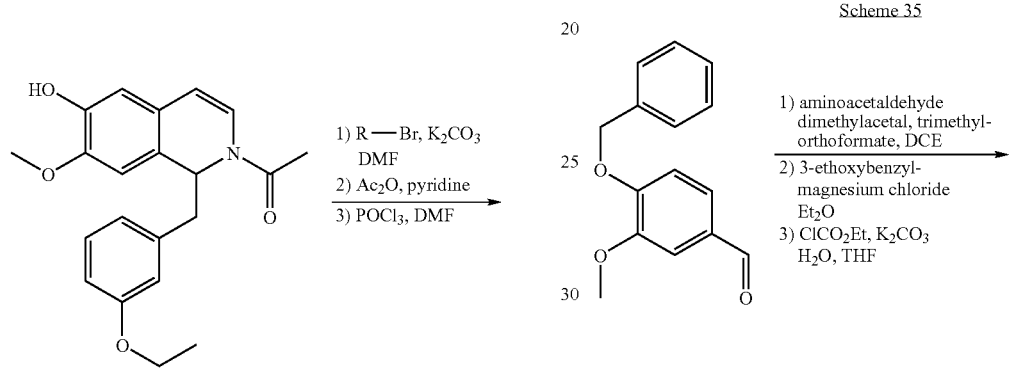
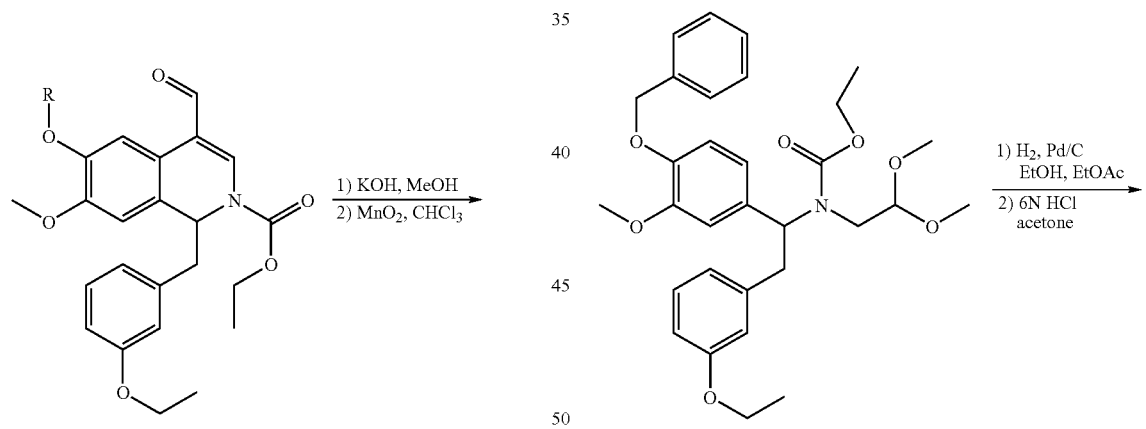
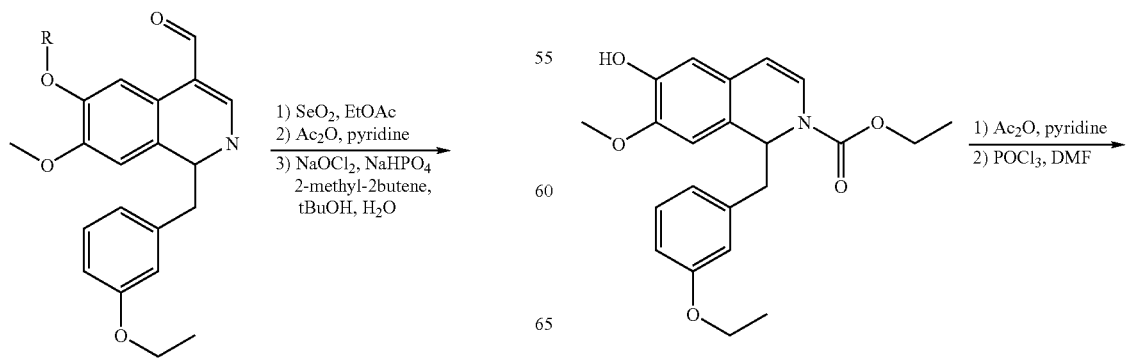

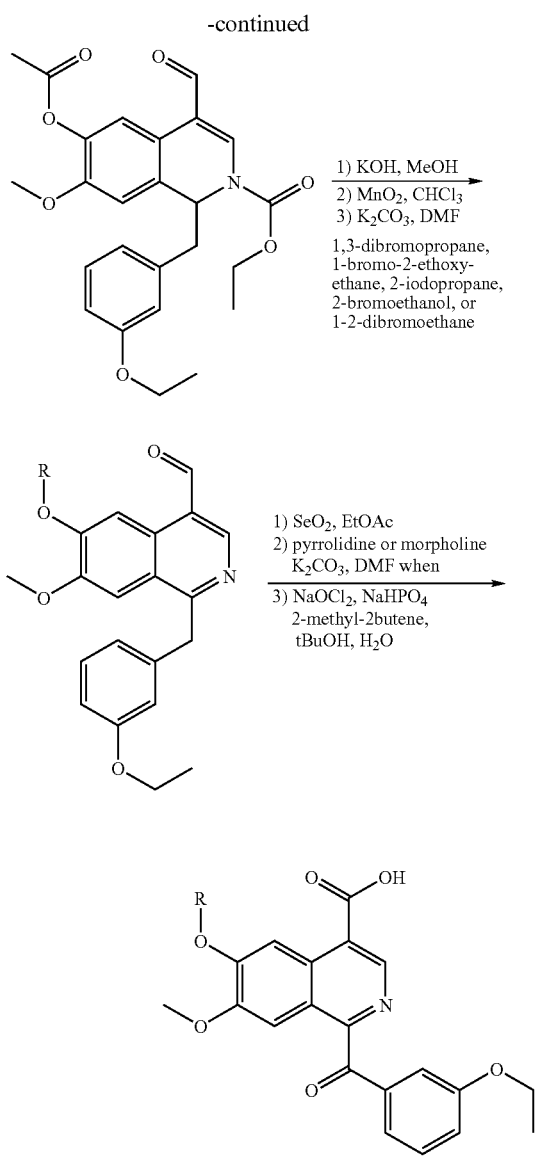
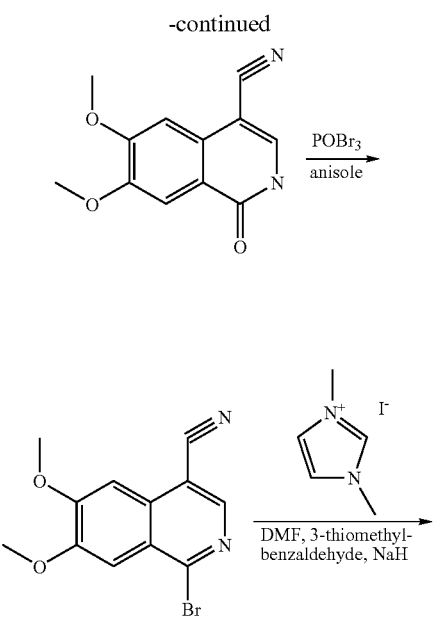
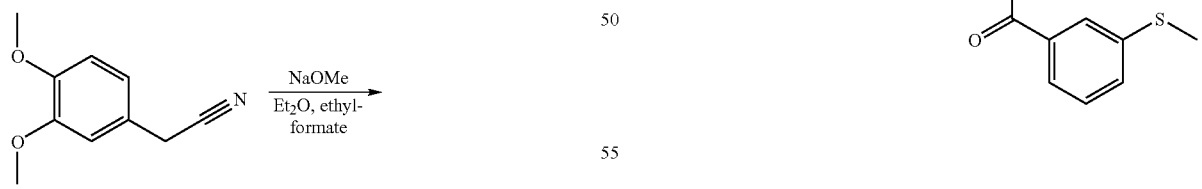
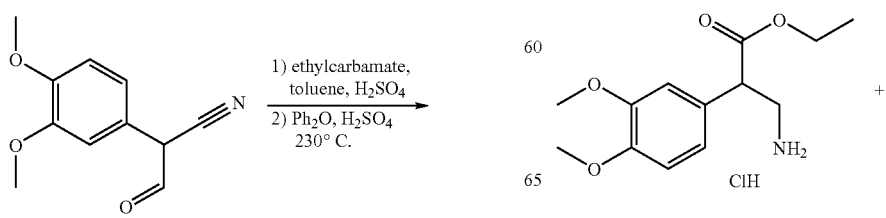

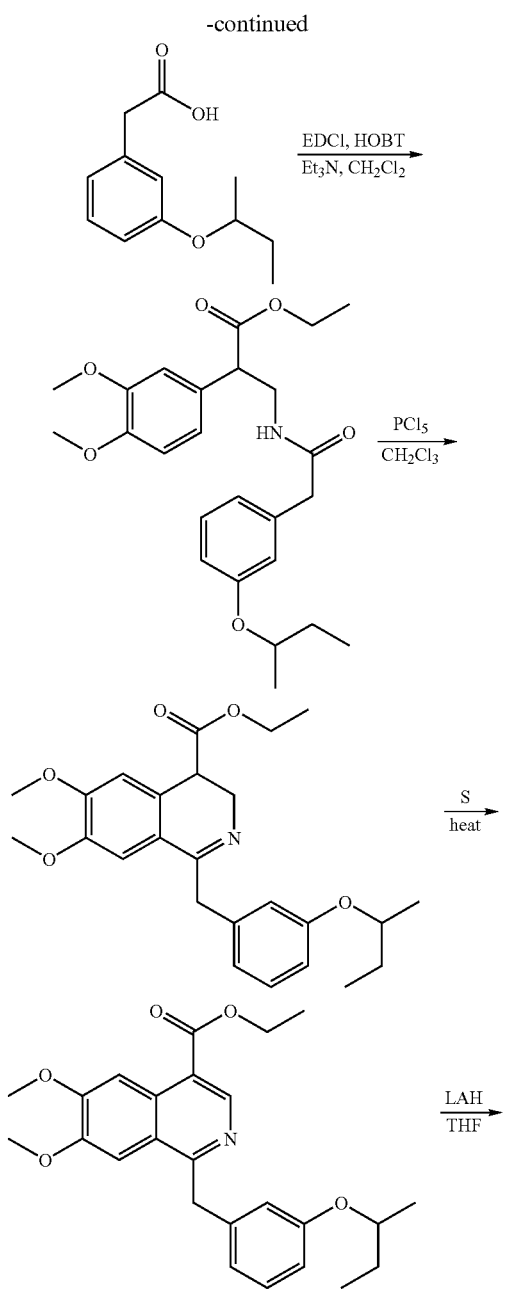
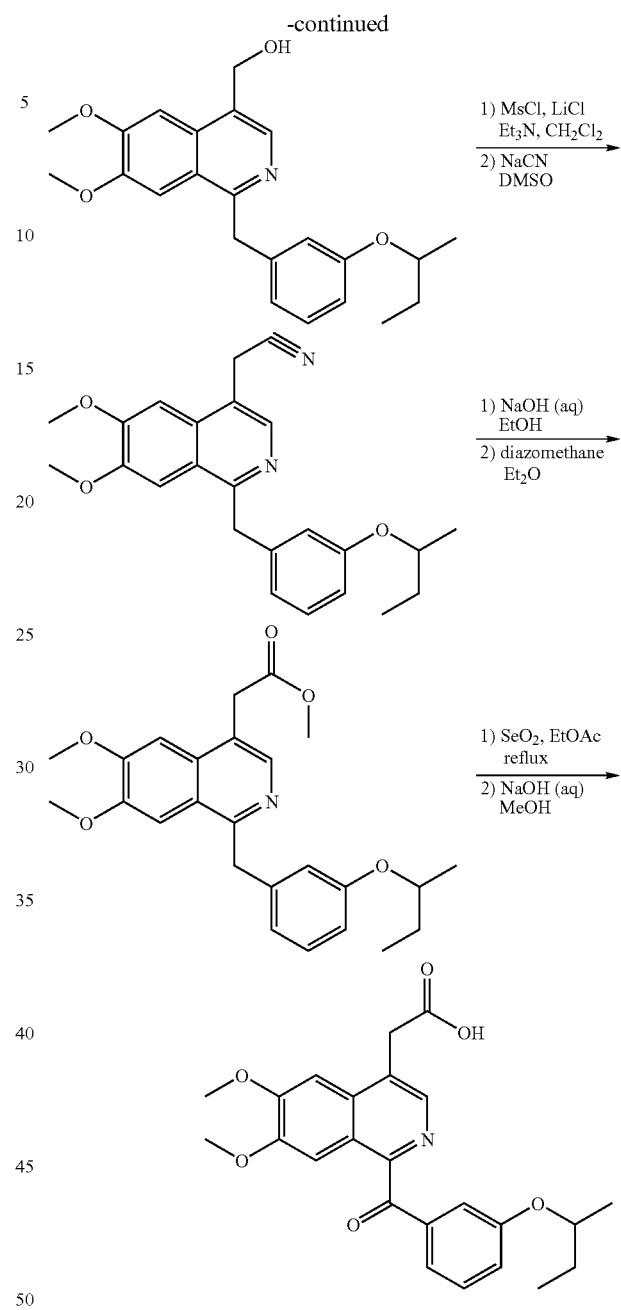
Scheme 38
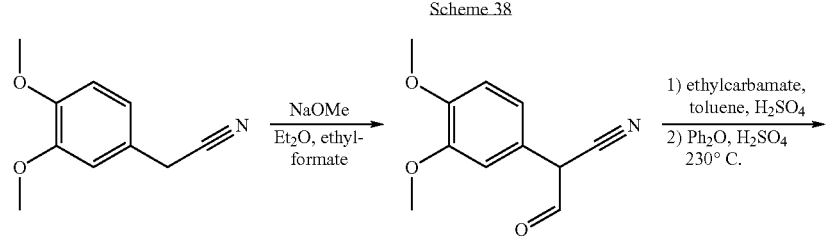

-continued
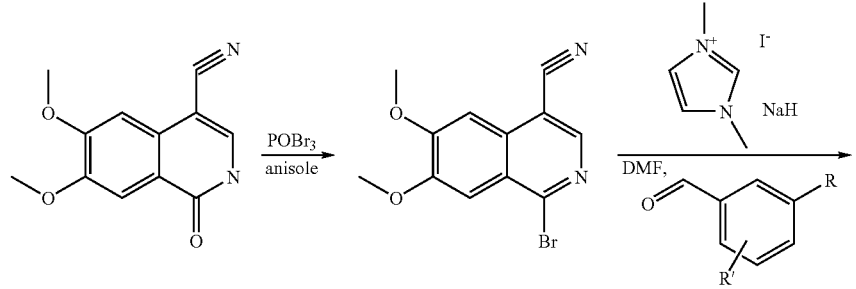
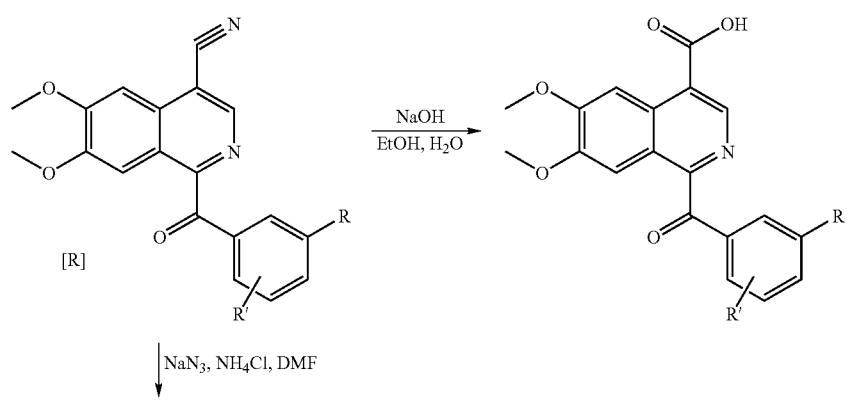
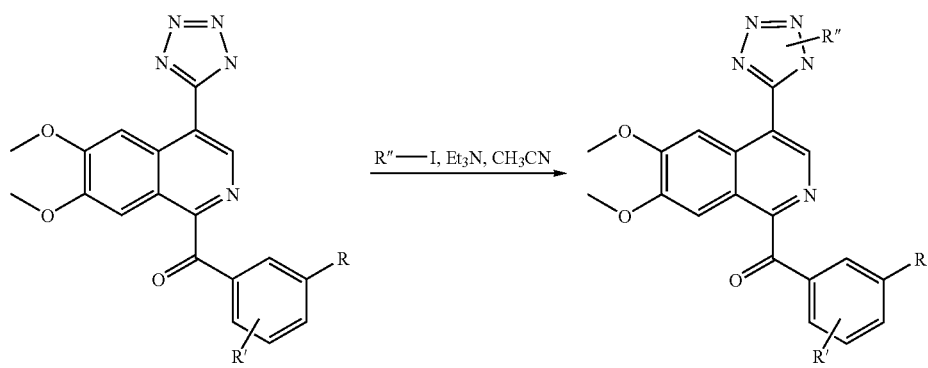
Scheme 39
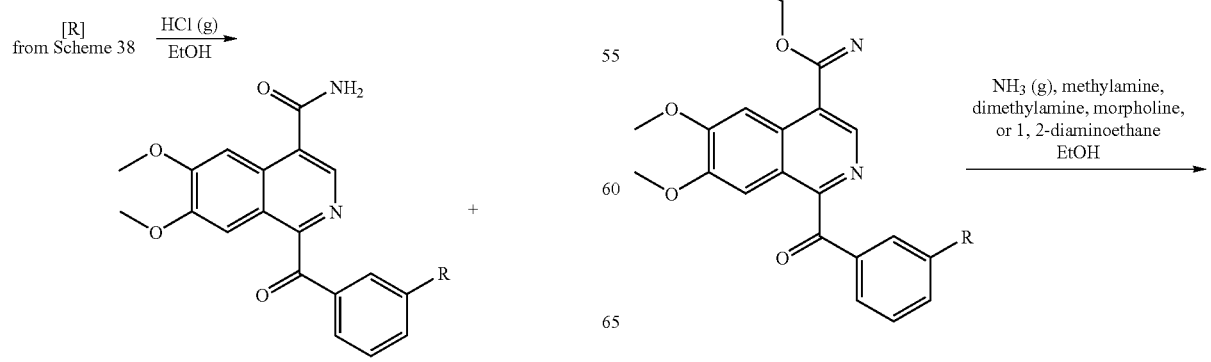

-continued
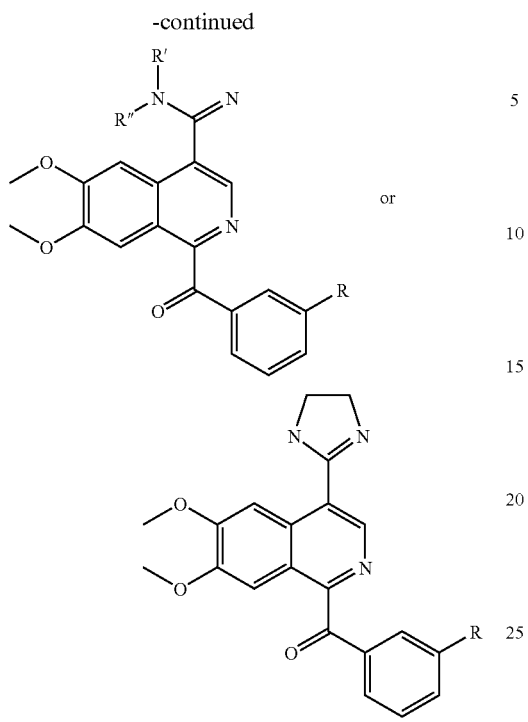
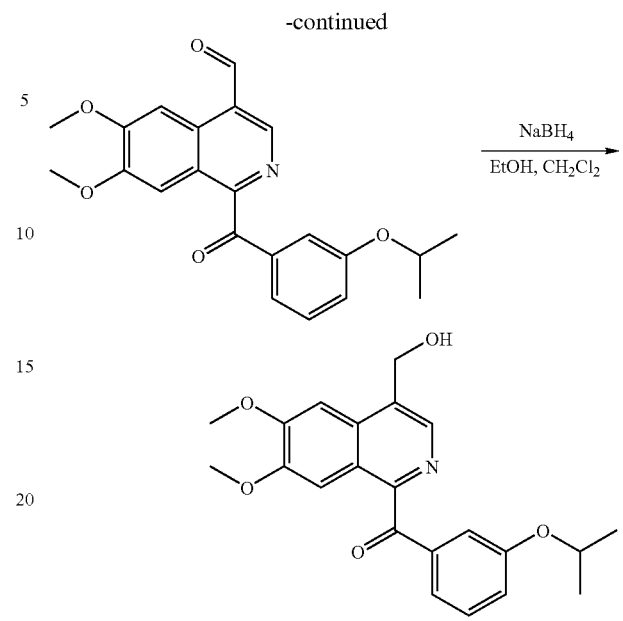
Scheme 40
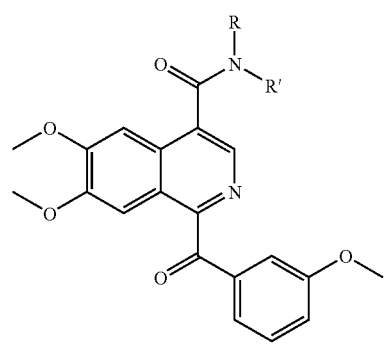
Scheme 41
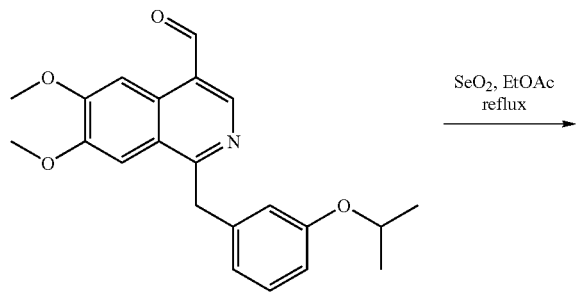
Scheme 42
Scheme 43
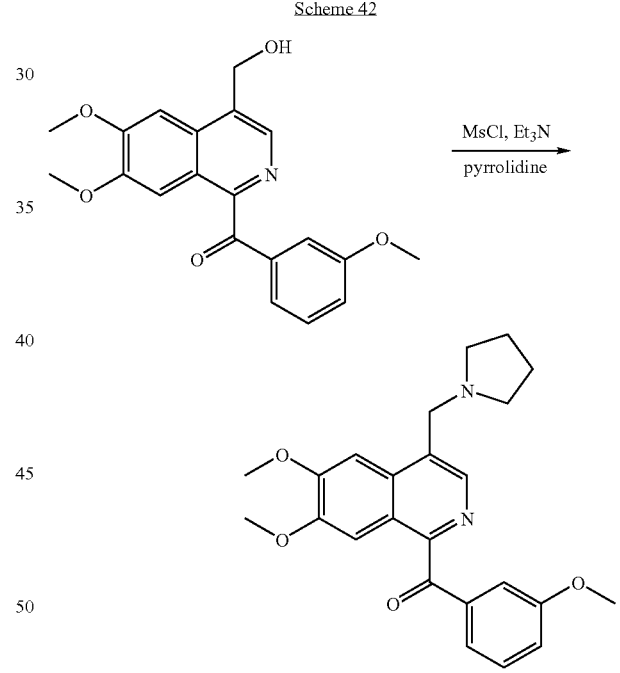
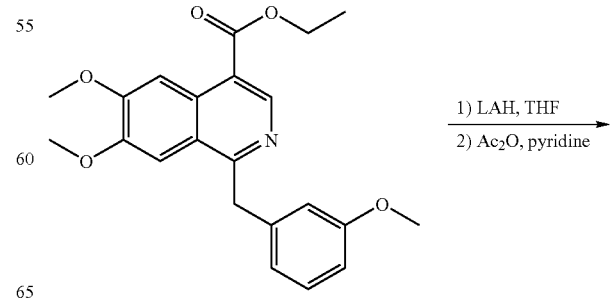

-continued
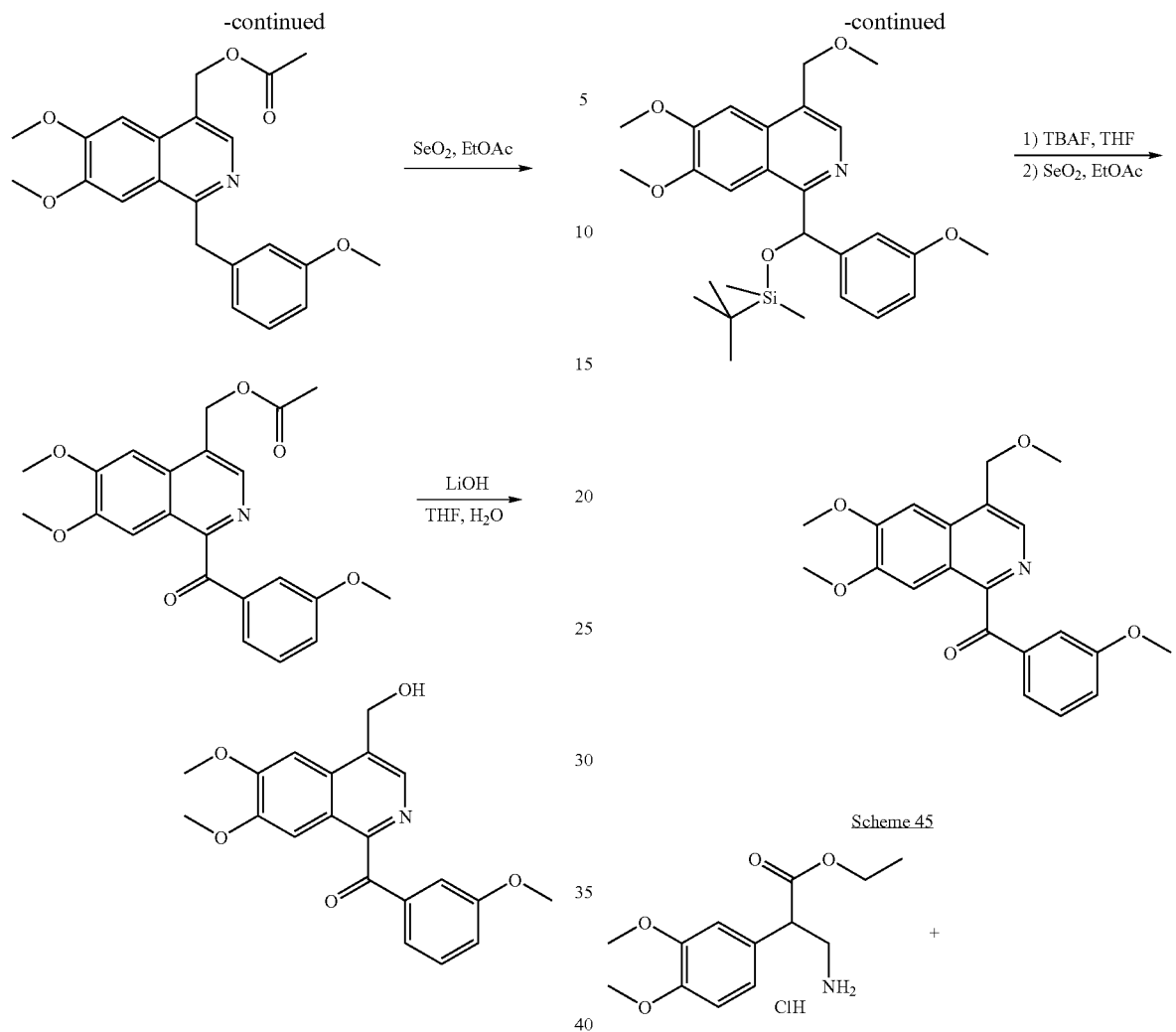
Scheme 44
Scheme 45
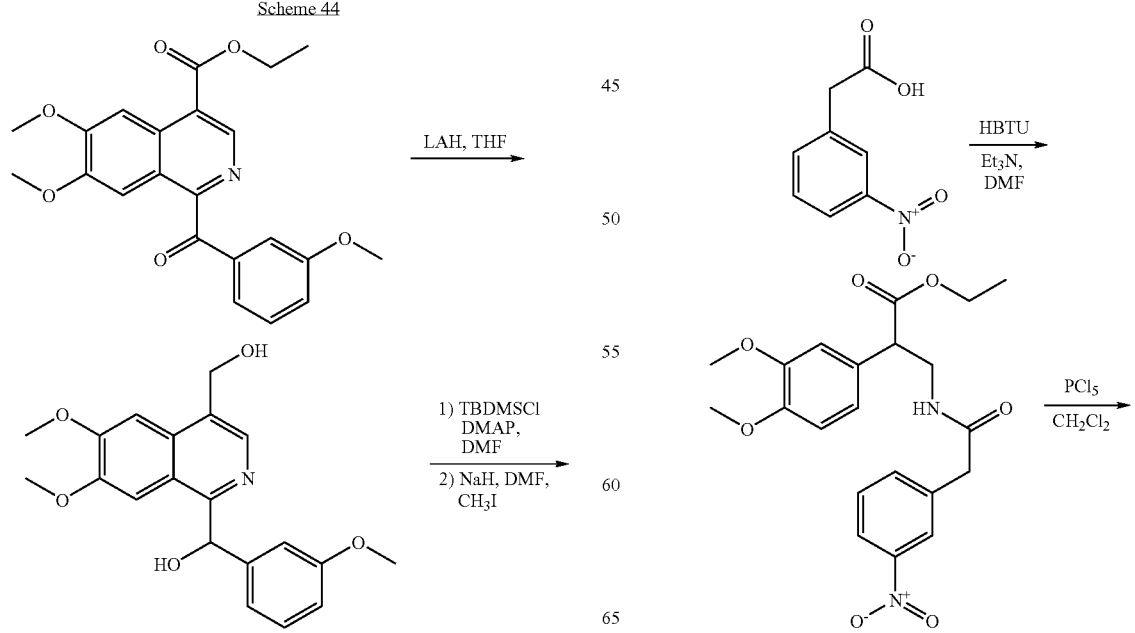

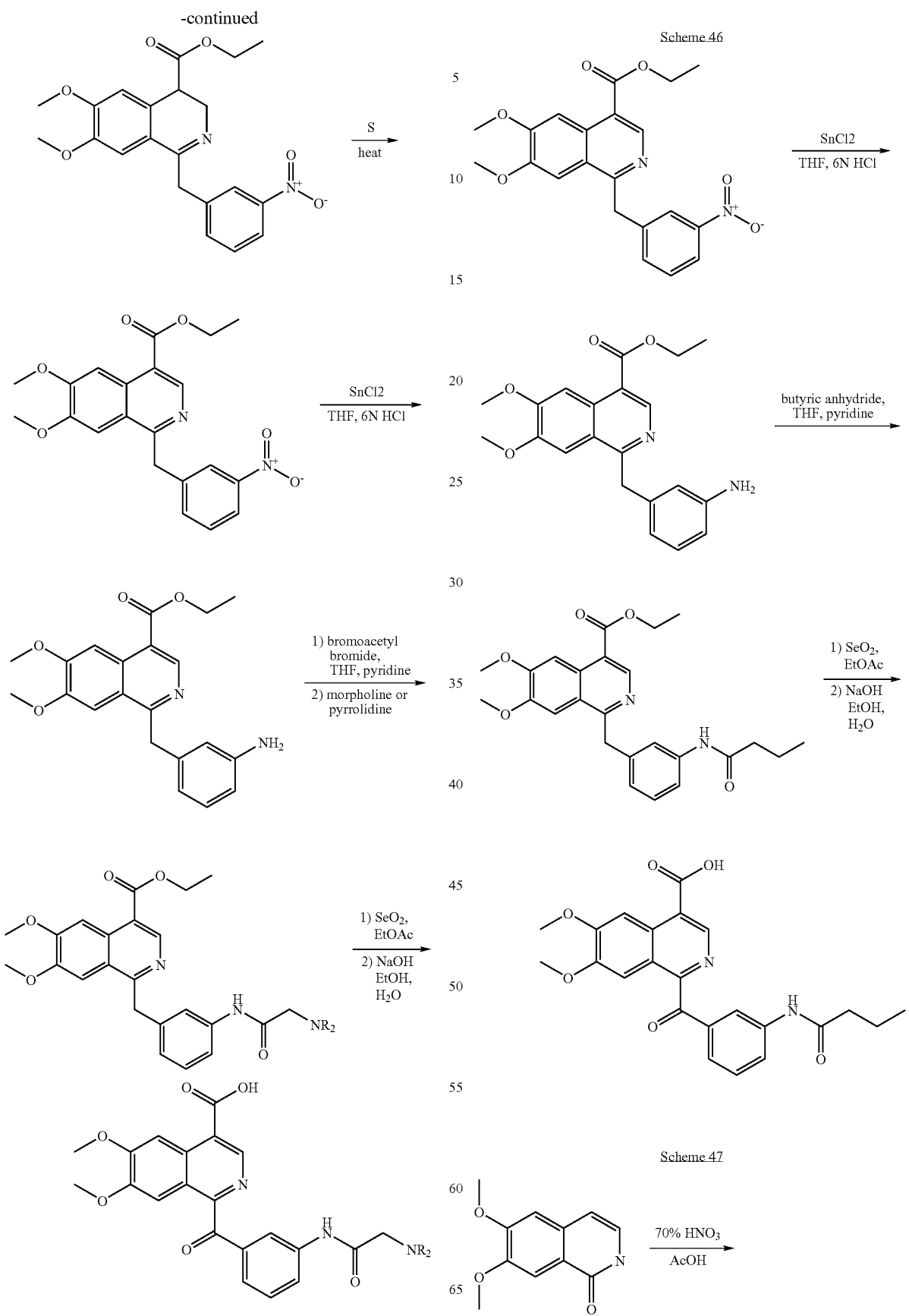

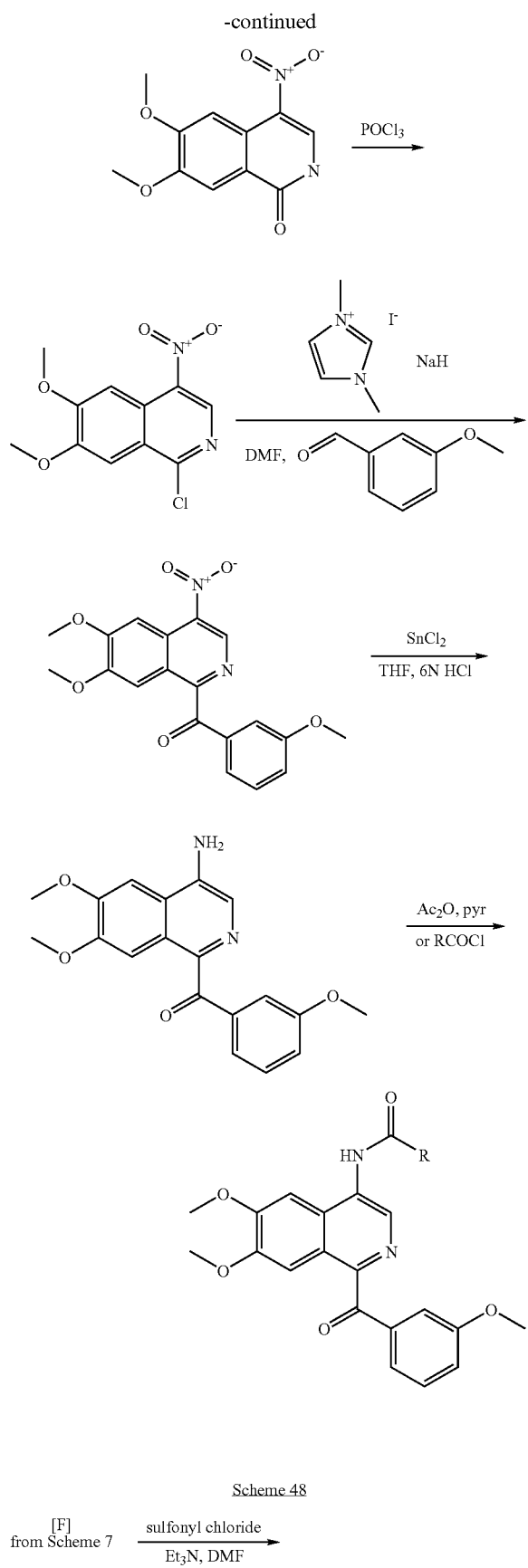

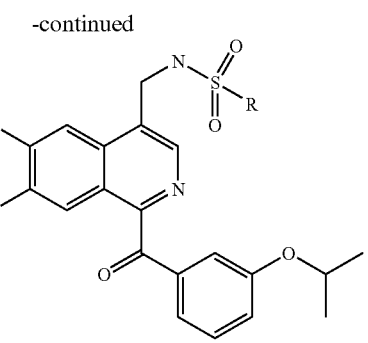

Example 58–61 and are synthetic intermediates. The Examples, with the exception of the noted synthetic intermediates, are within the scope of the present invention.

EXAMPLES

Example 1

6,7-Dimethoxy-2-[3-(2-oxo-2-pyrrolidin-1-yl-ethoxy)-benzoyl]-isoquinoline-4-carboxylic acid trifluoroacetate

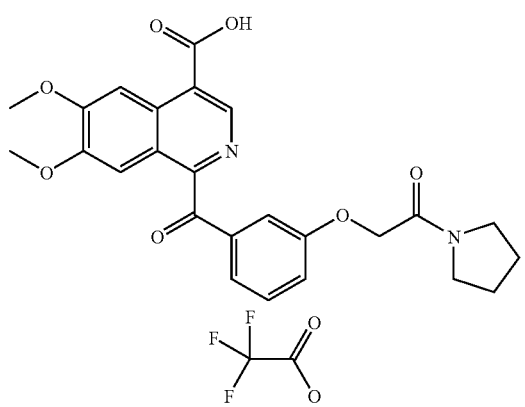

To a one liter round bottom flask was added sodium 12.1 g (0.526 mol) and 225 ml of toluene. The mixture was heated to 100° C. and then stirred to give a fine suspension. Then absolute ethanol 44 ml (1.50 eq) was added through a dropping funnel at 80° C. The mixture was heated at 85° C. for 2 hrs until all sodium was consumed. To this white turbid mixture was added 3,4-dimethoxyphenylacetonitrile (88.5 g, 0.5 mol) and diethyl carbonate (64.5 g, 1.10 eq). The mixture was stirred at 80° C. for 2 hrs. This mixture was distilled until 100 ml of liquids were collected. The mixture was then cooled down to room temperature. Then with an ice bath, a mixture of 250 ml of toluene and 400 ml of 1N hydrochloric acid was added. The mixture was extracted with toluene. The organic layer was dried with sodium sulfate and filtered through a layer of Celite. After the evaporation of solvents, a deep brown oil was obtained (119 g, 95.6%). TLC indicated the product had the same $R_f$ value as the starting material. HNMR showed the pure desired product.

The above crude product (31 g, 0.1245 mol) was dissolved into 100 ml of ethanol. Then 10% of palladium on carbon (7.0 g) was added. To this mixture was added concentrated hydrochloric acid (12N, 12 ml, 0.144 mol). The mixture was hydrogenated at 55 PSI overnight until no further hydrogen consumption was observed. The mixture was put on a steam bath to dissolve the most of the insoluble product. The hot mixture was filtered through a layer of Celite and washed with hot ethanol. The filtrate was kept at room temperature overnight to give a pale yellow crystal. The crystal was filtered and washed with ether to give α-aminomethyl-(3,4-dimethoxy)benzene acetic acid ethyl ester hydrochloride (14.2 g). The mother liquor was concentrated to about 150 ml and then crystallized. Total product obtained was 26.6 g (73.8%).

To 50 ml of methanol was added 3-hydroxyphenyl acetic acid (7.61 g, 0.05 mol). The mixture was cooled in an ice bath and then thionyl chloride was added (3.6 ml, 0.05 mol). The mixture was refluxed for 4 hrs and methanol was evaporated. The residue was extracted with ethyl acetate and sodium bicarbonate solution. The organic layer was dried and evaporated to give an oil (8.90 g). This oil was dissolved in 150 ml of acetone containing benzyl bromide (9.17 g, 0.053 mol) and potassium carbonate (16.9 g, 0.16 mol). The mixture was stirred at room temperature overnight. The solid was removed through filtration and solvents was evaporated. The residue was extracted with ethyl acetate and sodium bicarbonate solution. The organic layer was dried and evaporated. The residue was suspended in 70 ml of methanol and 1N sodium hydroxide solution was added (70 ml). The mixture was refluxed for 1 hr and solvents were evaporated. The residue was dissolved in 150 ml of water and extracted with ether. The aqueous layer was acidified with 1N hydrochloric acid and the white precipitate was filtered to give 3-benzyloxyphenyl acetic acid (11.0 g, 91%).

To a suspension of α-aminomethyl-(3,4-dimethoxy)benzene acetic acid ethyl ester hydrochloride (5.80 g, 20 mmol) in 150 ml of methylene chloride was added 3-benzyloxyphenylacetic acid (4.84 g, 20 mmol). Then triethylamine (5.53 ml, 2.0 eq) was added followed by the addition of HBTU (7.58 g, 20 mmol). The mixture was stirred at room temperature overnight and then extracted with methylene chloride and 1N hydrochloride solution. The organic layer was washed with water, concentrated sodium bicarbonate solution and finally brine. TLC showed one spot of the crude solution. After the drying and the evaporation of solvents, an oil was obtained (10.20 g).

The above crude oil product (10.20 g) was dissolved in 100 ml of methylene chloride. Then phosphorus pentachloride (6.70 g, 1.50 eq) was added. The mixture was stirred at room temperature overnight to give a deeply red colored solution. TLC showed the complete disappearance of the starting material. This solution was poured into an ice. The mixture was extracted with methylene chloride. The organic layer was washed with dilute ammonium hydroxide solution. After the evaporation of the solvents, the oily red residue was purified by flash column chromatography using ethyl acetate to give a desired dihydroisoquinoline derivative (4.03 g, 44% for 2 steps).

The above dihydroisoquinoline derivative (2.76 g, 6.01 mmol) was mixed with sulfur (230 mg, 7.18 mmol). The mixture was heated in an oil bath preheated to 165° C. and stirred at that temperature for 15 minutes. Then ethanol (100 ml) was added and the mixture was filtered. MS indicated complete disappearance of the starting material and the formation of the desired product. The red solution was evaporated and the residue was purified through a flash column chromatography to give a aromatized product 1-(3-benzyloxy)benzyl-6,7-dimethoxy-4-ethoxycarbonylisoquinoline (1.34 g, 49%).

The above isoquinoline (1.13 g, 2.47 mmol) was dissolved in ethanol and palladium on carbon was added (550 mg). The mixture was hydrogenated at 55 psi overnight. TLC showed complete disappearance of the starting material. The mixture was filtered and the solution was evaporated to dryness. The residue was dissolved in ethyl acetate and passed through a thin layer of silica gel. After the evaporation of solvents, an oil was obtained (760 mg, 84%) as 1-(3-hydroxy)benzyl-6,7-dimethoxy-4-ethoxycarbonyl-isoquinoline.

The above phenol derivative (760 mg, 2.07 mmol) was mixed with tert-butyl bromoacetate (464 mg, 2.38 mmol) in 20 ml of DMF. Then potassium carbonate (714 mg, 2.50 eq) was added. The mixture was stirred at room temperature for 4 hrs. MS indicated all the starting material was converted to the desired product. The mixture was evaporated and the residue was suspended in ethyl acetate. The solid was filtered and the filtrate was washed with water. After the evaporation of solvents, the residue was purified through a flash column chromatography using hexane and ethyl acetate (1.5:1) to give a pale yellow oil (700 mg, 70%).

The above tert-butyl ester (252 mg, 0.524 mmol) was dissolved into 10 ml of ethyl acetate. Then selenium dioxide (117 mg, 1.05 mmol) was added and the mixture was refluxed for 1.5 hr. TLC showed complete disappearance of the starting material. The mixture was filtered through a thin layer of silica gel to give an intermediate as a pale yellow solid. ES-MS calcd for $C_{27}H_{29}NO_8$ (m/e) 495.5, obsd 496.4 (M+H).

This intermediate (217 mg, 0.438 mmol) was dissolved into 8 ml of methylene chloride. Then trifluoroacetic acid (3 ml) was added and the mixture was stirred at room temperature for 2 hrs. MS indicated complete disappearance of the starting material. The mixture was evaporated to dryness and the residue was dried over vacuum pump. The residue was dissolved in 5 ml of methylene chloride and gaseous hydrogen chloride in ether was added. The solution was evaporated to dryness. The residue was dried over vacuum pump and washed with ether to give 1-(3-carboxymethoxybenzoyl)-6,7-dimethoxy-isoquinoline-4-carboxylic acid ethyl ester (176 mg, 87%).

The above 1-(3-carboxymethoxybenzoyl)-6,7-dimethoxy-isoquinoline-4-carboxylic acid ethyl ester (88.5 mg, 0.19 mmol) was suspended in 8 ml of methylene chloride containing 10 equivalent of pyrrolidine, 2.0 equivalent of HBTU and 3.0 equivalent of triethylamine. The mixture was stirred at room temperature overnight and then evaporated to remove solvents. The residue was extracted with ethyl acetate and water. The organic layer was dried and solvents were evaporated. The residue was dissolved in 4 ml of methanol and aqueous lithium hydroxide was added (0.5N, 1 ml). The mixture was stirred overnight until all starting material disappeared. The reaction was loaded to a preparative HPLC for purification to give 6,7-Dimethoxy-1-[3-(2-oxo-2-pyrrolidin-1-yl-ethoxy)-benzoyl]-isoquinoline-4-carboxylic acid as a fluffy solid (29 mg, 33%). ES-MS calcd for $C_{25}H_{24}N_2O_7$ (m/e) 464.5, obsd 465.4 (M+H).

Example 2

6,7-Dimethoxy-1-{3-[2-(4-methyl-piperazin-1-yl)-2-oxo-ethoxy]-benzoyl}-isoquinoline-4-carboxylic acid trifluoroacetate

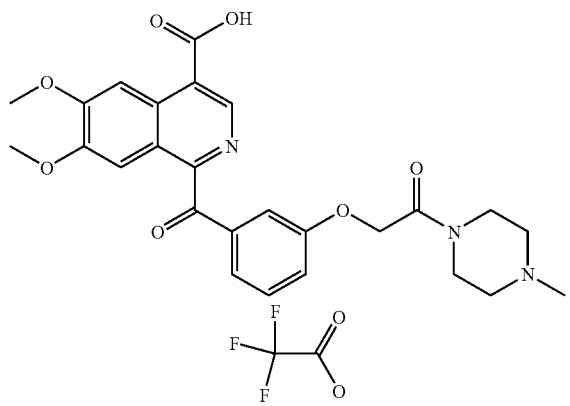

The 1-(3-carboxymethoxybenzoyl)-6,7-dimethoxy-isoquinoline-4-carboxylic acid ethyl ester (119 mg, 0.23 mmol) was suspended in 8 ml of methylene chloride containing 10 equivalent of N-methylpiperizine, 1.1 equivalent of HBTU and 4.0 equivalent of triethylamine. The mixture was stirred at room temperature overnight and then evaporated to remove solvents. The residue was extracted with ethyl acetate and water. The organic layer was dried and solvents were evaporated. The residue was dissolved in 4 ml of methanol and aqueous lithium hydroxide was added (0.5N, 1 ml). The mixture was stirred overnight until all starting material disappeared. The reaction was loaded on a preparative HPLC for purification to give 6,7-Dimethoxy-1-{3-[2-(4-methyl-piperazin-1-yl)-2-oxo-ethoxy]-benzoyl}-isoquinoline-4-carboxylic acid as a fluffy solid (39 mg, 35%). ES-MS calcd for $C_{26}H_{27}N_3O_7$ (m/e) 493.5, obsd 494.4 (M+H).

Example 3

6,7-Dimethoxy-1-[3-(2-morpholin-4-yl-2-oxo-ethoxy)-benzoyl]-isoquinoline-4-carboxylic acid trifluoroacetate

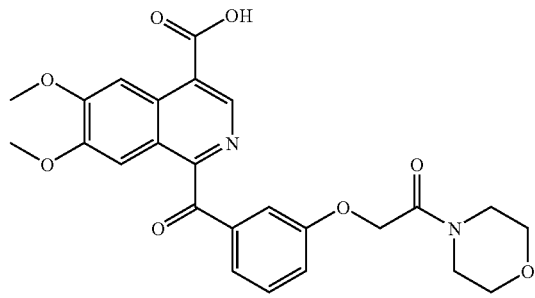

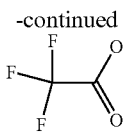

To a solution of 1-(3-carboxymethoxybenzoyl)-6,7-dimethoxy-isoquinoline-4-carboxylic acid ethyl ester (93.3 mg, 0.20 mmol) in 8 ml of methylene chloride was added 10 equivalent of morpholine, 1.2 equivalent of HBTU and 4 equivalent of triethylamine. The mixture was stirred at room temperature overnight. The solvents were evaporated and the residue was extracted with ethyl acetate and water. The organic phase was dried and solvents were evaporated. The residue was dissolved in 4 ml of methanol and aqueous lithium hydroxide was added (0.5N, 1 ml). The mixture was stirred overnight until all starting material disappeared. The reaction was loaded on a preparative HPLC for purification to give 6,7-Dimethoxy-1-[3-(2-morpholin-4-yl-2-oxo-ethoxy)-benzoyl]-isoquinoline-4-carboxylic acid as a fluffy solid (20 mg, 21%). ES-MS calcd for $C_{25}H_{24}N_2O_8$ (m/e) 480.5, obsd 481.3 (M+H).

Example 4

1-{3-[(Benzyl-methyl-carbamoyl)-methoxy]-benzoyl}-6,7-dimethoxy-isoquinoline-4-carboxylic acid trifluoroacetate

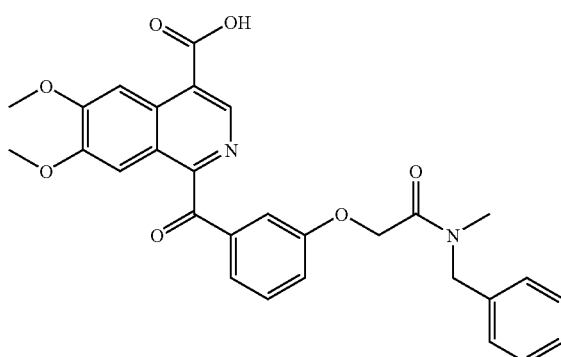

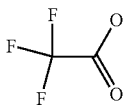

To a solution of 1-(3-carboxymethoxybenzoyl)-6,7-dimethoxy-isoquinoline-4-carboxylic acid ethyl ester (103.7 mg, 0.22 mmol) in 8 ml of methylene chloride was added 1.5 equivalent of N-methyl-N-benzylamine, 1.05 equivalent of HBTU and 4 equivalent of triethylamine. The mixture was stirred at room temperature overnight. The solvents were evaporated and the residue was extracted with ethyl acetate and water. The organic phase was dried and solvents were evaporated. The residue was dissolved in 4 ml of methanol and aqueous lithium hydroxide was added (0.5N, 1 ml). The mixture was stirred overnight until all starting material disappeared. The reaction was loaded on a preparative HPLC for purification to give 1-{3-[(Benzyl-methyl-carbamoyl)-methoxy]-benzoyl}-6,7-dimethoxy-isoquinoline-4-carboxylic acid as a fluffy solid (60 mg, 53%). ES-MS calcd for $C_{29}H_{26}N_2O_7$ (m/e) 514.5, obsd 515.3 (M+H).

Example 5

1-{3-[2-(4-Benzyl-piperazin-1-yl)-2-oxo-ethoxy]-benzoyl}-6,7-dimethoxy-isoquinoline-4-carboxylic acid trifluoroacetate

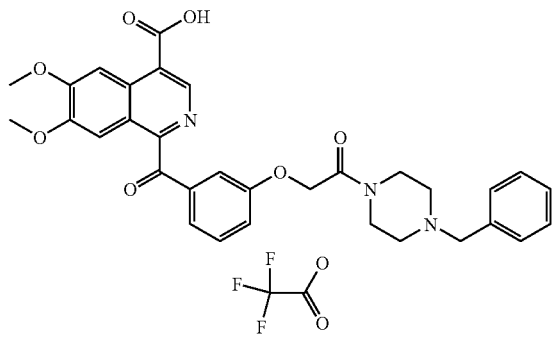

To a solution of 1-(3-carboxymethoxybenzoyl)-6,7-dimethoxy-isoquinoline-4-carboxylic acid ethyl ester (103.5 mg, 0.22 mmol) in 8 ml of methylene chloride was added 1.0 equivalent of N-benzylpiperazine, 1.05 equivalent of HBTU and 4 equivalent of triethylamine. The mixture was stirred at room temperature overnight. The solvents were evaporated and the residue was extracted with ethyl acetate and water. The organic phase was dried and solvents were evaporated. The residue was dissolved in 4 ml of methanol and aqueous lithium hydroxide was added (0.5N, 1 ml). The mixture was stirred overnight until all starting material disappeared. The reaction was loaded on a preparative HPLC for purification to give 1-{3-[2-(4-Benzyl-piperazin-1-yl)-2-oxo-ethoxy]-benzoyl}-6,7-dimethoxy-isoquinoline-4-carboxylic acid as a fluffy solid (43 mg, 35%). ES-MS calcd for $C_{32}H_{31}N_3O_7$ (m/e) 569.6, obsd 570.3 (M+H).

Example 6

1-(3-Carboxymethoxy-benzoyl)-6,7-dimethoxy-isoquinoline-4-carboxylic acid trifluoroacetate

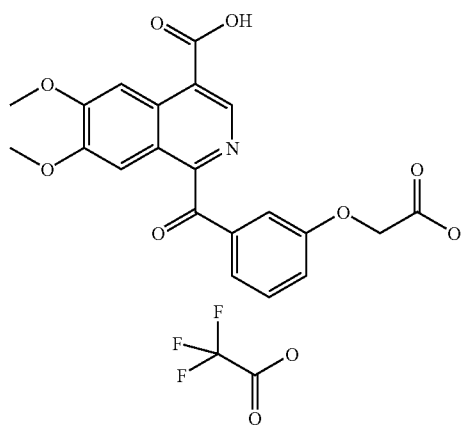

To a solution of 1-(3-carboxymethoxybenzoyl)-6,7-dimethoxy-isoquinoline-4-carboxylic acid ethyl ester (89 mg, 0.19 mmol) in 5 ml of methanol was added lithium hydroxide solution (0.5 N, 1.0 ml). The mixture was stirred at room temperature overnight. The reaction mixture was loaded to a preparative HPLC for purification to give 1-(3-Carboxymethoxy-benzoyl)-6,7-dimethoxy-isoquinoline-4-carboxylic acid as a fluffy solid (72.6 mg, 92%). ES-MS calcd for $C_{21}H_{17}NO_8$ (m/e) 411.4, obsd 412.3 (M+H).

Example 7

[6,7-Dimethoxy-1-(3-methoxy-benzoyl)-isoquinolin-4-yl]-acetic acid trifluoroacetate

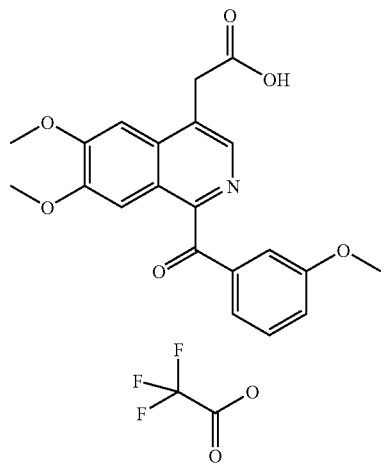

α-Aminomethyl-3,4-dimethoxybenzene-acetic acid ethyl ester hydrochloride (2.895 g, 10 mmol) was mixed with 3-methoxyphenylacetic acid (1.66 g, 10 mmol), EDCI (1.925 g, 10 mmol), and HOBT (1.35 g, 10 mmol) in 100 ml of methylene chloride containing triethylamine (2.75 ml, 20 mmol). The mixture was stirred overnight and then extracted with methylene chloride and 1N hydrochloric acid. The organic layer was washed first with 1N hydrochloric acid, then with brine and finally with saturated sodium bicarbonate solution. After the evaporation of solvents, an oil was obtained (3.79 g, 95%).

The above oil (3.79 g, 9.45 mmol) was dissolved into 50 ml of methylene chloride. Then phosphorus pentachloride (3.94 g, 2.0 eq) was added. The mixture was stirred at room temperature overnight. The mixture was then poured into ice and the resulted solution was extracted with methylene chloride. The organic layer was washed with brine followed by saturated sodium bicarbonate solution. After the evaporation of solvents, an oil was obtained (3.8 g). ES-MS showed molecular weight (M+H) 384 which is consistent with the desired dihydroisoquinoline structure.

The above dihydroisoquinoline derivative (3.8 g, 9.92 mmol) was mixed with sulfur (333 mg, 1.05 eq) and the mixture was heated at 165° C. for 25 minutes until no further gas was observed. Then ethanol (60 ml) was added to the hot mixture with stirring. The solid was removed by filtering. The filtrate was evaporated and the residue was purified through a flash column chromatography using ethyl acetate and hexane (1/2 ratio) to give a solid product 1-(3-methoxybenzyl)-6,7-dimethoxyisoquinoline-4-carboxylic acid ethyl ester (1.60 g, 44% with 2 steps).

The above 1-(3-methoxybenzyl)-6,7-dimethoxyisoquinoline-4-carboxylic acid ethyl ester (1.50 g, 3.94 mmol) was dissolved into 30 ml of THF. To this solution was added lithium aluminum hydride (240 mg, 6.49 mmol). The mixture was refluxed for 30 minutes and then poured into ice and extracted with methylene chloride and saturated ammonium chloride solution. The organic layer was dried with sodium sulfate and solvents were evaporated. The residue was washed with ether to give a white solid 1-(3-methoxy-benzyl)-4-hydroxymethyl-6,7-dimethoxyisoquinoline (1.13 g, 85%). ES-MS calculated for $C_{20}H_{21}O_4N$ (m/e) 339.39, observed 340.5 (M+1). 1H-NMR is consistent with the desired structure.

The above 1-(3-methoxybenzyl)-4-hydroxymethyl-6,7-dimethoxyisoquinoline (339 mg, 1.0 mmol) was dissolved in 5 ml of methylene chloride. Then at −30° C., triethylamine (160 ul, 1.10 eq) and methanesulfonyl chloride (85 ul, 1.10 eq) was added. The mixture was stirred at −30° C. for 30 minutes and then at room temperature overnight. The mixture was extracted with methylene chloride and water. After evaporation of solvents, a solid was obtained to give 1-(3-methoxybenzyl)-4-chloromethyl-6,7-dimethoxyisoquinoline (361 mg, 100%). ES-MS calculated for $C_{20}H_{20}O_3NCl$ (m/e) 357.39, observed 358.5 (M+1).

The above 1-(3-methoxybenzyl)-4-chloromethyl-6,7-dimethoxyisoquinoline (361 mg, 1.0 mmol) was suspended into 15 ml of 90% ethanol. Then sodium cyanide (392 mg, 8.0 mmol) and sodium iodide (83 mg, 0.5 mmol) was added. The mixture was refluxed for 4 hrs. solvents were evaporated and the residue was extracted with ethyl acetate. After the evaporation of solvents, the residue was purified by flash column chromatography using ethyl acetate and hexane (2/1) to give 1-(3-methoxybenzyl)-4-cyanomethyl-6,7-dimethoxyisoquinoline as a solid (165 mg, 47.4%). ES-MS calculated for $C_{21}H_{20}O_3N_2$ (m/e) 348.41, observed 349.5.5 (M+1). 1H-NMR is consistent with the desired structure.

The above 1-(3-methoxybenzyl)-4-cyanomethyl-6,7-dimethoxyisoquinoline (152.7 mg, 0.438 mmol) was dissolved in 10 ml of ethyl acetate, then selenium dioxide (48.8 mg, 58.8 mg, 0.529 mmol) was added. The mixture was refluxed for 1 hr. The crude mixture was filtered through a thin layer of silica gel and washed with ethyl acetate. After the evaporation of solvents, the residue was purified through a flash column chromatography using ethyl acetate and hexane (2/1) to give 1-(3-methoxybenzoyl)-4-cyanomethyl-6,7-dimethoxyisoquinoline as a solid (68 mg, 42.8%).

The 1-(3-methoxybenzoyl)-4-cyanomethyl-6,7-dimethoxyisoquinoline (58 mg, 0.16 mmol) was suspended in a mixture of 2 ml of ethanol and 2 ml of water. To this solution was added sodium hydroxide (51 mg, 1.27 mmol). The mixture was refluxed for 3 hrs and TLC showed complete disappearance of the starting material. The mixture was purified by a reverase phase preparative HPLC to give two fractions. The fraction with a later retention time is the desired compound [6,7-Dimethoxy-1-(3-methoxy-benzoyl)-isoquinolin-4-yl]-acetic acid (16.6 mg). ES-MS calculated for $C_{21}H_{19}NO_5$ (m/e) 381.40, observed 382.4 (M+1).

Example 8

2-[6,7-Dimethoxy-1-(3-methoxy-benzoyl)-isoquinolin-4-yl]-acetamide trifluoroacetate

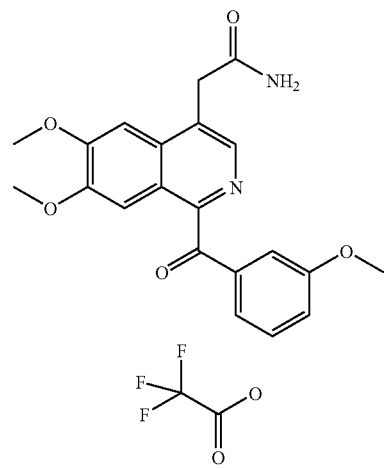

The second fraction with an earlier retention time from the last step HPLC purification of [6,7-Dimethoxy-1-(3-methoxy-benzoyl)-isoquinolin-4-yl]-acetic acid (Example 7) was identified as 2-[6,7-Dimethoxy-1-(3-methoxy-benzoyl)-isoquinolin-4-yl]-acetamide (14.5 mg). ES-MS calculated for $C_{21}H_{20}N_2O_5$ (m/e) 380.40, observed 381.4 (M+1).

Example 9

6,7-Dimethoxy-1-(3-methoxy-benzoyl)-isoquinoline-4-carboxylic acid

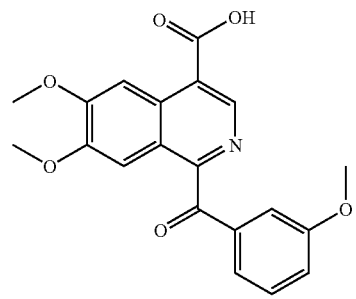

1-(3-methoxybenzyl)-6,7-dimethoxyisoquinoline-4-carboxylic acid ethyl ester (159 mg, 0.417 mmol, the intermediate in the preparation of [6,7-Dimethoxy-1-(3-methoxy-benzoyl)-isoquinolin-4-yl]-acetic acid) (Example 7) was dissolved into 4 ml of acetic acid. Then selenium dioxide (69.5 mg, 1.50 eq) was added. The mixture was refluxed for 20 minutes and then evaporated to dryness. The residue was suspended into ethyl acetate and the mixture was passed through a layer of silica gel. The filtrate was evaporated to give 1-(3-methoxybenzoyl)-6,7-dimethoxyisoquinoline-4-carboxylic acid ethyl ester as a solid (135 mg, 82%). This material (95.6 mg, 0.242 mmol) was suspended in 5 ml of methanol. Then 1N sodium hydroxide solution (0.5 ml) was added. The mixture was refluxed for 1 hr. TLS showed complete disappearance of the starting material. The mixture was evaporated and the residue was dissolved into 5 ml of water and then filtered. The filtrate was acidified with 1N hydrochloric acid to give 6,7-Dimethoxy-1-(3-methoxy-benzoyl)-isoquinoline-4-carboxylic acid as a solid (76 mg, 86%). ES-MS calculated for $C_{20}H_{17}NO_6$ (m/e) 367.36, observed 368.4 (M+1). $^1$H-NMR is consistent with the desired structure.

Example 10

1-(3-Isopropoxy-benzoyl)-6,7-dimethoxy-isoquinoline-4-carboxylic acid trifluoroacetate

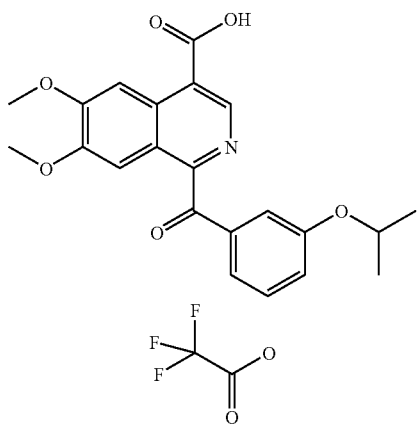

To a solution of 3-hydroxyphenyl acetic acid (7.61 g, 50 mmol) in 50 ml of methanol was added acetyl chloride (3.6 ml). The mixture was refluxed for 4 hrs. Then methanol was evaporated and the residue was extracted with ethyl acetate and concentrated sodium bicarbonate solution. The organic layer was dried and evaporated to give an oil (8.90 g). This oil (4.24 g, 25 mmol) was dissolved in 30 ml of DMF. Then 2-iodopropane (10 g, 58 mmol) and potassium carbonate (5.21 g, 2.0 eq) were added. The mixture was stirred and heated to 50° C. for 1 hr and then cooled down. The reaction mixture was poured into 120 ml of water and extracted with methylene chloride. The organic layer was washed three times with water and then dried. After the evaporation of solvents, the residue was dissolved in 75 ml of methanol and 1N sodium hydroxide solution (75 ml) was added. The mixture was refluxed for 2 hrs and solvents were evaporated. The residue was extracted with water and ether. The aqueous solution was acidified with 1N hydrochloric acid and then extracted with ether. The organic layer was dried and evaporated to give an oil as 3-isopropoxyphenyl acetic acid (3.80 g). 1H-NMR is consistent with the desired structure.

To a mixture of 3-isopropoxyphenyl acetic acid (3.79 g, 19.54 mmol) and α-aminomethyl-3,4-dimethoxybenzeneacetic acid ethyl ester hydrochloride (5.656 g, 19.54 mmol) in 150 ml of methylene chloride was added triethylamine (5.44 ml, 2.0 eq) and HBTU (8.15 g, 21.50 mmol). The mixture was stirred at room temperature overnight and then extracted with 3N hydrochloric acid and methylene chloride. The organic layer was washed with water and sodium bicarbonate solution. After the evaporation of solvents, an oil was obtained (10.20 g). This oil (10.2 g) was dissolved in 100 ml of methylene chloride. The solution was cooled in an ice bath and then phosphorus pentachloride (10.0 g, 47.96 mmol) was added. The mixture was stirred at room temperature overnight and then poured into ice. The mixture was extracted with methylene chloride. The organic layer was washed with concentrated sodium bicarbonate solution and then dried. After the evaporation of solvents, an oil was obtained. This oil (8.81 g, 21.43 mmol) was mixed with sulfur (755 mg, 23.6 mmol) and the mixture was put into an oil bath preheated to 165° C. and stirred at this temperature for 20 minutes. Then ethanol (100 ml) was added and the mixture was filtered. The filtrate was evaporated and the residue was suspended into ethyl acetate. The solid was removed by filtration and the filtrate was washed with sodium bicarbonate solution. After the evaporation of solvents, the residue was purified through a flash column chromatography using ethyl acetate and hexane (2/1 ratio) to give 1-(3-isopropoxybenzyl)-6,7-dimethoxyisoquinoline-4-carboxylic acid ethyl ester (4.40 g, 55% for 3 steps).

The above 1-(3-isopropoxybenzyl)-6,7-dimethoxyisoquinoline-4-carboxylic acid ethyl ester (2.20 g, 5.38 mmol) was dissolved into 100 ml of ethyl acetate. Then selenium dioxide (1.08 g, 9.73 mmol) was added and the mixture was refluxed for 30 minutes. The reaction mixture was filtered through a thin layer of silica gel. The filtrate was concentrated and then purified through a flash column chromatography using hexane and ethyl acetate (2.5/1 ratio) to give 1-(3-isopropoxybenzoyl)-6,7-dimethoxyisoquinoline-4-carboxylic acid ethyl ester as a solid (1.50 g, 66%).

The above give 1-(3-isopropoxybenzoyl)-6,7-dimethoxyisoquinoline-4-carboxylic acid ethyl ester (1.05 g, 2.48 mmol) was suspended in 20 ml of methanol. Then 1N sodium hydroxide solution (5.0 ml) was added. The mixture was refluxed for 1 hr. HPLC showed the purity of the crude mixture to be 91.2%. The mixture was acidified with 1N hydrochloric acid and extracted with ethyl acetate. After the evaporation of solvents, a solid was obtained (900 mg). This solid (40 mg) was further purified through preparative HPLC to give 1-(3-Isopropoxy-benzoyl)-6,7-dimethoxy-isoquinoline-4-carboxylic acid as a fluffy solid (25.8 mg). ES-MS calcd for $C_{22}H_{21}NO_6$ (m/e) 395.44, obsd 396.4 (M+H).

Example 11

3-[1-(3-Isopropoxy-benzoyl)-6,7-dimethoxy-isoquinolin-4-yl]-propionamid trifluoroacetate

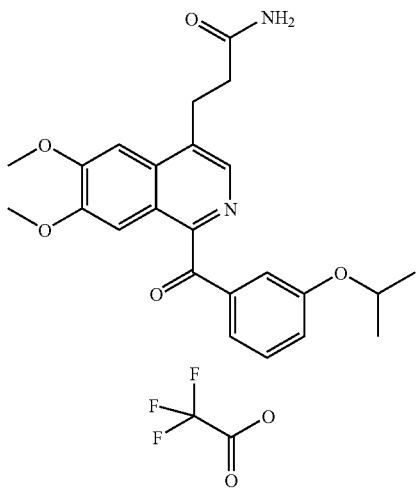

To a THF solution containing 2.20 g (5.38 mmol) of 1-(3-isopropoxybenzyl)-6,7-dimethoxyisoquinoline-4-carboxylic acid ethyl ester (intermediate of 1-(3-Isopropoxy-benzoyl)-6,7-dimethoxy-isoquinoline-4-carboxylic acid (Example 10)) was added lithium aluminum hydride (400 mg, 10.8 mmol) under an ice bath. The mixture was stirred at room temperature overnight. Then another batch of lithium aluminum hydride (300 mg) was added and the mixture was refluxed for 1 hr until all starting material disappeared. The mixture was poured into an ice and extracted with methylene chloride. After the evaporation of solvents, a solid (1.50 g) was obtained as 1-(3-isopropoxybenzyl)-6,7-dimethoxyisoquinoline-4-methanol (76%).

The above alcohol (657 mg, 1.79 mmol) was suspended into 30 ml of methylene chloride. To this mixture was added Dess-Martin reagent (888 mg, 2.09 mmol) at room temperature. The mixture was stirred at room temperature for 25 minutes until all starting material disappeared. The mixture was poured into water and extracted with ethyl acetate and sodium bicarbonate solution. After the evaporation of solvents, the organic layer was dried and evaporated. The residue was dissolved into 30 ml of toluene and methyl (triphenylphosporanylidene) acetate (1.50 eq) was added. The mixture was refluxed for 1 hr and then cooled down. The crude solution was extracted with ethyl acetate and sodium bicarbonate solution. The organic layer was washed with brine and dried. After the evaporation of solvents, the residue was purified through a flash column chromatography using hexane and ethyl acetate (2/1 ratio) to give an olefin (700 mg).

The above olefin (700 mg) was dissolved in 20 ml of methanol and catalytic amount of palladium on carbon was added. The mixture was hydrogenated at 45 PSI for three hrs. The mixture was filtered and solvents were evaporated. The residue was dissolved in 15 ml of ethyl acetate and selenium dioxide (88 mg) was added. The mixture was refluxed for 30 minutes. Another batch of selenium dioxide (75 mg) was added and the mixture was refluxed for 20 more minutes. The mixture was filtered and the filtrate was evaporated. The residue was purified through a flash column chromatography using ethyl acetate and hexane (1/1 ratio) to give 1-(3-isopropoxybenzoyl)-6,7-dimethoxyisoquinoline-4-propionic acid methyl ester as an oil (193 mg).

The above oil (193 mg) was hydrolyzed in methanol with 1N sodium hydroxide solution (2 ml) at room temperature. After 1 hr, TLC showed all starting material disappeared. The mixture was purified through a reverse phase preparative HPLC to give 1-(3-isopropoxybenzoyl)-6,7-dimethoxy-isoquinoline-4-propionic acid (116 mg).

The above carboxylic acid (70.3 mg) was dissolved in 6 ml of THF. Then at −30° C., triethylamine (0.055 ml) was added followed by isobutyl chloroformate (0.034 ml). The mixture was stirred at −20° C. for 30 minutes. Then 30% ammonia hydroxide solution (0.15 ml) was added. The mixture was stirred at room temperature overnight and then purified through a reverse preparative HPLC to give 3-[1-(3-Isopropoxy-benzoyl)-6,7-dimethoxy-isoquinolin-4-yl]-propionamid as a fluffy solid (47.2 mg). ES-MS calcd for $C_{24}H_{26}N_2O_5$ (m/e) 422.5, obsd 423.4 (M+H).

Example 12

N-[11-(3-Isopropoxy-benzoyl)-6,7-dimethoxy-isoquinolin-4-yl]-acetamide trifluoroacetate

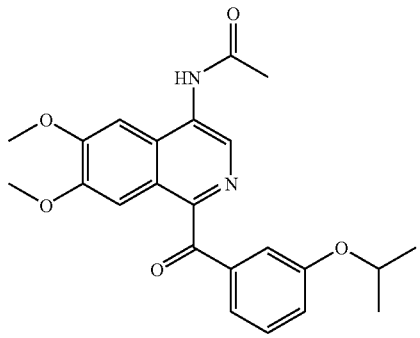

-continued

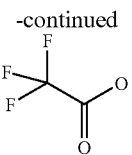

To a solution of 1-(3-isopropoxybenzoyl)-6,7-dimethoxyisoquinoline-4-carboxylic acid (198 mg) in 8 ml of tert-butanol was added diphenylphosphoryl azide (DPPA, 0.119 ml, 1.10 eq) and triethylamine (0.084 ml, 1.20 eq). The mixture was refluxed for 3 hrs and then solvents were evaporated. The residue was extracted with ethyl acetate and saturated sodium bicarbonate solution. The organic layer was dried and then evaporated. The residue was dissolved in a mixture of 4 ml of methylene chloride and 4 ml of trifluoroacetic acid. The mixture was kept at room temperature for 1 hr and then solvents were evaporated. The residue was extracted with ethyl acetate and saturated sodium bicarbonate solution. After the evaporation of solvents, the residue was purified through a flash column chromatography using ethyl acetate and hexane (2/1 ratio) to give an oil. This oil was dissolved in methylene chloride and hydrogen chloride (gas) in ether was added. After the evaporation of solvents, a yellow solid was obtained as 1-(3-isopropoxybenzoyl)-4-amino-6,7-dimethoxyisoquinoline hydrochloride (106 mg, 48% in two steps).

The above amine hydrochloride (32 mg, 0.073 mmol) was suspended in 5 ml of methylene chloride and acetyl chloride (0.020 ml, 4.0 eq) was added followed by the addition of pyridine (6.0 eq). The mixture was stirred at room temperature over night. Solvents were evaporated and the residue was dissolved in methanol. The crude methanol solution was purified through a reverse phase preparative HPLC to give N-[1-(3-Isopropoxy-benzoyl)-6,7-dimethoxy-isoquinolin-4-yl]-acetamide as a fluffy solid (25.8 mg). ES-MS calcd for $C_{23}H_{24}N_2O_5$ (m/e) 408.46, obsd 409.4 (M+H).

Example 13

(4-Aminomethyl-6,7-dimethoxy-isoquinolin-1-yl)-(3-isopropoxy-phenyl)-methanone trifluoroacetate

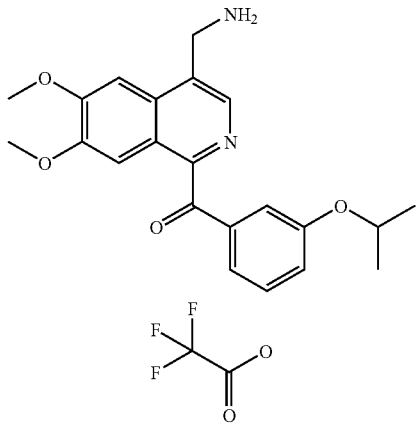

The 1-(3-isopropoxybenzyl)-6,7-dimethoxyisoquinoline-4-methanol (3.67 g, 10.0 mmol) was suspended in 50 ml of methylene chloride. Then at 0° C., triethylamine (1.53 ml, 11 mmol) and methanesulfonyl chloride (0.85 ml) was added. The mixture was stirred at 0° C. for 20 minutes. Then lithium chloride (0.83 g) was added. The mixture was stirred at room temperature overnight. The crude mixture was extracted with methylene chloride. After the evaporation of solvents, a pale brown solid was obtained as 1-(3-isopropoxy)benzyl-4-chloromethyl-6,7-di-methoxyisoquinoline.

Sodium azide (2.10 g, 32 mmol) was suspended in 20 ml of DMSO and the mixture was heated to 70° C. to give a clear solution. Then the above chloride compound (2.50 g, crude) was added. The mixture was stirred at 65° C. for 1 hr. MS indicated complete disappearance of the starting material. The mixture was extracted with ethyl acetate and water. The organic layer was dried and evaporated. The residue was dissolved in methylene chloride and purified through a flash column chromatography using ethyl acetate and hexane (1/1 ratio) to give 1-(3-isopropoxy)benzyl-4-azidomethyl-6,7-dimethoxyisoquinoline as a solid (1.85 g, 66% in two steps).

The above azide compound (1.76 g, 4.489 mmol) was dissolved in 100 ml of THF. To that solution was added di-tert-butyl dicarbonate (1.08 g, 1.10 eq) and catalytic amount of 10% palladium on activated carbon. The mixture was hydrogenated at 40 PSI for 1 hr. TLC showed complete disappearance of the starting material. The mixture was passed through a layer of Celite. Then solvents were evaporated and the residue was washed with hexane to give a solid as 1-(3-isopropoxy)benzyl-4-(N-Boc-aminomethyl)-6,7-dimethoxyisoquinoline (1.75 g, 84% in 2 steps).

The above solid (1.75 g, 3.76 mmol) was dissolved in 30 ml of ethyl acetate. Then selenium dioxide (417 mg, 1.20 eq) was added. The mixture was refluxed for 1 hr. TLC showed some remaining starting material. So another portion of selenium dioxide (139 mg) was added and the mixture was refluxed for 30 minutes further. TLC showed complete disappearance of the starting material. The mixture was filtered through a layer of silica gel and washed with ethyl acetate. After the evaporation of solvents, a solid was obtained as 1-(3-isopropoxy)benzoyl-4-(N-Boc-aminomethyl)-6,7-di-methoxyisoquinoline (1.92 g, 100%).

The above solid (1.92 g) was dissolved in 5 ml of methylene chloride. Then trifluoroacetic acid (10 ml) was added. The mixture was kept at room temperature for 2 hrs. Solvents were evaporated and the residue was dissolved in 20 ml of methylene chloride. Then gaseous hydrogen chloride in ether was added. The mixture was evaporated and the residue was dried under vacuum. The resulting solid was dissolved in methylene chloride (5 ml) and gaseous hydrogen chloride in ether (2N, 10 ml) was added. Solvents were evaporated and the residue was dried on vacuum. The solid was washed with dry ether to give a crude product (1.50 g) as a hydrochloride salt. HPLC showed purity to be 94.2%. This material was further purified through a reverse phase preparative HPLC to give a pure (4-Aminomethyl-6,7-dimethoxy-isoquinolin-1-yl)-(3-isopropoxy-phenyl)-methanone trifluoroacetate salt. ES-MS calcd for $C_{22}H_{24}N_2O_4$ (m/e) 380.47, obsd 381.3 (M+H).

Example 14

N-[1-(3-Isopropoxy-benzoyl)-6,7-dimethoxy-isoquinolin-4-ylmethyl]-acetamide trifluoroacetate

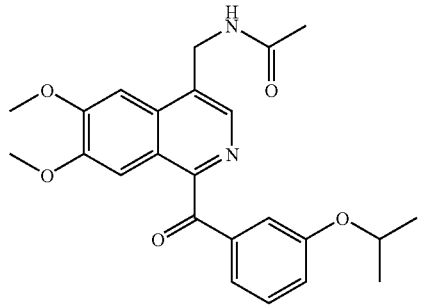

-continued

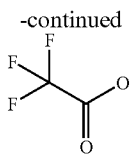

To a solution of 1-(3-isopropoxy)benzoyl-4-aminomethyl-6,7-dimethoxy-isoquinoline hydrochloride (65.3 mg, 0.157 mmol) in 3 ml of methylene chloride was added triethylamine (0.08 ml) and acetic anhydride (0.015 ml). The mixture was stirred for 6 hrs and solvents were evaporated. The residue was dissolved in methanol and purified through a reverse phase preparative HPLC to give N-[1-(3-Isopropoxy-benzoyl)-6,7-dimethoxy-isoquinolin-4-ylmethyl]-acetamide as a fluffy solid (59.2 mg). ES-MS calcd for $C_{24}H_{26}N_2O_5$ (m/e) 422.51, obsd 423.4 (M+H).

Example 15

N-[1-(3-Isopropoxy-benzoyl)-6,7-dimethoxy-isoquinolin-4-ylmethyl]-nicotinamide trifluoroacetate

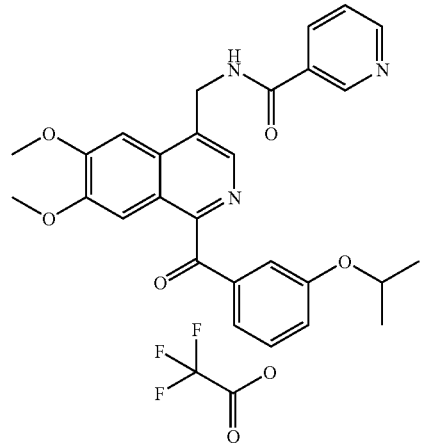

To a solution of 1-(3-isopropoxy)benzoyl-4-aminomethyl-6,7-dimethoxy-isoquinoline hydrochloride (78.2 mg, 0.1876 mmol) in 4 ml of methylene chloride was added triethylamine (0.13 ml), nicotinic acid (23.1 mg, 1.0 eq) and EDCI (39.7 mg, 1.10 eq). The mixture was stirred at room temperature overnight. Solvents were evaporated and the residue was purified through a reverse phase preparative HPLC to give N-[1-(3-Isopropoxy-benzoyl)-6,7-isoquinolin-4-ylmethyl]-nicotinaide as a fluffy solid (25.9 mg). ES-MS calcs for $C_{28}H_{27}N_3O_5$ (m/e) 485.57, obsd 486.3 (M+H).

Example 16

Pyrazine-2-carboxylic acid [1-(3-isopropoxy-benzoyl)-6,7-dimethoxy-isoquinolin-4-ylmethyl]-amide trifluoroacetate

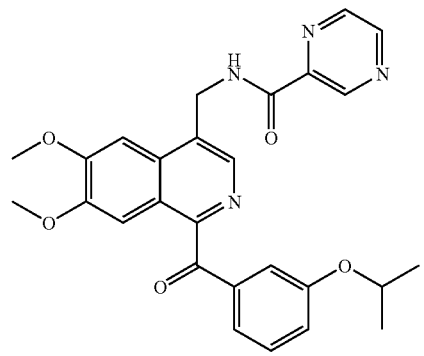

-continued

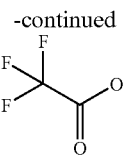

Pyrazine-2-carboxylic acid (38.6 mg, 0.31 mmol) was suspended in 5 ml of methylene chloride. Then oxalyl chloride (0.055 ml) and one drop of DMF was added. The mixture was stirred at room temperature for 15 minutes. A second portion of oxalyl chloride (0.1 ml) was added and the mixture was stirred for 1 hr. Solvents were evaporated and the residue was dried under vacuum. The residue was dissolved in methylene chloride and the amine salt (70.51 mg) was added followed by the addition of triethylamine (0.12 ml). The mixture was stirred at room temperature overnight. Solvents were evaporated and the residue was purified through a reverse phase preparative HPLC to give Pyrazine-2-carboxylic acid [1-(3-isopropoxy-benzoyl)-6,7-dimethoxy-isoquinolin-4-ylmethyl]-amide (30.2 mg). ES-MS calcd for $C_{27}H_{26}N_4O_5$ (m/e) 486.56, obsd 487.3 (M+H).

Example 17

N-[1-(3-Isopropoxy-benzoyl)-6,7-dimethoxy-iso-quinolin-4-ylmethyl]-2-pyridin-3-yl-acetamide trifluoroacetate

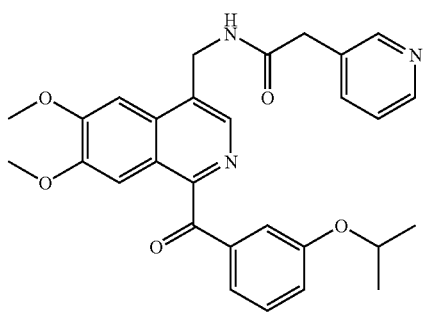

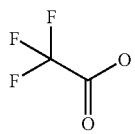

To a solution of 1-(3-isopropoxy)benzoyl-4-aminomethyl-6,7-dimethoxy-isoquinoline hydrochloride (70.2 mg, 0.1549 mmol) in 4 ml of methylene chloride was added triethylamine (0.065 ml, 3.0 eq), 3-pyridineacetic acid (23.3 mg, 1.1 eq) and EDCI (34.0 mg, 1.10 eq). The mixture was stirred at room temperature overnight. Solvents were evaporated and the residue was purified through a reverse phase preparative HPLC to give N-[1-(3-Isopropoxy-benzoyl)-6,7-dimethoxy-isoquinolin-4-ylmethyl]-2-pyridin-3-yl-acetamide as a fluffy solid (48.6 mg). ES-MS calcd for $C_{29}H_{29}N_3O_5$ (m/e) 499.58, obsd 500.3

Example 18

3H-Imidazole-4-carboxylic acid [1-(3-isopropoxy-benzoyl)-6,7-dimethoxy-isoquinolin-4-ylmethyl]-amide trifluoroacetate

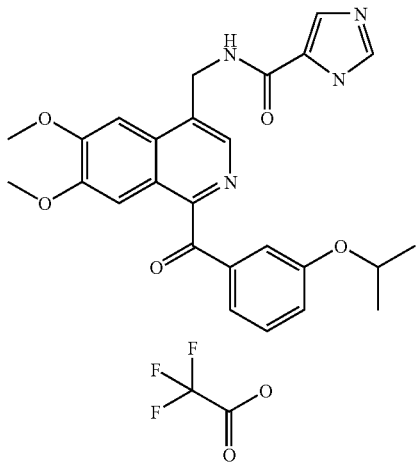

To a solution of 1-(3-isopropoxy)benzoyl-4-aminomethyl-6,7-dimethoxy-isoquinoline hydrochloride (70 mg, 0.1545 mmol) in 4 ml of methylene chloride was added triethyl amine (0.085 ml, 4.0 eq), imidazole-4-carboxylic acid (20.8 mg, 0.1856 mmol) and HBTU (70 mg, 0.1846 mmol). The mixture was stirred at room temperature overnight. Solvents were evaporated and the residue was purified through a reverse phase preparative HPLC to give 3H-Imidazole-4-carboxylic acid [1-(3-isopropoxy-benzoyl)-6,7-dimethoxy-isoquinolin-4-ylmethyl]-amide as a fluffy solid (25.6 mg). ES-MS calcd for $C_{26}H_{26}N_4O_5$ (m/e) 474.53, obsd 475.2 (M+H).

Example 19

N-[1-(3-Isopropoxy-benzoyl)-6,7-dimethoxy-iso-quinolin-4-ylmethyl]-isonicotinamide trifluoroacetate

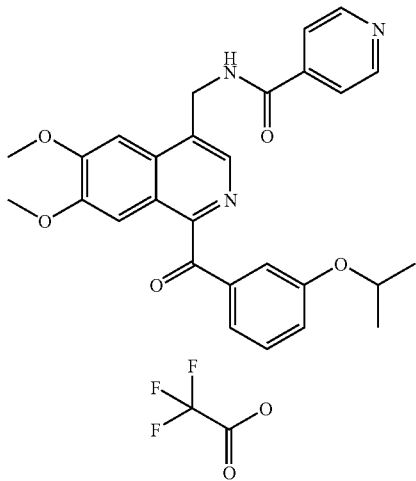

To a solution of 1-(3-isopropoxy)benzoyl-4-aminomethyl-6,7-dimethoxy-isoquinoline hydrochloride (72.1 mg, 0.1592 mmol) in 4 ml of methylene chloride was added triethylamine (0.14 ml), isonicotinoyl chloride hydrochloride (28.4 mg, 0.1595 mmol). The mixture was stirred at room temperature overnight. Solvents were evaporated and the residue was purified through a reverse phase preparative HPLC to give N-[1-(3-Isopropoxy-benzoyl)-6,7-dimethoxy-isoquinolin-4-ylmethyl]-isonicotinamide as a fluffy solid (73 mg). ES-MS calcd for $C_{28}H_{27}N_3O_5$ (m/e) 485.55, obsd 486.3 (M+H).

Example 20

Morpholine-4-carboxylic acid [1-(3-isopropoxy-benzoyl)-6,7-dimethoxy-isoquinolin-4-ylmethyl]-amide trifluoroacetate

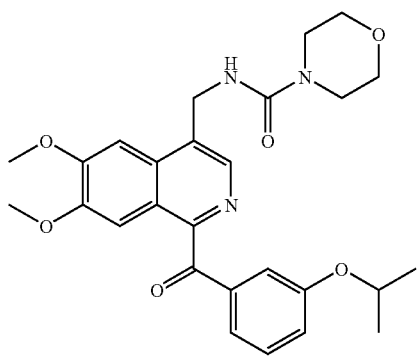

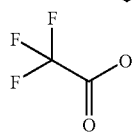

To a solution of 1-(3-isopropoxy)benzoyl-4-aminomethyl-6,7-dimethoxy-isoquinoline hydrochloride (70.5 mg) in 4 ml of methylene chloride was added triethylamine (0.085 ml) and 4-morpholinecarbonyl chloride (0.0197 ml). The mixture was stirred at room temperature overnight. Solvents were evaporated and the residue was purified through a reverse phase preparative HPLC to give Morpholine-4-carboxylic acid [1-(3-isopropoxy-benzoyl)-6,7-dimethoxy-isoquinolin-4-ylmethyl]-amide as a fluffy solid (60 mg). ES-MS calcd for $C_{27}H_{31}N_3O_6$ (m/e) 493.57, obsd 494.2 (M+H).

Example 21

N-[1-(3-Isopropoxy-benzoyl)-6,7-dimethoxy-isoquinolin-4-ylmethyl]-methanesulfonamide trifluoroacetate

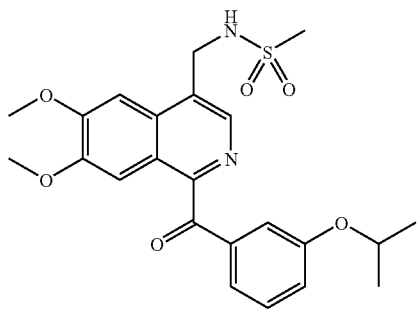

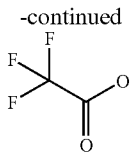

To a solution of 1-(3-isopropoxy)benzoyl-4-aminomethylene-6,7-dimethoxy-isoquinoline hydrochloride (96 mg, 0.2119 mmol) in 5 ml of methylene chloride was added methanesulfonyl chloride (0.025 ml) and triethylamine (0.15 ml). The mixture was stirred at room temperature for 1 hr. Solvents were evaporated and the residue was purified through a reverse phase preparative HPLC to give N-[1-(3-Isopropoxy-benzoyl)-6,7-dimethoxy-isoquinolin-4-ylmethyl]-methanesulfonamide as a fluffy solid (76.4 mg). ES-MS calcd for $C_{23}H_{26}N_2O_6S$ (m/e) 458.56, obsd 459.1 (M+H).

Example 22

Ethanesulfonic acid [1-(3-isopropoxy-benzoyl)-6,7-dimethoxy-isoquinolin-4-ylmethyl]-amide trifluoroacetate

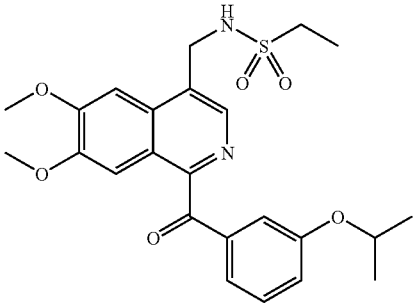

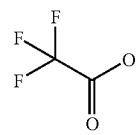

To a solution of 1-(3-isopropoxy)benzoyl-4-aminomethyl-6,7-dimethoxy-isoquinoline hydrochloride (96 mg, 0.2119 mmol) in 5 ml of methylene chloride was added ethanesulfonyl chloride (0.030 ml) and triethylamine (0.15 ml). The mixture was stirred at room temperature for 1 hr. Solvents were evaporated and the residue was purified through a reverse phase preparative HPLC to give Ethanesulfonic acid [1-(3-isopropoxy-benzoyl)-6,7-dimethoxy-isoquinolin-4-ylmethyl]-amide as a fluffy solid (54 mg). ES-MS calcd for $C_{24}H_{28}N_2O_6S$ (m/e) 472.57, obsd 473.1 (M+H).

Example 23

C,C,C-Trifluoro-N-[1-(3-isopropoxy-benzoyl)-6,7-dimethoxy-isoquinolin-4-ylmethyl]-methanesulfonamide trifluoroacetate

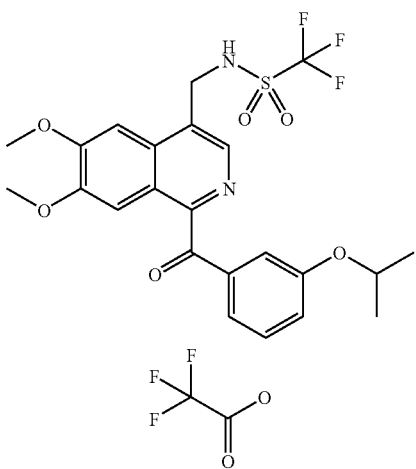

To a suspension 1-(3-isopropoxy)benzoyl-4-aminomethyl-6,7-dimethoxy-isoquinoline hydrochloride (161.7 mg, 0.3579 mmol) in 5 ml of methylene chloride was added N,N-diisopropylethylamine (0.187 ml). The solution was cooled down to −78° C. and trifluoromethanesulfonic anhydride (0.060 ml) was added. The mixture was stirred at −78° C. for 1 hr and then at room temperature for 2 hrs. The mixture was evaporated and the residue was purified through a flash column chromatography using ethyl acetate and hexane (1/2 ratio) to give C,C,C-Trifluoro-N-[1-(3-isopropoxy-benzoyl)-6,7-dimethoxy-isoquinolin-4-ylmethyl]-methanesulfonamide (122 mg, 67%). ES-MS calcd for $C_{23}H_{23}F_3N_2O_6S$ (m/e) 512.51, obsd 513.2 (M+H).

Example 24

[1-(3-Isopropoxy-benzoyl)-6,7-dimethoxy-isoquinolin-4-yl]-acetic acid trifluoroacetate

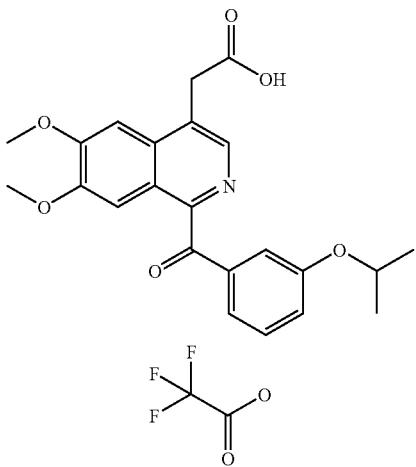

To a suspension of crude 1-(3-isopropoxy)benzyl-4-chloromethyl-6,7-di-methoxyisoquinoline (770 mg, 2.0 mmol) in 60 ml of ethanol was added sodium cyanide (980 mg, 10 eq) and water (8 ml). The mixture was refluxed for 2 hrs. MS indicated all starting material was consumed. Solvents were evaporated and the residue was extracted with ethyl acetate. The organic layer was dried and solvents were removed. The residue was purified through a flash column chromatography using ethyl acetate and hexane (2/1 ratio) to give a corresponding nitrile (421.7 mg).

The above nitrile (390.5 mg) was dissolved in 15 ml of ethyl acetate and selenium dioxide (138 mg, 1.20 eq) was added. The mixture was refluxed for 1.5 hr. The mixture was filtered through a layer of Celite. The filtrate was concentrated and the residue was purified through a flash column chromatography using ethyl acetate and hexane (1/1 ratio) to give 1-(3-isopropoxy)benzoyl-4-cyanomethyl-6,7-di-methoxyisoquinolin (277 mg).

The above 1-(3-isopropoxy)benzoyl-4-cyanomethyl-6,7-di-methoxyisoquinolin (260 mg, 0.67 mmol) was suspended in 4 ml of ethanol. To that mixture was added solid sodium hydroxide (150 mg) and water (4 ml). The mixture was refluxed for 2 hrs and TLC showed complete disappearance of the starting material. Analytical HPLC showed two major products. The crude mixture was purified through a reverse phase preparative HPLC to give two pure fractions. The fraction with a later retention time was identified as [1-(3-Isopropoxy-benzoyl)-6,7-dimethoxy-isoquinolin-4-yl]-acetic acid (111.5 mg). ES-MS calcd for $C_{23}H_{23}NO_6$ (m/e) 409.45, obsd 410.3 (M+H).

Example 25

2-[1-(3-Isopropoxy-benzoyl)-6,7-dimethoxy-isoquinolin-4-yl]-acetamide trifluoroacetate

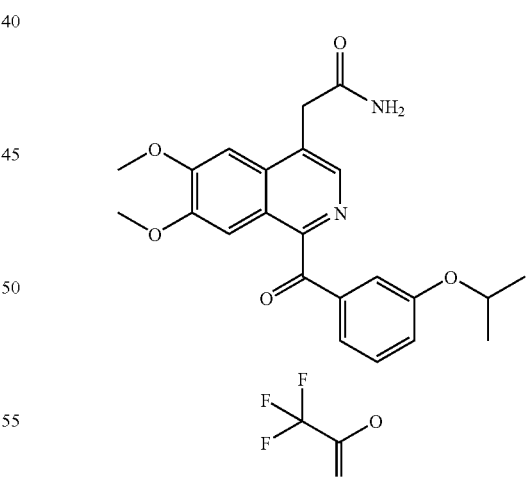

This compound was obtained during the last step preparative HPLC purification in the preparation of [1-(3-Isopropoxy-benzoyl)-6,7-dimethoxy-isoquinolin-4-yl]-acetic acid (Example 24). One of the two fractions with the earlier retention time was identified as 2-[1-(3-Isopropoxy-benzoyl)-6,7-dimethoxy-isoquinolin-4-yl]-acetamide (114 mg). ES-MS calcd for $C_{23}H_{24}N_2O_5$ (m/e) 408.46, obsd 409.4 (M+H).

Example 26

1-(2-Fluoro-5-methoxy-benzoyl)-6,7-dimethoxy-isoquinoline-4-carboxylic acid trifluoroacetate

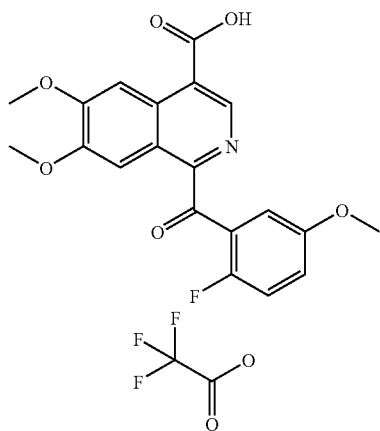

The 4-fluoro-3-methylanisole (7.32 g, 52.28 mmol) was dissolved in 30 ml of carbon tetrachloride. To this solution was added N-bromosuccinimide (9.772 g, 1.05 eq) and AIBN 428 mg, 5% eq). The mixture was refluxed for 1 hr and then cooled. The solid was filtered out and the filtrate was evaporated. The residue was extracted with ethyl acetate and washed with concentrated sodium bicarbonate. The organic layer was dried and solvents were removed to give an oil (13.0 g). The crude oil was dissolved in 150 ml of ethanol and sodium cyanide (12.8 g, 261 mmol) was added followed by the addition of water (20 ml). The mixture was refluxed for 2.5 hrs. The insoluble material was filtered out and the filtrate was concentrated. The residue was extracted with water and ether. The organic layer was dried and solvents were evaporated to give an oil (8.0 g). This oil was dissolved in 120 ml of ethanol. To that solution was added water (40 ml) and solid sodium hydroxide (20.9 g, 10.0 eq). The mixture was refluxed overnight to give a clear solution. Solvents were evaporated and the residue was suspended in 200 ml of hot water. The solution was cooled down and extracted with ether twice. The aqueous layer was acidified with 6N hydrochloric acid and then extracted with ether. The organic layer was washed with brine and dried. After the evaporation of solvents, 2-fluoro-5-methoxyphenylacetic acid was obtained (6.56 g, 68% in three steps).

The 2-fluoro-5-methoxyphenylacetic acid (2.30 g, 12.5 mmol) was mixed with α-aminomethyl-(3,4-dimethoxy) benzene acetic acid ethyl ester (α-aminomethyl-3,4-dimethoxybenzene-acetic acid ethyl ester hydrochloride (3.62 g) in 100 ml of methylene chloride. To this suspension was added triethylamine (3.5 ml), HOBT (1.68 g) and EDCI (2.52 g, 1.05 eq). The mixture was stirred at room temperature for 12 hrs. The mixture was extracted with 1N hydrochloric acid and methylene chloride. The organic layer was washed with sodium bicarbonate solution and then dried. After the evaporation of solvents, a crude oil was obtained (5.25 g). This oil was dissolved in 60 ml of methylene chloride and phosphorus pentachloride (3.90 g, 18.70 mmol) was added. The mixture was stirred at room temperature for 2.5 hrs and then poured into ice. The mixture was extracted with methylene chloride and the organic layer was washed with water, sodium bicarbonate solution and brine. The organic layer was dried and solvents were evaporated to give a brownish oil (4.79 g). This brownish oil was mixed with sulfur (440 mg, 1.10 eq) and the mixture was put in an oil bath preheated to 165° C. The mixture was stirred at 165° C. for 20 minutes until no gas was observed. Then ethanol (50) ml was added to the hot mixture and the solution was filtered. The filtrate was cooled down to give 1-(2-fluoro-5-methoxybenzyl)-4-ethoxycarbonyl-6,7-dimethoxyisoquinoline (2.60 g).

The above 1-(2-fluoro-5-methoxybenzyl)-4-ethoxycarbonyl-6,7-dimethoxyisoquinoline was dissolved in ethyl acetate (25 ml) and selenium dioxide was added (723 mg). The mixture was refluxed for 1 hr until all starting material was consumed. The solution was filtered through a layer of Celite and the filtrate was concentrated. The residue was purified through a flash column chromatography using hexane and ethyl acetate (3/1 ratio) to give 1-(2-fluoro-5-methoxybenzoyl-6,7-dimethoxyisoquinoline-4-caboxylic acid ethyl ester (1.28 g). This ester (200 mg, 0.48 mmol) was suspended in 10 ml of methanol and 1N sodium hydroxide solution (2.0 ml) was added. The mixture was refluxed for 30 minutes and the solution was loaded to a preparative HPLC for purification to give 1-(2-Fluoro-5-methoxy-benzoyl)-6,7-dimethoxy-isoquinoline-4-carboxylic acid (138 mg). ES-MS calcd for $C_{20}H_{16}FNO_6$ (m/e) 385.36, obsd 386.2 (M+H).

Example 27

(4-Aminomethyl-6,7-dimethoxy-isoquinolin-1-yl)-(2-fluoro-5-methoxy-phenyl)-methanone hydrogenchloride

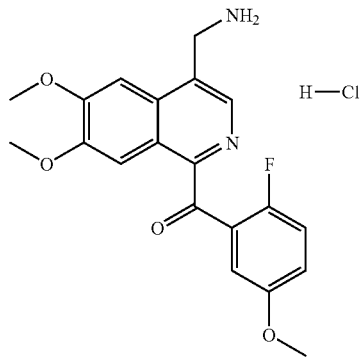

The 1-(2-fluoro-5-methoxybenzyl)-4-ethoxycarbonyl-6,7-dimethoxyisoquinoline (4.0 g, 10 mmol, intermediate for 1-(2-Fluoro-5-methoxy-benzoyl)-6,7-dimethoxy-isoquinoline-4-carboxylic acid (Example 26) was dissolved in 60 ml of THF. At 0° C., lithium aluminum hydride (371 mg, 1.0 eq) was added and the mixture was stirred at room temperature overnight. TLC showed complete disappearance of the starting material. The mixture was evaporated to remove solvents and the residue was extracted with methylene chloride and saturated ammonium chloride solution. The organic layer was washed with water and brine. After the evaporation of solvents a solid was obtained. The solid was washed with dry ether and hexane to give 1-(2-fluoro-5-methoxybenzyl)-4-hydroxymethyl-6,7-dimethoxyisoquinoline (3.12 g, 87%).

The above alcohol (3.0 g, 8.40 mmol) was dissolved into 75 ml of methylene chloride. At 0° C., methanesulfonyl chloride (0.715 ml) was added followed by the addition of triethylamine (1.28 ml, 1.1 eq). The mixture was stirred at 0° C. for 2 hrs and then lithium chloride (697 mg) was added. The mixture was stirred at room temperature overnight. The solution was extracted with methylene chloride and water. The organic layer was washed with brine and dried. After the evaporation of solvents, a pale yellow solid was obtained (3.25 g).

The above solid (2.05 g) was suspended in a mixture containing sodium azide (1.78 g) and DMSO (15 ml) which was preheated to 65° C. The mixture was stirred at 65° C. for 2 hrs and the solution was extracted with methylene chloride. After the evaporation of solvents, the residue was purified through a flash column chromatography using hexane and ethyl acetate (2/1 ratio) to give a desired azide (1.53 g, 73%).

The above azide (1.53 g) was dissolved into 100 ml of THF and di-tert-butyldicarbonate (1.0 g, 1.15 eq) was added followed by the addition of 10% palladium on activated carbon (350 mg). The mixture was hydrogenated at 40 PSI for 2 hrs. The solution was filtered through a layer of Celite and solvents were removed. The residue was dissolved into 100 ml of warm ethyl acetate and selenium dioxide (613 mg, 1.50 eq) was added. The mixture was refluxed for 3 hrs until all starting material was consumed. The mixture was filtered through a layer of silica gel and washed with ethyl acetate. The filtrate was concentrated and the residue was purified through a flash column chromatography using hexane and ethyl acetate (1.5/1 ratio) to give 1-(2-fluoro-5-methoxybenzoyl)-4-N-Boc-aminomethyl-6,7-dimethoxyisoquinoline (1.69 g, 90% in 3 steps).

The above 4-N-Boc-aminomethyl-1-(2-fluoro-5-methoxybenzoyl)-6,7-dimethoxy-isoquinoline (1.69 g) was dissolved into 4 ml of methylene chloride. To this solution was added trifluoroacetic acid (8 ml). The mixture was kept at room temperature for 2 hrs. Solvents were evaporated and the residue dried under vacuum. The residue was dissolved in methylene chloride and 2N gaseous hydrogen chloride in ether was added (6 ml). The solvents were evaporated and the residue was first dried, then washed with ether and finally filtered to give a hydrochloride salt (4-Aminomethyl-6,7-dimethoxy-isoquinolin-1-yl)-(2-fluoro-5-methoxy-phenyl)-methanone (1.546 g). ES-MS calcd for $C_{20}H_{19}FN_2O_4$ (m/e) 370.34, obsd 371.3 (M+H).

Example 28

N-[1-(2-Fluoro-5-methoxy-benzoyl)-6,7-dimethoxy-isoquinolin-4-ylmethyl]-methanesulfonamide

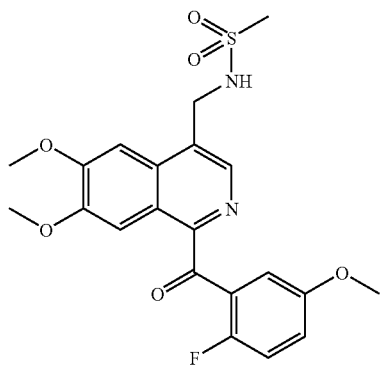

(4-Aminomethyl-6,7-dimethoxy-isoquinolin-1-yl)-(2-fluoro-5-methoxy-phenyl)-methanone (Example 27) (100.5 mg, 0.2269 mmol) was suspended in 5 ml of methylene chloride. The solution was cooled to −78° C. and methanesulfonyl chloride (0.0195 ml, 1.10 eq) was added followed by the addition of N,N-diisopropylethylamine (0.122 ml, 3.0 eq). The mixture was stirred at −78° C. for 1 hr and then at room temperature overnight. The mixture was evaporated and the residue was purified through a flash column chromatography using ethyl acetate and hexane (4/1 ratio) to give N-[1-(2-Fluoro-5-methoxy-benzoyl)-6,7-dimethoxy-isoquinolin-4-ylmethyl]-methanesulfonamide (70 mg, 69%). ES-MS calcd for $C_{21}H_{21}N_2O_6S$ (m/e) 448.47, obsd 449.0 (M+H).

Example 29

C,C,C-Trifluoro-N-[1-(2-fluoro-5-methoxy-benzoyl)-6,7-dimethoxy-isoquinolin-4-ylmethyl]-methanesulfonamide

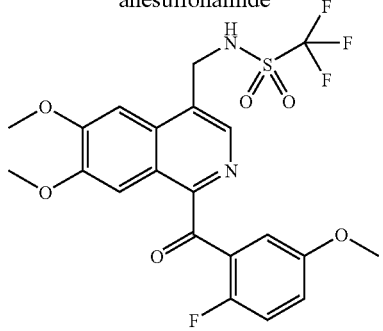

(4-Aminomethyl-6,7-dimethoxy-isoquinolin-1-yl)-(2-fluoro-5-methoxy-phenyl)-methanone (Example 27) (100.75 mg, 0.22739 mmol) was suspended in 6 ml of methylene chloride. The solution was cooled to −78° C. and trifluoromethanesulfonic anhydride (0.042 ml, 1.10 eq) was added followed by the addition of N,N-diisopropylethylamine (0.118 ml, 3.0 eq). The mixture was stirred at −78° C. for 1 hr and then at room temperature for 2 hrs. The mixture was evaporated and the residue was purified through a flash column chromatography using ethyl acetate and hexane (1/2 ratio) to give C,C,C-Trifluoro-N-[1-(2-fluoro-5-methoxy-benzoyl)-6,7-dimethoxy-isoquinolin-4-ylmethyl]-methanesulfonamide (45.6 mg, 40%). ES-MS calcd for $C_{21}H_{18}F_4N_2O_6S$ (m/e) 502.44, obsd 503.01 (M+H).

Example 30

1-(2-Fluoro-5-isopropoxy-benzoyl)-6,7-dimethoxy-isoquinoline-4-carboxylic acid trifluoroacetate

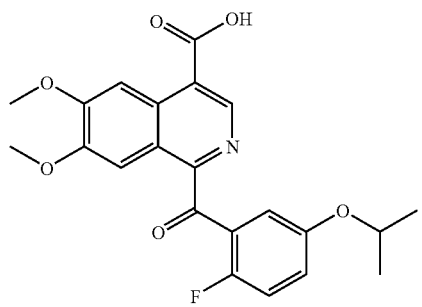

-continued

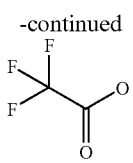

The 4-fluoro-3-methylphenol (13.1 g, 104 mmol) was dissolved in 200 ml of acetone. To this solution was added 2-iodopropane (35.3 g, 2.0 eq) and potassium carbonate (28.6 g, 2.0 eq). The mixture was refluxed overnight and TLC showed some staring material. Another portion of 2-iodopropane (17.6 g) was added and the mixture was refluxed for 24 hrs until all starting material disappeared. The mixture was filtered and the filtrate was evaporated. The residue was extracted with ether and 1N sodium hydroxide solution. The organic layer was dried and evaporated to give an oil (17.1 g). This oil was dissolved into 60 ml of carbon tetrachloride. To the solution was added N-bromosuccinimide (19.12 g, 1.05 eq) and AIBN (840 mg). The mixture was refluxed for 1 hr. The solid was filtered out and the filtrate was evaporated. The residue was extracted with ether and washed with sodium bicarbonate solution. After the removal of solvents, an oil was obtained (26.03 g).

The above crude oil (23.5 g) was suspended into 300 ml of ethanol and water was added (50 ml). Then sodium cyanide (23.5 g, 5.0 eq) was added and the mixture was refluxed for 4 hrs. The mixture was filtered out. The filtrate was concentrated and then extracted with ether. The organic layer was dried and evaporated to give an oil which was purified through a flash column chromatography using hexane and ethyl acetate (10/1 ratio) to give 2-cyanomethyl-4-isopropoxyfluorobene as a colorless oil (7.5 g, 40% in three steps). This nitrile (7.5 g, 38.87 mmol) was dissolved into ethanol (102 ml) and then sodium hydroxide (15.54 g, 10 eq) was added followed by the addition of water (33.7 ml). The mixture was refluxed for 24 hrs and the solvents were evaporated. The residue was dissolved into water and extracted with ether. The aqueous layer was acidified with 6N hydrochloric acid and then extracted with ethyl acetate. After the evaporation of solvents, 2-fluoro-5-isopropoxyphenylacetic acid was obtained (7.62 g, 93%).

The 2-fluoro-5-isopropoxyphenylacetic acid (4.0 g, 18.87 mmol) was mixed with α-aminomethyl-3,4-dimethoxybenzene-acetic acid ethyl ester hydrochloride (5.47 g, 18.89 mmol) in 100 ml of methylene chloride. To that mixture was added triethylamine (5.2 ml), EDCI (3.82 g, 1.05 eq), and HOBT (2.54 g, 1.0 eq). The mixture was stirred at room temperature overnight. TLC showed one major spot. The mixture was worked up with methylene chloride and 1N hydrochloric acid. The organic layer was washed with sodium bicarbonate solution. After the removal of solvents, an oil was obtained (9.63 g). This crude oil was dissolved into 150 ml of methylene chloride. To that solution was added phosphorus pentachloride (5.9 g, 28.3 mmol). The mixture was stirred overnight and then poured into an ice. The mixture was extracted with methylene chloride. The organic layer was washed with brine and then sodium bicarbonate solution. After the evaporation of solvents, a brownish oil was obtained (8.44 g). This oil was mixed with sulfur (629 mg, 19.66 mmol) and the mixture was stirred at 165° C. for 20 minutes. Then ethanol (100 ml) was added and the mixture was filtered. The solvents was evaporated and the residue was suspended in ethyl acetate and hexane (150 ml, 3/1 ratio). The insoluble material was filtered out. The filtrate was concentrated and purified through a flash column chromatography using hexane and ethyl acetate (2.4/1 ratio) to give 1-(2-fluoro-5-isopropoxy)benzyl-6,7-dimethoxyisoquinoline-4-carcoxylic acid ethyl ester (4.40 g).

The 1-(2-fluoro-5-isopropoxy)benzyl-6,7-dimethoxyisoquinoline-4-carcoxylic acid ethyl ester (657 mg, 1.538 mmol) was dissolved into 3 ml of ethyl acetate and selenium dioxide (171 mg) was added. The mixture was refluxed for 1.5 hrs. The mixture was passed through a layer of silica gel and washed with ethyl acetate. The organic layer was dried to give a crude solid which was carried on to the next step without further purification. One third of the crude solid was suspended in 5 ml of methanol and 1N sodium hydroxide solution (2 ml) was added. The mixture was refluxed for 40 minutes and then evaporated. The residue was dissolved into 6 ml of water and filtered. The filtrate was loaded to a preparative HPLC for purification to give 1-(2-Fluoro-5-isopropoxy-benzoyl)-6,7-dimethoxy-isoquinoline-4-carboxylic acid as a fluffy solid (126 mg). ES-MS calcd for $C_{22}H_{20}FNO_6$ (m/e) 413.41, obsd 414.3 (M+H).

Example 31

[1-(2-Fluoro-5-isopropoxy-benzoyl)-6,7-dimethoxy-isoquinolin-4-yl]-acetic acid trifluoroacetate

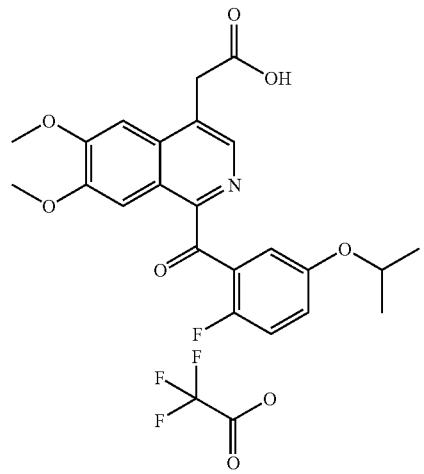

The 1-(2-fluoro-5-isopropoxy)benzyl-6,7-dimethoxyisoquinoline-4-carcoxylic acid ethyl ester (1.95 g, 4.57 mmol) was dissolved into 50 ml of THF. To this solution was added lithium aluminum hydride (340 mg, 2.0 eq). The mixture was stirred at room temperature for 1 hr. TLC showed complete disappearance of the starting material. The mixture was evaporated and the residue was worked up with ammonium chloride and then extracted with methylene chloride. After the evaporation of solvents, the residue was washed with ether to give a white solid (1.76 g, 100%). This solid (1.464 g, 3.8025 mmol) was suspended in 50 ml of methylene chloride and cooled to 0° C. Then methanesulfonyl chloride (0.323 ml, 1.10 eq) was added followed by the addition of triethylamine (0.529 ml, 1.10 eq). The mixture was stirred at 0° C. for 2 hrs and at room temperature overnight. Solvents were evaporated and the residue was extracted with methylene chloride and water. After the evaporation of solvents, a crude solid was obtained (1.10 g). This solid was dissolved into 15 ml of DMSO and sodium cyanide (614 mg, 5.0 eq) was added. The mixture was stirred at 85° C. for 1 hr until all starting material disappeared. The mixture was extracted with water and methylene chloride. The organic layer was dried and the residue was purified through a flash column chromatography using ethyl acetate and hexane (1.5/1 ratio) to give 1-(2-fluoro-5-isopropoxy) benzyl-4-cyanomethyl-6,7-dimethoxyisoquinoline (951 mg).

The above nitrile compound (940 mg, 2.386 mmol) was suspended in 25 ml of ethanol. Then water (7 ml) was added followed by the addition of sodium hydroxide (954 mg, 10 eq). The mixture was refluxed overnight and then acidified with 6N hydrochloric acid. The solution was extracted with methylene chloride and the organic layer was dried and then evaporated to give a carboxylic acid (950 mg). This carboxylic acid was dissolved into 20 ml of methylene chloride and a ether solution of diazomethane (0.15 N, 20 ml) was added. The mixture was stirred at room temperature for 10 minutes and then solvents were evaporated to give 1-(2-fluoro-5-isopropoxy)benzyl-6,7-dimethoxyisoquinoline-4-acetic acid methyl ester.

The above ester (133.5 mg, 0.3126 mmol) was dissolved into 10 ml of ethyl acetate. To this solution was added selenium dioxide (51.7 mg). The mixture was refluxed for 1.5 hrs. TLC showed complete disappearance of the staring material and the formation of two major product. The mixture was passed through a layer of silica gel and the filtrate was purified through a flash column chromatography using ethyl acetate and hexane (1/2 ratio) to give 1-(2-fluoro-5-isopropoxy)benzoyl-6,7-dimethoxyisoquinoline-4-acetic acid methyl ester (97.5 mg). This ester was dissolved into 5 ml of methanol and 1N sodium hydroxide solution (0.2 ml) was added. The mixture was refluxed for 30 minutes and the crude mixture was purified through a preparative HPLC to give [1-(2-Fluoro-5-isopropoxy-benzoyl)-6,7-dimethoxy-isoquinolin-4-yl]-acetic acid (49 mg). ES-MS calcd for $C_{23}H_{22}FNO_6$ (m/e) 427.44, obsd 428.2 (M+H).

Example 32

2-[1-(2-Fluoro-5-isopropoxy-benzoyl)-6,7-dimethoxy-isoquinolin-4-yl]-propionic acid trifluoroacetate

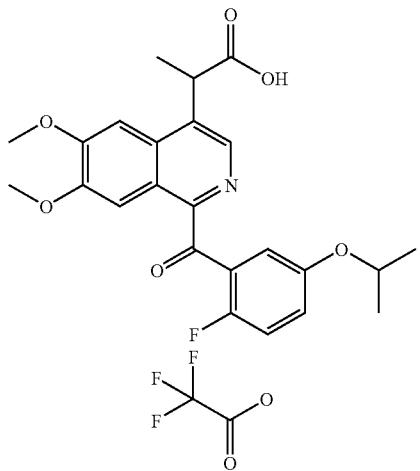

The 1-(2-fluoro-5-isopropoxy)benzyl-6,7-dimethoxyisoquinoline-4-acetic acid methyl ester (363 mg, 0.85 mmol) was dissolved in 5 ml of DMF. To this solution was added potassium tert-butyl oxide (209 mg, 2.20 eq). A deeply red colored solution was observed. To this solution was added methyl iodide (0.106 ml) and the mixture was stirred at room temperature overnight. The solvents were evaporated and the residue was extracted with ethyl acetate. After the removal of solvents, the residue was dissolved in 10 ml of ethyl acetate and selenium dioxide (94.5 mg) was added. The mixture was refluxed for 2 hrs and then passed through a layer of silica gel. The filtrate was concentrated and purified through a flash column chromatography to give a solid (66.8 mg). This solid (62 mg) was dissolved into 4 ml of methanol and 0.2 ml of 1N sodium hydroxide solution was added. The mixture was refluxed for 30 minutes. The crude mixture was purified through a reverse phase preparative HPLC to give 2-[1-(2-Fluoro-5-isopropoxy-benzoyl)-6,7-dimethoxy-isoquinolin-4-yl]-propionic acid (24 mg). ES-MS calcd for $C_{24}H_{24}FNO_6$ (m/e) 441.46, obsd 442.11 (M+H).

Example 33

1-(2,6-Difluoro-benzoyl)-6,7-dimethoxy-isoquinoline-4-carboxylic acid trifluoroacetate

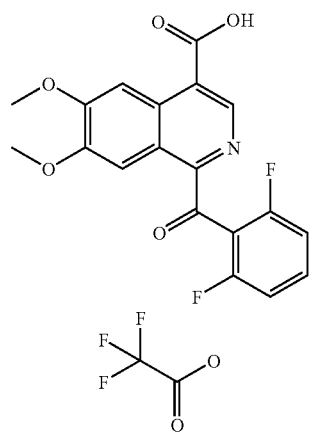

To a solution of 2,6-difluorophenylacetic acid (5.0 g, 29.07 mmol) and α-aminomethyl-3,4-dimethoxybenzene-acetic acid ethyl ester hydrochloride (8.42 g, 19.08 mmol) in 200 ml of methylene chloride was added triethylamine (8.2 ml, 58.4 mmol), EDCI (6.16 g, 1.10 eq) and HOBT (3.91 g, 1.0 eq). The mixture was stirred at room temperature overnight and then extracted with methylene chloride and 1N hydrochloric acid. The organic layer was washed sequentially with 1N hydrochloric acid, water, concentrated sodium bicarbonate solution and brine. TLC showed one major spot (ethyl acetate and hexane, 2/1 ratio). After the evaporation of solvents, an oil was obtained (10.90 g). This oil was dissolved in 100 ml of methylene chloride and phosphorus pentachloride (7.26 g, 1.30 eq) was added. The mixture was stirred at room temperature overnight and then poured into ice and extracted with methylene chloride. The organic layer was washed with brine and concentrated sodium bicarbonate solution. After the evaporation of solvents, an oil was obtained (9.93 g). This oil (9.93 g) was mixed with sulfur (980 mg, 1.20 eq) and the mixture was put into an oil bath preheated to 160° C. The dark brown solution was stirred at 160° C. for 30 minutes until no more gas was observed. Then ethanol (150 ml) was added to give a clear solution.

This solution was cooled down to room temperature to give a needle crystal. The solid was filtered and washed with ethanol to give 1-(2,6-difluoro)benzyl-6,7-dimethoxyisoquinoline-4-carboxylic acid ethyl ester as a needle crystal (6.88 g, 61% over three steps).

The above 1-(2,6-difluoro)benzyl-6,7-dimethoxyisoquinoline-4-carboxylic acid ethyl ester (158 mg, 0.4093 mmol) was mixed with selenium dioxide (77.2 mg, 1.70 eq) in 5 ml of acetic acid. The mixture was refluxed for 20 minutes and then solvents were evaporated. The residue was dissolved in ethyl acetate and the mixture was passed through a layer of silica gel. The filtrate was concentrated and the residue was purified through a flash column chromatography using hexane and ethyl acetate (2/1 ratio) to give 1-(2,6-difluoro)benzoyl-6,7-dimethoxyisoquinoline-4-carboxylic acid ethyl ester as a solid (85 mg). This solid (27.0 mg) was suspended in 3 ml of methanol and 1N sodium hydroxide solution (0.15 ml) was added. The mixture was refluxed for 1.5 hr and then loaded to a preparative HPLC for purification to give 1-(2,6-Difluoro-benzoyl)-6,7-dimethoxy-isoquinoline-4-carboxylic acid (23.1 mg). ES-MS calcd for $C_{19}H_{13}F_2NO_5$ (m/e) 373.32, obsd 374.3 (M+H).

Example 34

N-[1-(2,6-Difluoro-benzoyl)-6,7-dimethoxy-isoquinolin-4-ylmethyl]-C,C,C-trifluoro-methanesulfonamide

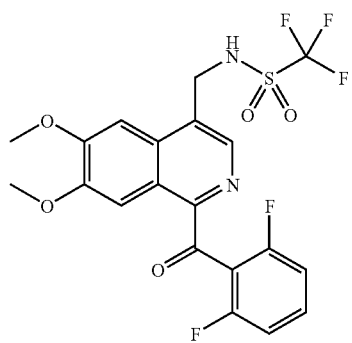

The needle crystal 1-(2,6-difluoro)benzyl-6,7-dimethoxyisoquinoline-4-carboxylic acid ethyl ester (4.0 g, 10.33 mmol, intermediate of 1-(2,6-Difluoro-benzoyl)-6,7-dimethoxy-isoquinoline-4-carboxylic acid (Example 33) was dissolved in 60 ml of dry THF. To this solution was added lithium aluminum hydride (382 mg, 1.0 eq). And the mixture was stirred at room temperature overnight. The solvents were evaporated and the residue was suspended into methylene chloride. The mixture was extracted with methylene chloride and ammonium chloride solution. The organic layer was washed with brine. The solution was dried over sodium sulfate and solvents were removed. The residue was washed with ether to give a white solid (3.15 g, 89%). This solid (3.0 g, 8.69 mmol) was suspended in 75 ml of methylene chloride and the solution was cooled to 0° C. To this solution was added methanesulfonyl chloride (0.74 ml, 1.10 eq) and triethylamine (1.33 ml, 1.10 eq). The mixture was stirred at 0° C. for 2 hrs and then lithium chloride (360 mg, 2.0 eq) was added. The resulting solution was stirred at room temperature overnight and then extracted with methylene chloride and water. After the evaporation of solvents, a solid was obtained (3.29 g). This solid (2.09 g) was suspended into a mixture containing DMSO (15 ml) and sodium azide (1.80 g). The mixture was stirred at 65° C. for 2 hrs and then cooled to room temperature. The waxy material was extracted with methylene chloride and water. After the evaporation of solvents, the residue was purified through a flash column chromatography using hexane and ethyl acetate (2/1 ratio) to give 1-(2,6-difluoro)benzyl-4-azidomethyl-6,7-dimethoxyisoquinoline (1.66 g) as a white solid.

The above azide (1.66 g, 4.48 mmol) was mixed with di-tert-butyldicarbonate (1.96 g, 2.0 eq) in 40 ml of THF. Catalytic amount of 10% palladium on carbon (350 mg) was added and the mixture was hydrogenated at 40 PSI for 2 hrs. The solution was filtered through a layer of Celite and the filtrate was concentrated. The residue was washed with hexane to give a waxy material (1.79 g). This material (1.79 g) was dissolved in 40 ml of ethyl acetate and selenium dioxide ((537 mg, 1.20 eq) was added. The mixture was refluxed for 3 hrs until all starting material was consumed. The mixture was filtered through a thin layer of silica gel. The filtrate was evaporated and the residue was purified through a flash column chromatography using hexane and ethyl acetate (1.6/1 ratio) to give 4-N-Boc-aminomethyl-1-(2,6-difluoro)benzoyl-6,7-dimethoxyisoquinoline (1.52 g).

The above 4-N-Boc-aminomethyl-1-(2,6-difluoro)benzoyl-6,7-dimethoxyisoquinoline (1.52 g) was dissolved into 3 ml of methylene chloride. To this solution was added trifluoroacetic acid (8 ml). The mixture was stirred at room temperature for 2 hrs. Solvents were evaporated and the residue was dried under vacuum. The brownish oil was dissolved in methylene chloride and treated with 2N gaseous hydrogen chloride in ether (6 ml). The solvents were evaporated and the residue was dried and then washed with ether to give 4-aminomethyl-1-(2,6-difluoro)benzoyl-6,7-dimethoxyisoquinoline as a hydrochloride salt (1.524 g, 64% over 6 steps).

The above amine hydrochloride (100.3 mg, 0.2327 mmol) was dissolved into 6 ml of methylene chloride. At −78° C., trifluorosulfonic anhydride (0.043 ml, 1.10 eq) was added followed by the addition of diisopropylethylamine (0.122 ml, 3.0 eq). The mixture was stirred at −78° C. for 1 hr and then at room temperature for 2 hrs. After the evaporation of solvents, the residue was purified through a flash column chromatography using hexane and ethyl acetate (2/1 ratio) to give N-[1-(2,6-Difluoro-benzoyl)-6,7-dimethoxy-isoquinolin-4-ylmethyl]-C,C,C-trifluoro-methanesulfonamide as a pale yellow solid (44 mg). ES-MS calcd for $C_{20}H_{15}F_5N_2O_5S$ (m/e) 490.40, obsd 491.0 (M+H).

Example 35

6,7-Dimethoxy-1-[3-(3-oxo-3-pyrrolidin-1-yl-propenyl)-benzoyl]-isoquinoline-4-carboxylic acid trifluoroacetate

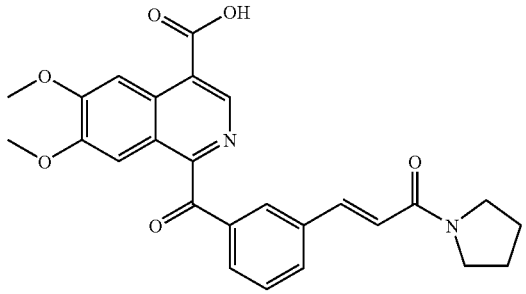

-continued

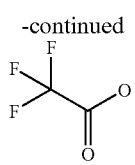

To a mixture of 3-bromophenylacetic acid (3.23 g, 15 mmol) and α-aminomethyl-3,4-dimethoxybenzene-acetic acid ethyl ester hydrochloride (4.35 g, 15 mmol) in 100 ml of methylene chloride was added triethylamine (4.50 ml, 32 mmol) and HBTU (6.25 g, 16.5 mmol). The mixture was stirred at room temperature for 2 days. The resulting solution was extracted with methylene chloride and 1N hydrochloric acid. The organic layer was washed with water and sodium bicarbonate solution. After the evaporation of solvents, a crude material was obtained (6.30 g). TLC showed a good purity. This material (6.30 g, 14 mmol) was dissolved in 100 ml of methylene chloride and phosphorus pentachloride (5.84 g, 2.0 eq) was added. The mixture was stirred at room temperature overnight and then poured into ice. The solution was extracted with methylene chloride. The organic layer was washed with brine and sodium bicarbonate solution. After the evaporation of solvents, a brownish oil was obtained (6.62 g). This oil (6.62 g) was mixed with sulfur (588 mg, 1.20 eq) and the mixture was stirred at 165° C. for 20 minutes until no gas was observed. The mixture was worked up by the addition of hot ethanol. The insoluble material was filtered out and solvents were evaporated. The resulting crude material was purified through a flash column chromatography using ethyl acetate and hexane (1/1 ratio) to give 1-(3-bromo)benzyl-6,7-dimethoxy-4-carboxylic acid ethyl ester (3.20 g) as a solid.

The above 1-(3-bromo)benzyl-6,7-dimethoxy-4-carboxylic acid ethyl ester (200 mg, 0.4651 mmol) was dissolved in 5 ml of triethylamine. To this solution was added tert-butyl acrylate (238 mg, 4.0 eq), palladium acetate (10 mg, 0.1 eq), and tri-(o-tolyl)phosphine (14.1 mg, 0.10 eq). The mixture was refluxed over night. The solvents were evaporated. The residue was suspended in methylene chloride and the mixture was passed through a layer of Celite. The filtrate was concentrated and then purified through a flash column chromatography using ethyl acetate and hexane (1/1 ratio) to give 1-(3-trans-tert-butoxycarbonylvinyl)benzyl-6,7-dimethoxy-4-carboxylic acid ethyl ester as a solid (188 mg, 85%).

The above solid (97 mg) was dissolved into 10 ml of ethyl acetate and selenium dioxide (34.8 mg) was added. The mixture was refluxed for 1.5 hr until all starting material was consumed. The mixture was filtered through a thin layer of silica gel and the filtrate was concentrated to give a solid (78 mg). This solid (78 mg) was dissolved in 3 ml of methylene chloride and trifluoroacetic acid (1 ml) was added. The mixture was stirred at room temperature for 3 hrs. The solvents were evaporated and the residue was dried under vacuum. The residue was dissolved in methylene chloride and gaseous hydrogen chloride in ether was added. Solvents were evaporated and the residue was dried under vacuum to give a hydrochloride salt (69.6 mg). The hydrochloride salt (69.6 mg) was suspended in 5 ml of dry THF and the solution was cooled to −20° C. To this solution was added isobutyl chloroformate (24.2 mg, 1.20 eq), triethylmine (44.7 mg, 3.0 eq) and pyrrolidine (21 mg, 2.0 eq). The mixture was stirred at room temperature overnight and solvents were evaporated. The residue was dissolved in 3 ml of methanol and treated with 0.5N lithium hydroxide solution (1 ml). Two drops of THF was added to give a homogeneous solution and the mixture was stirred at room temperature for 1 hr. The crude mixture was purified through a reverse phase preparative HPLC to give 6,7-Dimethoxy-1-[3-(3-oxo-3-pyrrolidin-1-yl-propenyl)-benzoyl]-isoquinoline-4-carboxylic acid as a fluffy solid (23 mg). ES-MS calcd for $C_{26}H_{24}N_2O_6$ (m/e) 460.49, obsd 461.4 (M+H).

Example 36

6,7-Dimethoxy-1-[3-(3-oxo-3-pyrrolidin-1-yl-propyl)-benzoyl]-isoquinoline-4-carboxylic acid trifluoroacetate

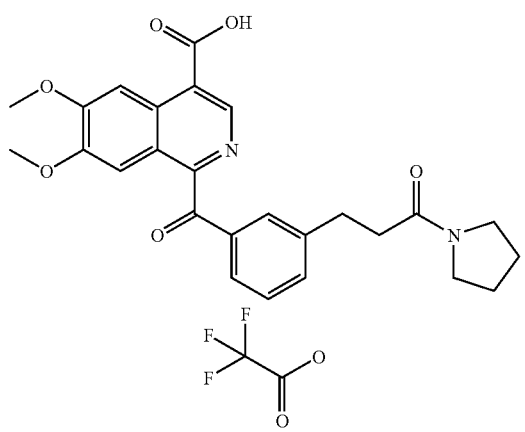

The 1-(3-trans-tert-butoxycarbonylvinyl)benzyl-6,7-dimethoxy-4-carboxylic acid ethyl ester (165 mg) was dissolved in a mixture of methanol and THF (4/1 ratio, 25 ml). Catalytic amount of 10% palladium on carbon was added and the mixture was hydrogenated at 35 PSI for 1 hr. The resulting solution was filtered through a layer of Celite. The filtrate was concentrated and the residue (158 mg) was dissolved in 10 ml of ethyl acetate. Selenium dioxide (45 mg, 1.20 eq) was added and the mixture was refluxed for 2 hrs until all starting material was consumed. The solution was filtered through a thin layer of silica gel and washed with ethyl acetate. The filtrate was evaporated to give an oxidized product (163 mg). This material (163 mg) was dissolved in 4 ml of methylene chloride and trifluoroacetic acid (1 ml) was added. The mixture was stirred at room temperature for 2 hrs. The solvents were evaporated and the residue was first dried under vacuum and then dissolved in methylene chloride and treated with gaseous hydrogen chloride in ether. Solvents were evaporated and the residue was dried to give a hydrochloride salt (138 mg). This hydrochloride salt (88.5 mg) was suspended in 6 ml of THF. At −20° C., isobutyl chloroformate (0.030 ml, 1.20 eq), triethylamine (0.103 ml, 4.0 eq) and pyrrolidine (0.040 ml, 2.50 eq) were added. The mixture was stirred at room temperature overnight. Solvents were evaporated and the crude material was dissolved in 4 ml of methanol. To this solution was added 0.5N lithium hydroxide (1 ml) and 2 drops of THF. The solution was stirred at room temperature for 1 hr. The mixture was loaded to a reverse phase preparative HPLC for purification to give 6,7-Dimethoxy-1-[3-(3-oxo-3-pyrrolidin-1-yl-propyl)-benzoyl]-isoquinoline-4-carboxylic acid as a fluffy solid (60 mg). ES-MS calcd for $C_{26}H_{26}N_2O_6$ (m/e) 462.51, obsd 463.4 (M+H).

Example 37

1-[3-(Isopropylcarbamoyl-methoxy)-benzoyl]-6,7-dimethoxy-isoquinoline-4-carboxylic acid; compound with trifluoro-acetic acid

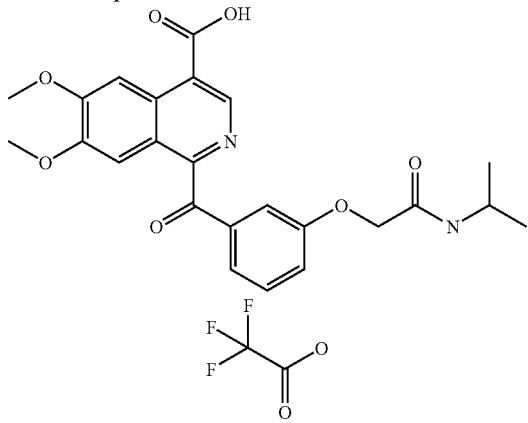

The 1-(3-carboxymethoxybenzoyl)-6,7-dimethoxy-isoquinoline-4-carboxylic acid ethyl ester (intermediate in the preparation of 6,7-Dimethoxy-1-[3-(2-oxo-2-pyrrolidin-1-yl-ethoxy)-benzoyl]-isoquinoline-4-carboxylic acid (Example 1)) (550 mg, 1.155 mmol) was mixed with N-methyl morpholine (0.32 ml, 2.9 mmol) in 5 ml of THF. The mixture was stirred at −12° C. and isobutylchloroformate (0.155 ml, 1.19 mmol) was added. The mixture was stirred at that temperature for 7 minutes and then a suspension of resin bound 1-hydroxy-2-nitro-4-benzophenone (1.0 g, 1.6 mmol/g) in 5 ml of DMF was added. The mixture was stirred at room temperature for 18 hrs and then filtered. The resinous amber solid was washed with dichloromethane (3×10 ml) followed by ether washing (3×10 ml). This material was dried in vacuum to give a resin bound activated ester (1.54 g, equivalent to 1.147 mmol of ester).

The above resin bound activated ester (225 mg, 0.19 mmol) was suspended in 3 ml of dichloromethane. Then isopropylamine (0.035 ml, 0.4 mmol) was added and the mixture was shaken under a stream of argon for 15 minutes. The mixture was filtered and the filter cake was washed with dichloromethane (3×1 ml). The filtrate was evaporated to dryness and the residue was dissolved in 1 ml of methanol containing 0.5 ml of 1N sodium hydroxide solution. The mixture was stirred for 4 hr until the completion of saponification. The mixture was evaporated and the residue was purified through a reverse phase C18 HPLC system eluted with acetonitrile and water. The pure desired fraction was dried to give 1-[3-(Isopropylcarbamoyl-methoxy)-benzoyl]-6,7-dimethoxy-isoquinoline-4-carboxylic acid; compound with trifluoro-acetic acid, as a fluffy solid (30 mg).

Example 38

6,7-Dimethoxy-1-[3-(2-oxo-2-thiomorpholin-4-yl-ethoxy)-benzoyl]-isoquinoline-4-carboxylic acid; compound with trifluoro-acetic acid

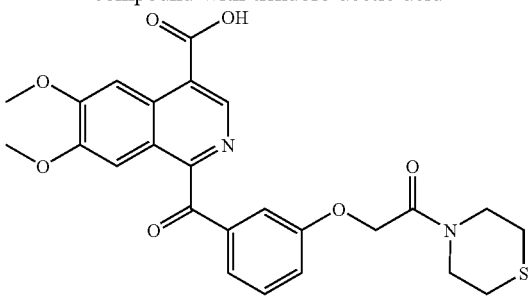

-continued

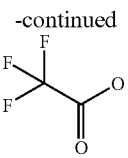

The resin bound activated ester (intermediate in the preparation of 1-[3-(Isopropyl-carbamoyl-methoxy)-benzoyl]-6,7-dimethoxy-isoquinoline-4-carboxylic acid; compound with trifluoro-acetic acid (Example 37)) (225 mg, 0.19 mmol) was combined with 3 ml of methylene chloride and 0.04 ml of thiomorpholine (0.4 mmol). The mixture was shaken for 15 minutes at room temperature. The mixture was filtered and the filter cake was washed with methylene chloride. The filtrate was evaporated to dryness. The residue was saponified by dissolving in 1 ml of methanol containing 0.5 ml of 1N sodium hydroxide solution and several drops of tetrahydrofuran. The mixture was stirred at room temperature for 4 hrs and then evaporated to dryness. The residue was purified through a reverse phase preparative HPLC to give 6,7-Dimethoxy-1-[3-(2-oxo-2-thiomorpholin-4-yl-ethoxy)-benzoyl]-isoquinoline-4-carboxylic acid; compound with trifluoro-acetic acid, as a fluffy solid (30 mg).

Example 39

6,7-Dimethoxy-1-{3-[(1-phenyl-ethylcarbamoyl)-methoxy]-benzoyl}-isoquinoline-4-carboxylic acid; compound with trifluoro-acetic acid

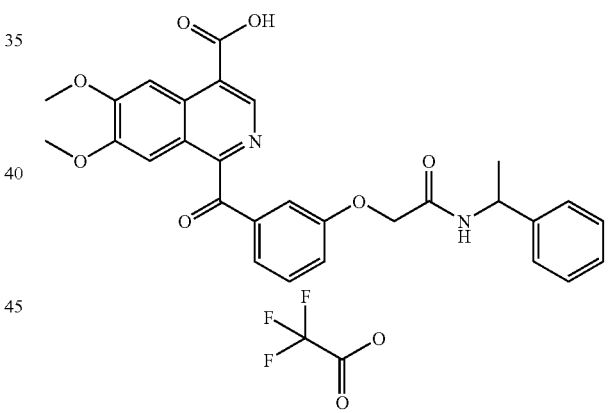

The resin bound activated ester (intermediate in the preparation of 1-[3-(Isopropylcarbamoyl-methoxy)-benzoyl]-6,7-dimethoxy-isoquinoline-4-carboxylic acid; compound with trifluoro-acetic acid (Example 37)) (225 mg, 0.19 mmol) was combined with 3 ml of methylene chloride and 0.05 ml of α-methylbenzyl amine (0.4 mmol). The mixture was shaken for 15 minutes under argon at room temperature. The mixture was filtered and the filter cake was washed with methylene chloride. The filtrate was evaporated to dryness. The residue was saponified by dissolving in 1 ml of methanol containing 0.5 ml of 1N sodium hydroxide solution and several drops of tetrahydrofuran. The mixture was stirred at room temperature for 4 hrs and then evaporated to dryness. The residue was purified through a reverse phase preparative HPLC to give 6,7-Dimethoxy-1-{3-[(1-phenyl-ethylcarbamoyl)-methoxy]-benzoyl}-isoquinoline-4-carboxylic acid; compound with trifluoro-acetic acid, as a fluffy solid (30 mg).

Example 40

1-[3-[(Ethyl-methyl-carbamoyl)-methoxy]-benzoyl]-6,7-dimethoxy-isoquinoline-4-carboxylic acid; compound with trifluoro-acetic acid

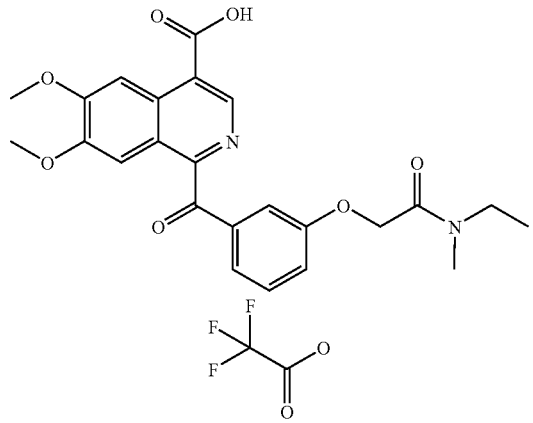

The resin bound activated ester (intermediate in the preparation of 1-[3-(Isopropylcarbamoyl-methoxy)-benzoyl]-6,7-dimethoxy-isoquinoline-4-carboxylic acid; compound with trifluoro-acetic acid (Example 37)) (225 mg, 0.19 mmol) was combined with 3 ml of methylene chloride and 0.035 ml of ethylmethylamine (0.4 mmol). The mixture was shaken for 15 minutes under argon at room temperature. The mixture was filtered and the filter cake was washed with methylene chloride. The filtrate was evaporated to dryness. The residue was saponified by dissolving in 1 ml of methanol containing 0.5 ml of 1N sodium hydroxide solution and several drops of tetrahydrofuran. The mixture was stirred at room temperature for 4 hrs and then evaporated to dryness. The residue was purified through a reverse phase preparative HPLC to give 1-{3-[(Ethyl-methyl-carbamoyl)-methoxy]-benzoyl}-6,7-dimethoxy-isoquinoline-4-carboxylic acid; compound with trifluoro-acetic acid, as a fluffy solid (27 mg).

Example 41

6,7-Dimethoxy-1-{3-[2-oxo-2-(4-phenyl-piperazin-1-yl)-ethoxy]-benzoyl}-isoquinoline-4-carboxylic acid; compound with trifluoro-acetic acid

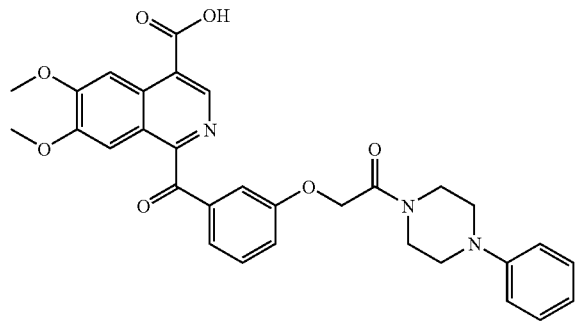

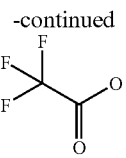

The resin bound activated ester (intermediate in the preparation of 1-[3-(Isopropylcarbamoyl-methoxy)-benzoyl]-6,7-dimethoxy-isoquinoline-4-carboxylic acid; compound with trifluoro-acetic acid (Example 37)) (225 mg, 0.19 mmol) was combined with 3 ml of methylene chloride and 0.060 ml of N-phenylpiperazine (0.388 mmol). The mixture was shaken for 15 minutes under argon at room temperature. The mixture was filtered and the filter cake was washed with methylene chloride. The filtrate was evaporated to dryness. The residue was saponified by dissolving in 1 ml of methanol containing 0.5 ml of 1N sodium hydroxide solution and several drops of tetrahydrofuran. The mixture was stirred at room temperature for 4 hrs and then evaporated to dryness. The residue was purified through a reverse phase preparative HPLC to give 6,7-Dimethoxy-1-{3-[2-oxo-2-(4-phenyl-piperazin-1-yl)-ethoxy]-benzoyl}-isoquinoline-4-carboxylic acid; compound with trifluoro-acetic acid, as a fluffy solid (30 mg).

Example 42

6,7-Dimethoxy-1-{3-[(1-phenyl-ethylcarbamoyl)-methoxy]-benzoyl}-isoquinoline-4-carboxylic acid; compound with trifluoro-acetic acid

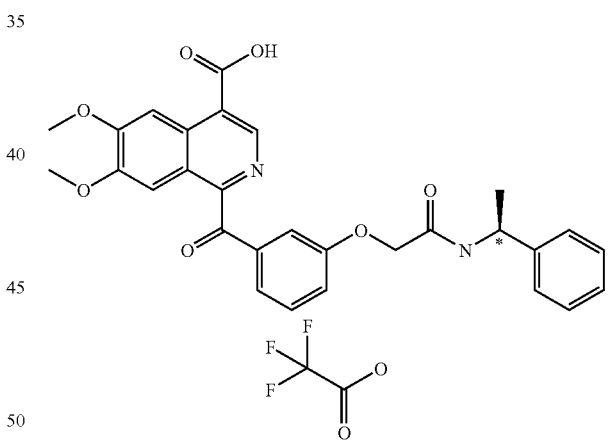

The asterisk signifies a chiral carbon.

The 1-(3-carboxymethoxybenzoyl)-6,7-dimethoxy-isoquinoline-4-carboxylic acid ethyl ester (intermediate in the preparation of 6,7-Dimethoxy-1-[3-(2-oxo-2-pyrrolidin-1-yl-ethoxy)-benzoyl]-isoquinoline-4-carboxylic acid (Example 1)) (100 mg, 0.21 mmol) was dissolved in 3 ml of THF and the stirring solution was chilled to −10° C. Then isobutylchloroformate (0.35 ml, 0.269 mmol) was added followed by triethylamine (0.09 ml: 0.644 mmol). The solution was stirred for 10 minutes and then (S)-1-phenyl-ethylamine (0.032 ml, 0.25 mmol) in a small amount of THF was added. The cooling bath was withdrawn after 5 minutes and the mixture was stirred at ambient temperature for 75 minutes. The reaction mixture was evaporated to dryness and the residue was partitioned between water (10 ml) and ethyl acetate (5 ml). The organic phase was washed with two 5 ml portions of water and the aqueous washes was back-extracted with a 5 ml portion of ethyl acetate. The organic extracts were dried over sodium sulfate, filtered and evaporated to give a crude oil which was purified by chromatography (ethyl acetate/hexanes in gradient) to provide about 25 mg of the purified amide. This amide ethyl ester (22 mg, 0.0405 mmol) was dissolved in 0.5 ml of methanol. The stirring solution was treated with 0.1 ml of 1.0 N sodium hydroxide solution. The mixture was stirred at room temperature for 15 hours. The reaction mixture was evaporated to dryness and then dissolved in a small quantity of acetic acid. The crude product was purified by a $C_{18}$ reverse phase HPLC system to give 6,7-Dimethoxy-1-{3-[(1-phenyl-ethylcarbamoyl)-methoxy]-benzoyl}-isoquinoline-4-carboxylic acid; compound with trifluoro-acetic acid, as a white foam (15 mg).

Example 43

1-(3-Isobutoxy-benzoyl)-6,7-dimethoxy-isoquinoline-4-carboxylic acid; compound with trifluoro-acetic acid

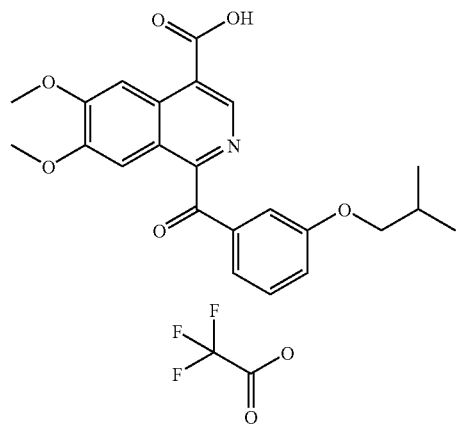

To a solution of 1-(3-hydroxy)benzyl-6,7-dimethoxy-4-ethoxycarbonylisoquinoline (250 mg, 0.68 mmol, intermediate in the preparation of 6,7-Dimethoxy-1-[3-(2-oxo-2-pyrrolidin-1-yl-ethoxy)-benzoyl]-isoquinoline-4-carboxylic acid (Example 1)) in 5 ml of ethanol was added a solution containing 18 mg of sodium in 3 ml of ethanol. The solution was stirred for about 10 minutes at room temperature and then evaporated to dryness. The residue was dried in vacuum to give a yellow solid as the sodium salt of the phenol (280 mg). This solid (140 mg, 0.34 mmol) was dissolved in 1 ml of dry DMF and 1-bromo-2-methylpropane (0.1 ml, 0.92 mmol) was added. The mixture was stirred at 45° C. for 30 minutes and then evaporated to dryness. The residue was dissolved in methanol and THF (1/1 volume ratio) and treated with 1N sodium hydroxide solutions (1.0 ml). The mixture was stirred at room temperature for 17 hrs. Solvents were evaporated and the residue was dissolved in water. The resulting solution was treated with 0.2 ml of acetic acid (3.4 mmol). The milky mixture was extracted with ethyl acetate (3×5 ml). The organic layer was dried with sodium sulfate and solvents were evaporated to give a crude oil (200 mg) which was purified through a reverse phase HPLC to give carboxylic acid as a brown solid (61 mg). The carboxylic acid was dissolved in 05 ml of acetic acid and treated with selenium dioxide (20 mg, 0.18 mmol). The mixture was stirred at 115° C. for 45 minutes and then cooled to room temperature. The mixture was filtered through Celite and washed with acetic acid. The filtrate was concentrated and then purified through reverse phase preparative HPLC to give 1-(3-Isobutoxy-benzoyl)-6,7-dimethoxy-isoquinoline-4-carboxylic acid; compound with trifluoro-acetic acid, as a yellow solid (35 mg).

Example 44

1-(3-sec-Butoxy-benzoyl)-6,7-dimethoxy-isoquinoline-4-carboxylic acid; compound with trifluoro-acetic acid

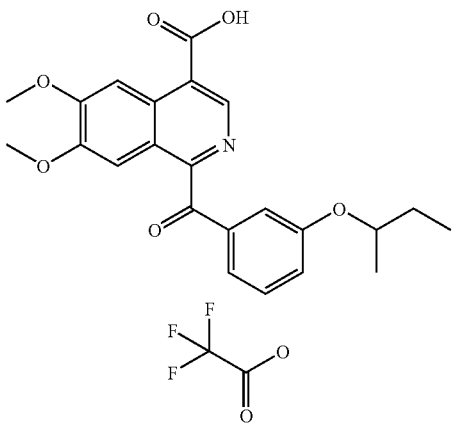

To a solution of 1-(3-hydroxy)benzyl-6,7-dimethoxy-4-ethoxycarbonylisoquinoline (250 mg, 0.68 mmol, intermediate in the preparation of 6,7-Dimethoxy-1-[3-(2-oxo-2-pyrrolidin-1-yl-ethoxy)-benzoyl]-isoquinoline-4-carboxylic acid (Example 1)) in 5 ml of ethanol was added a solution containing 18 mg of sodium in 3 ml of ethanol. The solution was stirred for about 10 minutes at room temperature and then evaporated to dryness. The residue was dried in vacuum to give a yellow solid as the sodium salt of the phenol (280 mg). This solid (140 mg, 0.34 mmol) was dissolved in 1 ml of dry DMF and 2-bromobutane (0.1 ml, 0.91 mmol) was added. The mixture was stirred at room temperature for 18 hrs and then evaporated to dryness. The residue was dissolved in methanol and THF (2 ml, 1/1 volume ratio) and treated with 1N sodium hydroxide solutions (1.0 ml). The mixture was stirred at room temperature for 17 hrs. Solvents were evaporated and the residue was dissolved in brine (20 ml). The resulting solution was treated with 0.25 ml of acetic acid. The milky mixture was extracted with ethyl acetate (3×5 ml). The organic layer was dried with sodium sulfate and solvents were evaporated. The resulting residue was purified through a reverse phase HPLC to give a carboxylic acid. This carboxylic acid was dissolved in 05 ml of acetic acid and treated with selenium dioxide (20 mg, 0.18 mmol). The mixture was stirred at 115° C. for 45 minutes and then cooled to room temperature. The mixture was filtered through Celite and washed with acetic acid. The filtrate was concentrated and then purified through reverse phase preparative HPLC to give 1-(3-sec-Butoxy-benzoyl)-6,7-dimethoxy-isoquinoline-4-carboxylic acid; compound with trifluoro-acetic acid, as a yellow solid (35 mg).

Example 45

1-[3-(1,1-Dimethyl-2-oxo-2-pyrrolidin-1-yl-ethoxy)-benzoyl]-6,7-dimethoxy-isoquinoline-4-carboxylic acid; compound with trifluoro-acetic acid

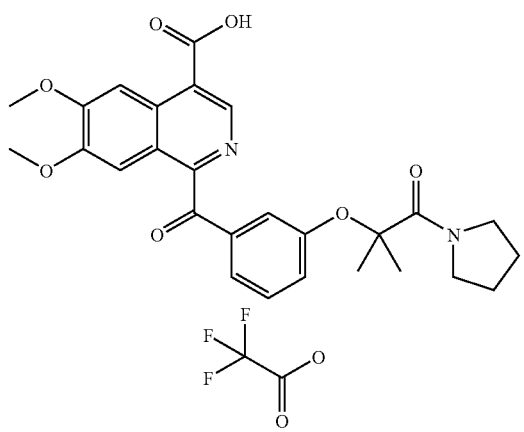

To a solution of 1-(3-hydroxybenzyl)-6,7-dimethoxy-4-ethoxycarbonylisoquinoline (367 mg, 1.0 mmol) in 10 ml of ethyl acetate was added selenium dioxide (166 mg, 1.50 mmol) and the mixture was refluxed for 1.5 hr until all starting material was consumed. The mixture was filtered through a layer of silica gel and washed with ethyl acetate. After evaporation of solvents, a solid was obtained as 1-(3-hydroxybenzoyl)-6,7-dimethoxy-4-ethoxycarbonylisoquinoline (370 mg). This solid (325 mg, 0.85 mmol) was dissolved in 3 mL of DMF and the stirring solution was treated with potassium carbonate (300 mg, 2.17 mmol) followed by t-butyl-2-bromoisobutyrate (210 mg, 0.94 mmol). The resulting mixture was heated (50° C. in an oil-bath) and stirred for 25 hours. Mass spectrum and TLC indicated partial conversion to the desired product and additional potassium carbonate (330 mg, 2.17 mmol) and isobutyrate (210 mg, 0.94 mmol) were added. The mixture was heated with stirring for additional 25 hours. The reaction mixture was evaporated and the residue was partitioned with ethyl acetate (50 ml) and brine (25 ml). The organic layer was dried over sodium sulfate, filtered and evaporated to give an oil which was purified by silica gel chromatography, using gradient mixtures of ethyl acetate and hexanes, to produce 248 mg of the isobutyrate as a yellow oil.

The above yellow oil was dissolved in 3 mL of dichloromethane and treated with 1 ml of trifluoroacetic acid. The mixture was stirred for 1 hour at room temperature. The solution was evaporated and the residue was dissolved in dichloromethane. The resulting solution was treated with gaseous hydrogen chloride for 3 minutes. After the evaporation of solvents, the residue was triturated with ethyl ether and the solid was filtered to give about 250 mg of a deliquescent solid as 1-[3-(2-methyl-2-carboxy)ethoxy]benzoyl-6,7-dimethoxy-4-ethoxycarbonylisoquinoline. H-NMR suggested a pure product containing ethyl ether as solvate.

The above carboxylic acid (115 mg, 0.228 mmol) was dissolved in dry THF (3 mL) and 100 µl of triethyl amine (0.717 mmol) was added. The mixture was stirred at −10° C. and isobutyl chloroformate (37 µl, 0.285 mmol) was added. The solution was stirred for 10 minutes and then pyrollidine (22 µl, 0.263 mmol) was added. The mixture was stirred at that temperature for 10 minutes and the cooling bath was withdrawn. The mixture was stirred for 66 hours at room temperature. The reaction mixture was evaporated to dryness and the residue was partitioned with ethyl acetate (5 ml) and saturated sodium bicarbonate solution. The organic phase was washed in turn with brine (5 ml), water containing a few drops of acetic acid, and finally with brine. Each aqueous phase was extracted again with a portion (3 ml) of ethyl acetate. Upon drying over sodium sulfate, filtration and evaporation of the solvent, the crude mixture was purified by reverse phase preparative HPLC to provide the desired amide as an orange oil (40 mg) as well as the recovered starting material carboxylic acid (45 mg).

The above amide (40 mg, 0.063 mmol) was stirred with a mixture of methanol (1 ml) and 0.2 ml of 1.0 N sodium hydroxide at room temperature for 17 hours. The mixture was evaporated and the residue was first dissolved in acetic acid and then purified by reverse phase preparative HPLC to provide 1-[3-(1,1-Dimethyl-2-oxo-2-pyrrolidin-1-yl-ethoxy)-benzoyl]-6,7-dimethoxy-isoquinoline-4-carboxylic acid; compound with trifluoro-acetic acid, as a colorless foam (25 mg).

Example 46

1-[3-(1-Isopropylcarbamoyl-1-methyl-ethoxy)-benzoyl]-6,7-dimethoxy-isoquinoline-4-carboxylic acid; compound with trifluoro-acetic acid

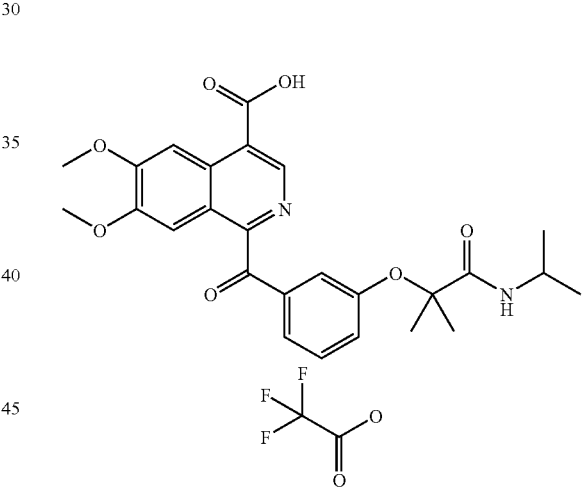

To a solution of 1-[3-(2-methyl-2-carboxy)ethoxy]benzoyl-6,7-dimethoxy-4-ethoxycarbonylisoquinoline hydrochloride (115 mg, 0.228 mmol, intermediate in the preparation of 1-[3-(1,1-Dimethyl-2-oxo-2-pyrrolidin-1-yl-ethoxy)-benzoyl]-6,7-dimethoxy-isoquinoline-4-carboxylic acid; compound with trifluoro-acetic acid (Example 45)) in 3 ml of dry THF was added Et$_3$N (100 µl, 0.717 mmol) and the mixture was chilled to −10° C. Then isobutyl chloroformate (37 µl, 0.285 mmol) was added and the mixture was stirred for 10 minutes. Isopropylamine (23 µl, 0.27 mmol) was added and the solution was stirred at room temperature for 66 hours. Solvent was removed in vacuo and the remainder was partitioned with methylene chloride (20 ml) and saturated aqueous sodium bicarbonate solution. The organic phase was washed with brine, dried over sodium sulfate, filtered and evaporated to yield a clear orange oil (about 120 mg). This oil material was dissolved in methanol (1.5 ml) and treated with 0.5 ml of 1.0 N aqueous sodium hydroxide.

The mixture was stirred at room temperature for 3 hours, stored in a freezer for 16 hours and the solvent was removed in vacuo. The residue was dissolved in acetic acid and purified by reverse preparative HPLC to yield a pink solid as 1-[3-(1-Isopropylcarbamoyl-1-methyl-ethoxy)-benzoyl]-6,7-dimethoxy-isoquinoline-4-carboxylic acid; compound with trifluoro-acetic acid (51 mg).

Example 47

1-[3-(1-Isopropylcarbamoyl-1-methyl-ethoxy)-benzoyl]-6,7-dimethoxy-isoquinoline-4-carboxylic acid; compound with trifluoro-acetic acid

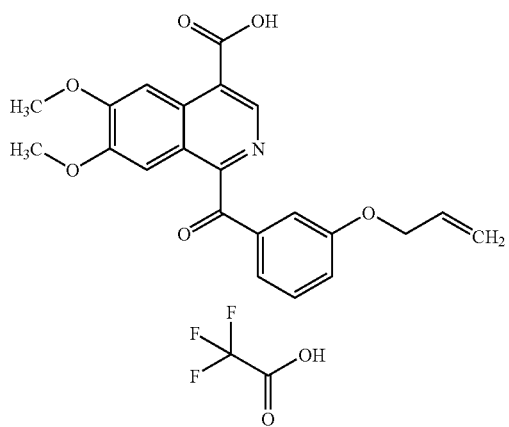

α-Aminomethyl-3,4-dimethoxybenzene-acetic acid ethyl ester hydrochloride (11.9 g, 41.2 mmol) was mixed with 3-alloxyphenylacetic acid (8.3 g, 43.2 mmol), diisopropylethylamine (25 ml, 143 mmol), and O-benzotriazol-1-yl-N,N,N',N'-tetramethyluronium hexafluorophosphate (17.2 g, 45.3 mmol) in DMF (250 ml). The mixture was stirred at room temperature for 16 hours. The solvent was removed in vacuo and the residue was partitioned with dichloromethane (250 ml) and 1N hydrochloric acid (150 ml). The organic phase was washed with saturated aqueous sodium bicarbonate solution. The aqueous phase was extracted with another portion of dichloromethane The combined extracts were dried from sodium sulfate, filtered an d evaporated to dryness and the residue was purified by silica gel chromatography (2:1 ethyl acetate:hexanes) to give an amide as a pale yellow oil (16.0 g).

The above amide (15.5 g, 36.25 mmol) was dissolved in 150 ml of dichloromethane and treated while stirring with 13 g of $PCl_5$ (62.4 mmol). Stirring was continued for 17 hours under a $CaSO_4$ drying tube. The solvent was evaporated and the residue was partitioned with 250 ml of dichloromethane and 200 ml of saturated aqueous sodium bicarbonate. The organic phase was washed with brine. Each aqueous phase was extracted with another portion of dichloromethane. The organic phase was combined, dried over sodium sulfate, filtered and evaporated to give the ring-closed substance dihydroisoquinoline as an orange oil (15 g).

The above dihydroisoquinoline was combined with 1.8 g of elemental sulfur (56 mmol) and the stirring mixture was heated at 155° C. in an oil-bath for one hour during which time the mixture became a dark, thick paste. The mixture was cooled to 50° C. and stirred with 150 ml of ethyl alcohol. A small amount of yellow precipitate was removed by filtering through a layer of Celite. Solvent was removed in vacuo and the residue was purified through silica gel chromatography (gradient mixtures of ethyl acetate and hexanes) to produce 1-(3-alloxybenzyl)-6,7-dimethoxy-4-ethoxycarbonylisoquinoline (4.1 g) as well as 1-(3-alloxy-benzoyl)-6,7-dimethoxy-4-ethoxycarbonylisoquinoline (150 mg).

The above 1-benzoylisoquinoline (150 mg, 0.34 mmol) was combined with 5 ml of methanol, 2 ml of THF and 1.0 ml of 1.0 M sodium hydroxide solution. The mixture was stirred for 2 hours at room temperature then at 42° C. for 2 hours. The reaction mixture was evaporated to dryness, then dissolved in a small amount of methanol and purified by reverse phase preparative HPLC. The purified fraction was lyophilized to give 1-[3-(1-Isopropylcarbamoyl-1-methyl-ethoxy)-benzoyl]-6,7-dimethoxy-isoquinoline-4-carboxylic acid; compound with trifluoro-acetic acid, as a tan solid (25 mg)

Example 48

1-(3-Butoxy-benzoyl)-6,7-dimethoxy-isoquinoline-4-carboxylic acid

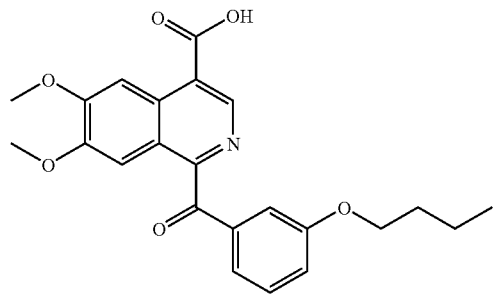

The 3-phenylacetic acid was refluxed in methanol containing gaseous hydrogen chloride. The resulting methyl ester was alkylated with n-butyl bromide in DMF containing potassium carbonate. The methyl ester was finally saponified in refluxing ethanol with 1.0 N sodium hydroxide solution to provide 3-butoxyphenylacetic acid.

The above 3-butoxyphenyl acetic acid (440 mg, 2.11 mmol) was mixed with α-aminomethyl-3,4-dimethoxybenzene-acetic acid ethyl ester hydrochloride (580 mg, 2.0 mmol) in 30 mL of DMF. Then HBTU (837 mg, 2.2 mmol) and diisopropylethyl amine (1.22 ml, 7.0 mmol) were added. The mixture was stirred at room temperature for 16 hours. Solvent was removed in vacuo and the residue was partitioned with ethyl acetate (50 ml) and saturated aqueous sodium bicarbonate (35 ml). The ethyl acetate was washed with brine then with 35 ml of 0.5 M hydrochloric acid and again with brine. The Organic layers were combined, dried over sodium sulfate, filtered and evaporated to give about 1 g of the crude product which was purified by silica gel chromatography, eluting with gradient mixtures of ethyl acetate and hexanes to produce the amide as a pale yellow liquid (860 mg).

The above amide (860 mg, 1.94 mmol) was combined in 50 ml of dichloromethane with 700 mg of phosphorous pentachloride (3.36 mmol) and the mixture was stirred under a $CaSO_4$ drying tube for 17 hours. The solution was evaporated and the residue was partitioned with saturated aqueous sodium bicarbonate (50 ml) and dichloromethane (75 ml).

The extract was dried from sodium sulfate, filtered and evaporated to give an amber oil as a dihydroisoquinoline (825 mg).

The dihydroisoquinoline (825 mg, 2 mmol) was combined with 100 mg of sulfur (3.1 mmol) and the mixture was heated and stirred at 155° C. in an oil-bath for 45 minutes. The paste was cooled and stirred with 3 mL of ethyl alcohol and filtered through Celite. The filtrate was evaporated to dryness giving a dark oil (800 mg). This oil was dissolved in 25 ml of acetic acid and treated with 260 mg (2.34 mmol) of selenium dioxide and the mixture was heated (122° C. oil bath) and stirred for 45 minutes. The mixture was evaporated to dryness and the residue was partitioned with saturated aqueous sodium bicarbonate and dichloromethane. The organic phase was dried from sodium sulfate, filtered and evaporated to give 900 mg of a dark oil which was purified on silica gel, eluting with gradient mixtures of ethyl acetate and hexanes. One of the fractions, rich in desired material, precipitated 205 mg of yellow crystals. Other fractions containing the desired material were evaporated to produce an additional 260 mg of the 1-(3-butoxybenzoyl)-6,7-dimethoxy-4-ethoxycarbonylisoquinoline.

The above intermediate, 1-(3-butoxybenzoyl)-6,7-dimethoxy-4-ethoxycarbonyl-isoquinoline (390 mg, 0.89 mmol) was dissolved in a solution of ethanol (10 ml), THF (5 ml) and 4N sodium hydroxide (1 ml). The mixture was refluxed until all starting material was consumed. Solvents were evaporated and 25 ml of water was added. The solution was washed with ethyl ether (2×10 ml). The aqueous phase was neutralized by the addition of 4 ml of 1.0 N hydrochloric acid. The milky mixture was extracted with two 25 ml portions of ethyl acetate. The organic layer was washed with brine. The organic extracts were dried over sodium sulfate, filtered and evaporated to give 350 mg of yellow solid which was stirred in 25 ml of ethyl ether. The solid was filtered and washed with cold ethyl ether to produce 310 mg of the carboxylic acid as a yellow solid 1-(3-Butoxy-benzoyl)-6,7-dimethoxy-isoquinoline-4-carboxylic acid.

Example 49

1-(3-Furan-2-yl-benzoyl)-6,7-dimethoxy-isoquinoline-4-carboxylic acid; compound with trifluoroacetic acid

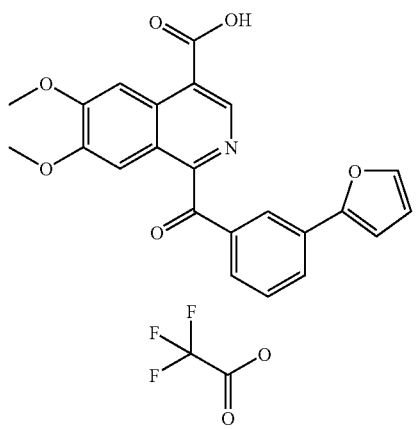

To a mixture of 1-(3-bromobenzyl)-6,7-dimethoxy-4-carboxylic acid ethyl ester (200 mg, 0.46 mmol, intermediate in the preparation of 6,7-Dimethoxy-1-[3-(3-oxo-3-pyrrolidin-1-yl-propenyl)-benzoyl]-isoquinoline-4-carboxylic acid (Example 35)) in 5 ml of acetic acid was added selenium dioxide (65 mg, 0.585 mmol). The stirring mixture was heated at 120° C. in an oil bath for 45 minutes at which time a TLC (1:1 EtOAc/Hexanes) suggested complete conversion to a slightly less polar product. The crude mixture was filtered through Celite, washed with a little acetic acid and the filtrate evaporated to dryness. The residue was partitioned with dichloromethane (20 ml) and saturated aqueous sodium bicarbonate (10 mL). The organic phase was dried over magnesium sulfate, filtered, evaporated and the residue was purified by silica gel chromatography (EtOAc/hexanes) to yield 1-(3-bromobenzoyl)-6,7-dimethoxy-4-carboxylic acid ethyl ester, as yellow crystals (125 mg, 61%).

The intermediate, 1-(3-bromobenzoyl)-6,7-dimethoxy-4-carboxylic acid ethyl ester (170 mg, 0.38 mmol) and tetrakistriphenylphosphine palladium (48 mg, 0.0415 mmol) were combined in 10 ml of DMF and the mixture was stirred at room temperature under argon for 15 minutes. Then 2-furanboronic acid (75 mg, 0.67 mmol) and potassium carbonate (200 mg, 1.447 mmol) were added and the reaction mixture was heated in an oil bath (120° C.) with vigorous stirring for 17 hours. Since TLC analysis indicated a slow reaction to a more polar product, an additional 2-furanboronic acid (25 mg, 0.0216 mmol), Pd(0) reagent and potassium carbonate (100 mg, 0.72 mmol) were added to the reaction mixture and heating was resumed for 42 hours. Heating was discontinued and the mixture was stirred at ambient temperature for another 72 hours. The reaction mixture was evaporated under reduced pressure and the residue was partitioned with saturated aqueous ammonium chloride solution (25 ml) and dichloromethane (25 ml). The organic phase was washed in turn with saturated aqueous sodium bicarbonate (20 ml) and brine (20 ml). The organic extract was dried over sodium sulfate, filtered and evaporated in vacuo and the crude product was chromatographed on silica gel (ethyl ether/hexanes) to provide about 37 mg of a mixture containing the starting material bromide and the desired 2-furan derivative. This mixture was combined in 1 ml of ethyl alcohol with 0.4 ml of 1.0 N sodium hydroxide solution. The mixture was refluxed until the saponification was complete. The cooled aqueous solution was diluted with water and extracted twice with ethyl ether (3 mL). The aqueous layer was neutralized by the addition of 0.4 ml of 1.0 M hydrochloric acid. The milky mixture was extracted with ethyl acetate, dried over sodium sulfate, evaporated and purified by reverse phase preparative HPLC to provide 1-(3-Furan-2-yl-benzoyl)-6,7-dimethoxy-isoquinoline-4-carboxylic acid; compound with trifluoro-acetic acid, as a brown semi-solid (25 mg, 56%).

Example 50

6,7-Dimethoxy-1-(3-thiophen-3-yl-benzoyl)-isoquinoline-4-carboxylic acid; compound with trifluoro-acetic acid

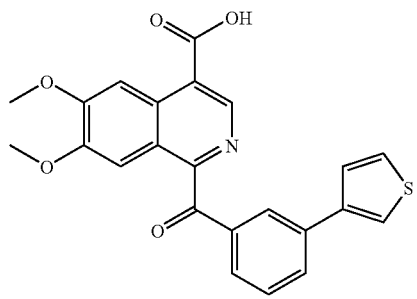

-continued

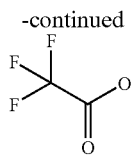

1-(3-bromobenzoyl)-6,7-dimethoxy-4-carboxylic acid ethyl ester (intermediate in the preparation of Example 49) (170 mg, 0.38 mmol) and tetrakistriphenylphosphine palladium (48 mg, 0.0415 mmol) were combined in 10 ml of DMF and the mixture was stirred at room temperature under argon for 15 minutes. Then 2-thiopheneboronic acid (86 mg, 0.67 mmol) and potassium carbonate (200 mg, 1.45 mmol) were added and the reaction mixture was heated in an oil bath at 120° C. with vigorous stirring for 17 hours. An additional portion of 2-thiopheneboronic acid (45 mg, 0.35 mmol), tetrakistriphenylphosphine palladium (25 mg, 0.022 mmol) and potassium carbonate (100 mg, 0.725 mmol) were added. The stirring at 120° C. was continued for 42 hours. The reaction mixture was evaporated to dryness in vacuo at 50° C. and then partitioned with saturated aqueous sodium bicarbonate solution (50 ml) and dichloromethane (100 ml). The organic phase was dried with anhydrous sodium sulfate, filtered, evaporated to dryness and the residue was purified by chromatography on silica gel (ethyl ether/hexane) to provide a thiophene derivative as a yellow powder (68 mg, 44%).

The above powder (65 mg, 0.145 mmol) was dissolved in 2 ml of ethyl alcohol, and 0.6 ml of 1N sodium hydroxide solution was added. The mixture was refluxed, allowing the volatile solvent to boil out. Water was added in small increments over 30 minutes. Analysis by TLC (CHCl$_3$/MeOH/H$_2$O/HOAc) suggested complete transformation to a crude mixture of products which was purified by reverse phase preparative HPLC to provide 6,7-Dimethoxy-1-(3-thiophen-3-yl-benzoyl)-isoquinoline-4-carboxylic acid; compound with trifluoro-acetic acid, as a pale yellow powder (20.1 mg).

Example 51

2-[1-(3-Isopropoxy-benzoyl)-6,7-dimethoxy-isoquinolin-4-ylmethyl]-[1,2,4]oxadiazolidine-3,5-dione; compound with trifluoro-acetic acid

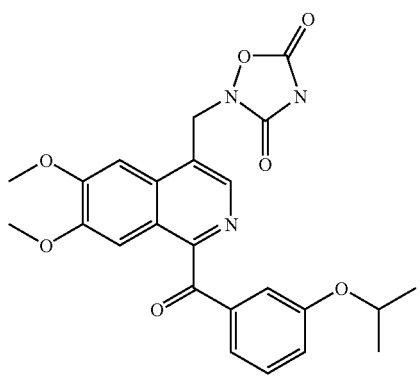

1-(3-Isopropoxybenzyl)-6,7-dimethoxyisoquinoline-4-methanol (368 mg, 1.0 mmol, intermediate in the preparation of Example 11) was combined with t-butyl N-t-butoxycarbonyloxy)carbamate (280 mg, 1.2 mmol) and triphenylphosphine (315 mg, 1.2 mmol) in 10 ml of THF. The stirring solution was chilled to −20° C. under argon and diethylazodicarboxylate (0.19 ml, 1.2 mmol) in 2 ml of THF was added dropwise by syringe. The mixture was stirred at −20° C. for 5 minutes then −5° C. for 60 minutes. The mixture was evaporated to dryness and the residue was partitioned with ethyl acetate (50 ml) and water (25 ml). The organic phase was first dried over sodium sulfate, then filtered and evaporated. The residue was purified by silica gel chromatography using gradient mixtures of hexane and ethyl acetate to give a carbamate as a colorless oil (460 mg).

The above carbamate (460 mg, 0.79 mmol) was combined with a solution composed of 2 ml of dichloromethane and 2 ml of trifluoroacetic acid and the solution was stirred for 6 hours at room temperature. After evaporation to dryness the residue was partitioned with dichloromethane (25 ml) and 1N sodium hydroxide (20 ml). The organic phase was dried from sodium sulfate. The mixture was filtered and solvent was evaporated to produce the hydroxyamine derivative as a pale yellow oil (295 mg).

The above hydroxyamine derivative (290 mg, 0.758 mmol) was dissolved in 5 ml of dry THF and chilled while stirring to 0° C. Then N-chlorocarbonyl isocyanate (0.063 ml, 0.837 mmol) in 1 ml of THF was added dropwise and the solution was stirred at 0° C. for 30 minutes. The mixture was quenched with saturated ammonium chloride solution (10 ml) and then extracted with dichloromethane (2×25 ml). The organic layer was dried over magnesium sulfate and the solvent was evaporated to produce the oxadiazolidenedione as a white solid (350 mg).

The above white solid (120 mg, 0.264 mmol) was dissolved in 5 ml of ethyl acetate, treated with 36 mg of selenium dioxide (0.324 mmol) and heated to reflux for 60 minutes. The reaction mixture was cooled and passed through filter aid, evaporated to dryness, and the residue was dissolved in methanol and subjected to reverse phase HPLC purification to give the title compound as a white powder (35 mg).

Example 52

3-[1-(3-Isopropoxy-benzoyl)-6,7-dimethoxy-isoquinolin-4-ylmethyl]-thiazolidine-2,4-dione; compound with trifluoro-acetic acid

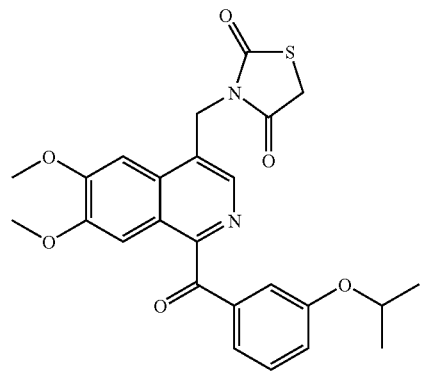

-continued

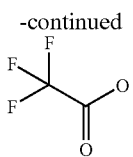

1-(3-Isopropoxybenzyl)-6,7-dimethoxyisoquinoline-4-methanol (3.55 g, 9.66 mmol, intermediate in the preparation of Example 11) was dissolved in 50 ml of methylene chloride and chilled to 0° C. while stirring. Then triethylamine (1.5 ml, 10.7 mmol) was added, followed by methanesulfonyl chloride (0.825 ml, 10.6 mmol). The mixture was stirred for 20 minute at 0° C. Lithium chloride (1 g, 23.5 mmol) was then added. The cooling bath was withdrawn and stirring was continued for 17 hours. The reaction mixture was partitioned with brine (50 ml) and 100 ml of additional methylene chloride. The organic phase was dried over sodium sulfate, filtered and evaporated to provide a chloride derivative as a beige semi-solid (3.6 g).

The above chloride (385 mg, 1 mmol) was dissolved in THF (5 mL) and 80 mg of sodium hydride (60% oil dispersion, 2 mmol) was added. Within 5 minutes a white solid came out of solution which was dissolved by the portion-wise addition of DMF (5 ml). The mixture was warmed with stirring at 50° C. for 2 hours. The orange red solution was cooled to room temperature and 120 mg (1.02 mmol) of 2,4-thiazolidene-dione in 3 ml of THF was added and the mixture was stirred at room temperature for 66 hours. Solvents were evaporated and the residue was partitioned with methylene chloride (25 ml) and saturated aqueous ammonium chloride solution. The organic phase was washed with brine and dried over sodium sulfate. Evaporation of solvents gave an orange oil (460 mg) which was used as such for the next reaction.

The above crude compound (455 mg, 0.97 mmol) was dissolved in ethyl acetate (10 ml) and heated at reflux and stirred in the presence of SeO$_2$ (1.08 mmol) for 1 hour. The mixture was cooled, passed through a plug of filter aid. The filtrate was evaporated and the residue was dissolved in about 10 ml of methanol. One half of this methanol solution was applied to a reserve phase preparative HPLC for purification to give the title compound (25 mg) as a beige powder.

Example 53

(2-Fluoro-5-isopropoxy-phenyl)-[4-(2-hydroxy-ethyl)-6,7-dimethoxy-isoquinolin-1-yl]-methanone

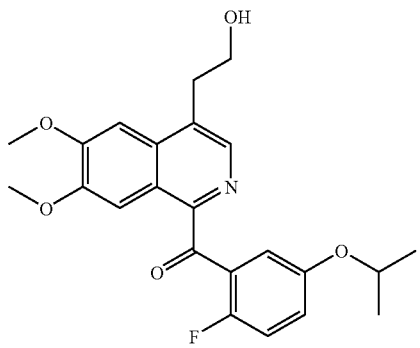

To a solution of 1-(2-fluoro-5-isopropoxy)benzyl-6,7-dimethoxyisoquinoline-4-acetic acid methyl ester (200 mg, 0.467 mmol, intermediate in the preparation of Example 31) in 5 ml of dry THF was added while stirring under argon 0.5 ml of a 1.0 M lithium aluminum hydride solution in THF. After stirring at room temperature for 15 minutes, the mixture was cooled to 5° C. and was treated with 5 ml of saturated ammonium chloride solution. The fluid was decanted from a thick white precipitate. The liquid layer was diluted with 25 ml of ethyl acetate and washed with 20 ml of 10% aqueous sodium potassium tartrate solution, followed by brine. The organic layer was dried from sodium sulfate, filtered and evaporated to give the alcohol as a pale yellow oil (195 mg).

The above crude compound (195 mg) was dissolved in 5 ml of ethyl acetate and the stirring solution was heated to 78° C. in an oil-bath and 90 mg of selenium dioxide (90 mg, 0.81 mmol) was added and the mixture was refluxed for 90 minutes. The mixture was cooled and applied to a silica gel column, eluted with gradient mixtures of ethyl acetate and hexanes and the appropriate fractions were evaporated to provide the title compound as an amorphous solid (45 mg). Collection of less pure fractions gave an additional 90 mg of cruder product which was reserved for further purification.

Example 54

2-[1-(2-Fluoro-5-isopropoxy-benzoyl)-6,7-dimethoxy-isoquinolin-4-yl]-4-methyl-pentanoic acid; compound with trifluoro-acetic acid

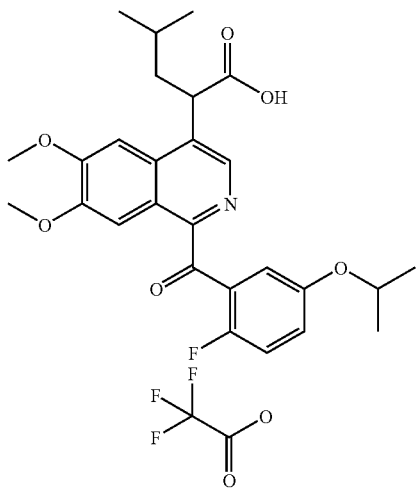

Elemental sodium (15 mg, 0.65 mmol) was added to and stirred with 5 ml of methanol. The sodium methoxide solution, thus prepared, was added to a solution of 1-(2-fluoro-5-isopropoxy)benzyl-6,7-dimethoxyisoquinoline-4-acetic acid methyl ester (188 mg, 0.44 mmol, intermediate in the preparation of Example 31) in 5 ml of methanol. The mixture was stirred at room temperature for 10 minutes and the solvent was evaporated. The residue was dissolved in 5 ml of DMF and the resulting cherry red solution was cooled to 5° C. Then 1-bromo-2-methyl propane (0.070 mL) was added and the mixture was stirred at 5° C. for 20 minutes and at room temperature for 16 hours. The mixture was evaporated to dryness and then partitioned with ethyl acetate and saturated aqueous NH$_4$Cl solution. The ethyl acetate extract was dried over sodium sulfate, filtered and evaporated to give an oil. The crude mixture was purified by silica gel chromatography with elution of gradient mixtures of ethyl acetate and hexanes to give 33 mg of the desired alkylated material as well as 50 mg of the starting material.

The above alkylated ester (30 mg, 0.62 mmol) was dissolved in 1 ml of ethyl acetate, treated with 12 mg of selenium dioxide (0.108 mmol) and heated at reflux for 60 minutes. The reaction mixture was cooled, filtered through a layer of Celite, and then evaporated. The residue was purified by silica gel chromatography, eluting with 1/1 ethyl acetate and hexanes to provide 30 mg of the ketone.

The above ketone (30 mg, 0.6 mmol) was dissolved in 2 ml of methanol. The mixture was brought to reflux and 1 ml of 1 N sodium hydroxide solution was added. After refluxing for 15 minutes, solvent was evaporated and the residue was dissolved in water (1 ml). The mixture was acidified with 1.0 ml of 1 N hydrochloric acid. The milky mixture was extracted with ethyl acetate. The organic extracts were washed with brine, dried over sodium sulfate, filtered and evaporated. The residue was purified by reverse phase preparative HPLC to give 23 mg of the title compound.

Example 55

1-(2,6-Difluoro-3-methoxy-benzoyl)-6,7-dimethoxy-isoquinoline-4-carboxylic acid; compound with trifluoro-acetic acid

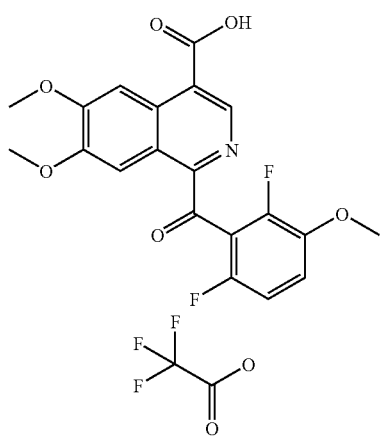

13 g (100 mmol) of 2,4-difluorophenol was dissolved in 100 ml of acetone and was treated with $K_2CO_3$ (55 g, 400 mmol), followed by iodomethane (25 ml, 400 mmol) and the mixture was stirred at room temperature for about 66 hours. The mixture was taken almost to dryness in vacuo and the residue was dissolved in dichloromethane (150 ml) and washed with brine (100 ml). The organic phase was dried over sodium sulfate, filtered and evaporated in vacuo to yield 6.1 g of the difluoro anisole as a colorless liquid. This compound was converted to 2,6-difluoro-3-methoxyphenyl acetic acid with the same procedure described in the preparation of Example 56.

α-Aminomethyl-3,4-dimethoxybenzene-acetic acid ethyl ester hydrochloride (intermediate in the preparation of Example 30)) (1.25 g, 4.33 mmol), 2,6-difluoro-3-methoxyphenyl acetic acid (0.8 g, 3.95 mmol), 1.8 g (4.745 mmol) of HBTU and 2.3 ml (13.2 mmol) of diisopropylethylamine were combined in 25 ml of DMF and the solution was stirred at room temperature for 17 hours. The resulting mixture was warmed to 50° C. under argon for 24 hours. The mixture was evaporated to dryness and the residue was partitioned with ethyl acetate (100 ml) and 1N HCl (50 ml). The ethyl acetate solution was washed with 5% $K_2CO_3$ (aq.), then with brine (50 ml). Each aqueous extracted with 50 ml ethyl acetate. The organic layers were combined, dried ($Na_2SO_4$), filtered and the residue was purified by silica gel chromatography, using gradient mixtures of ethyl acetate and hexanes to give the amide as a white solid (1.10 g).

The above amide (1.05 g, 2.4 mmol) was combined with phosphorous pentachloride (0.8 g, 3.84 mmol) in 50 ml of $CH_2Cl_2$ and the mixture was stirred for 36 hours at room temperature under a calcium sulfate drying tube. The reaction mixture was evaporated to dryness and then dissolved in 100 ml of dichloromethane and washed with two 50 ml portions of saturated (aq.) sodium bicarbonate solution, followed by brine. The organic solution was dried from sodium sulfate, filtered, and evaporated to give 1.05 g of the dihydroisoquinoline as an amber oil.

The above dihydroisoquinoline (1.05 g, 2.4 mmol) was combined with sulfur (120 mg, 3.74 mmol) in 10 ml of methylene chloride and solvent was gently evaporated to produce a uniform paste which was heated at 155° C. in an oil-bath with magnetic stirring for 1 hour and 15 minutes. The mixture was cooled, stirred in 25 ml of ethyl alcohol, and filtered through Celite. The filtrate was evaporated to dryness and the residue was purified by silica gel chromatography (ethyl acetate/hexanes elution) to yield 330 mg of the isoquinoline as a white solid.

The above isoquinoline (320 mg, 0.766 mmol) was dissolved in 10 ml of ethyl acetate and treated with 240 mg (2.16 mmol) of $SeO_2$ and the mixture was heated at reflux for 3 hours. The mixture was evaporated to dryness and then crystallized from ethyl ether and hexanes to produce the ketone (295 mg) as a yellow solid. This yellow solid (290 mg, 0.067 mmol) was dissolved in EtOH (10 mL) and the solution was heated to reflux. Then 0.2 mL of 10 N NaOH was added and the mixture was heated at 100° C. in an oil bath. Ethanol was allowed to boil out gradually with the addition of water. Heating was continued for 20 minutes, the mixture was cooled, filtered and evaporated to eliminate residual ethanol. The mixture was diluted with 25 ml of water and extracted with ethyl ether to eliminate neutral impurities. The aqueous was adjusted to pH 4.1 with the addition of 0.1 N HCl. The resulting solid was filtered and washed with water. The solid was dissolved in a small amount of THF and was purified by reverse phase preparative HPLC to give the title compound as a yellow solid.

Example 56

1-(2,6-Difluoro-3-isopropoxy-benzoyl)-6,7-dimethoxy-isoquinoline-4-carboxylic acid; compound with trifluoro-acetic acid

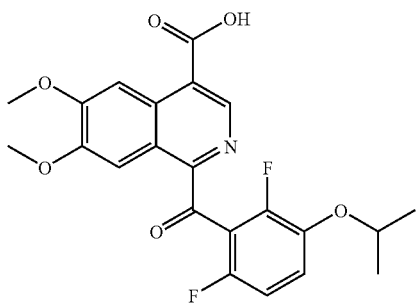

-continued

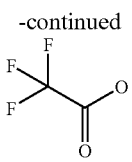

18.5 g (141 mmol) of 2,4-difluorophenol was dissolved in 150 mL acetone and potassium carbonate (0.56 mol) was added with stirring followed by 42 mL (0.42 mol) of 2-iodopropane and the mixture refluxed under mechanical stirring for 20 hours. The reaction mixture was cooled, filtered through filter-aid and the filtrate evaporated (at 35° C.). The residue was partitioned with 250 mL of dichloromethane and 100 mL 1N NaOH; the organic phase was washed with brine. Each aqueous was extracted with a portion of dichloromethane. Organic extracts were combined, dried from sodium sulfate, filtered and evaporated to give 22 g of a pale yellow oil.

22 g (140 mmol) of 1,3-difluoro-4-isopropoxybenzene was dissolved in 175 mL of freshly distilled THF and the stirring mixture chilled to −78° C. under argon. 165 mL of 1.3 M sec-butyl lithium solution in cyclohexane (215 mmol) was added slowly (over 20 minutes) by cannula under argon pressure. When addition was complete the mixture was stirred at −75° C. for 10 minutes. A solution of DMF (19 mL: 245 mmol) and THF (25 mL) was added to the stirring mixture all at once. Temperature rose to −40° C. then subsided. The mixture was then stirred at 0° C. for 40 minutes. The mixture was 200 mL of hexanes and stirred with 200 mL of saturated aqueous ammonium chloride. Phases were separated; the organic phase was washed with brine; the aqueous phase was extracted further with 200 mL of ethyl ether. Organic solutions were combined, dried (magnesium sulfate), filtered and evaporated to give 24 g of the crude aldehyde which was purified by silica gel chromatography, eluting with gradient mixtures of ethyl acetate and hexanes. The process yielded 14.6 g of purified aldehyde as a pale green oil.

16.3 g (81.42 mmol) of the aldehyde was dissolved in dry THF and treated while stirring and under argon with 3.1 g lithium aluminum hydride (81.79 mmol) gradually over 20 minutes in ten approximately equal portions. The reaction mixture's temperature reaches ~45° C. Within 10 minutes of final addition, the mixture is cooled to 0° C. and treated dropwise and carefully with 100 mL of NH$_4$Cl. The resulting mixture of thick grey solids was filtered through Celite and washed with a small portion of THF, then in portions with 300 mL of hexanes. The resulting organic solution was stirred with 200 mL of saturated aqueous sodium potassium tartrate. The phases were separated and the aqueous phase extracted with a portion of ethyl ether. The organic phases were washed in turn with 100 mL of brine. The extracts were combined, dried (MgSO$_4$) filtered, and evaporated to provide 17 g of the benzyl alcohol as a colorless liquid.

17 g (81 mmol) of the benzyl alcohol was dissolved in dichloromethane (350 mL) along with triethylamine (13 mL:93.3 mmol). Methanesulfonyl chloride (7.1 mL:91.77 mmol) was added in a dropwise manner at room temperature with stirring and under argon. Mixture stirred for 10 minutes, then (10 g:235 mmol) was and the mixture stirred for 18 hours. In order to drive the reaction to completion the mixture was warmed under a reflux condenser in an oil-bath at 40° C. for 5 hours. The mixture was cooled and washed with 200 mL of 1 N HCl followed by 100 mL of 0.5 M NaOH followed by brine. Each aqueous phase was extracted with 100 mL of dichloromethane. The extracts were dried (Na$_2$SO$_4$), filtered and evaporated to give the chloride (19 g: slightly higher than theoretical) as a pale green oil.

~19 g (~81 mmol) of the chloride was dissolved in 20 mL of warm DMSO and was added to a stirring solution of sodium cyanide (0.408 mol) which had been dissolved in 200 mL of DMSO at 95° C. The mixture was heated at 95° C. for 1 hour, then cooled and diluted to about 800 mL with water and extracted with three 200 mL portions of ethyl ether; each organic phase was washed in turn with a 150 mL of water. The organic layers were combined and the purple solution was dried over MgSO$_4$, filtered and evaporated to yield 17.5 g of the nitrile as a pale red oil.

17.5 g (81 mmol) was dissolved in 200 mL of ethyl alcohol and the stirring mixture brought to reflux. 10 N NaOH (50 mL) was added in a slow stream. The reaction mixture was heated at 102° C., allowing alcohol to boil out and gradually replacing the alcohol with water. After 90 minutes the mixture was cooled and evaporated further to replace the last traces of alcohol. The milky aqueous mixture was extracted with two 50 mL portions of ethyl ether and these discarded. The aqueous mixture was treated with 100 mL of 6N HCl and 25 g NaCl and extracted with three 100 mL portions of ethyl acetate. The organic phases were washed brine. The extracts were combined, dried from MgSO$_4$, stirred with charcoal, filtered and evaporated to dryness. The residue was dissolved in 75 mL of warm hexanes and allowed to crystallize. The mixture was filtered to give 16.05 g of the phenyl acetic acid as beige crystals.

The amine hydrochloride (3.18 g:11.0 mmol), the phenyl acetic acid (2.3 g:10 mmol), HBTU (4.55 g:11.99 mmol) were combined in 75 mL of DMF and treated with diisopropylethylamine (5.8 mL:33.3 mmol). The stirring mixture was warmed at 50° C. for 4.5 hours. Solvent was removed in vacuo. The residue was dissolved in dichloromethane and purified by silica gel chromatography, eluting with gradient mixtures of ethyl acetate and hexanes, to produce 4.2 g of the amide as a colorless oil.

4.2 g (~9 mmol) of the amide was dissolved in 100 mL of CH$_2$Cl$_2$ and the mixture stirred at room temperature for 18 hours. The mixture was evaporated to an oil which was partitioned with CH$_2$Cl$_2$ (100 mL) and 50 mL of NaHCO$_3$ solution (saturated). The organic phase was dried over sodium sulfate, filtered and evaporated to give 4.2 g of the amine as an oil.

4.2 g (9 mmol) of the amine was combined in 10 mL of dichloromethane along with 450 mg (14 mmol) of sulfur and the mixture gently evaporated to produce a smooth paste which was heated and stirred at 155° C. for 90 minutes. The mixture was cooled and stirred with ethyl alcohol (25 mL), filtered through Celite, the filtrate evaporated to dryness and applied to a silica gel column. The column was eluted with gradient mixture of ethyl acetate and hexanes to produce 2.1 g of the isoquinoline.

200 mg (0.45 mmol) of the isoquinoline was dissolved in 4 mL of ethyl acetate, treated with SeO$_2$ (150 mg:1.35 mmol) and heated while stirring at 80° C. for 2 hours. An additional SeO$_2$ (150 mg:1.35 mmol) was added and heating continued for 2 hours. The mixture was cooled, filtered through Celite and the filtrate evaporated to give 215 mg of the ketone as a dark semi-solid.

215 mg (0.45 mmol) of the ester was dissolved in 2 mL of ethanol; 2 mL of THF was added. To the stirring mixture 2.0 mL of 1N NaOH was added and the mixture stirred at room temperature for 17 hours. The mixture was evaporated to dryness, added 2 mL of water and extracted with ethyl

Example 57

[6,7-Dimethoxy-4-(1H-tetrazol-5-ylmethyl)-isoquinolin-1-yl]-(2-fluoro-5-methoxy-phenyl)-methanone

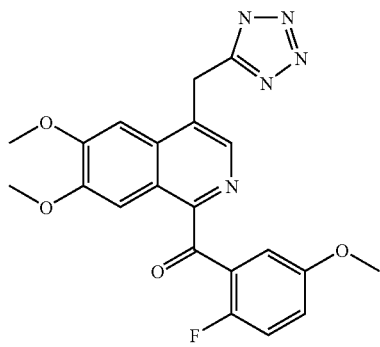

1.6 g (4.3 mmol) 4-hydroxymethyl-1-(2-fluoro-5-methoxy-benzyl)-6,7-dimethoxy-isoquinoline (intermediate in the preparation of Example 27) was dissolved in dichloromethane (50 mL) and triethylamine (0.75 mL:5.38 mmol) was added with stirring followed by the dropwise addition of methanesulfonyl chloride (0.39 mL:5.04 mmol). After 30 minutes the stirring mixture was treated with lithium chloride (110 mg:2.59 mmol) and stirring continued for 3 hours. The mixture was treated with an additional 100 mg of lithium chloride (2.35 mmol) and stirring continued for 17 hours. The reaction mixture was diluted with 50 mL of dichloromethane and washed with three 50 mL portions of brine. The organic extracts were combined and dried from sodium sulfate, filtered and the filtrate evaporated to provide the chloride as ~1.6 g of a light brown solid.

1.6 g (4.3 mmol) 4-Chloromethyl-1-(2-fluoro-5-methoxy-benzyl)-6,7-dimethoxy-isoquinoline was dissolved in 15 mL DMSO and was added with stirring to a solution of 900 mg of sodium cyanide (18.36 mmol) in 10 mL of DMSO at 95 C. Heating at 95 C. was continued for 60 minutes before being cooled and diluted with 500 ml of brine. The aqueous mixture was extracted with three 75 mL portions of dichloromethane. Each organic extract was washed again in turn with 50 ml of brine. The extracts were combined, dried from sodium sulfate filtered and evaporated to give ~1.3 g of the crude nitrile as a dark oil. The nitrile was purified by silica gel chromatography, eluting with gradient mixtures of ethyl acetate and hexanes. Appropriate cuts were combined to give 950 mg of the desired material as a brown solid.

183 mg (0.5 mmol) of [1-(2-Fluoro-5-methoxy-benzyl)-6,7-dimethoxy-isoquinolin-4-yl]-acetonitrile was dissolved in 15 mL toluene. The solution was warmed to 95 C. and 100 mg (1.53 mmol) of sodium azide and 210 mg (1.52 mmol) of triethyl amine hydrochloride was added and the mixture heated at 100 C for 60 minutes. Because ms and tlc suggest significant quantities of starting material is present an additional 100 mg of sodium azide and 210 mg of triethyl amine hydrochloride were added and heating at 100 C continued for 150 minutes at which time another 100 mg of sodium azide and 210 mg of triethyl amine hydrochloride and heating at 100 C continued for 120 minutes followed by room temperature stirring for 16 hours. The mixture was diluted with 15 mL of toluene and 20 mL of water. The stirring mixture was treated with 2 drops of conc. HCl in the fume hood and the resulting solid filtered giving ~65 mg of the tetrazole as a white solid. The aqueous phase of the filtrate was separated and treated with stirring with another 2 drops of conc. HCl and solid filtered and washed with water to provide an additional 30 mg of the tetrazole. Thin layer chromatography show both crops to be homogeneous. Spectroscopy (nmr and ms) are compatible.

Example 58

[1-(3-Benzyloxy-4-methoxy-phenyl)-2-(3-methoxy-phenyl)-ethyl]-(2,2-dimethoxy-ethyl)-carbamic acid ethyl ester

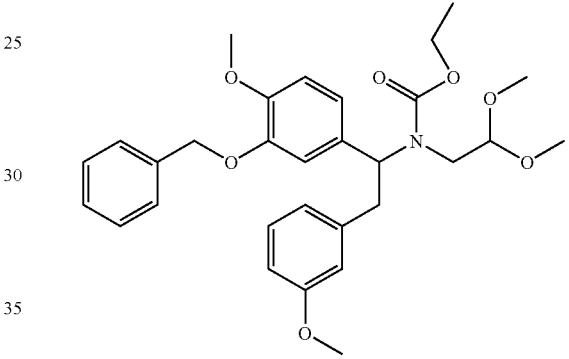

3-Benzyloxy-4-methoxybenzaldehyde (2.42 g, 10 mmol), aminoacetaldehyde dimethylacetal (1.08 g, 10 mmol), and trimethylorthoformate (2.5 mL) were mixed in 1,2-dichloroethane (10 mL) at room temperature and stirred×2 hours. The solvent was removed in vacuo to give (3-benzyloxy-4-methoxy-benzylidene)-(2,2-dimethoxy-ethyl)-amine as a viscous oil, which was dissolved in diethyl ether (10 mL).

3-Methoxybenzyl chloride (3.13 g, 20 mmol) was dissolved in 10 mL of diethyl ether and magnesium metal (0.49 g, 20.5 mmol) was added without stirring. Several crystals of iodine were added. After the reaction was initiated, stirring was begun and external cooling was applied as necessary to maintain gentle refluxing. Once the initial reaction had subsided, the mixture was refluxed×1 hour. The mixture was diluted to 40 mL with diethyl ether and cooled in an ice-bath. The etheral solution of (3-benzyloxy-4-methoxy-benzylidene)-(2,2-dimethoxy-ethyl)-amine was added dropwise to the cold solution. After the addition was complete, the resulting suspension was heated at reflux×2 hours. The mixture was cooled in an ice-bath and saturated aqueous ammonium chloride solution (20 mL) was added dropwise. The mixture was stirred at 0° C.×15 minutes and then at room temperature×1 hour. Water (20 mL) was added, and the mixture was filtered. The organic layer was separated, washed with water (1×20 mL), saturated aqueous sodium chloride solution (1×20 mL) and dried over anhydrous magnesium sulfate. The solvent was concentrated in vacuo to give a viscous oil. The oil was dissolved in tetrahydrofuran (20 mL) and water (10 mL) was added. Then potassium carbonate (2.5 g) was added at room temperature followed by dropwise addition of ethyl chloroformate (1.08 g, 10 mmol, 0.95 mL). The mixture was stirred×1 hour at room temperature. The mixture was diluted with diethyl ether (50 mL), and the organic layer was separated and dried over anhydrous magnesium sulfate. The solvent was concentrated in vacuo. The resulting viscous oil was used purified by silica gel chromatography (25% to 35% ethyl acetate in hexanes to give [1-(3-Benzyloxy-4-methoxy-phenyl)-2-(3-methoxy-phenyl)-ethyl]-(2,2-dimethoxy-ethyl)-carbamic acid ethyl ester (4.51 g, 8.6 mmol, 86%) as pale yellow viscous oil.

Example 59

7-Benzyloxy-6-methoxy-1-(3-methoxy-benzyl)-1H-isoquinoline-2-carboxylic acid ethyl ester

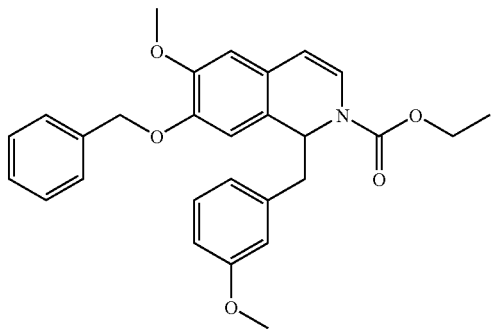

[1-(3-Benzyloxy-4-methoxy-phenyl)-2-(3-methoxy-phenyl)-ethyl]-(2,2-dimethoxy-ethyl)-carbamic acid ethyl ester (3.15 g, 6.01 mmol) was dissolved in acetone (125 mL) at 0° C., and 6M aqueous hydrochloric acid (25 mL) was added dropwise. After the addition was complete, the mixture was stored at 0° C. overnight (14 hours). The mixture was warmed to room temperature and stirred×4 hours. The mixture was cooled in an ice bath and diluted with water (150 mL). The mixture was extracted with ethyl acetate (3×60 mL). The combined organic extracts were washed with water (60 mL), saturated aqueous sodium chloride solution (60 mL) and dried over anhydrous magnesium sulfate. Concentration of the solvent gave an oily solid that was crystallized from ethyl acetate/hexanes to give 7-benzyloxy-6-methoxy-1-(3-methoxy-benzyl)-1H-isoquinoline-2-carboxylic acid ethyl ester (1.32 g, 2.87 mmol, 48%) as a white solid.

Example 60

7-Benzyloxy-6-methoxy-1-(3-methoxy-benzyl)-isoquinoline-4-carbaldehyde

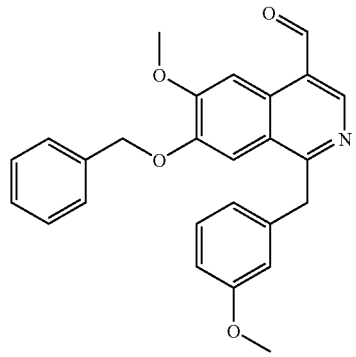

To N,N-dimethylformamide (0.36 mL) at 0° C. was added phosphorous oxychloride (0.84 mL, 0.80 g, 10.9 mmol.) dropwise. The mixture was warmed to room temperature and stirred×30 minutes. The mixture was recooled in an ice-bath, and 7-benzyloxy-6-methoxy-1-(3-methoxy-benzyl)-1H-isoquinoline-2-carboxylic acid ethyl ester (2.15 g, 2.11 mmol) in N,N-dimethylformamide (5 mL) was added dropwise. After addition was complete, the mixture was heated on an oil bath×2 hours at 60° C. The mixture was cooled, poured into water (50 mL) and extracted with ethyl acetate (3×20 mL). The combined organic extracts were washed with water (3×20 mL), saturated aqueous sodium chloride solution (1×20 mL) and dried over anhydrous magnesium sulfate. Concentration of the solvent in vacuo gave a viscous oil that was dissolved methanol (20 mL), and a solution of powdered potassium hydroxide (0.63 g, 10.5 mmol) in methanol (5 mL) was added dropwise. The mixture was stirred overnight (14 hours) at room temperature. The mixture was poured into water (100 mL) and extracted with diethyl ether (3×30 mL). The combined organic extracts were washed with water (30 mL), saturated aqueous sodium chloride solution (30 mL) and dried over anhydrous magnesium sulfate. Concentration gave an orange foam that was dissolved in dichloromethane (100 mL), and maganese (IV) oxide (3 g, 34.8 mmol.) was added in one portion. The mixture was stirred at room temperature×2 hours. Silica gel (5 g) was added to the mixture. The mixture was filtered through a silica gel pad. The silica gel pad was washed with 50% ethyl acetate in hexanes (200 mL). Concentration of the combined filtrates and precipitation from ethyl acetate with hexanes gave 7-benzyloxy-6-methoxy-1-(3-methoxy-benzyl)-isoquinoline-4-carbaldehyde (1.00 g, 2.42 mmol, 53%) as a yellow solid.

Example 61

7-Hydroxy-6-methoxy-1-(3-methoxy-benzyl)-isoquinoline-4-carbaldehyde

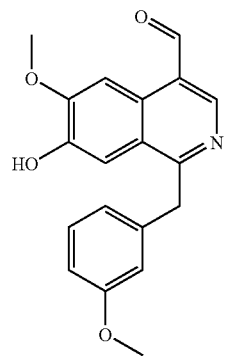

10% Palladium on carbon (500 mg) was added the mixture was stirred under hydrogen (balloon) for 16 hours. The excess hydrogen was evaculated from the reaction vessel, and the mixture was filtered through a pad of celite. The filtrate was concentrated in vacuo, and the residue was dissolved in dichloromethane (100 mL) and maganese (IV) oxide (3.00 g, 34.8 mmol) was added in one portion. The mixture was stirred at room temperature×30 minutes, and then the mixture was filtered through a pad of celite. Concentration of the solvent gave a solid that was dissolved in ethyl acetate and precipitated with hexanes to give 7-hydroxy-6-methoxy-1-(3-methoxy-benzyl)-isoquinoline-4-carbaldehyde as a yellow solid (323 mg, 1.00 mmol, 22%).

Example 62

7-Benzyloxy-6-methoxy-1-(3-methoxy-benzoyl)-isoquinoline-4-carboxylic acid

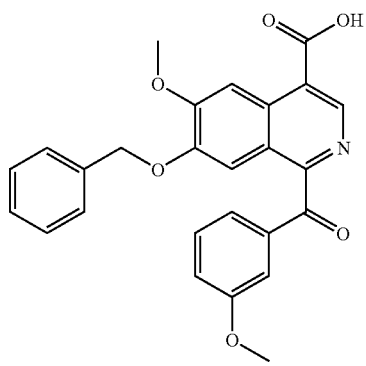

7-Hydroxy-6-methoxy-1-(3-methoxy-benzyl)-isoquinoline-4-carbaldehyde (53 mg, 0.13 mmol) was dissolved in ethyl acetate (5 mL). Selenium (IV) oxide (29 mg, 0.26 mmol) was added, and the mixture was heated at reflux×1 hour. The mixture was cooled and applied to a silica gel column. The column was eluted with 27% ethyl acetate in hexanes to give a yellow solid (46 mg). The solid, sodium chlorite (43 mg, 0.47 mmol), sodium dihydrogenphosphate hydrate (44 mg (0.32 mmol), and 2-methyl-2-butene (0.5 mL) were combined in a mixture of t-butyl alcohol and water (5:1)(2 mL). The mixture was stirred at room temperature×4 hours. The mixture was partitioned between dichloromethane (10 mL) and saturated aqueous sodium chloride solution (10 mL). The organic layer was separated, and the aqueous layer was extracted with dichloromethane (3×10 mL). The combined organic layers were dried over anhydrous magnesium sulfate. The solvent was concentrated in vacuo to give a solid that was recrystallized from ethyl acetate to give 7-benzyloxy-6-methoxy-1-(3-methoxy-benzoyl)-isoquinoline-4-carboxylic acid (12 mg, 0.027 mmol, 21%) as a yellow solid.

HR-EI m/e calcd for $C_{26}H_{21}NO_6$: $(M)^+$ 443.1368, found 443.1369.

Example 63

7-Butoxy-6-methoxy-1-(3-methoxy-benzoyl)-isoquinoline-4-carboxylic acid

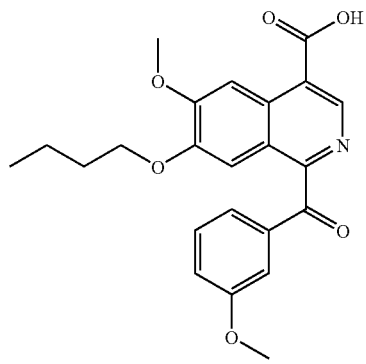

n-Butyl iodide (175 mg, 0.95 mmol), 7-hydroxy-6-methoxy-1-(3-methoxy-benzyl)-isoquinoline-4-carbaldehyde (60 mg, 0.19 mmol), and anhydrous potassium carbonate (262 mg, 1.9 mmol) were combined in anhydrous N,N-dimethylformamide (2 mL) and heated on an oil bath at 80° C. The mixture was cooled and poured into water (20 mL). The mixture was extracted with ethyl acetate (3×30 mL). The combined organic extracts were washed with water (3×30 mL), saturated aqueous sodium chloride solution (30 mL), and dried over anhydrous magnesium sulfate. The solvent was removed in vacuo, and the residue was dissolved in ethyl acetate (5 mL). Selenium (IV) oxide (50 mg, 0.45 mmol) was added and the mixture was heated at reflux×1 hour. The mixture was cooled and applied to a silica gel column. The column was eluted with 25% ethyl acetate in hexanes to give a yellow solid (66 mg). The solid, sodium chlorite (43 mg, 0.47 mmol), sodium dihydrogenphosphate hydrate (44 mg, 0.32 mmol), and 2-methyl-2-butene (0.5 mL) were combined in a mixture of acetonitrile, t-butyl alcohol, and water (3:1:1)(5 mL). The mixture was stirred at room temperature×20 hours. The mixture was partitioned between dichloromethane (10 mL) and saturated aqueous sodium chloride solution (10 mL). The organic layer was separated, and the aqueous layer was extracted with dichloromethane (3×10 mL). The combined organic layers were dried over anhydrous magnesium sulfate. The solvent was concentrated in vacuo to give a solid that was recrystallized from ethyl acetate to give 7-butoxy-6-methoxy-1-(3-methoxy-benzoyl)-isoquinoline-4-carboxylic acid (32 mg, 0.078 mmol, 41%) as a yellow solid.

$ES^+$-HRMS m/e calcd for $C_{23}H_{23}NO_6$: $(M-H)^+$ 408.1442, found 408.1445.

Example 64

7-(2-Hydroxy-ethoxy)-6-methoxy-1-(3-methoxy-benzoyl)-isoquinoline-4-carboxylic acid

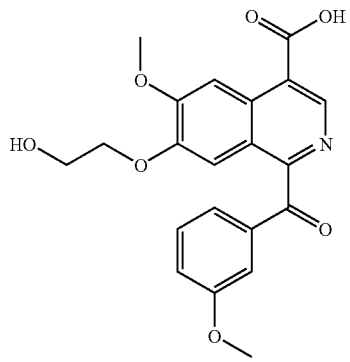

2-Bromoethanol (129 mg, 1 mmol), 7-hydroxy-6-methoxy-1-(3-methoxy-benzyl)-isoquinoline-4-carbaldehyde (60 mg, 0.19 mmol), and anhydrous potassium carbonate (138 mg, 1 mmol) were combined in anhydrous N,N-dimethylformamide (1 mL) and heated on an oil bath at 80° C. The mixture was cooled and poured into water (20 mL). The mixture was extracted with ethyl acetate (3×30 mL). The combined organic extracts were washed with water (3×30 mL), saturated aqueous sodium chloride solution (30 mL), and dried over anhydrous magnesium sulfate. The solvent was removed in vacuo, and the residue was dissolved in ethyl acetate (10 mL). Selenium (IV) oxide (50 mg, 0.45 mmol) was added, and the mixture was heated at reflux×1 hour. The mixture was cooled and applied to a silica gel column. The column was eluted with 80% ethyl acetate in hexanes to give a yellow solid (43 mg). The solid, sodium chlorite (43 mg, 0.47 mmol), sodium dihydrogenphosphate hydrate (44 mg, 0.32 mmol) and 2-methyl-2-butene (0.5 mL) were combined in a mixture of acetonitrile, t-butylalcohol, and water (3:1:1) (2.5 mL). The mixture was stirred at room temperature×16 hours. The mixture was partitioned between dichloromethane (10 mL) and saturated aqueous sodium chloride solution (10 mL). The organic layer was separated, and the aqueous layer was extracted with dichloromethane (3×10 mL). The combined organic layers were dried over anhydrous magnesium sulfate. The solvent was concentrated in vacuo to give a solid that was recrystallized from ethyl acetate to give 7-(2-hydroxy-ethoxy)-6-methoxy-1-(3-methoxy-benzoyl)-isoquinoline-4-carboxylic acid (21 mg, 0.052 mmol, 28%) as an orange solid.

HR-EI m/e calcd for $C_{21}H_{19}NO_7$: $(M)^+$ 397.1161, found 397.1162.

Example 65

7-Carbamoylmethoxy-6-methoxy-1-(3-methoxy-benzoyl)-isoquinoline-4-carboxylic acid

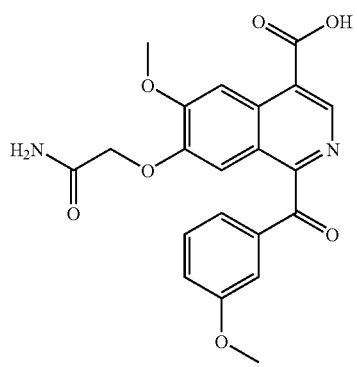

2-Chloroacetamide (93 mg, 1 mmol), 7-hydroxy-6-methoxy-1-(3-methoxy-benzyl)-isoquinoline-4-carbaldehyde (60 mg, 0.19 mmol), and anhydrous potassium carbonate (276 mg, 2 mmol) were combined in anhydrous N,N-dimethylformamide (2 mL) and heated on an oil bath at 80° C.×16 hours. The mixture was cooled and poured into water (20 mL). The mixture was extracted with ethyl acetate (3×30 mL). The combined organic extracts were washed with water (3×30 mL), saturated aqueous sodium chloride solution (30 mL), and dried over anhydrous magnesium sulfate. The solvent was removed in vacuo, and the residue was dissolved in ethyl acetate (10 mL). Selenium (IV) oxide (42 mg, 0.38 mmol) was added and the mixture was heated at reflux×1 hour. The mixture was cooled and applied to a silica gel column. The column was eluted with ethyl acetate in hexanes to give a yellow solid (23 mg). The solid, sodium chlorite (43 mg, 0.47 mmol), sodium dihydrogenphosphate hydrate (44 mg, 0.32 mmol), and 2-methyl-2-butene (0.5 mL) were combined in a mixture of acetonitrile, t-butylalcohol, and water (3:1:1)(2.5 mL). The mixture was stirred at room temperature×4 days. The mixture was partitioned between dichloromethane (10 mL) and saturated aqueous sodium chloride solution (10 mL). The organic layer was separated, and the aqueous layer was extracted with dichloromethane (3×10 mL). The combined organic layers were dried over anhydrous magnesium sulfate. The solvent was concentrated in vacuo to give a solid that was triturated with hot ethyl acetate to give 7-carbamoylmethoxy-6-methoxy-1-(3-methoxy-benzoyl)-isoquinoline-4-carboxylic acid as an off-white solid (13 mg, 0.032 mmol, 17%).

$ES^+$-HRMS m/e calcd for $C_{21}H_{18}N_2O_7$: $(M+H)^+$ 411.1187, found 411.1182

Example 66

6-Methoxy-1-(3-methoxy-benzoyl)-7-(2-pyrrolidin-1-yl-ethoxy)-isoquinoline-4-carboxylic acid hydrochloride

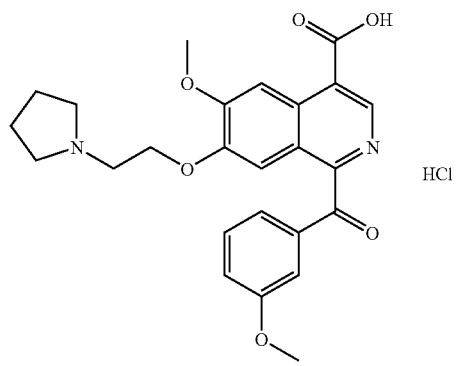

1,2-Dibromoethane (376 mg, 2 mmol), 7-hydroxy-6-methoxy-1-(3-methoxy-benzyl)-isoquinoline-4-carbaldehyde (120 mg, 0.37 mmol), and anhydrous potassium carbonate (276 mg, 2 mmol) were combined in anhydrous N,N-dimethylformamide (2 mL) and heated on an oil bath at 80° C. The mixture was cooled and poured into water (20 mL). The mixture was extracted with ethyl acetate (3×30 mL). The combined organic extracts were washed with water (3×30 mL), saturated aqueous sodium chloride solution (30 mL), and dried over anhydrous magnesium sulfate. The solvent was removed in vacuo, and the residue was dissolved in ethyl acetate (10 mL). Selenium (IV) oxide (81 mg, 0.74 mmol) was added and the mixture was heated at reflux×1 hour. The mixture was cooled and applied to a silica gel column. The column was eluted with 40% ethyl acetate in hexanes to give a yellow solid (92 mg). The solid (50 mg, 0.11 mmol) and pyrrolidine (17 mg, 0.24 mmol) were combined in N,N-dimethylformamide (1 mL) and heated on an oil bath at 85 C×30 minutes. The mixture was cooled, poured into dilute sodium hydroxide solution (20 mL) and extracted with ethyl acetate (3×20 mL). The combined organic extracts were washed with water (2×20 mL), saturated aqueous sodium chloride solution (1×20 mL) and dried over anhydrous magnesium sulfate. Concentration of the solvent gave 60 mg of a brownish/orange oil. The oil, sodium chlorite (43 mg, 0.47 mmol), sodium dihydrogenphosphate hydrate (44 mg, 0.32 mmol), and 2-methyl-2-butene (0.5 mL) were combined in a mixture of acetonitrile, t-butyl alcohol, and water (3:1:1)(2.5 mL). The mixture was stirred at room temperature×16 hours. The mixture was partitioned between dichloromethane (10 mL) and saturated aqueous sodium chloride solution (10 mL). The organic layer was separated, and the aqueous layer was extracted with dichloromethane (3×10 mL). The combined organic layers were dried over anhydrous magnesium sulfate. Concentration gave an oil that was dissolved in methanolic hydrogen chloride solution. The volatiles were removed and the residue was triturated with a mixture of toluene, methanol, and diethyl ether to give 6-methoxy-1-(3-methoxy-benzoyl)-7-(2-pyrrolidin-1-yl-ethoxy)-isoquinoline-4-carboxylic acid hydrochloride as an orange precipitate (17 mg, 0.034 mmol, 18%)

ES$^+$-HRMS m/e calcd for $C_{25}H_{26}N_2O_6$: (M+H)$^+$ 451.1864, found 451.1861

Example 67

6-Benzyloxy-7-methoxy-1-(3-methoxy-benzoyl)-isoquinoline-4-carboxylic acid

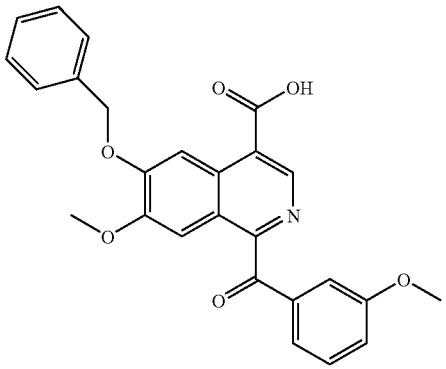

4-Benzyloxy-3-methoxybenzyladehyde (4.84 g, 20 mmol), aminoacetaldehyde dimethylacetal (1.48 mL, 20 mmol) and trimethylorthoformate (4 mL) were mixed in 1,2-dichloroethane (20 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Methoxybenzylchloride (7.26 mL, 50 mmol) was dissolved in diethyl ether (50 mL) and magnesium metal (1.28 g, 52.5 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (6.58 g, 20 mmol) in diethyl ether (30 mL) was added dropwise (a precipitate forms with each drop). After addition was complete, the resulting suspension was heated at reflux for 2 hours. The mixture was cooled in an ice-bath and saturated ammonium chloride solution (50 mL) was carefully added dropwise. The mixture was stirred at 0° C. for 15 minutes and then room temperature for 1 h. Water (50 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-methoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-methoxy-phenyl)-ethyl]-(2,2-dimethoxy-ethyl)-amine (10.46 g, 20 mmol) in tetrahydrofuran (40 mL) and water (20 mL) was added potassium carbonate (5 g, 36 mmol) and ethyl chloroformate (1.91 mL, 20 mmol) dropwise. The mixture was stirred for 1 h at room temperature. The mixture was diluted with diethyl ether (100 mL), and the organic layer was separated. The aqueous phase was extracted with ethyl acetate (3×100 mL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-methoxy-phenyl)-2-phenyl-ethyl]-(2,2-dimethoxy-ethyl)-carbamic acid ethyl ester (7 g, 67% yield in three steps) as a colorless oil.

To a stirred solution of [1-(4-benzyloxy-3-methoxy-phenyl)-2-phenyl-ethyl]-(2,2-dimethoxy-ethyl)-carbamic acid ethyl ester (100 mg, 0.19 mmol) in acetone (5 mL) was added 6N hydrochloric acid (1 mL) at 0° C. The reaction mixture was stirred at room temperature for 18 hrs and neutralized by addition of 6N aqueous sodium hydroxide solution. The solvent was evaporated and the aqueous phase was extracted with dichloromethane (3×25 μL). The combined extracts were washed with saturated aqueous sodium chloride solution (10 mL), dried over anhydrous magnesium sulfate, filtered and concentrated in vacuo. Flash chromatography (Merck Silica gel 60, 70–230 mesh, 50% ethyl acetate/hexane) afforded 6-benzyloxy-7-methoxy-1-(3-methoxy-benzyl)-1H-isoquinoline-2-carboxylic acid ethyl ester (60 g, 85% yield) as a colorless oil.

To anhydrous N,N-dimethylformamide (0.078 mL, 1.02 mmol) at 0° C. was added phosphorus oxychloride (0.042 mL, 0.44 mmol) dropwise. The mixture was warmed to room temperature and stirred for 30 minutes. The mixture was cooled in an ice-bath, and 6-benzyloxy-7-methoxy-1-(3-methoxy-benzyl)-1H-isoquinoline-2-carboxylic acid ethyl ester (156 mg, 0.34 mmol) in dichloromethane (3 mL) was added dropwise. After addition was complete, the mixture was heated on an oil bath for 4 hrs at 80° C. The mixture was cooled to 0° C. and a solution of potassium acetate (154 mg, 1.56 mmol) in water (2 mL) was added slowly. The mixture was then heated at 80° C. for 20 minutes. The mixture was cooled, poured into water and diluted with dichloromethane (60 mL). The organic layer was washed water (2×20 mL), saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 20% ethyl acetate/hexane,) afforded 6-benzyloxy-4-formyl-7-methoxy-1-(3-methoxy-benzyl)-1H-isoquinoline-2-carboxylic acid ethyl ester as a colorless oil (85 mg, 52% yield).

To a solution of 6-benzyloxy-4-formyl-7-methoxy-1-(3-methoxy-benzyl)-1H-isoquinoline-2-carboxylic acid ethyl ester (85 mg, 0.17 mmol) in methanol (3 mL) was added powdered potassium hydroxide (97.7 mg, 1.75 mmol) at room temperature. The mixture was stirred at room temperature for 14 hrs. The solvent was evaporated and the residue was diluted with water (20 mL). The aqueous phase was extracted with ethyl acetate (2×20 mL). The combined extracts were washed with saturated aqueous sodium chloride solution (20 mL), dried over anhydrous magnesium sulfate, filtered and concentrated in vacuo to afford a crude oil. Flash chromatography (Merck Silica gel 60, 70–230 mesh, 50% ethyl acetate/hexane, 75% ethyl acetate/hexane, ethyl acetate) afforded 6-benzyloxy-7-methoxy-1-(3-methoxy-benzyl)-isoquinoline-4-carbaldehyde as a colorless oil (30 mg, 42% yield).

To a stirred solution of 6-benzyloxy-7-methoxy-1-(3-methoxy-benzyl)-isoquinoline-4-carbaldehyde (90 mg, 0.22 mmol) in acetic acid (3 mL) was added selenium dioxide (120 mg, 1.08 mmol). The reaction mixture was heated at 120° C. for 1 hr. The solvent was evaporated and the residue was diluted with dichloromethane (30 mL). The organic layer was washed with saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 6-benzyloxy-7-methoxy-1-(3-methoxy-benzoyl)-isoquinoline-4-carbaldehyde as a yellow solid (50 mg, 57% yield).

To a stirred solution of 6-benzyloxy-7-methoxy-1-(3-methoxy-benzoyl)-isoquinoline-4-carbaldehyde (55 mg, 0.13 mmol) in t-butanol (2 mL) and water (2 mL) solution was added sodium dihydrogenphosphate monohydrate (71.1 mg, 0.52 mmol), 2-methyl-2-butene (0.087 mL, 0.77 mmol) and sodium chlorite (69.9 mg, 0.77 mmol) at room temperature. The reaction suspension was then stirred at room temperature for 14 hrs. The resulting two-phase mixture was partitioned between dichloromethane and water and acidified to pH=3 by addition of acetic acid. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in methanol to afford 6-Benzyloxy-7-methoxy-1-(3-methoxy-benzoyl)-isoquinoline-4-carboxylic acid (35 mg, 62% yield) as a light yellow solid. HR-MS m/e calcd for $C_{26}H_{21}N_1O_6$ (M–H$^+$) 444.1442, found 444.1442; $^1$H NMR (300 MHz) compatible.

Example 68

6-Butoxy-7-methoxy-1-(3-methoxy-benzoyl)-isoquinoline-4-carboxylic acid

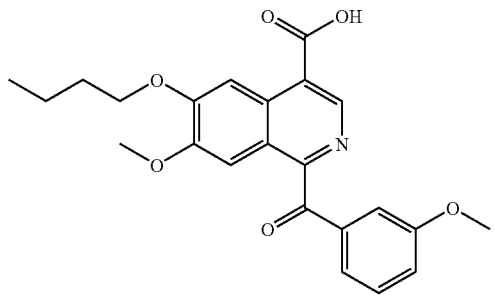

4-Benzyloxy-3-methoxybenzyladehyde (4.84 g, 20 mmol), aminoacetaldehyde dimethylacetal (1.48 mL, 20 mmol) and trimethylorthoformate (4 mL) were mixed in 1,2-dichloroethane (20 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Methoxybenzylchloride (7.26 mL, 50 mmol) was dissolved in diethyl ether (50 mL) and magnesium metal (1.28 g, 52.5 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (6.58 g, 20 mmol) in diethyl ether (30 mL) was added dropwise (a precipitate forms with each drop). After addition was complete, the resulting suspension was heated at reflux for 2 hours. The mixture was cooled in an ice-bath and saturated ammonium chloride solution (50 mL) was carefully added dropwise. The mixture was stirred at 0° C. for 15 minutes and then room temperature for 1 h. Water (50 mL) was added, and the mixture was filtered. The organic layer was separated, washed with water (50 mL), saturated sodium chloride solution (40 mL), dried over magnesium sulfate, filtered and concentrated in vacuo to afford [1-(4-benzyloxy-3-methoxy-phenyl)-2-(3-methoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-methoxy-phenyl)-ethyl]-(2,2-dimethoxy-ethyl)-amine (10.46 g, 20 mmol) in tetrahydrofuran (40 mL) and water (20 mL) was added potassium carbonate (5 g, 36 mmol) and ethyl chloroformate (1.91 mL, 20 mmol) dropwise. The mixture was stirred for 1 h at room temperature. The mixture was diluted with diethyl ether (100 mL), and the organic layer was separated. The aqueous phase was extracted with ethyl acetate (3×100 mL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-methoxy-phenyl)-2-phenyl-ethyl]-(2,2-dimethoxy-ethyl)-carbamic acid ethyl ester (7 g, 67% yield in three steps) as a colorless oil.

To a stirred solution of [1-(4-benzyloxy-3-methoxy-phenyl)-2-phenyl-ethyl]-(2,2-dimethoxy-ethyl)-carbamic acid ethyl ester (10.5 g, 20 nmol) in ethyl acetate (100 mL) and ethanol (50 mL) was added 10% palladium on activated carbon (2 g). The mixture was hydrogenated at 1 atm for 15 hrs. The solution was filtered through a Celite® plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (4.87 g, 56% yield).

To a stirred solution of (2,2-dimethoxy-ethyl)-[1-(4-hydroxy-3-methoxy-phenyl)-2-(3-methoxy-phenyl)-ethyl-carbamic acid ethyl ester (3.7 g, 8.55 mmol) in acetone (150 mL) was added 6N hydrochloric acid (38 mL) at 0° C. The reaction mixture was stirred at room temperature for 15 hrs. The mixture was diluted with water. The solvent was evaporated and the aqueous layer was extracted with ethyl acetate (3×100 mL). The combined extracts were washed with saturated aqueous sodium chloride solution (80 mL), dried over anhydrous magnesium sulfate, filtered and concentrated in vacuo. Flash chromatography (Merck Silica gel 60, 70–230 mesh, 50% ethyl acetate/hexane) afforded 6-hydroxy-7-methoxy-1-(3-methoxy-benzyl)-1H-isoquinoline-2-carboxylic acid ethyl ester (1.17, 37% yield) as a colorless oil.

To a stirred solution of 6-hydroxy-7-methoxy-1-(3-methoxy-benzyl)-1H-isoquinoline-2-carboxylic acid ethyl ester (840 mg, 2.28 mmol) in anhydrous N,N-dimethylformamide (25 mL) was added potassium carbonate (1.89 g, 13.6 mmol) and butyl iodide (0.78 mL, 6.83 mmol) dropwise. The reaction mixture was heated with stirring at 85° C. for 18 hrs. The solvent was evaporated and the residue was diluted with ethyl acetate (50 mL) and water (50 mL). The aqueous phase was extracted with ethyl acetate (3×50 mL). The combined extracts were washed with saturated aqueous sodium chloride solution (50 mL), dried over anhydrous magnesium sulfate, filtered and concentrated in vacuo. Flash chromatography (Merck Silica gel 60, 70–230 mesh, 20% ethyl acetate/hexane) afforded 6-Butoxy-7-methoxy-1-(3-methoxy-benzyl)-1H-isoquinoline-2-carboxylic acid ethyl ester (560 mg, 56% yield) as a colorless oil.

To anhydrous N,N-dimethylformamide (0.102 mL, 1.32 mmol) at 0° C. was added phosphorus oxychloride (0.053 mL, 0.58 mmol) dropwise. The mixture was warmed to room temperature and stirred for 30 minutes. The mixture was cooled in an ice-bath, 6-butoxy-7-methoxy-1-(3-methoxy-benzyl)-1H-isoquinoline-2-carboxylic acid ethyl ester (230 mg, 0.53 mmol) in dichloromethane (3 mL) was added dropwise. After addition was complete, the mixture was heated on an oil bath for 4 hrs at 80° C. The mixture was cooled to 0° C. and a solution of potassium acetate (154 mg, 1.56 mmol) in water (2 mL) was added slowly. The mixture was then heated at 80° C. for 20 minutes. The mixture was cooled, poured into water and diluted with dichloromethane (60 mL). The organic layer was washed water (2×20 mL), saturated aqueous sodium bicarbonate solution (20 mL), saturated aqueous sodium chloride solution (20 mL), dried over anhydrous magnesium sulfate, filtered and concentrated in vacuo to afford 6-butoxy-4-formyl-7-methoxy-1-(3-methoxy-benzyl)-1H-isoquinoline-2-carboxylic acid ethyl ester (243 mg, 99% yield) as a yellow oil. The crude product was used without further purification.

To a stirred solution of 6-butoxy-4-formyl-7-methoxy-1-(3-methoxy-benzyl)-1H-isoquinoline-2-carboxylic acid ethyl ester (286 mg, 0.60 mmol) in methanol (12 mL) was added powdered potassium hydroxide (341 mg, 6.08 mmol). The reaction mixture was stirred at room temperature for 15 hrs. The solvent was evaporated and the residue was diluted with ethyl acetate (20 mL) and water (20 mL). The aqueous phase was extracted with ethyl acetate (3×20 mL). The combined extracts were washed with saturated aqueous sodium chloride solution (20 mL), dried over anhydrous magnesium sulfate, filtered and concentrated in vacuo to afford 6-butoxy-7-methoxy-1-(3-methoxy-benzyl)-1,2-dihydro-isoquinoline-4-carbaldehyde (200 mg, 87% yield) as a yellow oil. The crude product was used without further purification.

To a stirred solution of 6-butoxy-7-methoxy-1-(3-methoxy-benzyl)-1,2-dihydro-isoquinoline-4-carbaldehyde (200 mg, 0.53 mmol) in chloroform (6 mL) was added manganese (IV) oxide (536 mg, 5.34 mmol). The reaction mixture was stirred at room temperature for 15 hrs, filtered through a Celite® pad, and washed with chloroform. The filtrate was concentrated in vacuo to afford 6-butoxy-7-methoxy-1-(3-methoxy-benzyl)-isoquinoline-4-carbaldehyde (200 mg, 99% yield). The crude product was without further purification.

To a stirred solution of 6-butoxy-7-methoxy-1-(3-methoxy-benzyl)-isoquinoline-4-carbaldehyde (200 mg, 0.53 mmol) in acetic acid (5 mL) was added selenium dioxide (175 mg, 1.58 mmol). The reaction mixture was heated at 120° C. for 1 h. The solvent was evaporated and the residue was diluted with dichloromethane (30 mL). The organic layer was washed with saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 6-butoxy-7-methoxy-1-(3-methoxy-benzoyl)-isoquinoline-4-carbaldehyde as a yellow solid (131 mg, 63% yield).

To a stirred solution of afforded 6-butoxy-7-methoxy-1-(3-methoxy-benzoyl)-isoquinoline-4-carbaldehyde (131 mg, 0.33 mmol) in t-butanol (2 mL) and water (2 mL) solution was added sodium dihydrogenphosphate monohydrate (184 mg, 1.33 mmol), 2-methyl-2-butene (0.226 mL, 2.00 mmol) and sodium chlorite (181 mg, 2.00 mmol) at room temperature. The reaction suspension was then stirred at room temperature for 14 hrs. The resulting two-phase mixture was partitioned between dichlormethane and water and acidified to pH=3 by addition of acetic acid. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in ethyl acetate and hexane to afford 6-butoxy-7-methoxy-1-(3-methoxy-benzoyl)-isoquinoline-4-carboxylic acid (35 mg, 62% yield) as a light yellow solid. HR-MS m/e calcd for $C_{26}H_{21}N_1O_6$ (M–H$^+$) 444.1442, found 444.1442; $^1$H NMR (300 MHz) compatible.

Example 69

6-Cyclopentyloxy-7-methoxy-1-(3-methoxy-benzoyl)-isoquinoline-4-carboxylic acid

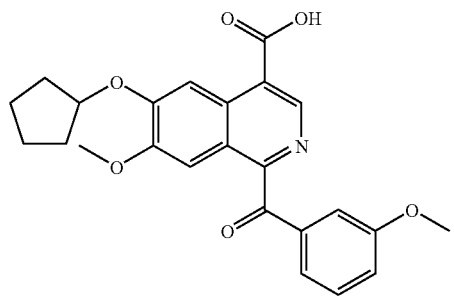

4-Benzyloxy-3-methoxybenzyladehyde (4.84 g, 20 mmol), aminoacetaldehyde dimethylacetal (1.48 mL, 20 mmol) and trimethylorthoformate (4 mL) were mixed in 1,2-dichloroethane (20 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Methoxybenzylchloride (7.26 mL, 50 mmol) was dissolved in diethyl ether (50 mL) and magnesium metal (1.28 g, 52.5 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (6.58 g, 20 mmol) in diethyl ether (30 mL) was added dropwise (a precipitate forms with each drop). After addition was complete, the resulting suspension was heated at reflux for 2 hours. The mixture was cooled in an ice-bath and saturated ammonium chloride solution (50 mL) was carefully added dropwise. The mixture was stirred at 0° C. for 15 minutes and then room temperature for 1 h. Water (50 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-methoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-methoxy-phenyl)-ethyl]-(2,2-dimethoxy-ethyl)-amine (10.46 g, 20 mmol) in tetrahydrofuran (40 mL) and water (20 mL) was added potassium carbonate (5 g, 36 mmol) and ethyl chloroformate (1.91 mL, 20 mmol) dropwise. The mixture was stirred for 1 h at room temperature. The mixture was diluted with diethyl ether (100 mL), and the organic layer was separated. The aqueous phase was extracted with ethyl acetate (3×100 mL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-methoxy-phenyl)-2-phenyl-ethyl]-(2,2-dimethoxy-ethyl)-carbamic acid ethyl ester (7 g, 67% yield in three steps) as a colorless oil.

To a stirred solution of [1-(4-benzyloxy-3-methoxy-phenyl)-2-phenyl-ethyl]-(2,2-dimethoxy-ethyl)-carbamic acid ethyl ester (10.5 g, 20 mmol) in ethyl acetate (100 mL) and ethanol (50 mL) was added 10% palladium on activated carbon (2 g). The mixture was hydrogenated at 1 atm for 15 hrs. The solution was filtered through a Celite plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (4.87 g, 56% yield)

To a stirred solution of (2,2-dimethoxy-ethyl)-[1-(4-hydroxy-3-methoxy-phenyl-2-(3-methoxy-phenyl)-ethyl-carbamic acid ethyl ester (3.7 g, 8.55 mmol) in acetone (150 mL) was added 6N hydrochloric acid (38 mL) at 0° C. The reaction mixture was stirred at room temperature for 15 hrs. The mixture was diluted with water. The solvent was evaporated and the aqueous layer was extracted with ethyl acetate (3×100 mL). The combined extracts were washed with saturated aqueous sodium chloride solution (80 mL), dried over anhydrous magnesium sulfate, filtered and concentrated in vacuo. Flash chromatography (Merck Silica gel 60, 70–230 mesh, 50% ethyl acetate/hexane) afforded 6-hydroxy-7-methoxy-1-(3-methoxy-benzyl)-1H-isoquinoline-2-carboxylic acid ethyl ester (1.17, 37% yield) as a colorless oil.

To a stirred solution of 6-hydroxy-7-methoxy-1-(3-methoxy-benzyl)-1H-isoquinoline-2-carboxylic acid ethyl ester (890 mg, 2.41 mmol) in anhydrous N,N-dimethylformamide (25 mL) was added potassium carbonate (2.0 g, 14.5 mmol) and cyclopentyl iodide (0.84 mL, 7.24 mmol) dropwise. The reaction mixture was heated with stirring at 85° C. for 18 h. The solvent was evaporated and the residue was diluted with ethyl acetate (50 mL) and water (50 mL). The aqueous phase was extracted with ethyl acetate (3×50 mL). The combined extracts were washed with saturated aqueous sodium chloride solution (50 mL), dried over anhydrous magnesium sulfate, filtered and concentrated in vacuo. Flash chromatography (Merck Silica gel 60, 70–230 mesh, 20% ethyl acetate/hexane) afforded 6-cyclopentyloxy-7-methoxy-1-(3-methoxy-benzyl)-1H-isoquinoline-2-carboxylic acid ethyl ester (350 mg, 32% yield) as a colorless oil.

To anhydrous N,N-dimethylformamide (0.151 mL, 1.95 mmol) at 0° C. was added phosphorus oxychloride (0.079 mL, 0.85 mmol) dropwise. The mixture was warmed to room temperature and stirred for 30 minutes. The mixture was cooled in an ice-bath, 6-cyclopentyloxy-7-methoxy-1-(3-methoxy-benzyl)-1H-isoquinoline-2-carboxylic acid ethyl ester (350 mg, 0.78 mmol) in dichloromethane (2 mL) was added dropwise. After addition was complete, the mixture was heated on an oil bath for 4 hrs at 80° C. The mixture was cooled to 0° C. and a solution of potassium acetate (228 mg, 2.32 mmol) in water (2 mL) was added slowly. The mixture was then heated at 80° C. for 20 minutes. The mixture was cooled, poured into water and diluted with dichloromethane (60 mL). The organic layer was washed water (2×20 mL), saturated aqueous sodium bicarbonate solution (20 mL), saturated aqueous sodium chloride solution (20 mL), dried over anhydrous magnesium sulfate, filtered and concentrated in vacuo to afford 6-cyclopentyloxy-4-formyl-7-methoxy-1-(3-methoxy-benzyl)-1H-isoquinoline-2-carboxylic acid ethyl ester (386 mg, 99% yield) as a yellow oil. The crude product was used without further purification.

To a stirred solution of 6-cyclopentyloxy-4-formyl-7-methoxy-1-(3-methoxy-benzyl)-1H-isoquinoline-2-carboxylic acid ethyl ester (386 mg, 0.83 mmol) in methanol (15 mL) was added powdered potassium hydroxide (465 mg, 8.30 mmol). The reaction mixture was stirred at room temperature for 15 hrs. The solvent was evaporated and the residue was diluted with ethyl acetate (20 mL) and water (20 mL). The aqueous phase was extracted with ethyl acetate (3×20 mL). The combined extracts were washed with saturated aqueous sodium chloride solution (20 mL), dried over anhydrous magnesium sulfate, filtered and concentrated in vacuo to afford 6-cyclopentyloxy-7-methoxy-1-(3-methoxy-benzyl)-1,2-dihydro-isoquinoline-4-carbaldehyde (280 mg, 86% yield) as a yellow oil. The crude product was used without further purification.

To a stirred solution of 6-cyclopentyloxy-7-methoxy-1-(3-methoxy-benzyl)-1,2-dihydro-isoquinoline-4-carbaldehyde (280 mg, 0.71 mmol) in chloroform (8 mL) was addend manganese (IV) oxide (728 mg, 7.12 mmol). The reaction mixture was stirred at room temperature for 15 hrs, filtered through a Celite® pad, and washed with chloroform. The filtrate was concentrated in vacuo to afford 6-cyclopentyloxy-7-methoxy-1-(3-methoxy-benzyl)-isoquinoline-4-carbaldehyde (280 mg, 99% yield). The crude product was without further purification.

To a stirred solution of 6-cyclopentyloxy-7-methoxy-1-(3-methoxy-benzyl)-isoquinoline-4-carbaldehyde (300 mg, 0.77 mmol) in acetic acid (7 μL) was added selenium dioxide (255 mg, 2.30 mmol). The reaction mixture was heated at 120° C. for 1 h. The solvent was evaporated and the residue was diluted with dichloromethane (30 mL). The organic layer was washed with saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 6-cyclopentyloxy-7-methoxy-1-(3-methoxy-benzoyl)-isoquinoline-4-carbaldehyde as a yellow solid (200 mg, 64% yield).

To a stirred solution of afforded 6-cyclopentyloxy-7-methoxy-1-(3-methoxy-benzoyl)-isoquinoline-4-carbaldehyde (200 mg, 0.49 mmol) in t-butanol (2 mL) and water (2 mL) solution was added sodium dihydrogenphosphate monohydrate (184 mg, 1.33 mmol), 2-methyl-2-butene (0.226 mL, 2.00 mmol) and sodium chlorite (181 mg, 2.00 mmol) at room temperature. The reaction suspension was then stirred at room temperature for 14 hrs. The resulting two-phase mixture was partitioned between dichloromethane and water and acidified to pH=3 by addition of acetic acid. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in ethyl acetate and hexane to afford 6-cyclopentyloxy-7-methoxy-1-(3-methoxy-benzoyl)-isoquinoline-4-carboxylic acid (120 mg, 58% yield) as a yellow solid: HR-MS m/e calcd for $C_{24}H_{23}N_1O_6$ (M–H$^+$) 421.1525, found 421.1526; $^1$H NMR (300 MHz) compatible.

Example 70

6-(3-Acetoxy-propoxy)-7-methoxy-1-(3-methoxy-benzoyl)-isoquinoline-4-carboxylic acid

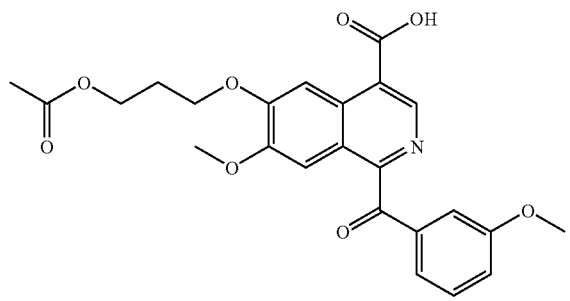

4-Benzyloxy-3-methoxybenzyladehyde (4.84 g, 20 mmol), aminoacetaldehyde dimethylacetal (1.48 mL, 20 mmol) and trimethylorthoformate (4 mL) were mixed in 1,2-dichloroethane (20 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Methoxybenzylchloride (7.26 mL, 50 mmol) was dissolved in diethyl ether (50 mL) and magnesium metal (1.28 g, 52.5 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (6.58 g, 20 mmol) in diethyl ether (30 mL) was added dropwise (a precipitate forms with each drop). After addition was complete, the resulting suspension was heated at reflux for 2 hours. The mixture was cooled in an ice-bath and saturated ammonium chloride solution (50 mL) was carefully added dropwise. The mixture was stirred at 0° C. for 15 minutes and then room temperature for 1 h. Water (50 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-methoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-methoxyphenyl)-ethyl]-(2,2-dimethoxy-ethyl)-amine (10.46 g, 20 mmol) in tetrahydrofuran (40 mL) and water (20 mL) was added potassium carbonate (5 g, 36 mmol) and ethyl chloroformate (1.91 mL, 20 mmol) dropwise. The mixture was stirred for 1 h at room temperature. The mixture was diluted with diethyl ether (100 mL), and the organic layer was separated. The aqueous phase was extracted with ethyl acetate (3×100 mL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-methoxy-phenyl)-2-phenyl-ethyl]-(2,2-dimethoxy-ethyl)-carbamic acid ethyl ester (7 g, 67% yield in three steps) as a colorless oil.

To a stirred solution of [1-(4-benzyloxy-3-methoxy-phenyl)-2-phenyl-ethyl]-(2,2-dimethoxy-ethyl)-carbamic acid ethyl ester (10.5 g, 20 mmol) in ethyl acetate (100 mL) and ethanol (50 mL) was added 10% palladium on activated carbon (2 g). The mixture was hydrogenated at 1 atm for 15 hrs. The solution was filtered through a Celite® plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (4.87 g, 56% yield)

To a stirred solution of (2,2-dimethoxy-ethyl)-[1-(4-hydroxy-3-methoxy-phenyl)-2-(3-methoxy-phenyl)-ethyl-carbamic acid ethyl ester (400 mg, 0.95 mmol) in acetone (10 mL) was added potassium carbonate (766 g, 5.67 mmol) and 3-bromo-2-propanol (0.25 mL, 2.84 mmol) dropwise. The reaction mixture was heated with stirring at 85° C. for 18 hrs. The solvent was evaporated and the residue was diluted with ethyl acetate (50 mL) and water (50 mL). The aqueous phase was extracted with ethyl acetate (3×50 mL). The combined extracts were washed with saturated aqueous sodium chloride solution (50 mL), dried over anhydrous magnesium sulfate, filtered and concentrated in vacuo. The crude product (2,2-dimethoxy-ethyl)-[1-[4-(3-hydroxy-propoxy)-3-methoxy-phenyl]-2-(3-methoxy-phenyl)-ethyl]-carbamic acid ethyl ester was used without further purification.

To a stirred solution of crude (2,2-dimethoxy-ethyl)-[1-[4-(3-hydroxy-propoxy)-3-methoxy-phenyl]-2-(3-methoxy-phenyl)-ethyl]-carbamic acid ethyl ester in acetone (30 mL) was added 6N hydrochloric acid (10 mL) at 0° C. The reaction mixture was stirred at room temperature for 15 hrs. The mixture was diluted with water. The solvent was evaporated and the aqueous layer was extracted with ethyl acetate (3×30 mL). The combined extracts were washed with saturated aqueous sodium chloride solution (20 mL), dried over anhydrous magnesium sulfate, filtered and concentrated in vacuo. Flash chromatography (Merck Silica gel 60, 70–230 mesh, 50% ethyl acetate/hexane) afforded 6-(3-hydroxy-propoxy)-7-methoxy-1-(3-methoxy-benzyl)-1H-isoquinoline-2-carboxylic acid ethyl ester (130, 32% yield in two steps) as a colorless oil.

To a stirred solution of 6-(3-hydroxy-propoxy)-7-methoxy-1-(3-methoxy-benzyl)-1H isoquinoline-2-carboxylic acid ethyl ester (130 mg, 0.30 mmol) in pyridine (2 μL) was added acetic anhydride (1 mL). The reaction mixture was stirred at room temperature for 15 hrs. The solvent was evaporated and toluene was added to remove pyridine completely. The crude product 6-(3-acetoxy-propoxy)-7- methoxy-1-(3-methoxy-benzyl)-1H-isoquinoline-2-carboxylic acid ethyl ester (142, 99% yield) was used without further purification.

To anhydrous N,N-dimethylformamide (0.129 mL, 1.51 mmol) at 0° C. was added phosphorus oxychloride (0.068 mL, 0.67 mmol) dropwise. The mixture was warmed to room temperature and stirred for 30 minutes. The mixture was cooled in an ice-bath, 6-(3-acetoxy-propoxy)-7-methoxy-1-(3-methoxy-benzyl)-1H-isoquinoline-2-carboxylic acid ethyl ester (142 mg, 0.30 mmol) in dichloromethane (2 mL) was added dropwise. After addition was complete, the mixture was heated on an oil bath for 4 hrs at 80° C. The mixture was cooled to 0° C. and a solution of potassium acetate (196 mg, 1.82 mmol) in water (2 mL) was added slowly. The mixture was then heated at 80° C. for 20 minutes. The mixture was cooled, poured into water and diluted with dichloromethane (60 m]L). The organic layer was washed water (2×20 mL), saturated aqueous sodium bicarbonate solution (20 mL), saturated aqueous sodium chloride solution (20 mL), dried over anhydrous magnesium sulfate, filtered and concentrated in vacuo to afford 6-(3-acetoxy-propoxy)-4-formyl-7-methoxy-1-(3-methoxy-benzyl)-1H-isoquinoline-2-carboxylic acid ethyl ester (150 mg, 99% yield) as a yellow oil. The crude product was without further purification.

To a stirred solution of 6-(3-acetoxy-propoxy)-4-formyl-7-methoxy-1-(3-methoxy-benzyl)-1H-isoquinoline-2-carboxylic acid ethyl ester (150 mg, 0.30 mmol) in methanol (6 mL) was added powdered potassium hydroxide (169 mg, 3.0 mmol). The reaction mixture was stirred at room temperature for 3 hrs. The solvent was evaporated and the residue was diluted with ethyl acetate (20 mL) and water (20 mL). The aqueous phase was extracted with ethyl acetate (3×20 mL). The combined extracts were washed with saturated aqueous sodium chloride solution (20 mL), dried over anhydrous magnesium sulfate, filtered and concentrated in vacuo to afford 6-(3-acetoxy-propoxy)-7-methoxy-1-(3-methoxy-benzyl)-1,2-dihydro-isoquinoline-4-carbaldehyde (78 mg, 67% yield) as a yellow oil. The crude product was used without further purification. To a stirred solution of 6-(3-acetoxy-propoxy)-7-methoxy-1-(3-methoxy-benzyl)-1,2-dihydro-isoquinoline-4-carbaldehyde (78 mg, 0.20 mmol) in chloroform (3 mL) was added manganese (IV) oxide (208 mg, 2.0 mmol). The reaction mixture was stirred at room temperature for 15 hrs, filtered through a Celite® pad, and washed with chloroform. The filtrate was concentrated in vacuo to afford 6-(3-acetoxy-propoxy)-7-methoxy-1-(3-methoxy-benzyl)-isoquinoline-4-carbaldehyde (20 mg, 23% yield). The crude product was used without further purification.

To a stirred solution of 6-(3-acetoxy-propoxy)-7-methoxy-1-(3-methoxy-benzyl)-isoquinoline-4-carbaldehyde (20 mg, 0.047 mmol) in acetic acid (1 mL) was added selenium dioxide (16 mg, 1.44 mmol). The reaction mixture was heated at 120° C. for 1 h. The solvent was evaporated and the residue was diluted with dichloromethane (30 mL). The organic layer was washed with saturated sodium bicarbonate solution (20 mL), saturated sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 6-(3-acetoxy-propoxy)-7-methoxy-1-(3-methoxy-benzoyl)-isoquinoline-4-carbaldehyde as a yellow solid (20 mg, 97% yield).

To a stirred solution of afforded 6-(3-acetoxy-propoxy)-7-methoxy-1-(3-methoxy-benzoyl)-isoquinoline-4-carbaldehyde (20 mg, 0.045 mmol) in t-butanol (1 mL) and water (1 mL) solution was added sodium dihydrogenphosphate monohydrate (25.3 mg, 0.18 mmol), 2-methyl-2-butene (0.030 mL, 0.27 mmol) and sodium chlorite (24.8 mg, 0.27 mmol) at room temperature. The reaction suspension was then stirred at room temperature for 14 hrs. The resulting two-phase mixture was partitioned between dichloromethane and water and acidified to pH=3 by addition of acetic acid. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in ethyl acetate and hexane to afford 6-(3-acetoxy-propoxy)-7-methoxy-1-(3-methoxy-benzoyl)-isoquinoline-4-carboxylic acid (8.0 mg, 39% yield) as a white solid: HR-MS m/e calcd for $C_{24}H_{23}N_1O_8$ $(M-H^+)$ 454.1496, found 454.1502; $^1H$ NMR (300 MHz) compatible.

Example 71

6-(3-Hydroxy-propoxy)-1-(3-isopropoxy-benzoyl)-7-methoxy-isoquinoline-4-carboxylic acid; compound with trifluoroacetic acid

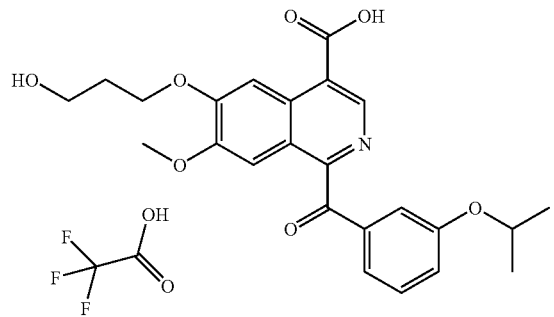

To a stirred solution of 6-hydroxy-1-(3-isopropoxy-benzoyl)-7-methoxy-isoquinoline-4-carboxylic acid ethyl ester (30 mg, 0.073 mmol) in N,N-dimethylformamide (1 mL) was added potassium carbonate (81.1 mg, 0.58 mmol) and 3-bromo-1-propanol (0.033 mL, 0.22 mmol) at room temperature. The reaction mixture was heated 85° C. for 2 hrs. The solvent was evaporated and the residue was purified on a flash chromatography (Merck Silica gel 60, 70–230 mesh, 50% ethyl acetate/hexane) to afford product 6-(3-hydroxy-propoxy)-1-(3-isopropoxy-benzoyl)-7-methoxy-isoquinoline-4-carboxylic acid ethyl ester as a colorless oil (34 mg, 99% yield).

To a stirred solution of 6-(3-hydroxy-propoxy)-1-(3-isopropoxy-benzoyl)-7-methoxy-isoquinoline-4-carboxylic acid ethyl ester (34 mg, 0.073 mmol) in pyridine (1 mL) was added acetic anhydride (0.5 mL). The mixture was stirred at room temperature for 15 hrs. The solvent was evaporated and the residue was used in the next step reaction without further purification. To a stirred solution of 6-(3-acetoxy-propoxy)-1-(3-isopropoxy-benzoyl)-7-methoxy isoquinoline-4-carboxylic acid ethyl ester (78.5 mg, 0.15 mmol) in ethanol (0.8 mL) and tetrahydrofuran (0.4 mL) was added 4N aqueous sodium hydroxide (0.078 mL). The mixture was heated at 60° C. for 1 hr. The solvent was evaporated and the residue was diluted with dichloromethane and water. The aqueous phase was acidified to pH=3 by addition of 1N hydrochloride solution and then was extracted with dichlo-

Example 72

1-(3-Isopropoxy-benzoyl)-7-methoxy-6-(2-pyrrolidin-1-yl-ethoxy)-isoquinoline-4-carboxylic acid hydrochloride

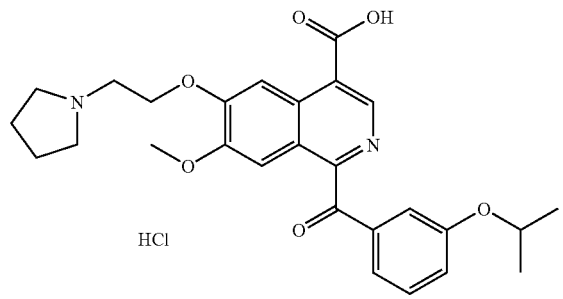

To a stirred solution of 6-hydroxy-1-(3-isopropoxy-benzoyl)-7-methoxy-isoquinoline-4-carboxylic acid ethyl ester (73 mg, 0.18 mmol) in N,N dimethylformamide (2 mL) was added potassium carbonate (197 mg, 1.42 mmol) and 1,2-dibromoethane (0.046 mL, 0.89 mmol) at room temperature. The reaction mixture was heated 85° C. for 2 hrs. The solvent was evaporated and the crude product was diluted with ethyl acetate and water. The aqueous phase was extracted with ethyl acetate (3×20 mL). The combined extracts were washed with saturated aqueous sodium chloride solution (20 mL), dried over anhydrous magnesium sulfate, filtered and concentrated in vacuo. Flash chromatography (Merck Silica gel 60, 70–230 mesh, 30% ethyl acetate/hexane) afforded 6-(2-bromo-ethoxy)-1-(3-isopropoxy-benzoyl)-7-methoxy-isoquinoline-4-carboxylic acid ethyl ester as a white solid (70 mg, 75% yield).

To a stirred solution of 6-(2-bromo-ethoxy)-1-(3-isopropoxy-benzoyl)-7-methoxy-isoquinoline-4-carboxylic acid ethyl ester (70 mg, 0.14 mmol) in N,N dimethylformamide (2 mL) was added potassium carbonate (157 mg, 1.35 mmol) and pyrrolidine (0.033 mL, 0.67 mmol) at room temperature. The reaction mixture was heated 85° C. for 2 hrs. The solvent was evaporated and the crude product, 1-(3-isopropoxy-benzoyl)-7-methoxy-6-(2-pyrrolidin-1-yl-ethoxy)-isoquinoline-4-carboxylic acid ethyl ester, was without further purification.

To a stirred solution of 1-(3-isopropoxy-benzoyl)-7-methoxy-6-(2-pyrrolidin-1-yl-ethoxy)-isoquinoline-4-carboxylic acid ethyl ester (73.0 mg, 0.14 mmol) in ethanol (1.0 mL) and tetrahydrofuran (0.5 mL) was added 4N aqueous sodium hydroxide (0.144 mL, 0.56 mmol). The mixture was heated at 60° C. for 1 h. The solvent was evaporated and the residue was diluted with dichloromethane and water. The aqueous phase was acidified to pH=3 by addition of 1N hydrochloric acid solution and then was extracted with dichloromethane (3×20 mL). The combined extracts were washed with saturated aqueous sodium chloride solution (20 mL), dried over anhydrous magnesium sulfate, filtered and concentrated in vacuo. The crude product recrystallized from ethyl acetate to afford 1-(3-isopropoxy-benzoyl)-7-methoxy-6-(2-pyrrolidin-1-yl-ethoxy)-isoquinoline-4-carboxylic acid hydrochloride as a light brown solid (12 mg, 18% yield). HR-MS m/e calcd for $C_{27}H_{30}N_2O_6$ (M–H$^+$) 479.2177, found 479.2177; $^1$H NMR (300 MHz) compatible.

Example 73

6-Carboxymethoxy-1-(3-isopropoxy-benzoyl)-7-methoxy-isoquinoline-4-carboxylic acid

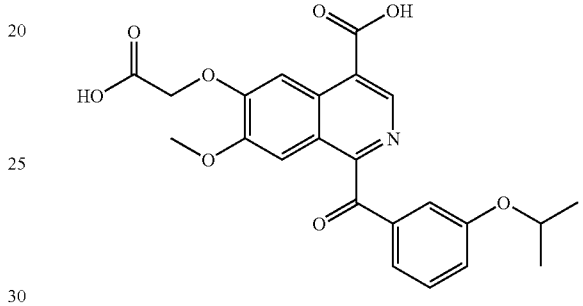

To a stirred solution of 6-hydroxy-1-(3-isopropoxy-benzoyl)-7-methoxy-isoquinoline-4-carboxylic acid ethyl ester (70 mg, 0.17 mmol) in N,N dimethylformamide (2 mL) was added potassium carbonate (237 mg, 1.71 mmol) and 2-chloro-N,N-dimethyl-acetamide (0.088 mL, 0.86 mmol) at room temperature. The reaction mixture was heated 85° C. for 2 hrs. The solvent was evaporated and the crude product was diluted with ethyl acetate and water. The aqueous phase was extracted with ethyl acetate (3×20 mL). The combined extracts were washed with saturated aqueous sodium chloride solution (20 mL), dried over anhydrous magnesium sulfate, filtered and concentrated in vacuo. Flash chromatography (Merck Silica gel 60, 70–230 mesh, 30% ethyl acetate/hexane) afforded 6-dimethylcarbamoylmethoxy-1-(3-isopropoxy-benzoyl)-7-methoxy-isoquinoline-4-carboxylic acid ethyl ester. To a stirred solution of 1-(3-isopropoxy-benzoyl)-7-methoxy-6-(2-pyrrolidin-1-yl-ethoxy)-isoquinoline-4-carboxylic acid ethyl ester (73.0 mg, 0.14 mmol) in ethanol (1.0 mL) and tetrahydrofuran (0.5 mL) was added 4N aqueous sodium hydroxide (0.144 mL, 0.56 mmol) at room temperature. The mixture was heated at 60° C. for 1 h. The solvent was evaporated and the residue was diluted with dichloromethane and water. The aqueous phase was acidified to pH=3 by addition of 1N hydrochloride solution and then was extracted with dichloromethane (3×20 mL). The combined extracts were washed with saturated aqueous sodium chloride solution (20 mL), dried over anhydrous magnesium sulfate, filtered and concentrated in vacuo. The crude product recrystallized from ethyl acetate to afford 1-(3-isopropoxy-benzoyl)-7-methoxy-6-(2-pyrrolidin-1-yl-ethoxy)-isoquinoline-4-carboxylic acid as a light brown solid (28 mg, 37% yield). HR-MS m/e calcd for $C_{23}H_{21}N_1O_6$ (M–H$^+$) 440.1340, found 440.1347; $^1$H NMR (300 MHz) compatible.

--- romethane (3×20 mL). The combined extracts were washed with saturated aqueous sodium chloride solution (20 mL), dried over anhydrous magnesium sulfate, filtered and concentrated in vacuo. The crude product was purified on a HPLC (with trifluoroacetic acid added in the eluent solvent) to afford 6-(3-hydroxy-propoxy)-1-(3-isopropoxy-benzoyl)-7-methoxy-isoquinoline-4-carboxylic acid trifluoroacetic acid salt as a light brown solid (5 mg, 6% yield). HR-MS m/e calcd for $C_{24}H_{25}N_1O_7$ (M–H$^+$) 440.1704, found 440.1707; $^1$H NMR (300 MHz) compatible.

Example 74

6-(3-Acetoxy-propoxy)-1-(3-ethoxy-benzoyl)-7-methoxy-isoquinoline-4-carboxylic acid

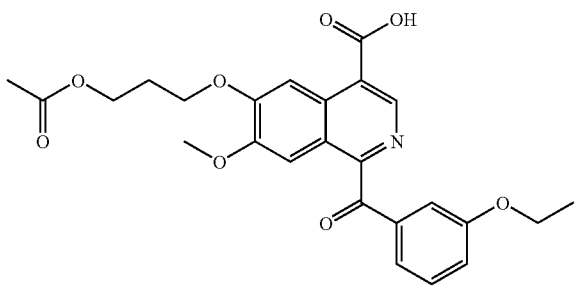

4-Benzyloxy-3-methoxybenzyladehyde (9.71 g, 40 mmol), aminoacetaldehyde dimethylacetal (2.97 mL, 40 mmol) and trimethylorthoformate (8 mL) were mixed in 1,2-dichloroethane (100 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Ethoxybenzylchloride (13.6 g, 80 mmol) was dissolved in diethyl ether (100 mL) and magnesium metal (2.04 g, 84 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (13.2 g, 40 mmol) in diethyl ether (60 mL) was added dropwise (a precipitate forms with each drop). After addition was complete, the resulting suspension was heated at reflux for 2 hours. The mixture was cooled in an ice-bath and saturated aqueous ammonium chloride solution (100 mL) was carefully added dropwise. The mixture was stirred at 0° C. for 15 minutes and then room temperature for 1 h. Water (80 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-ethoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-ethoxy-phenyl)-ethyl]-(2,2-dimethoxy-ethyl)-amine (22.2 g, 40 mmol) in tetrahydrofuran (120 mL) and water (60 mL) was added potassium carbonate (9.93 g, 72 mmol) and ethyl chloroformate (4.2 mL, 44 mmol) dropwise.). The mixture was stirred for 1 h at room temperature. The mixture was diluted with diethyl ether (100 mL), and the organic layer was separated. The aqueous phase was extracted with ethyl acetate (3×100 mL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-ethoxy-phenyl)-2-phenyl-ethyl]-(2,2-dimethoxy-ethyl)-carbamic acid ethyl ester (12 g, 56% yield in three steps) as a colorless oil.

To a stirred solution of [1-(4-benzyloxy-3-ethoxy-phenyl)-2-phenyl-ethyl]-(2,2-dimethoxy-ethyl)-carbamic acid ethyl ester (12.0 g, 28 mmol) in ethyl acetate (120 mL) and ethanol (60 mL) solution was added 10% Pd/C (2.4 g). The mixture was hydrogenated at 1 atm for 15 hrs. The solution was filtered through a Celite® plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (10 g, 80% yield).

To a stirred solution of (2,2-dimethoxy-ethyl)-[1-(4-hydroxy-3-ethoxy-phenyl)-2-(3-methoxy-phenyl)-ethyl-carbamic acid ethyl ester (10 g, 22 mmol) in acetone (300 mL) was added 6N aqueous hydrogen chloride solution (40 mL) at 0° C. The reaction mixture was stirred at room temperature for 15 hrs. The mixture was diluted with water. The solvent was evaporated and the aqueous layer was extracted with ethyl acetate (3×100 mL). The combined extracts were washed with saturated aqueous sodium chloride solution (80 mL), dried over anhydrous magnesium sulfate, filtered and concentrated in vacuo to afford 6-hydroxy-7-methoxy-1-(3-ethoxy-benzyl)-1H-isoquinoline-2-carboxylic acid ethyl ester. The crude product was used without further purification.

To a stirred solution of 6-hydroxy-7-methoxy-1-(3-ethoxy-benzyl)-1H-isoquinoline-2-carboxylic acid ethyl ester (737 mg, 1.92 mmol) in N,N-dimethylformamide (10 mL) was added potassium carbonate (2.6 g, 19.2 mmol) and 3-bromo-1-propanol (0.868 m]L, 9.62 mmol) at room temperature. The reaction mixture was heated 85° C. for 2 hrs. The solvent was evaporated and the residue was purified on a flash chromatography (Merck Silica gel 60, 70–230 mesh, 50% ethyl acetate/hexane) to afford product 6-(3-hydroxy-propoxy)-7-methoxy-1-(3-ethoxy-benzyl)-1H-isoquinoline-2-carboxylic acid ethyl ester as a colorless oil (260 mg, 31% yield).

To a stirred solution of 6-(3-hydroxy-propoxy)-7-methoxy-1-(3-ethoxy-benzyl)-1H-isoquinoline-2-carboxylic acid ethyl ester (160 mg, 0.59 mmol) in pyridine (4.2 mL) was added acetic anhydride (2.1 mL). The reaction mixture was stirred at room temperature for 15 hrs. The mixture was concentrated in vacuo to afford 6-(3-acetoxy-propoxy)-7-methoxy-1-(3-ethoxy-benzyl)-1H-isoquinoline-2-carboxylic acid ethyl ester (285 mg, 99% yield). The crude product was used without further purification.

To anhydrous N,N-dimethylformamide (0.228 mL, 2.95 mmol) at 0° C. was added phosphorus oxychloride (0.12 mL, 1.30 mmol) was added dropwise. The mixture was warmed to room temperature and stirred for 30 minutes. The mixture was cooled in an ice-bath, and afford 6-(3-acetoxy-propoxy)-7-methoxy-1-(3-ethoxy-benzyl)-1H-isoquinoline-2-carboxylic acid ethyl ester (285 mg, 0.59 mmol) in dichloromethane (3 mL) was added dropwise. After addition was complete, the mixture was heated on an oil bath for 4 hrs at 80° C. The mixture was cooled to 0° C. and a solution of potassium acetate (347 mg, 3.54 mmol) in water (2 mL) was added slowly. The mixture was then heated at 80° C. for 20 minutes. The mixture was cooled, poured into water and diluted with dichloromethane (60 mL). The organic layer was washed water (2×20 mL), saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 20% ethyl acetate/hexane,) afforded 6-(3-acetoxypropoxy)-1-(3-ethoxy-benzyl)-4-formyl-7-methoxy-1H-isoquinoline-2-carboxylic acid ethyl ester as a colorless oil (130 mg, 40% yield).

To a solution of 6-(3-acetoxy-propoxy)-1-(3-ethoxy-benzyl)-4-formyl-7-methoxy-1H-isoquinoline-2-carboxylic acid ethyl ester (130 mg, 0.25 mmol) in methanol (3.5 mL) was added powdered potassium hydroxide (85.5 mg, 1.53 mmol) at room temperature. The mixture was stirred at room temperature for 14 hrs. The solvent was evaporated and the residue was diluted with water (20 mL). The aqueous phase was extracted with ethyl acetate (2×20 mL). The combined extracts were washed with saturated aqueous sodium chloride solution (20 mL), dried over anhydrous magnesium sulfate, filtered and concentrated in vacuo to afford a crude oil. Flash chromatography (Merck Silica gel 60, 70–230 mesh, 50% ethyl acetate/hexane, 75% ethyl acetate/hexane, ethyl acetate) afforded 6-(3-acetoxy-propoxy)-7-methoxy-1-(3-ethoxy-benzyl)-1,2-dihydro-isoquinoline-4-carbaldehyde (120 mg, 42% yield).

To a stirred solution of 6-(3-acetoxy-propoxy)-7-methoxy-1-(3-ethoxy-benzyl)-1,2-dihydro-isoquinoline-4-carbaldehyde (120 mg, 0.27 mmol) in chloroform (3 mL) was addend manganese (IV) oxide (279 mg, 2.7 mmol). The reaction mixture was stirred at room temperature for 15 hrs, filtered through a celite pad®, and washed with chloroform. The filtrate was concentrated in vacuo to afford 6-(3-acetoxy-propoxy)-7-methoxy-1-(3-ethoxy-benzyl)-isoquinoline-4-carbaldehyde (120 mg, 99% yield). The crude product was used without further purification.

To a stirred solution of 6-(3-acetoxy-propoxy)-7-methoxy-1-(3-ethoxy-benzyl)-isoquinoline-4-carbaldehyde (120 mg, 0.27 mmol) was added selenium dioxide (120 mg, 1.08 mmol). The reaction mixture was heated at 120° C. for 1 h. The solvent was evaporated and the residue was diluted with dichloromethane (30 mL). The organic layer was washed with saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 6-(3-hydroxy-propoxy)-1-(3-ethoxy-benzoyl)-7-methoxy-isoquinoline-4-carbaldehyde as a major product (40 mg, 37% yield).

To a stirred solution of 6-(3-hydroxy-propoxy)-1-(3-ethoxy-benzoyl)-7-methoxy-isoquinoline-4-carbaldehyde (40 mg, 0.10 mmol) in pyridine (8 mL) was added acetic anhydride (0.4 mL). The reaction mixture was stirred at room temperature for 15 hrs. The mixture was concentrated in vacuo to afford 6-(3-acetoxy-propoxy)-1-(3-ethoxy-benzoyl)-7-methoxy-isoquinoline-4-carbaldehyde (60 mg, 99% yield). The crude product was used without further purification.

To a stirred solution of 6-(3-acetoxy-propoxy)-1-(3-ethoxy-benzoyl)-7-methoxy-isoquinoline-4-carbaldehyde (60 mg, 0.13 mmol) in t-butanol (0.5 mL) and water (0.5 mL) solution was added sodium dihydrogenphosphate monohydrate (73 mg, 0.53 mmol), 2-methyl-2-butene (0.090 mL, 0.80 mmol) and sodium chlorite (72.2 mg, 0.80 mmol) at room temperature. The reaction suspension was then stirred at room temperature for 14 hrs. The resulting two-phase mixture was partitioned between dichloromethane and water and acidified to pH=3 by addition of acetic acid. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in ethyl acetate to afford 6-(3-acetoxy-propoxy)-1-(3-ethoxy-benzoyl)-7-methoxy-isoquinoline-4-carboxylic acid (13 mg, 21% yield) as a yellow solid. HR-MS m/e calcd for $C_{25}H_{25}N_1O_8$ (M–H$^+$) 468.1653, found 468.1657; $^1$H NMR (300 MHz) compatible.

Example 75

6-(3-Acetoxy-propoxy)-1-(3-ethoxy-benzoyl)-7-methoxy-isoquinoline-4-carboxylic acid hydrochloride

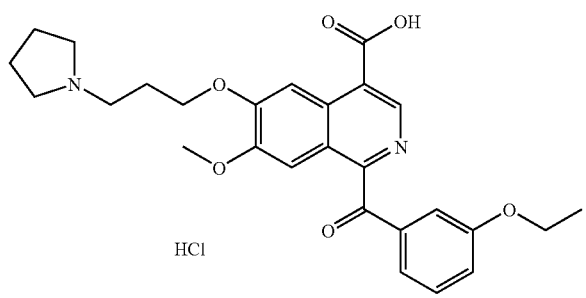

4-Benzyloxy-3-methoxybenzyladehyde (9.71 g, 40 mmol), aminoacetaldehyde dimethylacetal (2.97 mL, 40 mmol) and trimethylorthoformate (8 mL) were mixed in 1,2-dichloroethane (100 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Ethoxybenzylchloride (13.6 g, 80 mmol) was dissolved in diethyl ether (100 mL) and magnesium metal (2.04 g, 84 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (13.2 g, 40 mmol) in diethyl ether (60 mL) was added dropwise (a precipitate forms with each drop). After addition was complete, the resulting suspension was heated at reflux for 2 hours. The mixture was cooled in an ice-bath and saturated aqueous ammonium chloride solution (100 mL) was carefully added dropwise. The mixture was stirred at 0° C. for 15 minutes and then room temperature for 1 h. Water (80 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-ethoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-ethoxy-phenyl)-ethyl]-(2,2-dimethoxy-ethyl)-amine (22.2 g, 40 mmol) in tetrahydrofuran (120 mL) and water (60 mL) was added potassium carbonate (9.93 g, 72 mmol) and ethyl chloroformate (4.2 mL, 44 mmol) dropwise.). The mixture was stirred for 1 h at room temperature. The mixture was diluted with diethyl ether (100 mL), and the organic layer was separated. The aqueous phase was extracted with ethyl acetate (3×100 mL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-ethoxy-phenyl)-2-phenyl-ethyl]-(2,2-dimethoxy-ethyl)-carbamic acid ethyl ester (12 g, 56% yield in three steps) as a colorless oil.

To a stirred solution of [1-(4-benzyloxy-3-ethoxy-phenyl)-2-phenyl-ethyl]-(2,2-dimethoxy-ethyl)-carbamic acid ethyl ester (12.0 g, 28 mmol) in ethyl acetate (120 mL) and ethanol (60 mL) solution was added 10% Pd/C (2.4 g). The mixture was hydrogenated at 1 atm for 15 hrs. The solution was filtered through a Celite® plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (10 g, 80% yield).

To a stirred solution of (2,2-dimethoxy-ethyl)-[1-(4-hydroxy-3-ethoxy-phenyl)-2-(3-methoxy-phenyl)-ethyl-carbamic acid ethyl ester (10 g, 22 mmol) in acetone (300 mL) was added 6N aqueous hydrogen chloride solution (40 mL) at 0° C. The reaction mixture was stirred at room temperature for 15 hrs. The mixture was diluted with water. The solvent was evaporated and the aqueous layer was extracted with ethyl acetate (3×100 mL). The combined extracts were washed with saturated aqueous sodium chloride solution (80 mL), dried over anhydrous magnesium sulfate, filtered and concentrated in vacuo to afford 6-hydroxy-7-methoxy-1-(3-ethoxy-benzyl)-1H-isoquinoline-2-carboxylic acid ethyl ester. The crude product was used without further purification.

To a stirred solution of 6-hydroxy-7-methoxy-1-(3-ethoxy-benzyl)-1H-isoquinoline-2-carboxylic acid ethyl ester (6 g, 0.59 mmol) in pyridine (112 mL) was added acetic anhydride (56 mL). The reaction mixture was stirred at room temperature for 15 hrs. The mixture was concentrated in vacuo to afford 6-acetoxy-7-methoxy-1-(3-ethoxy-benzyl)-1H-isoquinoline-2-carboxylic acid ethyl ester. The crude product was used without further purification.

To anhydrous N,N-dimethylformamide (3.46 mL, 43.5 mmol) at 0° C. was added phosphorus oxychloride (1.83 mL, 19.2 mmol) dropwise. The mixture was warmed to room temperature and stirred for 30 minutes. The mixture was cooled in an ice-bath, and 6-acetoxy-7-methoxy-1-(3-ethoxy-benzyl)-1H-isoquinoline-2-carboxylic acid ethyl ester (3.7 mg, 8.70 mmol) in dichloromethane (8 mL) was added dropwise. After addition was complete, the mixture was heated on an oil bath for 4 hrs at 80° C. The mixture was cooled to 0° C. and a solution of potassium acetate (5.26 g, 52.2 mmol) in water (10 mL) was added slowly. The mixture was then heated at 80° C. for 20 minutes. The mixture was cooled, poured into water and diluted with dichloromethane (60 mL). The organic layer was washed water (2×80 mL), saturated aqueous sodium bicarbonate solution (50 mL), saturated aqueous sodium chloride solution (50 mL), dried over anhydrous magnesium sulfate, filtered and concentrated in vacuo to afford a crude oil. Flash chromatography (Merck Silica gel 60, 70–230 mesh, 20% ethyl acetate/hexane) afforded 6-acetoxy-1-(3-ethoxy-benzyl)-4-formyl-7-methoxy-1H-isoquinoline-2-carboxylic acid ethyl ester as a colorless oil (1.0 g, 25% yield).

To a solution of 6-acetoxy-1-(3-ethoxy-benzyl)-4-formyl-7-methoxy-1H-isoquinoline-2-carboxylic acid ethyl ester (1.0 g, 2.20 mmol) in methanol (50 mL) was added powdered potassium hydroxide (741 mg, 11.1 mmol) at room temperature. The mixture was stirred at room temperature for 14 hrs. The solvent was evaporated and the residue was diluted with water (50 mL). The aqueous phase was extracted with ethyl acetate (2×50 mL). The combined extracts were washed with saturated aqueous sodium chloride solution (50 mL), dried over anhydrous magnesium sulfate, filtered and concentrated in vacuo to afford 6-hydroxy-7-methoxy-1-(3-ethoxy-benzyl)-1,2-dihydro-isoquinoline-4-carbaldehyde (660 mg, 88% yield). The crude product was used without further purification.

To a stirred solution of 6-hydroxy-7-methoxy-1-(3-ethoxy-benzyl)-1,2-dihydro-isoquinoline-4-carbaldehyde (660 mg, 1.95 mmol) in chloroform (30 μL) was addend manganese (IV) oxide (1.99 mg, 19.5 mmol). The reaction mixture was stirred at room temperature for 15 hrs, filtered through a celite® pad, and washed with chloroform. The filtrate was concentrated in vacuo to afford 6-hydroxy-7-methoxy-1-(3-ethoxy-benzyl)-isoquinoline-4-carbaldehyde (600 mg, 89% yield). The crude product was used without further purification.

To a stirred solution of 6-hydroxy-7-methoxy-1-(3-ethoxy-benzyl)-isoquinoline-4-carbaldehyde (86 g, 0.24 mmol) in N,N-dimethylformamide (2 mL) was added potassium carbonate (337 mg, 2.40 mmol) and 1,3-dibromopropane (0.124 mL, 1.22 mmol) at room temperature. The reaction mixture was heated 85° C. for 2 hrs. The solvent was evaporated and the residue was purified on a flash chromatography (Merck Silica gel 60, 70–230 mesh, 50% ethyl acetate/hexane) to afford product 6-(3-bromo-propoxy)-7-methoxy-1-(3-ethoxy-benzyl)-isoquinoline-4-carbaldehyde as a colorless oil (70 mg, 62% yield).

To a stirred solution of 6-(3-bromo-propoxy)-7-methoxy-1-(3-ethoxy-benzyl)-isoquinoline-4-carbaldehyde (70 mg, 0.15 mmol) was added selenium dioxide (132 mg, 1.20 mmol). The reaction mixture was heated at 120° C. for 1 hr. The solvent was evaporated and the residue was diluted with dichloromethane (30 mL). The organic layer was washed with saturated sodium bicarbonate solution (20 mL), saturated sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 6-(3-bromo-propoxy)-1-(3-ethoxy-benzoyl)-7-methoxy-isoquinoline-4-carbaldehyde as a major product (62 mg, 88% yield).

To a stirred solution 6-(3-bromo-propoxy)-1-(3-ethoxy-benzoyl)-7-methoxy-isoquinoline-4-carbaldehyde (62 g, 0.13 mmol) in N,N-dimethylformamide (2 mL) was added potassium carbonate (181 mg, 1.30 mmol) and pyrrolidine (0.032 mL, 0.66 mmol) at room temperature. The reaction mixture was heated 85° C. for 2 hrs. The mixture was diluted with ethyl acetate and water. The aqueous phase was extracted with ethyl acetate (3×30 mL). The combined extracts were washed with saturated aqueous sodium chloride (50 mL), dried over anhydrous magnesium sulfate, filtered and concentrated to afford product 6-(3-pyrrolidin-1-yl-propoxy)-7-methoxy-1-(3-ethoxy-benzoyl)-isoquinoline-4-carbaldehyde as a colorless oil (63 mg, 99% yield).

To a stirred solution of 6-(3-pyrrolidin-1-yl-propoxy)-7-methoxy-1-(3-ethoxy-benzoyl)-isoquinoline-4-carbaldehyde (63 mg, 0.13 mmol) in t-butanol (0.5 mL) and water (0.5 mL) solution was added sodium dihydrogenphosphate monohydrate (73 mg, 0.53 mmol), 2-methyl-2-butene (0.089 mL, 0.80 mmol) and sodium chlorite (71.2 mg, 0.80 mmol) at room temperature. The reaction suspension was then stirred at room temperature for 14 hrs. The resulting two-phase mixture was partitioned between dichloromethane and water and acidified to pH=3 by addition of 1N hydrochloric acid. The aqueous phase was then extracted with dichloromethane (3×20 mL). The combined extracts were washed with saturated sodium chloride solution (30 mL), dried over anhydrous magnesium sulfate, filtered and concentrated in vacuo to afford a brown semi-solid oil. The crude product was recrystallized in ethyl acetate to afford 6-(3-pyrrolidin-1-yl-propoxy)-1-(3-ethoxy-benzoyl)-7-methoxy-isoquinoline-4-carboxylic acid hydrochloride (20 mg, 32% yield) as a light brown solid. HR-MS m/e calcd for $C_{27}H_{30}N_2O_6$ (M–H$^+$) 479.2177, found 479.2182; $^1$H NMR (300 MHz) compatible.

Example 76

1-(3-Ethoxy-benzoyl)-6-(2-ethoxy-ethoxy)-7-methoxy-isoquinoline-4-carboxylic acid

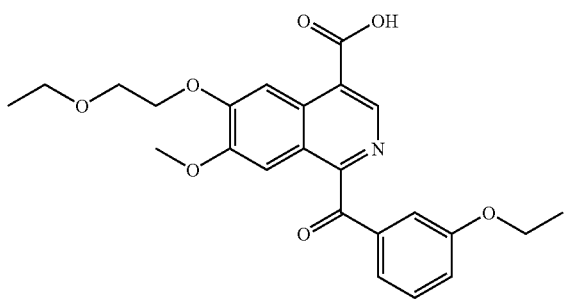

4-Benzyloxy-3-methoxybenzyladehyde (9.71 g, 40 mmol), aminoacetaldehyde dimethylacetal (2.97 mL, 40 mmol) and trimethylorthoformate (8 mL) were mixed in 1,2-dichloroethane (100 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Ethoxybenzylchloride (13.6 g, 80 mmol) was dissolved in diethyl ether (100 mL) and magnesium metal (2.04 g, 84 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (13.2 g, 40 mmol) in diethyl ether (60 mL) was added dropwise (a precipitate forms with each drop). After addition was complete, the resulting suspension was heated at reflux for 2 hours. The mixture was cooled in an ice-bath and saturated aqueous ammonium chloride solution (100 mL) was carefully added dropwise. The mixture was stirred at 0° C. for 15 minutes and then room temperature for 1 h. Water (80 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-ethoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-ethoxy-phenyl)-ethyl]-(2,2-dimethoxy-ethyl)-amine (22.2 g, 40 mmol) in tetrahydrofuran (120 mL) and water (60 mL) was added potassium carbonate (9.93 g, 72 mmol) and ethyl chloroformate (4.2 mL, 44 mmol) dropwise.). The mixture was stirred for 1 h at room temperature. The mixture was diluted with diethyl ether (100 mL), and the organic layer was separated. The aqueous phase was extracted with ethyl acetate (3×100 µL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-ethoxy-phenyl)-2-phenyl-ethyl]-(2,2-dimethoxy-ethyl)-carbamic acid ethyl ester (12 g, 56% yield in three steps) as a colorless oil.

To a stirred solution of [1-(4-benzyloxy-3-ethoxy-phenyl)-2-phenyl-ethyl]-(2,2-dimethoxy-ethyl)-carbamic acid ethyl ester (12.0 g, 28 mmol) in ethyl acetate (120 mL) and ethanol (60 mL) solution was added 10% Pd/C (2.4 g). The mixture was hydrogenated at 1 atm for 15 hrs. The solution was filtered through a Celite® plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (10 g, 80% yield).

To a stirred solution of (2,2-dimethoxy-ethyl)-[1-(4-hydroxy-3-ethoxy-phenyl)-2-(3-methoxy-phenyl)-ethyl-carbamic acid ethyl ester (10 g, 22 mmol) in acetone (300 mL) was added 6N aqueous hydrogen chloride solution (40 mL) at 0° C. The reaction mixture was stirred at room temperature for 15 hrs. The mixture was diluted with water. The solvent was evaporated and the aqueous layer was extracted with ethyl acetate (3×100 mL). The combined extracts were washed with saturated aqueous sodium chloride solution (80 mL), dried over anhydrous magnesium sulfate, filtered and concentrated in vacuo to afford 6-hydroxy-7-methoxy-1-(3-ethoxy-benzyl)-1H-isoquinoline-2-carboxylic acid ethyl ester. The crude product was used without further purification.

To a stirred solution of 6-hydroxy-7-methoxy-1-(3-ethoxy-benzyl)-1H-isoquinoline-2-carboxylic acid ethyl ester (6 g, 0.59 mmol) in pyridine (112 mL) was added acetic anhydride (56 mL). The reaction mixture was stirred at room temperature for 15 hrs. The mixture was concentrated in vacuo to afford 6-acetoxy-7-methoxy-1-(3-ethoxy-benzyl)-1H-isoquinoline-2-carboxylic acid ethyl ester. The crude product was used without further purification.

To anhydrous N,N-dimethylformamide (3.46 mL, 43.5 mmol) at 0° C. was added phosphorus oxychloride (1.83 mL, 19.2 mmol) dropwise. The mixture was warmed to room temperature and stirred for 30 minutes. The mixture was cooled in an ice-bath, and 6-acetoxy-7-methoxy-1-(3-ethoxy-benzyl)-1H-isoquinoline-2-carboxylic acid ethyl ester (3.7 mg, 8.70 mmol) in dichloromethane (8 mL) was added dropwise. After addition was complete, the mixture was heated on an oil bath for 4 hrs at 80° C. The mixture was cooled to 0° C. and a solution of potassium acetate (5.26 g, 52.2 mmol) in water (10 mL) was added slowly. The mixture was then heated at 80° C. for 20 minutes. The mixture was cooled, poured into water and diluted with dichloromethane (60 mL). The organic layer was washed water (2×80 mL), saturated aqueous sodium bicarbonate solution (50 mL), saturated aqueous sodium chloride solution (50 mL), dried over anhydrous magnesium sulfate, filtered and concentrated in vacuo to afford a crude oil. Flash chromatography (Merck Silica gel 60, 70–230 mesh, 20% ethyl acetate/ hexane) afforded 6-acetoxy-1-(3-ethoxy-benzyl)-4-formyl- 7-methoxy-1H-isoquinoline-2-carboxylic acid ethyl ester as a colorless oil (1.0 g, 25% yield).

To a solution of 6-acetoxy-1-(3-ethoxy-benzyl)-4-formyl-7-methoxy-1H-isoquinoline-2-carboxylic acid ethyl ester (1.0 g, 2.20 mmol) in methanol (50 mL) was added powdered potassium hydroxide (741 mg, 11.1 mmol) at room temperature. The mixture was stirred at room temperature for 14 hrs. The solvent was evaporated and the residue was diluted with water (50 mL). The aqueous phase was extracted with ethyl acetate (2×50 mL). The combined extracts were washed with saturated aqueous sodium chloride solution (50 mL), dried over anhydrous magnesium sulfate, filtered and concentrated in vacuo to afford 6-hydroxy-7-methoxy-1-(3-ethoxy-benzyl)-1,2-dihydro-isoquinoline-4-carbaldehyde (660 mg, 88% yield). The crude product was used without further purification.

To a stirred solution of 6-hydroxy-7-methoxy-1-(3-ethoxy-benzyl)-1,2-dihydro-isoquinoline-4-carbaldehyde (660 mg, 1.95 mmol) in chloroform (30 mL) was addend manganese (IV) oxide (1.99 mg, 19.5 mmol). The reaction mixture was stirred at room temperature for 15 hrs, filtered through a celite® pad, and washed with chloroform. The filtrate was concentrated in vacuo to afford 6-hydroxy-7-methoxy-1-(3-ethoxy-benzyl)-isoquinoline-4-carbaldehyde (600 mg, 89% yield). The crude product was used without further purification.

To a stirred solution of 6-hydroxy-7-methoxy-1-(3-ethoxy-benzyl)-isoquinoline-4-carbaldehyde (60 g, 0.17 mmol) in N,N-dimethylformamide (2 mL) was added potassium carbonate (234 mg, 1.70 mmol) and 1-bromo-2-ethoxy-ethane (0.095 mL, 0.85 mmol) at room temperature. The reaction mixture was heated 85° C. for 2 hrs. The solvent was evaporated and the residue was purified on a flash chromatography (Merck Silica gel 60, 70–230 mesh, 50% ethyl acetate/hexane) to afford product 1-(3-ethoxy-benzyl)-6-(2-ethoxy-ethoxy)-7-methoxy-isoquinoline-4-carbaldehyde as a colorless oil (61 mg, 88% yield).

To a stirred solution of 1-(3-ethoxy-benzyl)-6-(2-ethoxy-ethoxy)-7-methoxy-isoquinoline-4-carbaldehyde (61 mg, 0.15 mmol) was added selenium dioxide (132 mg, 1.20 mmol). The reaction mixture was heated at 120° C. for 1 h. The solvent was evaporated and the residue was diluted with dichloromethane (30 mL). The organic layer was washed with saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 1-(3-ethoxy-benzoyl)-6-(2-ethoxy-ethoxy)-7-methoxy-isoquinoline-4-carbaldehyde as a major product (60 mg, 95% yield).

To a stirred solution of 6-(3-ethoxy-benzoyl)-7-methoxy-1-(3-ethoxy-benzoyl)-isoquinoline-4-carbaldehyde (60 mg, 0.14 mmol) in t-butanol (0.5 mL) and water (0.5 mL) solution was added sodium dihydrogenphosphate monohydrate (78 mg, 0.56 mmol), 2-methyl-2-butene (0.095 mL, 0.85 mmol) and sodium chlorite (77.0 mg, 0.85 mmol) at room temperature. The reaction suspension was then stirred at room temperature for 14 hrs. The resulting two-phase mixture was partitioned between dichloromethane and water and acidified to pH=3 by addition of acetic acid. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in ethyl acetate to afford 1-(3-ethoxy-benzoyl)-6-(2-ethoxy-ethoxy)-7-methoxy-isoquinoline-4-carboxylic acid (22 mg, 36% yield) as a light brown solid. HR-MS m/e calcd for $C_{24}H_{25}N_1O_7$ (M–H$^+$) 440.1704, found 440.1708; $^1$H NMR (300 MHz) compatible.

Example 77

1-(3-Ethoxy-benzoyl)-6-(2-hydroxy-ethoxy)-7-methoxy-isoquinoline-4-carboxylic acid

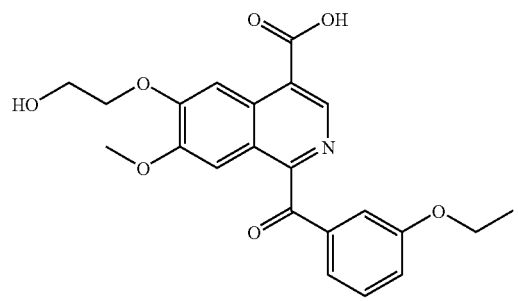

4-Benzyloxy-3-methoxybenzyladehyde (9.71 g, 40 mmol), aminoacetaldehyde dimethylacetal (2.97 mL, 40 mmol) and trimethylorthoformate (8 mL) were mixed in 1,2-dichloroethane (100 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Ethoxybenzylchloride (13.6 g, 80 mmol) was dissolved in diethyl ether (100 mL) and magnesium metal (2.04 g, 84 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (13.2 g, 40 mmol) in diethyl ether (60 mL) was added dropwise (a precipitate forms with each drop). After addition was complete, the resulting suspension was heated at reflux for 2 hours. The mixture was cooled in an ice-bath and saturated aqueous ammonium chloride solution (100 mL) was carefully added dropwise. The mixture was stirred at 0° C. for 15 minutes and then room temperature for 1 h. Water (80 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-ethoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-ethoxy-phenyl)-ethyl]-(2,2-dimethoxy-ethyl)-amine (22.2 g, 40 mmol) in tetrahydrofuran (120 mL) and water (60 mL) was added potassium carbonate (9.93 g, 72 mmol) and ethyl chloroformate (4.2 mL, 44 mmol) dropwise.). The mixture was stirred for 1 h at room temperature. The mixture was diluted with diethyl ether (100 mL), and the organic layer was separated. The aqueous phase was extracted with ethyl acetate (3×100 mL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-ethoxy-phenyl)-2-phenyl-ethyl]-(2,2-dimethoxy-ethyl)-carbamic acid ethyl ester (12 g, 56% yield in three steps) as a colorless oil.

To a stirred solution of [1-(4-benzyloxy-3-ethoxy-phenyl)-2-phenyl-ethyl]-(2,2-dimethoxy-ethyl)-carbamic acid ethyl ester (12.0 g, 28 mmol) in ethyl acetate (120 mL) and ethanol (60 mL) solution was added 10% Pd/C (2.4 g). The mixture was hydrogenated at 1 atm for 15 hrs. The solution was filtered through a Celite® plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (10 g, 80% yield).

To a stirred solution of (2,2-dimethoxy-ethyl)-[1-(4-hydroxy-3-ethoxy-phenyl)-2-(3-methoxy-phenyl)-ethyl-carbamic acid ethyl ester (10 g, 22 mmol) in acetone (300 mL) was added 6N aqueous hydrogen chloride solution (40 mL) at 0° C. The reaction mixture was stirred at room temperature for 15 hrs. The mixture was diluted with water. The solvent was evaporated and the aqueous layer was extracted with ethyl acetate (3×100 mL). The combined extracts were washed with saturated aqueous sodium chloride solution (80 mL), dried over anhydrous magnesium sulfate, filtered and concentrated in vacuo to afford 6-hydroxy-7-methoxy-1-(3-ethoxy-benzyl)-1H-isoquinoline-2-carboxylic acid ethyl ester. The crude product was used without further purification.

To a stirred solution of 6-hydroxy-7-methoxy-1-(3-ethoxy-benzyl)-1H-isoquinoline-2-carboxylic acid ethyl ester (6 g, 0.59 mmol) in pyridine (112 mL) was added acetic anhydride (56 mL). The reaction mixture was stirred at room temperature for 15 hrs. The mixture was concentrated in vacuo to afford 6-acetoxy-7-methoxy-1-(3-ethoxy-benzyl)-1H-isoquinoline-2-carboxylic acid ethyl ester. The crude product was used without further purification.

To anhydrous N,N-dimethylformamide (3.46 mL, 43.5 mmol) at 0° C. was added phosphorus oxychloride (1.83 mL, 19.2 mmol) dropwise. The mixture was warmed to room temperature and stirred for 30 minutes. The mixture was cooled in an ice-bath, and 6-acetoxy-7-methoxy-1-(3-ethoxy-benzyl)-1H-isoquinoline-2-carboxylic acid ethyl ester (3.7 mg, 8.70 mmol) in dichloromethane (8 mL) was added dropwise. After addition was complete, the mixture was heated on an oil bath for 4 hrs at 80° C. The mixture was cooled to 0° C. and a solution of potassium acetate (5.26 g, 52.2 mmol) in water (10 mL) was added slowly. The mixture was then heated at 80° C. for 20 minutes. The mixture was cooled, poured into water and diluted with dichloromethane (60 mL). The organic layer was washed water (2×80 mL), saturated aqueous sodium bicarbonate solution (50 mL), saturated aqueous sodium chloride solution (50 mL), dried over anhydrous magnesium sulfate, filtered and concentrated in vacuo to afford a crude oil. Flash chromatography (Merck Silica gel 60, 70–230 mesh, 20% ethyl acetate/hexane) afforded 6-acetoxy-1-(3-ethoxy-benzyl)-4-formyl-7-methoxy-1H-isoquinoline-2-carboxylic acid ethyl ester as a colorless oil (1.0 g, 25% yield).

To a solution of 6-acetoxy-1-(3-ethoxy-benzyl)-4-formyl-7-methoxy-1H-isoquinoline-2-carboxylic acid ethyl ester (1.0 g, 2.20 mmol) in methanol (50 mL) was added powdered potassium hydroxide (741 mg, 11.1 mmol) at room temperature. The mixture was stirred at room temperature for 14 hrs. The solvent was evaporated and the residue was diluted with water (50 mL). The aqueous phase was extracted with ethyl acetate (2×50 mL). The combined extracts were washed with saturated aqueous sodium chloride solution (50 mL), dried over anhydrous magnesium sulfate, filtered and concentrated in vacuo to afford 6-hydroxy-7-methoxy-1-(3-ethoxy-benzyl)-1,2-dihydro-isoquinoline-4-carbaldehyde (660 mg, 88% yield). The crude product was used without further purification.

To a stirred solution of 6-hydroxy-7-methoxy-1-(3-ethoxy-benzyl)-1,2-dihydro-isoquinoline-4-carbaldehyde (660 mg, 1.95 mmol) in chloroform (30 mL) was addend manganese (IV) oxide (1.99 mg, 19.5 mmol). The reaction mixture was stirred at room temperature for 15 hrs, filtered through a celite® pad, and washed with chloroform. The filtrate was concentrated in vacuo to afford 6-hydroxy-7-methoxy-1-(3-ethoxy-benzyl)-isoquinoline-4-carbaldehyde (600 mg, 89% yield). The crude product was used without further purification.

To a stirred solution of 6-hydroxy-7-methoxy-1-(3-ethoxy-benzyl)-isoquinoline-4-carbaldehyde (90 mg, 0.255 mmol) in N,N-dimethylformamide (2 mL) was added potassium carbonate (234 mg, 2.55 mmol) and 2-bromoethanol (0.090 mL, 1.27 mmol) at room temperature. The reaction mixture was heated 85° C. for 2 hrs. The solvent was evaporated and the residue was purified on a flash chromatography (Merck Silica gel 60, 70–230 mesh, 50% ethyl acetate/hexane) to afford product 1-(3-ethoxy-benzyl)-6-(2-hydroxy-ethoxy)-7-methoxy-isoquinoline-4-carbaldehyde as a colorless oil (50 mg, 52% yield).

To a stirred solution of 1-(3-ethoxy-benzyl)-6-(2-hydroxy-ethoxy)-7-methoxy-isoquinoline-4-carbaldehyde (50 mg, 0.13 mmol) was added selenium dioxide (146 mg, 1.30 mmol). The reaction mixture was heated at 120° C. for 1 hr. The solvent was evaporated and the residue was diluted with dichloromethane (30 mL). The organic layer was washed with saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 1-(3-ethoxy-benzoyl)-6-(2-hydroxy-ethoxy)-7-methoxy-isoquinoline-4-carbaldehyde as a major product (52 mg, 99% yield).

To a stirred solution of 1-(3-ethoxy-benzoyl)-6-(2-hydroxy-ethoxy)-7-methoxy-isoquinoline-4-carbaldehyde (70 mg, 0.17 mmol) in t-butanol (1 mL) and water (1 mL) solution was added sodium dihydrogenphosphate monohydrate (97 mg, 0.71 mmol), 2-methyl-2-butene (0.12 mL, 1.06 mmol) and sodium chlorite (98.0 mg, 1.06 mmol) at room temperature. The reaction suspension was then stirred at room temperature for 14 hrs. The resulting two-phase mixture was partitioned between dichloromethane and water and acidified to pH=3 by addition of acetic acid. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in ethyl acetate to afford 1-(3-ethoxy-benzoyl)-6-(2-hydroxy-ethoxy)-7-methoxy-isoquinoline-4-carboxylic acid (40 mg, 57% yield) as a light yellow solid. HR-MS m/e calcd for $C_{24}H_{25}N_1O_7$ (M–H$^+$) 412.1391, found 412.1394; $^1$H NMR (300 MHz) compatible.

Example 78

1-(3-Ethoxy-benzoyl)-6-isopropoxy-7-methoxy-isoquinoline-4-carboxylic acid

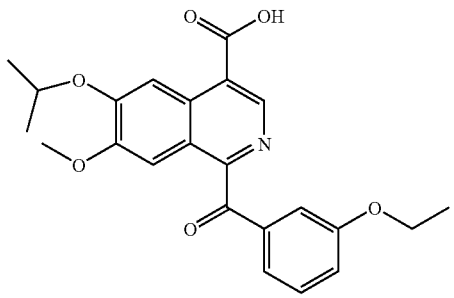

4-Benzyloxy-3-methoxybenzyladehyde (9.71 g, 40 mmol), aminoacetaldehyde dimethylacetal (2.97 mL, 40 mmol) and trimethylorthoformate (8 mL) were mixed in 1,2-dichloroethane (100 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Ethoxybenzylchloride (13.6 g, 80 mmol) was dissolved in diethyl ether (100 mL) and magnesium metal (2.04 g, 84 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (13.2 g, 40 mmol) in diethyl ether (60 mL) was added dropwise (a precipitate forms with each drop). After addition was complete, the resulting suspension was heated at reflux for 2 hours. The mixture was cooled in an ice-bath and saturated aqueous ammonium chloride solution (100 mL) was carefully added dropwise. The mixture was stirred at 0° C. for 15 minutes and then room temperature for 1 h. Water (80 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-ethoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-ethoxy-phenyl)-ethyl]-(2,2-dimethoxy-ethyl)-amine (22.2 g, 40 mmol) in tetrahydrofuran (120 mL) and water (60 mL) was added potassium carbonate (9.93 g, 72 mmol) and ethyl chloroformate (4.2 mL, 44 mmol) dropwise.). The mixture was stirred for 1 h at room temperature. The mixture was diluted with diethyl ether (100 mL), and the organic layer was separated. The aqueous phase was extracted with ethyl acetate (3×100 mL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-ethoxy-phenyl)-2-phenyl-ethyl]-(2,2-dimethoxy-ethyl)-carbamic acid ethyl ester (12 g, 56% yield in three steps) as a colorless oil.

To a stirred solution of [1-(4-benzyloxy-3-ethoxy-phenyl)-2-phenyl-ethyl]-(2,2-dimethoxy-ethyl)-carbamic acid ethyl ester (12.0 g, 28 mmol) in ethyl acetate (120 mL) and ethanol (60 mL) solution was added 10% Pd/C (2.4 g). The mixture was hydrogenated at 1 atm for 15 hrs. The solution was filtered through a Celite plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (10 g, 80% yield).

To a stirred solution of (2,2-dimethoxy-ethyl)-[1-(4-hydroxy-3-ethoxy-phenyl)-2-(3-methoxy-phenyl)-ethyl-carbamic acid ethyl ester (10 g, 22 mmol) in acetone (300 mL) was added 6N aqueous hydrogen chloride solution (40 m]L) at 0° C. The reaction mixture was stirred at room temperature for 15 hrs. The mixture was diluted with water. The solvent was evaporated and the aqueous layer was extracted with ethyl acetate (3×100 mL). The combined extracts were washed with saturated aqueous sodium chloride solution (80 mL), dried over anhydrous magnesium sulfate, filtered and concentrated in vacuo to afford 6-hydroxy-7-methoxy-1-(3-ethoxy-benzyl)-1H-isoquinoline-2-carboxylic acid ethyl ester. The crude product was used without further purification.

To a stirred solution of 6-hydroxy-7-methoxy-1-(3-ethoxy-benzyl)-1H-isoquinoline-2-carboxylic acid ethyl ester (6 g, 0.59 mmol) in pyridine (112 mL) was added acetic anhydride (56 mL). The reaction mixture was stirred at room temperature for 15 hrs. The mixture was concentrated in vacuo to afford 6-acetoxy-7-methoxy-1-(3-ethoxy-benzyl)-1H-isoquinoline-2-carboxylic acid ethyl ester. The crude product was used without further purification.

To anhydrous N,N-dimethylformamide (3.46 mL, 43.5 mmol) at 0° C. was added phosphorus oxychloride (1.83 mL, 19.2 mmol) dropwise. The mixture was warmed to room temperature and stirred for 30 minutes. The mixture was cooled in an ice-bath, and 6-acetoxy-7-methoxy-1-(3-ethoxy-benzyl)-1H-isoquinoline-2-carboxylic acid ethyl ester (3.7 mg, 8.70 mmol) in dichloromethane (8 mL) was added dropwise. After addition was complete, the mixture was heated on an oil bath for 4 hrs at 80° C. The mixture was cooled to 0° C. and a solution of potassium acetate (5.26 g, 52.2 mmol) in water (10 mL) was added slowly. The mixture was then heated at 80° C. for 20 minutes. The mixture was cooled, poured into water and diluted with dichloromethane (60 mL). The organic layer was washed water (2×80 mL), saturated aqueous sodium bicarbonate solution (50 mL), saturated aqueous sodium chloride solution (50 mL), dried over anhydrous magnesium sulfate, filtered and concentrated in vacuo to afford a crude oil. Flash chromatography (Merck Silica gel 60, 70–230 mesh, 20% ethyl acetate/hexane) afforded 6-acetoxy-1-(3-ethoxy-benzyl)-4-formyl-7-methoxy-1H-isoquinoline-2-carboxylic acid ethyl ester as a colorless oil (1.0 g, 25% yield).

To a solution of 6-acetoxy-1-(3-ethoxy-benzyl)-4-formyl-7-methoxy-1H-isoquinoline-2-carboxylic acid ethyl ester (1.0 g, 2.20 mmol) in methanol (50 mL) was added powdered potassium hydroxide (741 mg, 11.1 mmol) at room temperature. The mixture was stirred at room temperature for 14 hrs. The solvent was evaporated and the residue was diluted with water (50 mL). The aqueous phase was extracted with ethyl acetate (2×50 mL). The combined extracts were washed with saturated aqueous sodium chloride solution (50 mL), dried over anhydrous magnesium sulfate, filtered and concentrated in vacuo to afford 6-hydroxy-7-methoxy-1-(3-ethoxy-benzyl)-1,2-dihydro-isoquinoline-4-carbaldehyde (660 mg, 88% yield). The crude product was used without further purification.

To a stirred solution of 6-hydroxy-7-methoxy-1-(3-ethoxy-benzyl)-1,2-dihydro-isoquinoline-4-carbaldehyde (660 mg, 1.95 mmol) in chloroform (30 mL) was addend manganese (IV) oxide (1.99 mg, 19.5 mmol). The reaction mixture was stirred at room temperature for 15 hrs, filtered through a celite® pad, and washed with chloroform. The filtrate was concentrated in vacuo to afford 6-hydroxy-7-methoxy-1-(3-ethoxy-benzyl)-isoquinoline-4-carbaldehyde (600 mg, 89% yield). The crude product was used without further purification.

To a stirred solution of 6-hydroxy-7-methoxy-1-(3-ethoxy-benzyl)-isoquinoline-4-carbaldehyde (60 mg, 0.17 mmol) in N,N-dimethylformamide (2 mL) was added potassium carbonate (235 mg, 1.70 mmol) and 2-iodopropane (0.085 mL, 0.85 mmol) at room temperature. The reaction mixture was heated 85° C. for 2 hrs. The solvent was evaporated and the residue was purified on a flash chromatography (Merck Silica gel 60, 70–230 mesh, 50% ethyl acetate/hexane) to afford product 1-(3-ethoxy-benzyl)-6-isopropoxy-7-methoxy-isoquinoline-4-carbaldehyde as a colorless oil. The crude product was used without further purification. To a stirred solution of 1-(3-ethoxy-benzyl)-6-isopropoxy-7-methoxy-isoquinoline-4-carbaldehyde in acetic acid (2 mL) was added selenium dioxide (189 mg, 1.70 mmol). The reaction mixture was heated at 120° C. for 1 hr. The solvent was evaporated and the residue was diluted with dichloromethane (30 mL). The organic layer was washed with saturated aqueous sodium bicarbonate solution (20 mL), saturated aqueous sodium chloride solution (20 mL), dried over anhydrous magnesium sulfate, filtered and concentrated in vacuo to afford a crude oil. Flash chromatography (Merck Silica gel 60, 70–230 mesh, 40% ethyl acetate/hexane) afforded 1-(3-ethoxy-benzoyl)-6-isopropoxy-7-methoxy-isoquinoline-4-carbaldehyde as a major product (31 mg, 46% yield).

To a stirred solution of 1-(3-ethoxy-benzoyl)-6-isopropoxy-7-methoxy-isoquinoline-4-carbaldehyde (31 mg, 0.079 mmol) in t-butanol (1 mL) and water (1 mL) solution was added sodium dihydrogenphosphate monohydrate (44 mg, 0.32 mmol), 2-methyl-2-butene (0.053 mL, 0.48 mmol) and sodium chlorite (43 mg, 0.48 mmol) at room temperature. The reaction suspension was then stirred at room temperature for 14 hrs. The resulting two-phase mixture was partitioned between dichloromethane and water and acidified to pH=3 by addition of acetic acid. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in ethyl acetate to afford 1-(3-ethoxy-benzoyl)-6-isopropoxy-7-methoxy-isoquinoline-4-carboxylic acid (8 mg, 23% yield) as a light yellow solid. HR-MS m/e calcd for $C_{23}H_{23}N_1O_6$ (M–H$^+$) 410.1598, found 410.1601; $^1$H NMR (300 MHz) compatible.

Example 79

1-(3-Ethoxy-benzoyl)-7-methoxy-6-(2-morpholin-4-yl-ethoxy)-isoquinoline-4-carboxylic acid hydrochloride

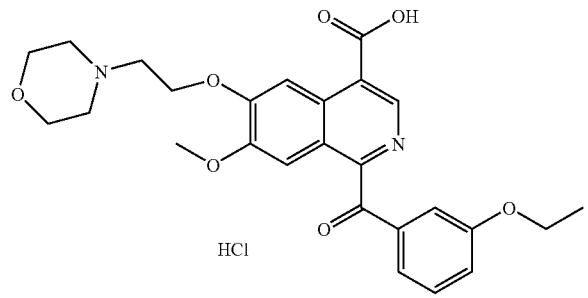

4-Benzyloxy-3-methoxybenzyladehyde (9.71 g, 40 mmol), aminoacetaldehyde dimethylacetal (2.97 mL, 40 mmol) and trimethylorthoformate (8 mL) were mixed in 1,2-dichloroethane (100 mL) and stirred at room temperature for 2 hrs. The solvent was removed in vacuo to afford (4-benzyloxy-3-methoxy-benzylidene)-(2,2-dimethoxy-ethyl)-amine as a light yellow solid which was used without further purification.

3-Ethoxybenzylchloride (13.6 g, 80 mmol) was dissolved in diethyl ether (100 mL) and magnesium metal (2.04 g, 84 mmol) was added without stirring. Several crystals of iodine were added to the magnesium "pile". When the reaction begins, stirring is started and external cooling is applied as necessary to maintain gentle refluxing. Once the initial reaction was complete, the mixture was refluxed for 1 h to complete the reaction. The resulting gray/green mixture was cooled in an ice-bath and (4-benzyloxy-3-methoxy-benzylidene)-(2,2-dimethoxy-ethyl)-amine (13.2 g, 40 mmol) in diethyl ether (60 mL) was added dropwise (a precipitate forms with each drop). After addition was complete, the resulting suspension was heated at reflux for 2 hours. The mixture was cooled in an ice-bath and saturated aqueous ammonium chloride solution (100 mL) was carefully added dropwise. The mixture was stirred at 0° C. for 15 minutes and then room temperature for 1 h. Water (80 mL) was added, and the mixture was filtered. The organic layer was separated, washed with water (50 mL), saturated aqueous sodium chloride solution (40 mL), dried over magnesium sulfate, filtered and concentrated in vacuo to afford [1-(4-benzyloxy-3-methoxy-phenyl)-2-(3-ethoxy-phenyl)-ethyl]-(2,2-dimethoxy-ethyl)-amine as a light tan solid which was used without further purification.

To a stirred solution of [1-(4-benzyloxy-3-methoxy-phenyl)-2-(3-ethoxy-phenyl)-ethyl]-(2,2-dimethoxy-ethyl)-amine (22.2 g, 40 mmol) in tetrahydrofuran (120 mL) and water (60 mL) was added potassium carbonate (9.93 g, 72 mmol) and ethyl chloroformate (4.2 mL, 44 mmol) dropwise.). The mixture was stirred for 1 h at room temperature. The mixture was diluted with diethyl ether (100 mL), and the organic layer was separated. The aqueous phase was extracted with ethyl acetate (3×100 μL) and the combined extracts were washed with saturated aqueous sodium chloride solution (100 mL), dried over anhydrous magnesium sulfate, filtered and concentrated in vacuo. Flash chromatography (Merck Silica gel 60, 70–230 mesh, 20% ethyl acetate/hexane) afforded [1-(4-benzyloxy-3-ethoxy-phenyl)-2-phenyl-ethyl]-(2,2-dimethoxy-ethyl)-carbamic acid ethyl ester (12 g, 56% yield in three steps) as a colorless oil.

To a stirred solution of [1-(4-benzyloxy-3-ethoxy-phenyl)-2-phenyl-ethyl]-(2,2-dimethoxy-ethyl)-carbamic acid ethyl ester (12.0 g, 28 mmol) in ethyl acetate (120 mL) and ethanol (60 mL) solution was added 10% Pd/C (2.4 g). The mixture was hydrogenated at 1 atm for 15 hrs. The solution was filtered through a Celite plug and evaporated to afford a crude oil. Flash chromatography (Merck Silica gel 60, 70–230 mesh, 50% ethyl acetate/hexane) afforded (2,2-dimethoxy-ethyl)-[1-(4-hydroxy-3-methoxy-phenyl)-2-(3-methoxy-phenyl)-ethyl-carbamic acid ethyl ester as a colorless oil. (10 g, 80% yield).

To a stirred solution of (2,2-dimethoxy-ethyl)-[1-(4-hydroxy-3-ethoxy-phenyl)-2-(3-methoxy-phenyl)-ethyl-carbamic acid ethyl ester (10 g, 22 mmol) in acetone (300 mL) was added 6N aqueous hydrogen chloride solution (40 mL) at 0° C. The reaction mixture was stirred at room temperature for 15 hrs. The mixture was diluted with water. The solvent was evaporated and the aqueous layer was extracted with ethyl acetate (3×100 mL). The combined extracts were washed with saturated aqueous sodium chloride solution (80 mL), dried over anhydrous magnesium sulfate, filtered and concentrated in vacuo to afford 6-hydroxy-7-methoxy-1-(3-ethoxy-benzyl)-1H-isoquinoline-2-carboxylic acid ethyl ester. The crude product was used without further purification.

To a stirred solution of 6-hydroxy-7-methoxy-1-(3-ethoxy-benzyl)-1H-isoquinoline-2-carboxylic acid ethyl ester (6 g, 0.59 mmol) in pyridine (112 mL) was added acetic anhydride (56 mL). The reaction mixture was stirred at room temperature for 15 hrs. The mixture was concentrated in vacuo to afford 6-acetoxy-7-methoxy-1-(3-ethoxy-benzyl)-1H-isoquinoline-2-carboxylic acid ethyl ester. The crude product was used without further purification.

To anhydrous N,N-dimethylformamide (3.46 mL, 43.5 mmol) at 0° C. was added phosphorus oxychloride (1.83 mL, 19.2 mmol) dropwise. The mixture was warmed to room temperature and stirred for 30 minutes. The mixture was cooled in an ice-bath, and 6-acetoxy-7-methoxy-1-(3-ethoxy-benzyl)-1H-isoquinoline-2-carboxylic acid ethyl ester (3.7 mg, 8.70 mmol) in dichloromethane (8 mL) was added dropwise. After addition was complete, the mixture was heated on an oil bath for 4 hrs at 80° C. The mixture was cooled to 0° C. and a solution of potassium acetate (5.26 g, 52.2 mmol) in water (10 mL) was added slowly. The mixture was then heated at 80° C. for 20 minutes. The mixture was cooled, poured into water and diluted with dichloromethane (60 mL). The organic layer was washed water (2×80 mL), saturated aqueous sodium bicarbonate solution (50 mL), saturated aqueous sodium chloride solution (50 mL), dried over anhydrous magnesium sulfate, filtered and concentrated in vacuo to afford a crude oil. Flash chromatography (Merck Silica gel 60, 70–230 mesh, 20% ethyl acetate/hexane) afforded 6-acetoxy-1-(3-ethoxy-benzyl)-4-formyl-7-methoxy-1H-isoquinoline-2-carboxylic acid ethyl ester as a colorless oil (1.0 g, 25% yield).

To a solution of 6-acetoxy-1-(3-ethoxy-benzyl)-4-formyl-7-methoxy-1H-isoquinoline-2-carboxylic acid ethyl ester (1.0 g, 2.20 mmol) in methanol (50 mL) was added powdered potassium hydroxide (741 mg, 11.1 mmol) at room temperature. The mixture was stirred at room temperature for 14 hrs. The solvent was evaporated and the residue was diluted with water (50 mL). The aqueous phase was extracted with ethyl acetate (2×50 mL). The combined extracts were washed with saturated aqueous sodium chloride solution (50 mL), dried over anhydrous magnesium sulfate, filtered and concentrated in vacuo to afford 6-hydroxy-7-methoxy-1-(3-ethoxy-benzyl)-1,2-dihydro-isoquinoline-4-carbaldehyde (660 mg, 88% yield). The crude product was used without further purification.

To a stirred solution of 6-hydroxy-7-methoxy-1-(3-ethoxy-benzyl)-1,2-dihydro-isoquinoline-4-carbaldehyde (660 mg, 1.95 mmol) in chloroform (30 μL) was addend manganese (IV) oxide (1.99 mg, 19.5 mmol). The reaction mixture was stirred at room temperature for 15 hrs, filtered through a celites pad, and washed with chloroform. The filtrate was concentrated in vacuo to afford 6-hydroxy-7-methoxy-1-(3-ethoxy-benzyl)-isoquinoline-4-carbaldehyde (600 mg, 89% yield). The crude product was used without further purification.

To a stirred solution of 6-hydroxy-7-methoxy-1-(3-ethoxy-benzyl)-isoquinoline-4-carbaldehyde (90 mg, 0.25 mmol) in N,N-dimethylformamide (2 mL) was added potassium carbonate (352 mg, 2.50 mmol) and 1,2-dibromoethane (0.129 μL, 1.25 mmol) at room temperature. The reaction mixture was heated 85° C. for 2 hrs. The solvent was evaporated and the residue was purified on a flash chromatography (Merck Silica gel 60, 70–230 mesh, 50% ethyl acetate/hexane) to afford product 1-(3-ethoxy-benzyl)-6-(2-bromo-ethoxy)-7-methoxy-isoquinoline-4-carbaldehyde as a colorless oil. The crude product was used without further purification. To a stirred solution of 1-(3-ethoxy-benzyl)-6-(2-bromo-ethoxy)-7-methoxy-isoquinoline-4-carbaldehyde in acetic acid (2 mL) was added selenium dioxide (278 mg, 2.50 mmol). The reaction mixture was heated at 120° C. for 1 hr. The solvent was evaporated and the residue was diluted with dichloromethane (30 mL). The organic layer was washed with saturated aqueous sodium bicarbonate solution (20 mL), saturated aqueous sodium chloride solution (20 μL), dried over anhydrous magnesium sulfate, filtered and concentrated in vacuo to afford a crude oil. Flash chromatography (Merck Silica gel 60, 70–230 mesh, 40% ethyl acetate/hexane) afforded 1-(3-ethoxy-benzoyl)-6-(2-bromo-ethoxy)-7-methoxy-isoquinoline-4-carbaldehyde as a major product (80 mg, 100% yield).

To a stirred solution of 1-(3-ethoxy-benzoyl)-6-(2-bromo-ethoxy)-7-methoxy-isoquinoline-4-carbaldehyde (85 mg, 0.19 mmol) in N,N dimethylformamide (2 mL) was added potassium carbonate (257 mg, 1.85 mmol) and morpholine (0.081 mL, 0.95 mmol) at room temperature. The reaction mixture was heated 85° C. for 2 hrs. The solvent was evaporated and the crude product, 1-(3-ethoxy-benzoyl)-6-(2-morpholin-4-yl-ethoxy)-7-methoxy-isoquinoline-4-carbaldehyde, was used without further purification.

To a stirred solution of 1-(3-ethoxy-benzoyl)-6-(2-morpholin-4-yl-ethoxy)-7-methoxy-isoquinoline-4-carbaldehyde (70 mg, 0.15 mmol) in t-butanol (1 mL) and water (1 mL) solution was added sodium dihydrogenphosphate monohydrate (83 mg, 0.60 mmol), 2-methyl-2-butene (0.102 mL, 0.90 mmol) and sodium chlorite (82 mg, 0.90 mmol) at room temperature. The reaction suspension was then stirred at room temperature for 14 hrs. The resulting two-phase mixture was partitioned between dichloromethane and water and acidified to pH=3 by addition of 1N aqueous hydrogen chloride. The aqueous phase was then extracted with dichloromethane (3×20 mL). The combined extracts were washed with saturated aqueous sodium chloride solution (30 mL), dried over anhydrous magnesium sulfate, filtered and concentrated in vacuo to afford a brown semi-solid oil. The crude product was recrystallized in ethyl acetate to afford 1-(3-ethoxy-benzoyl)-6-isopropoxy-7-methoxy-isoquinoline-4-carboxylic acid hydrochloride (12 mg, 16% yield) as a light brown solid. HR-MS m/e calcd for $C_{26}H_{28}N_2O_7$ (M−H$^+$) 481.1969, found 481.1974; $^1$H NMR (300 MHz) compatible.

Example 80

6,7-Dimethoxy-1-(3-methylsulfanyl-benzoyl)-isoquinoline-4-carboxylic acid; compound with trifluoroacetic acid

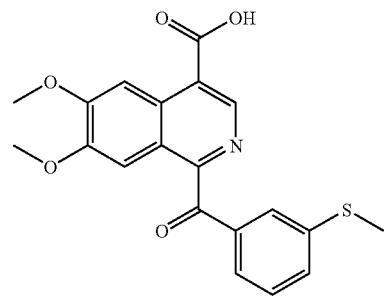

-continued

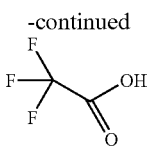

To a stirred solution of 3,4-dimethoxyphenyl acetonitrile (8.86 g, 50 mmol) in diethyl ether (150 mL) was added sodium methoxide (2.97 g, 55 mmol) and ethyl formate (4.04 mL, 50 mmol) in diethyl ether (50 mL) solution. The reaction mixture was stirred at room temperature for 24 hrs. A solid was precipitated. The mixture was filtered and the solid was collected and washed with diethyl ether. The solid was dissolved in water (50 mL). 10% acetic acid was then added dropwise to the solution. A white precipitation was formed and the mixture was filtered again. The while solid was washed with water and collected to afford 2-(3,4-dimethoxy-phenyl)-3-oxo-propionitrile (8.0 g, 78% yield).

To a stirred solution of 2-(3,4-dimethoxy-phenyl)-3-oxo-propionitrile (26 g, 127 mmol) in toluene ((275 mL) was added ethyl carbamate (11.3 g, 127 mmol) and concentrated sulfuric acid solution (2.0 mL). The reaction mixture was heated at 1110° C. with a Dean-Stark apparatus. The mixture was cooled and a solid was precipitated. The mixture was filtered and the solid was collected. The yellow solid was washed with diethyl ether to afford [2-cyano-2-(3,4-dimethoxy-phenyl)-vinyl]-carbamic acid ethyl ester (20 g, 57% yield).

To a stirred solution of [2-cyano-2-(3,4-dimethoxy-phenyl)-vinyl]-carbamic acid ethyl ester (8 g, 29.0 mmol) in diphenyl ether (70 mL) was added concentrated sulfuric acid (0.5 mL). The reaction mixture was heated at 230° C. for 4 hrs, cooled and diluted with diethyl ether (400 mL). A brown solid was precipitated, filtered, collected and washed with diethyl ether to afford 6,7-dimethoxy-1-oxo-1,2-dihydro-isoquinoline-4-carbonitrile. (3.5 g, 52% yield).

To a mixture of 6,7-dimethoxy-1-oxo-1,2-dihydro-isoquinoline-4-carbonitrile. (3.5 g, 15.2 mmol) and phosphorus oxybromide (30 g, 105 mmol) was added anisole (3.2 mL, 30.4 mmol). The reaction mixture was heated at 110° C. for 1 h. The excess phosphorus oxybromide was removed in vacuo. The mixture was then neutralized to pH=7 by addition of saturated aqueous sodium bicarbonate solution. The aqueous phase was extracted with dichloromethane (3×200 mL). The combined extracts were washed with saturated aqueous sodium chloride solution (100 mL), dried with anhydrous magnesium sulfate, filtered and concentrated in vacuo. The crude product was recrystallized from chloroform and diethyl ether to afford product 1-bromo-6,7-dimethoxy-isoquinoline-4-carbonitrile (1 g, 22.7% yield) as a white solid.

To a stirred solution of 1-bromo-6,7-dimethoxy-isoquinoline-4-carbonitrile (100 mg, 0.34 mmol), 3-methylsulfanyl-benzaldehyde (104 g, 0.68 mmol) and 1,3-dimethyl-1H-imidazolium iodide (153 mg, 0.68 mmol) in N,N-dimethylformamide (3 mL) was added sodium hydride (27.3 mg, 0.68 mmol). The mixture turned black instantly. The reaction mixture was stirred at room temperature for 1 h. Water was added and the aqueous phase was extracted with dichloromethane (3×20 mL). The combined extracts were washed with saturated sodium chloride solution (20 mL), dried over anhydrous magnesium sulfate, filtered and concentrated in vacuo. Flash chromatography (Merck Silica gel 60, 70–230 mesh, 20% ethyl acetate/hexane) afforded 6,7-dimethoxy-1-(3-methylsulfanyl-benzoyl)-isoquinoline-4-carbonitrile (70 mg, 57% yield) as a colorless oil.

To a stirred solution of 6,7-dimethoxy-1-(3-methylsulfanyl-benzoyl)-isoquinoline-4-carbonitrile (70 mg, 0.19 mmol) in ethanol (2 mL) was added 25% aqueous sodium hydroxide solution (1.2 mL). The reaction mixture was heated at 90° C. for 1 h and concentrated in vacuo. The mixture was acidified to pH=3 by addition of 6N aqueous hydrogen chloride solution. The aqueous phase was extracted with dichloromethane (3×15 mL). The combined extracts were washed with saturated aqueous sodium chloride solution (20 mL), dried with anhydrous magnesium sulfate, filtered and concentrated in vacuo. HPLC purification afforded 6,7-dimethoxy-1-(3-methylsulfanyl-benzoyl)-isoquinoline-4-carboxylic acid trifluoro-acetic acid (8 mg, 10% yield) as a light yellow solid. HR-MS m/e calcd for $C_{20}H_{17}N_1O_5S_1$ (M–H$^+$) 384.0900, found 384.0904; $^1$H NMR (300 MHz) compatible.

Example 81

[1-(3-sec-Butoxy-benzoyl)-6,7-dimethoxy-isoquinolin-4-yl]-acetic acid; 1:1 trifluoro-acetic acid

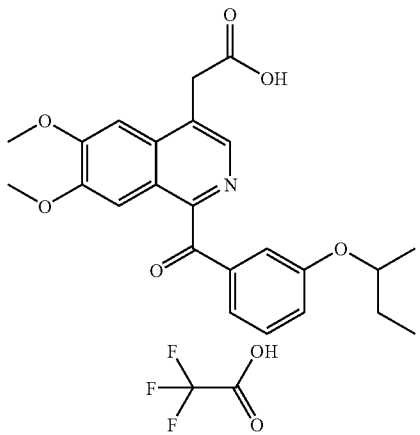

To methanol (300 mL) was added acetyl chloride (8.9 mL) dropwise in 10 minutes with stirring. 3-Hydroxyphenylacetic acid (25 g, 164 mmol) was added to the mixture at one time. The reaction mixture was stirred at room temperature for 15 hrs. The solvent was evaporated and the residue was concentrated in vacuo to afford 3-hydroxyphenyl acetic acid methyl ester (27.3 g, 99% yield) as a red oil.

To 3-hydroxyphenyl acetic acid methyl ester (27.3 g, 165 mmol) in acetone (200 mL) was added 2-iodobutane (55 mL, 478 mmol) and potassium carbonate (83 g, 601 mmol). The mixture was heated at 65° C. for 48 hrs and filtered through a Celite® pad. The filtrate was concentrated in vacuo and the residue was diluted with dichloromethane and water. The aqueous phase was extracted with dichloromethane (3×100 mL). The combined extracts were washed with saturated sodium chloride (50 mL), dried over anhydrous magnesium sulfate, filtered and concentrated in vacuo to afford (3-sec-butoxy-phenyl)-acetic acid methyl ester. To a solution of (3-sec-butoxy-phenyl)-acetic acid methyl ester in methanol (200 mL) was added 10N sodium hydroxide solution (50 mL). The reaction mixture was stirred at 60° C. for 4 hrs. The solvent was evaporated and the mixture was acidified to pH=3 by addition of 6N hydrogen chloride solution. The aqueous phase was extracted with dichloromethane (3×100 m]L). The combined extracts were washed with saturated aqueous sodium chloride solution (80 mL), dried over anhydrous magnesium sulfate, filtered and concentrated in vacuo to afford (3-sec-butoxy-phenyl) acetic acid (25 g, 73% yield) as a light brown oil.

Ethanol (13 mL, 225) was added to a suspension of sodium (3.6 g, 157 mmol) in toluene (125 mL) with stirring at 85° C. The reaction mixture turned to a slightly turbid white mixture. 3,4-Dimethoxy phenylacetonitrile (26.6 g, 150 mmol) was added to the reaction mixture at one time and the mixture was stirred at 85° C. for 30 minutes. Diethyl carbonate (20 mL, 16.5 mmol) was added to the mixture. The mixture was heated at 110° C. for 5 hrs. The solvent was evaporated and ice (250 g) was added. The mixture was neutralized to pH=7 by addition of acetic acid (20 mL). The aqueous phase was extracted with ethyl acetate (3×20 mL). The combined extracts were washed with saturated aqueous sodium chloride solution (50 mL), dried over anhydrous magnesium sulfate, filtered and concentrated in vacuo. Flash chromatography (Merck Silica gel 60, 70–230 mesh, 40% ethyl acetate/hexane) afforded cyano-(3,4-dimethoxy-phenyl)-acetic acid ethyl ester (18.1 g, 49% yield) as a colorless oil.

To a stirred solution of cyano-(3,4-dimethoxy-phenyl)-acetic acid ethyl ester (18.1 g, 72.6 mmol) in ethanol (100 mL) was added 10% palladium on activated carbon (3.6 g) and concentrated hydrogen chloride solution (6.6 mL). The reaction mixture was hydrogenated at 50 psi for 15 hrs. The mixture was filtered through a Celite® pad and the pad was washed with ethanol (500 mL). The filtrate was collected and concentrated in vacuo to afford 3-amino-2-(3,4-dimethoxy-phenyl)-propionic acid ethyl ester hydrochloride (15 g, 82% yield) as a white solid.

To a stirred solution 3-amino-2-(3,4-dimethoxy-phenyl)-propionic acid ethyl ester hydrochloride (6.5 g, 25.8 mmol) and (3-sec-butoxy-phenyl)-acetic acid (5.9 g, 28.4 mmol) in N,N-dimethylformamide (130 mL) was added O-benzotriazole-N,N,N',N'-tetramethyl-uronium hexaflurophosphate (HBTU) (11.8 g, 31.1 mmol) and diisopropylethylamine (14.8 mL, 85.0 mmol). The reaction mixture was stirred at room temperature for 15 hrs. The solvent was evaporated and the residue was diluted with ethyl acetate and saturated sodium bicarbonate solution. The aqueous phase was extracted with ethyl acetate (3×100 mL). The combined extracts were washed with 1N hydrogen chloride solution (50 mL), water (50 mL), saturated aqueous sodium chloride solution (50 mL), dried over anhydrous magnesium sulfate, filtered and concentrated in vacuo. Flash chromatography (Merck Silica gel 60, 70–230 mesh, 40% ethyl acetate/hexane, 100% ethyl acetate) afforded 3-[2-(3-sec-butoxy-phenyl)-acetylamino]-2-(3,4-dimethoxy-phenyl)-propionic acid ethyl ester (11.2 g, 98% yield) as a red oil.

To a stirred solution of 3-[2-(3-sec-butoxy-phenyl)-acetylamino]-2-(3,4-dimethoxy-phenyl)-propionic acid ethyl ester (11.2 g, 25.3 mmol) in dichloromethane (140 mL) was added phosphorus pentachloride (7.85 g, 37.7 mmol). The reaction mixture was stirred at room temperature for 15 hrs. The mixture was diluted with dichloromethane and washed with cold saturated aqueous sodium bicarbonate solution (50 mL) and saturated aqueous sodium chloride solution (50 mL). The aqueous phase was extracted with dichloromethane (3×50 mL). The combined extracts were dried over anhydrous magnesium sulfate, filtered and concentrated in vauo to afford 1-(3-sec-butoxy-benzyl)-6,7-dimethoxy-3,4-dihydro-isoquinoline-4-carboxylic acid ethyl ester (11.0 g, 99% yield) as a yellow oil. The crude product was used in the next step reaction without further purification.

To a stirred solution of 1-(3-sec-butoxy-benzyl)-6,7-dimethoxy-3,4-dihydro-isoquinoline-4-carboxylic acid ethyl ester (11.1 g, 25.9 mmol) in dichloromethane (10 mL) was added sulfur (2.5 g, 78.1 mmol). The solvent was evaporated to form a sulfur paste. The solid mixture was then heated at 155° C. for 1 h and dissolved in dichloromethane. Flash chromatography (Merck Silica gel 60, 70–230 mesh, 40% ethyl acetate/hexane) afforded 1-(3-sec-butoxy-benzyl)-6,7-dimethoxy-isoquinoline-4-carboxylic acid ethyl ester (2.67 g, 24% yield) as a yellow oil.

To a suspension of lithium aluminum hydride (309 mg, 7.73 mmol) in anhydrous tetrahydrofuran (15 mL) was added a solution of 1-(3-sec-butoxy-benzyl)-6,7-dimethoxy-isoquinoline-4-carboxylic acid ethyl ester (2.3 g, 5.44 mmol) in tetrahydrofuran (10 mL) dropwise at 0° C. The reaction mixture was stirred at 0° C. for 1 h and the excess lithium aluminum hydride was quenched with addition of water (1 mL), 15% aqueous sodium hydroxide solution (1 mL) and water (3 mL) at 0° C. The mixture was filtered through a Celite® pad and the filtrate was dried over anhydrous magnesium sulfate, filtered and concentrated in vacuo to afford [1-(3-sec-butoxy-benzyl)-6,7-dimethoxy-isoquinolin-4-yl]-methanol (2.1, 99% yield). The crude product was used without further purification.

To a stirred solution of [1-(3-sec-butoxy-benzyl)-6,7-dimethoxy-isoquinolin-4-yl]-methanol (2.7 g, 7.08 mmol) in dichloromethane (14 mL) was added triethylamine (3.0 mL, 21.2 mmol) and methanesulphonyl chloride (1.24 mL, 15.6 mmol) dropwise at 0° C. The reaction mixture was stirred at 0° C. for 15 minutes and lithium chloride (1.4 g, 33 mmol) was added at this temperature. The reaction mixture was stirred at room temperature for 15 hrs and diluted with dichloromethane (150 mL). The reaction mixture was washed with saturated aqueous sodium chloride solution (100 mL), dried over anhydrous magnesium sulfate, filtered and concentrated in vacuo to afford 1-(3-sec-butoxy-benzyl)-4-chloromethyl-6,7-dimethoxy-isoquinoline (2.1 g, 74% yield) as a brown oil. The crude product was used without further purification.

To a stirred solution of 1-(3-sec-butoxy-benzyl)-4-chloromethyl-6,7-dimethoxy-isoquinoline (950 mg, 2.38 mmol) in methyl sulfoxide (10 mL) was added sodium cyanide (582, 11.9 mmol). The reaction mixture was stirred at room temperature for 1 h and diluted with ethyl acetate and water. The aqueous phase was extracted with ethyl acetate (3×25 mL). The combined extracts were washed with saturated aqueous sodium chloride solution (20 mL), dried over anhydrous magnesium sulfate, filtered and concentrated in vacuo. Flash chromatography (Merck Silica gel 60, 70–230 mesh, 40% ethyl acetate/hexane) afforded [1-(3-sec-butoxy-benzyl)-6,7-dimethoxy-isoquinolin-4-yl]-acetonitrile (850 mg, 91% yield) as a colorless oil.

To a stirred solution of [1-(3-sec-butoxy-benzyl)-6,7-dimethoxy-isoquinolin-4-yl]-acetonitrile (250 mg, 0.64 mmol) in ethanol (4 mL) was added 10N sodium hydroxide solution (1 mL). The reaction mixture was stirred at 95° C. for 1 h. The solvent was evaporated and the residue was acidified to pH=3 by addition of 6N hydrogen chloride solution. The aqueous phase was then extracted with dichloromethane (3×20 mL). The combined extracts were washed with saturated aqueous sodium chloride solution (20 mL), dried with anhydrous magnesium sulfate, filtered and concentrated in vacuo to afford [1-(3-sec-butoxy-benzyl)-6,7- dimethoxy-isoquinolin-4-yl]-acetic acid (200 mg, 77% yield). The crude product was used without further purification.

To a stirred solution of [1-(3-sec-butoxy-benzyl)-6,7-dimethoxy-isoquinolin-4-yl]-acetic acid (200 mg, 0.49 mmol) in dichloromethane (4 Ml) was added 0.2N diazomethane in diethyl ether solution (6 mL). The reaction mixture was stirred at room temperature for 15 hrs. The solvent was evaporated to afford of [1-(3-sec-butoxy-benzyl)-6,7-dimethoxy-isoquinolin-4-yl]-acetic acid methyl ester (200 mg, 96% yield) as a light yellow oil. The crude product was used without further purification.

To a stirred solution of [1-(3-sec-butoxy-benzyl)-6,7-dimethoxy-isoquinolin-4-yl]-acetic acid methyl ester (200 mg, 0.47 mmol) in ethyl acetate (4 mL) was added selenium dioxide (65 mg, 0.59 mmol). The reaction mixture was heated at 85° C. for 1 hr. The solvent was evaporated and afford a crude product. Flash chromatography (Merck Silica gel 60, 70–230 mesh, 40% ethyl acetate/hexane) afforded [1-(3-sec-butoxy-benzoyl)-6,7-dimethoxy-isoquinolin-4-yl]-acetic acid methyl ester as a light brown oil (170 mg, 83% yield).

To a stirred solution of [1-(3-sec-butoxy-benzoyl)-6,7-dimethoxy-isoquinolin-4-yl]-acetic acid methyl ester (170 mg, 0.39 mmol) in methanol (3.5 mL) was added 1.0 N sodium hydroxide solution (2.0 mL, 1.56 mmol). The reaction mixture was heated at 90° C. for 1 h, concentrated in vacuo and diluted with water (3 mL). The aqueous phase was extracted with diethyl ether (1×10) and then acidified to pH=4 by addition of 1N hydrogen chloride solution. The aqueous phase was then extracted with dichloromethane (3×15 mL). The combined extracts were washed with saturated aqueous sodium chloride solution (20 mL), dried with anhydrous magnesium sulfate, filtered and concentrated in vacuo. HPLC purification afforded [1-(3-sec-butoxy-benzoyl)-6,7-dimethoxy-isoquinolin-4-yl]-acetic acid trfluoroacetic acid salt (59 mg, 36% yield) as a light yellow solid. HR-MS m/e calcd for $C_{24}H_{15}N_1O_6$ (M–H$^+$) 424.1755, found 424.1758; $^1$H NMR (300 MHz) compatible.

Example 82

Bromo-6,7-dimethoxy-isoquinoline-4-carbonitrile

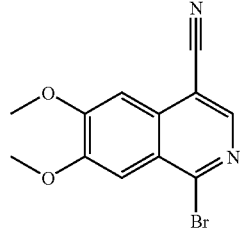

To the mixture of homoveratronitrile (17.7 g, 0.1 mol) and sodium methoxide (7.7 g, 0.11 mol) in ether (300 mL) was added the solution of ethyl formate (8.2 mL) in ether (100 mL). The mixture was stirred vigorously for 3 days. The precipitated solid was filtered, washed with ether. The solid was dissolved in water (100 mL). After adding 10% acetic acid to pH=3, the resulting precipitation was collected by filtration, washed with water and dried to afford 2-(3,4-Dimethoxy-phenyl)-3-oxo-propionitrile as white solid (19 g, 93%). LC-MS m/e calcd for $C_{11}H_{11}NO_3$ (MH$^+$) 206, found 206.

To the mixture of 2-(3,4-Dimethoxy-phenyl)-3-oxo-propionitrile (20.5 g, 0.1 mol), urethane (8.9 g, 0.1 mol) in toluene (400 mL) was added concentrated sulfuric acid (0.5 mL, 10 mmol). The mixture was refluxed and was concentrated by slow distillation to a volume to about 50 mL. The cooled mixture was filtered and the precipitate was washed with benzene and dried. Flash chromatography (Merck Silica gel 60, 70–230 mesh, 20% methylenechloride) afforded [2-Cyano-2-(3,4-dimethoxy-phenyl)-vinyl]-carbamic acid ethyl ester as a solid: LC-MS m/e calcd for $C_{14}H_{16}N_2O_4$ (MH$^+$) 277, found 277. $^1$H NMR (300 MHz) compatible.

Concentrated sulfuric acid (0.4 mL) was added the mixture of [2-Cyano-2-(3,4-dimethoxy-phenyl)-vinyl]-carbamic acid ethyl ester (33.5 g, 121 mmol) and diphenyl ether (230 mL). The mixture was heated to 230° C. for 6 hr. After cooling, ether was added to precipitate the solid. The resulting solid was collected by filtration, washed with ether and dried to afford 6,7-Dimethoxy-1-oxo-1,2-dihydro-isoquinoline-4-carbonitrile (20.7 g, 74.1%) as a brown solid which was used without further purification. LC-MS m/e calcd for $C_{12}H_{10}N_2O_3$ (MH$^+$) 231, found 231.

The mixture of 6,7-Dimethoxy-1-oxo-1,2-dihydro-isoquinoline-4-carbonitrile (8 g, 35 mmol) and phosphorus oxybromide (70 g, 244 mmol) in anisole (30 mL) was heated to 80° C. for 12 h. The solvent and excess POBr3 were removed by rotary evaporator. The resulting solid was washed with hexane and dried. The solid was slowly added to ice and the product was extracted with chloroform. The organic layer was washed with saturated aqueous sodium carbonate solution, saturated aqueous sodium chloride solution (20 mL), dried over magnesium sulfate, filtered and concentrated in vacuo to afford a brown solid. Flash chromatography (Merck Silica gel 60, 70–230 mesh, methylenechloride) afforded 1-Bromo-6,7-dimethoxy-isoquinoline-4-carbonitrile (7.5 g, 75%) as a brown solid. LC-MS m/e calcd for $C_{12}H_9BrN_2O_2$ (MH$^+$) 293, found 293.

Example 83

[6,7-Dimethoxy-4-(1H-tetrazol-5-yl)-isoquinolin-1-yl]-(3-ethoxy-phenyl)-methanone; compound, trifluoroacetic acid salt

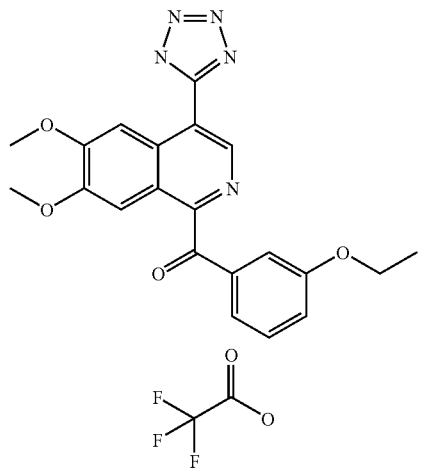

Sodium hydride (0.21 g, 5.1 mmol) was added to a stirred mixture of 1-Bromo-6,7-dimethoxy-isoquinoline-4-carbonitrile (1.0 g, 3.4 mmol), 3-Ethoxy-benzaldehyde (0.72 mL, 5.1 mmol), 1,3-dimethylimidazolium iodide (0.32 g, 1.36 mmol) in DMF (40 mL). The reaction mixture became dark color. After 30 min, water was added to the above mixture, and extracted with chloroform. The extract was washed with water, dried over sodium sulfate, filtered and concentrated in vacuo to afford a solid. Flash chromatography (Merck Silica gel 60, 70–230 mesh, methylenechloride) afforded 1-(3-Ethoxy-benzoyl)-6,7-dimethoxy-isoquinoline-4-carbonitrile (1.22 g, 98%) as a white solid. LC-MS m/e calcd for $C_{21}H_{18}N_2O_4$ (MH$^+$) 363, found 363.

The mixture of 1-(3-Ethoxy-benzoyl)-6,7-dimethoxy-isoquinoline-4-carbonitrile (50 mg, 140 mmol), sodium azide (20 mg, 310 mmol) and ammonium chloride (16.2 mg, 310 mmol) in DMF (2 mL) was stirred at 120° C. for 24 h. After removal of solvent, the crude product was purified directly by HPLC (Reverse C18, 10%-90% acetonitrile in water in 10 min) afforded our desired product [6,7-Dimethoxy-4-(1H-tetrazol-5-yl)-isoquinolin-1-yl]-(3-ethoxy-phenyl)-methanone with trifluoro-acetic (31 mg, 55%) as a light yellow solid. LC/MS m/e calcd for $C_{21}H_{19}N_5O_4$ (MH$^+$) 406, found 406.

Example 84

1-(3-Ethoxy-benzoyl)-6,7-dimethoxy-isoquinoline-4-carboxylic acid

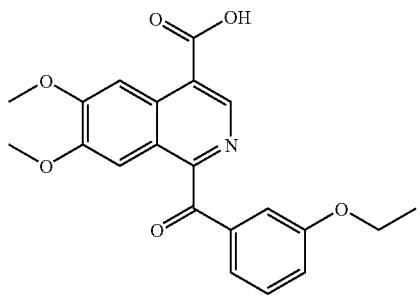

To the suspension of 1-(3-Ethoxy-benzoyl)-6,7-dimethoxy-isoquinoline-4-carbonitrile (from example 82) (2.0 g, 5.52 mmol) in methanol (120 mL) was added 25% of aqueous sodium hydroxide solution (30 mL, 190 mmol). The mixture was stirred at 100° C. for 12 h more. After cooling to room temperature, the reaction was adjusted to pH=2 with 2 N HCl solution. The product was extracted with chloroform (2×200 mL). The combined organic layers were washed with water (3×50 mL), dried over sodium sulfate, filtered, and concentrated in vacuo to give solid. Recrystallization from ethanol and ether to afford 1-(3-Ethoxy-benzoyl)-6,7-dimethoxy-isoquinoline-4-carboxylic acid yellow solid. LC/MS m/e calcd for $C_{21}H_{19}NO_6$ (MH$^+$) 382, Example 85A and B Compound A (3-Ethoxy-phenyl)-[1-(2-hydroxy-ethyl)-1H-tetrazol-5-yl]-6,7-dimethoxy-1-yl}-methanone, trifluoroacetic acid salt

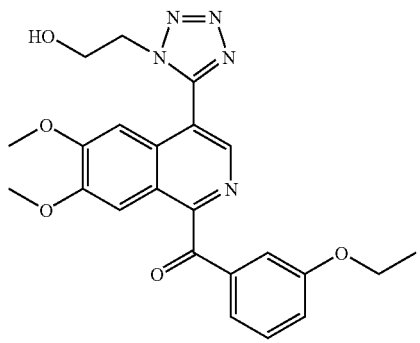

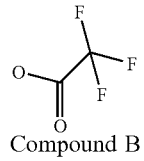

Compound B (3-Ethoxy-phenyl)-{4-[2-(2-hydroxy-ethyl)-1H-tetrazol-5-yl]-6,7-dimethoxy-isoquinolin-1-yl}-methanone, trifluoroacetic acid salt

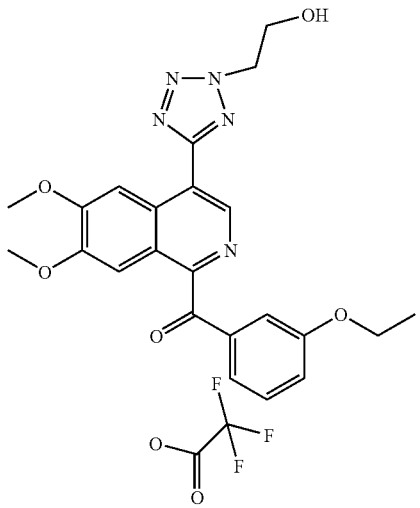

To the suspension of [6,7-Dimethoxy-4-(1H-tetrazol-5-yl)-isoquinolin-1-yl]-(3-ethoxy-phenyl)-methanone (100 mg, 0.25 mmol) and triethylamine (0.14 mL, 1 mmol) was added 2-iodoethanol (39 ul, 0.5 mmol) in acetonitrile (4 mL). The mixture was stirred at 80° C. for 3 h. After removal of solvent, the crude product was purified directly by HPLC (Reverse C18, acetonitrile in water in 10 min) afforded two isomers: 1-isomer, (3-Ethoxy-phenyl)-{4-[1-(2-hydroxy-ethyl)-1H-tetrazol-5-yl]-6,7-dimethoxy-isoquinolin-1-yl}-methanone with trifluoro-acetic acid (16 mg) as a light brown solid. LC/MS m/e calcd for $C_{23}H_{23}N_5O_5$ (MH$^+$) 450, found 450. $^1$H NMR (300 MHz) compatible; 2-isomer, (3-Ethoxy-phenyl)-{4-[2-(2-hydroxy-ethyl)-2H-tetrazol-5-yl]-6,7-dimethoxy-isoquinolin-1-yl}-methanone with trifluoro-acetic acid (9 mg) as a light brown solid; LC/MS m/e calcd for $C_{23}H_{23}N_5O_5$ (MH$^+$) 450, found 450. $^1$H NMR (300 MHz) compatible.

Example 86

[6,7-Dimethoxy-4-(1-methyl-1H-tetrazol-5-yl)-isoquinolin-1-yl]-(3-ethoxy-phenyl)-methanone, trifluoroacetic acid salt

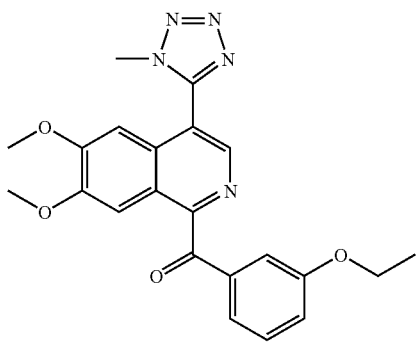

-continued

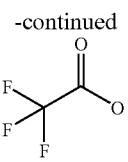

Similar to example 85 except that [6,7-Dimethoxy-4-(1H-tetrazol-5-yl)-isoquinolin-1-yl]-(3-ethoxy-phenyl)-methanone (100 mg, 0.25 mmol), triethylamine (0.14 mL, 1 mmol) was added iodomethane (31 ul, 0.5 mmol), acetonitrile (4 mL) were used. To give two isomers: 1-isomer, [6,7-dimethoxy-4-(1-methyl-1H-tetrazol-5-yl)-isoquinolin-1-yl]-(3-ethoxy-phenyl)-methanone with trifluoro-acetic acid (14 mg) as a solid. LC/MS m/e calcd for $C_{22}H_{21}N_5O_4$ (MH$^+$) 420, found 420. $^1$H NMR (300 MHz) compatible; 2-isomer, [6,7-Dimethoxy-4-(2-methyl-1H-tetrazol-5-yl)-isoquinolin-1-yl]-(3-ethoxy-phenyl)-methanone with trifluoro-acetic acid (15 mg) as a solid; LC/MS m/e calcd for $C_{22}H_{21}N_5O_4$ (MH$^+$) 420, found 420. $^1$H NMR (300 MHz) compatible.

Example 87

Compound A 1-(3-Ethoxy-benzoyl)-6,7-dimethoxy-isoquinoline-4-carboximidic acid ethyl ester, hydrochloride salt

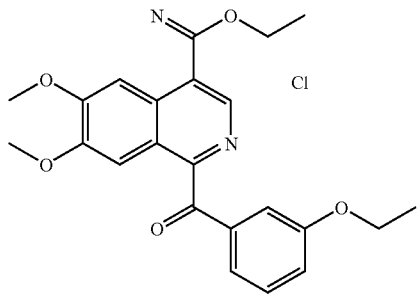

Compound B 1-(3-Ethoxy-benzoyl)-6,7-dimethoxy-isoquinoline-4-carboxylic acid amide, hydrochloride salt

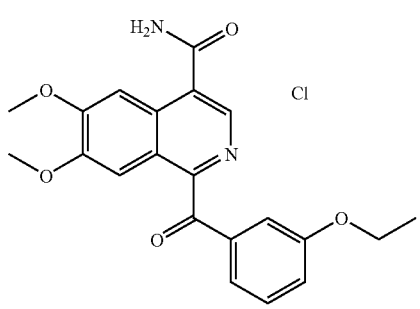

The dry hydrogen chloride gas was passed to the suspension of 1-(3-Ethoxy-benzoyl)-6,7-dimethoxy-isoquinoline-4-carbonitrile (200 mg, 0.55 mmol) in ethanol (5 mL) at 0° C. until the solution was saturated. The mixture was stirred at room temperature for 12 h. After removal of solvent and hydrogen chloride, ether was added to solidify the product. Flash chromatography (Merck Silica gel 60, 70–230 mesh, 0%–5% methanol in methylenechloride in 30 min) afforded two products: 1$^{st}$ product, 1-(3-Ethoxy-benzoyl)-6,7-dimethoxy-isoquinoline-4-carboximidic acid ethyl ester with hydrochloride as a solid. LC-MS m/e calcd for $C_{23}H_{24}N_2O_5$ (MH$^+$) 409, found 409. $^1$H NMR (300 MHz) compatible; 2$^{nd}$ product, 1-(3-Ethoxy-benzoyl)-6,7-dimethoxy-isoquinoline-4-carboxylic acid amide with hydrochloride as a solid. LC-MS m/e calcd for $C_{21}H_{20}N_2O_5$ (MH$^+$) 381, found 381. $^1$H NMR (300 MHz) compatible.

Example 88

1-(3-Ethoxy-benzoyl)-6,7-dimethoxy-isoquinoline-4-carboxamidine, trifluoroacetic acid salt

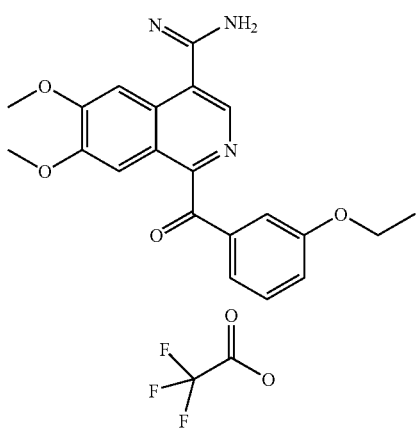

Dry ammonia gas was passed to the solution of 1-(3-Ethoxy-benzoyl)-6,7-dimethoxy-isoquinoline-4-carboximidic acid ethyl ester with hydrochloride (Example 87A) (224 mg, 0.55 mmol) in ethanol (10 mL) at 0° C. until the solution was saturated. The mixture was stirred at 65° C. for 12 h. After removal of solvent and ammonia, the crude product was purified directly by HPLC (Reverse C18, 5%–90% acetonitrile in water in 10 min) afforded 1-(3-Ethoxy-benzoyl)-6,7-dimethoxy-isoquinoline-4-carboxamidine with trifluoro-acetic acid (67.3 mg, 32%) as a brown solid. LC/MS m/e calcd for $C_{21}H_{21}N_3O_4$ (MH$^+$) 380, found 380. $^1$H NMR (300 MHz) compatible.

Example 89

4-(4,5-Dihydro-1H-imidazol-2-yl)-6,7-dimethoxy-isoquinolin-1-yl]-(3-ethoxy-phenyl)-methanone, trifluoroacetic acid salt

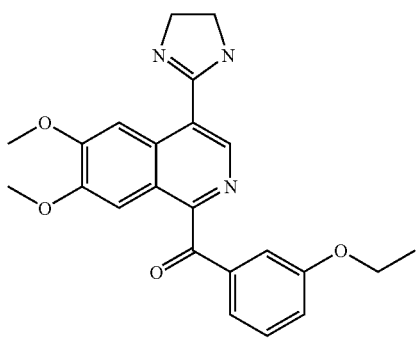

-continued

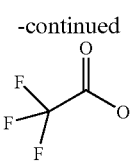

To the solution of 1-(3-Ethoxy-benzoyl)-6,7-dimethoxy-isoquinoline-4-carboximidic acid ethyl ester with hydrochloride (Example 87A) (25 mg, 0.06 mmol) in ethanol (10 mL) was added ethylenediamine (0.4 mL). The mixture was stirred at 65° C. for 12 h. LC-MS showed that N-(2-Amino-ethyl)-1-(3-ethoxy-benzoyl)-6,7-dimethoxy-isoquinoline-4-carboxamidine was formed. After removal of solvent, the residue was dissolved in ethanol (2 mL) and 2N HCl solution (2 mL) was added. The mixture was stirred for 12 h. After removal of solvent, the crude product was purified directly by HPLC (Reverse C18, 5%–90% acetonitrile in water in 10 min) afforded [4-(4,5-dihydro-1H-imidazol-2-yl)-6,7-dimethoxy-isoquinolin-1-yl]-(3-ethoxyphenyl)-methanone with trifluoro-acetic acid (7 mg) as a brown solid. LC/MS m/e calcd for $C_{23}H_{23}N_3O_4$ (MH$^+$) 406, found 406.

Example 90

(3-Ethoxy-phenyl)-[4-(imino-morpholin-4-yl-methyl)-6,7-dimethoxy-isoquinolin-1-yl]-methanone, trifluoroacetic acid salt

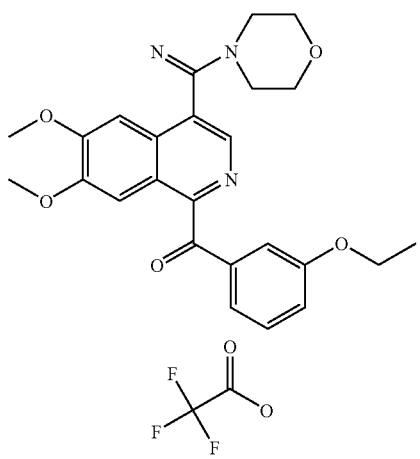

To the solution of 1-(3-Ethoxy-benzoyl)-6,7-dimethoxy-isoquinoline-4-carboximidic acid ethyl ester with hydrochloride (Example 87A) (100 mg, 0.25 mmol) in anhydrous ethanol (4 mL) was added morpholine (0.5 mL). The mixture was stirred at room temperature for 48 h. After removal of solvent, the crude product was purified directly by HPLC (Reverse C18, 5%–90% acetonitrile in water in 10 min) afforded 1-(3-Ethoxy-benzoyl)-6,7-dimethoxy-isoquinoline-4-carboxamidine with trifluoro-acetic acid (4.8 mg) as a brown solid. LC/MS m/e calcd for $C_{21}H_{21}N_3O_4$ (MH$^+$) 450, found 450.

Example 91

1-(3-Ethoxy-benzoyl)-6,7-dimethoxy-N,N-dimethyl-isoquinoline-4-carboxamidine, trifluoroacetic acid salt

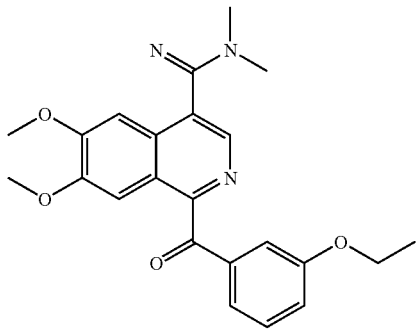

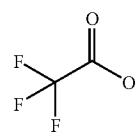

Similar to example 90 except that 2.0M of dimethyl amine in methanol (8 mL) was used instead of morpholine. LC/MS m/e calcd for $C_{23}H_{25}N_3O_4$ (MH$^+$) 408, found 408.

Example 92

1-(3-Ethoxy-benzoyl)-6,7-dimethoxy-N,N-dimethyl-isoquinoline-4-carboxamidine, trifluoroacetic acid salt

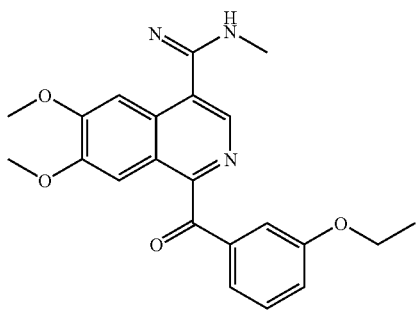

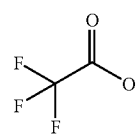

Similar to example 90 except that 2.0M of methyl amine in methanol (8 mL) was used instead of morpholine. LC/MS m/e calcd for $C_{22}H_{23}N_3O_4$ (MH$^+$) 394, found 394.

Example 93

[6,7-Dimethoxy-4-(1H-tetrazol-5-yl)-isoquinolin-1-yl]-[3-(2-hydroxy-ethoxy)-phenyl]-methanone, trifluoroacetic acid salt

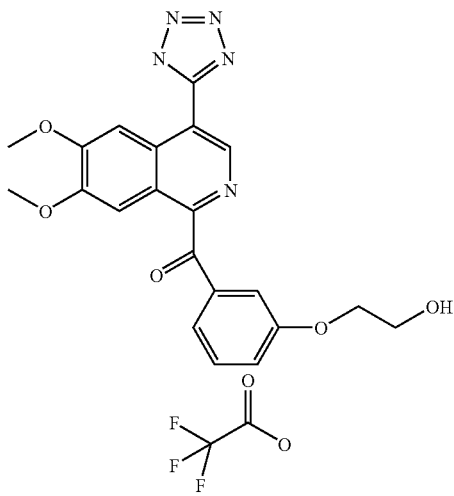

Sodium hydride (11 mg, 0.26 mmol) was added to a stirred mixture of 1-Bromo-6,7-dimethoxy-isoquinoline-4-carbonitrile (see example 1) (50 mg, 0.17 mmol), 3-(2-hydroxyethoxy)-benzaldehyde (43 mg, 0.26 mmol), 1,3-dimethylimidazolium iodide (16 mg, 0.26 mmol) in DMF (2 mL). The reaction mixture became dark color. After 1 h, water (4 mL) was added to the above mixture, and extracted with chloroform (6 mL). The extract was washed with water (4 mL), dried over sodium sulfate, filtered and concentrated in vacuo to afford a solid which was used without further purification.

The mixture of above solid (0.17 mmol), sodium azide (34 mg, 0.51 mmol) and ammonium chloride (27 mg, 0.51 mmol) in DMF (2 mL) was stirred at 100° C. for 24 h. After removal of solvent, the crude product was purified directly by HPLC (Reverse C18, 10%–90% acetonitrile in water in 10 min) afforded our desired product as a solid. LC/MS m/e calcd for $C_{21}H_{19}N_5O_5$ (MH$^+$) 422, found 422.

Example 94 rac-[3-(3-Azido-2-hydroxy-propoxy)-phenyl]-[6,7-dimethoxy-4-(1H-tetrazol-5-yl)-isoquinolin-1-yl]-methanone, trifluoroacetic acid salt

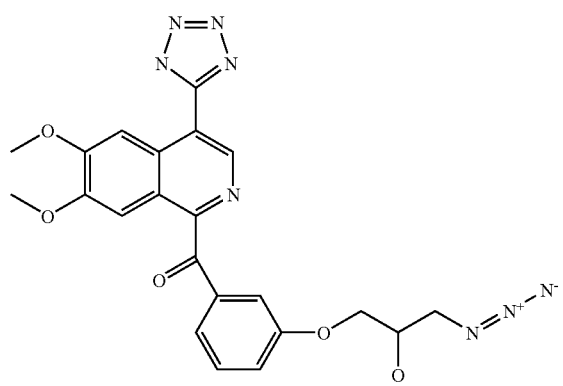

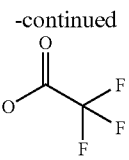

Similar to example 93 except that 3-(oxiranylmethoxy)-benzaldehyde (0.26 mmol) was used instead of 3-(2-hydroxyethoxy)-benzaldehyde (0.26 mmol) to afford the product as a solid. LC/MS m/e calcd for $C_{22}H_{20}N_8O_5$ (MH$^+$) 477 found 477.

Example 95

(3-Cyclopentyloxy-4-methoxy-phenyl)-[6,7-dimethoxy-4-(1H-tetrazol-5-yl)-isoquinolin-1-yl]-methanone, trifluoroacetic acid salt

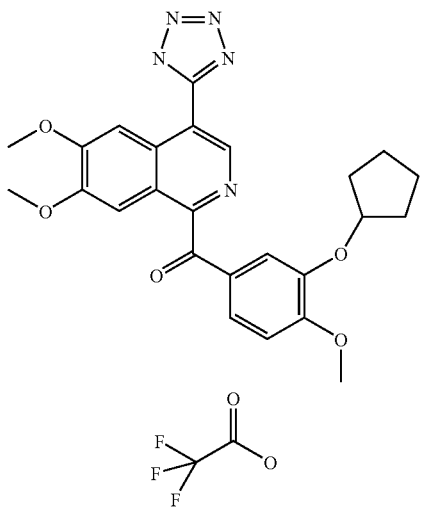

Similar to example 93 except that 3-Cyclopentyloxy-4-methoxy-benzaldehyde (0.26 mmol) was used instead of 3-(2-hydroxyethoxy)-benzaldehyde (0.26 mmol) to afford the product as a solid. LC/MS m/e calcd for $C_{25}H_{25}N_5O_5$ (MH$^+$) 476 found 476.

Example 96

[6,7-Dimethoxy-4-(1H-tetrazol-5-yl)-isoquinolin-1-yl]-(3-isopropoxy-phenyl)-methanone, trifluoroacetic acid salt

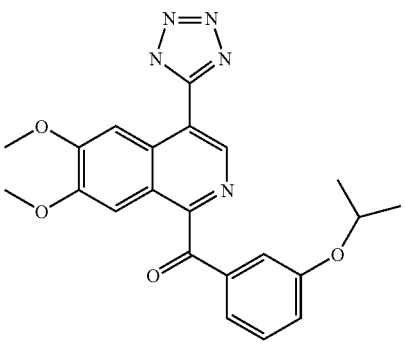

-continued

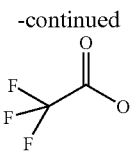

Similar to example 93 except that 3-Cyclopentyloxy-4-methoxy-benzaldehyde (0.26 mmol) was used instead of 3-(2-hydroxyethoxy)-benzaldehyde (0.26 mmol) to afford the product as a solid. LC/MS m/e calcd for $C_{22}H_{21}N_5O_4$ (MH$^+$) 420 found 420.

Example 97

(3-Allyloxy-phenyl)-[6,7-dimethoxy-4-(1H-tetrazol-5-yl)-isoquinolin-1-yl]-methanone, trifluoroacetic acid salt

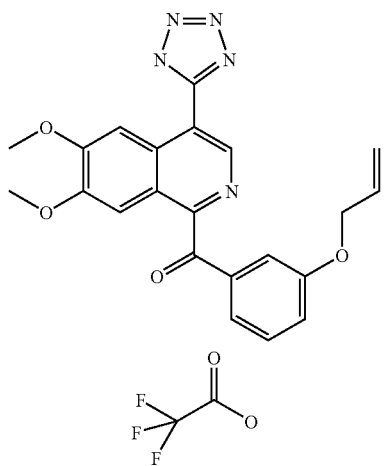

Similar to example 93 except that 3-allyloxy-benzaldehyde (0.26 mmol) was used instead of 3-(2-hydroxyethoxy)-benzaldehyde (0.26 mmol) to afford the product as a solid. LC/MS m/e calcd for $C_{22}H_{19}N_5O_4$ (MH$^+$) 418 found 418.

Example 98

(3-But-2-enyloxy-phenyl)-[6,7-dimethoxy-4-(1H-tetrazol-5-yl)-isoquinolin-1-yl]-methanone, trifluoroacetic acid salt

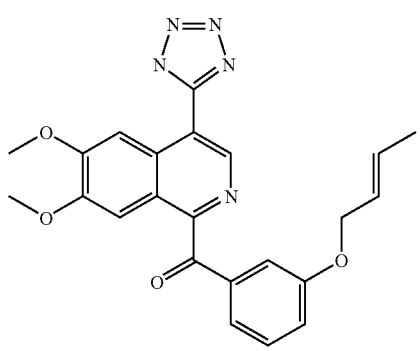

-continued

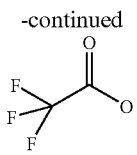

Similar to example 93 except that 3-But-2-enyloxy-benzaldehyde (0.26 mmol) was used instead of 3-(2-hydroxyethoxy)-benzaldehyde (0.26 mmol) to afford the product as a solid. LC/MS m/e calcd for $C_{23}H_{21}N_5O_4$ (MH$^+$) 432 found 432.

Example 99

(3-Cyclopentyloxy-phenyl)-[6,7-dimethoxy-4-(1H-tetrazol-5-yl)-isoquinolin-1-yl]-methanone, trifluoroacetic acid salt

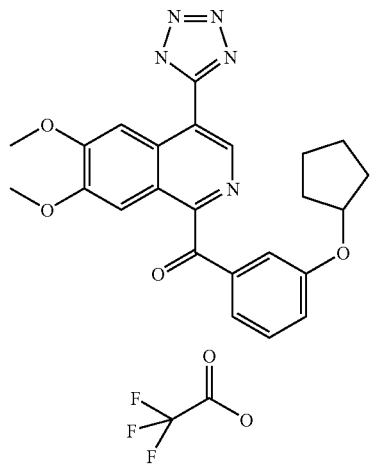

Similar to example 93 except that 3-Cyclopentyloxy-benzaldehyde (0.26 mmol) was used instead of 3-(2-hydroxyethoxy)-benzaldehyde (0.26 mmol) to afford the product as a solid. LC/MS m/e calcd for $C_{24}H_{23}N_5O_4$ (MH$^+$) 446 found 446.

Example 100

(3-Cyclopropylmethoxy-phenyl)-[6,7-dimethoxy-4-(1H-tetrazol-5-yl)-isoquinolin-1-yl]-methanone, trifluoroacetic acid salt

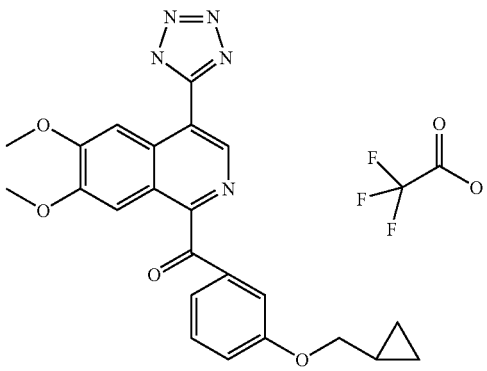

Similar to example 93 except that 3-Cyclopropyl-methoxy-benzaldehyde (0.26 mmol) was used instead of 3-(2-hydroxyethoxy)-benzaldehyde (0.26 mmol) to afford the product as a solid. LC/MS m/e calcd for $C_{23}H_{21}N_5O_4$ (MH$^+$) 432 found 432.

Example 101

(3-Cycloheptyloxy-phenyl)-[6,7-dimethoxy-4-(1H-tetrazol-5-yl)-isoquinolin-1-yl]-methanone, trifluoroacetic acid salt

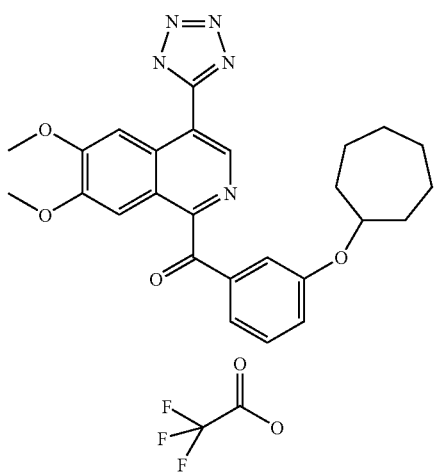

Similar to example 93 except that 3-Cycloheptyloxy-benzaldehyde (0.26 mmol) was used instead of 3-(2-hydroxyethoxy)-benzaldehyde (0.26 mmol) to afford the product as a solid. LC/MS m/e calcd for $C_{26}H_{27}N_5O_4$ (MH) 474 found 474.

Example 102

1-(3-hydroxyethoxy-benzoyl)-6,7-dimethoxy-isoquinoline-4-carboxylic acid, trifluoroacetic acid salt

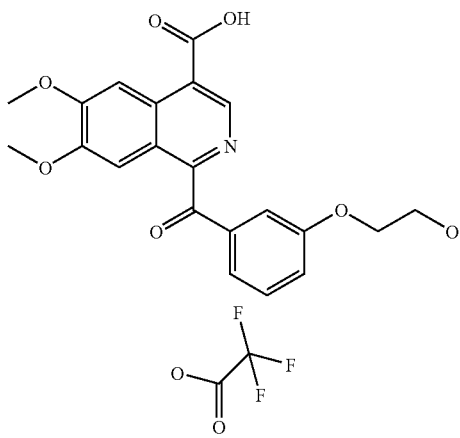

Sodium hydride (11 mg, 0.26 mmol) was added to a stirred mixture of 1-Bromo-6,7-dimethoxy-isoquinoline-4-carbonitrile (see example 82) (50 mg, 0.17 mmol), 3-(2-hydroxyethoxy)-benzaldehyde (43 mg, 0.26 mmol), 1,3-dimethylimidazolium iodide (16 mg, 0.26 mmol) in DMF (2 mL). The reaction mixture became dark color. After 1 h, water (4 mL) was added to the above mixture, and extracted with chloroform (6 mL). The extract was washed with water (4 mL), dried over sodium sulfate, filtered and concentrated in vacuo to afford a solid. Flash chromatography (Merck Silica gel 60, 70–230 mesh, 0–40% EtOAc in methylenechloride in 30 min) afforded 1-(3-hydroxyethoxy-benzoyl)-6,7-dimethoxy-isoquinoline-4-carbonitrile (31 mg, 41%) as a white solid. LC-MS m/e calcd for $C_{21}H_{18}N_2O_5$ (MH$^+$) 379, found 379.

To the suspension of 1-(3-hydroxyethoxy-benzoyl)-6,7-dimethoxy-isoquinoline-4-carbonitrile (31 mg, 0.082 mmol) in methanol (2 mL) was added 25% of aqueous sodium hydroxide solution (0.27 mL, 1.68 mmol). The mixture was stirred at 90° C. for 12 h. After cooling to room temperature, the reaction was adjusted to pH=2 with 2 N HCl solution. The product was extracted with chloroform (2×200 mL). The combined organic layers were washed with water (3×50 mL), dried over sodium sulfate, filtered, and concentrated in vacuo. The crude product was purified directly by HPLC (Reverse C18, 10%–90% acetonitrile in water in 10 min) afforded our desired product 1-(3-hydroxyethoxy-benzoyl)-6,7-dimethoxy-isoquinoline-4-carboxylic acid, trifluoroacetic acid salt (9 mg) as a solid. LC/MS m/e calcd for $C_{21}H_{19}NO_7$ (MH$^+$) 398, found 398.

Example 103

1-{3-[2-(2-Chloro-ethoxy)-ethoxy]-benzoyl}-6,7-dimethoxy-isoquinoline-4-carboxylic acid, trifluoroacetic acid salt

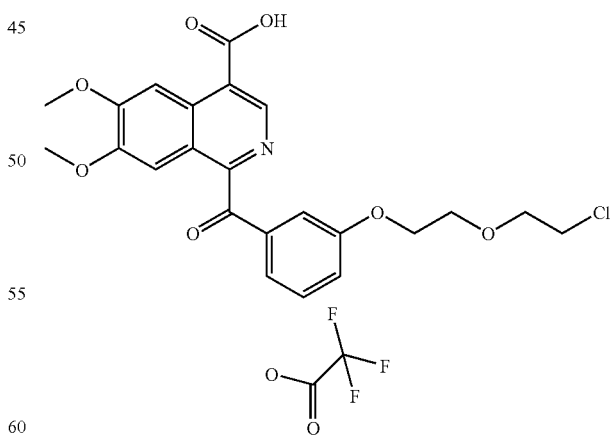

Similar to example 102 except that 3-[2-(2-Chloroethoxy)-ethoxy]-benzaldehyde (0.26 mmol) was used instead of 3-(2-hydroxyethoxy)-benzaldehyde (0.26 mmol) to afford the product as a solid. LC/MS m/e calcd for $C_{23}H_{22}ClNO_7$ (MH$^+$) 460 found 460.

Example 104

1-(3,5-Dimethoxy-benzoyl)-6,7-dimethoxy-isoquinoline-4-carboxylic acid, trifluoroacetic acid salt

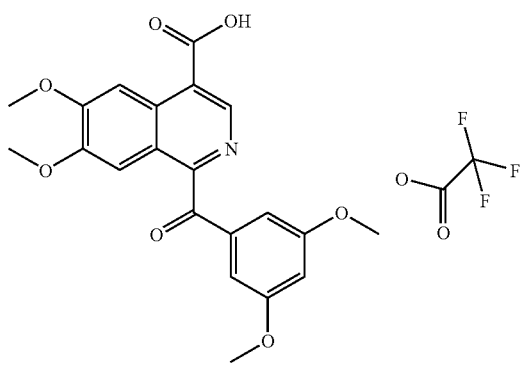

Similar to example 102 except that 3,5-dimethoxy-benzaldehyde (0.26 mmol) was used instead of 3-(2-hydroxy-ethoxy)-benzaldehyde (0.26 mmol) to afford the product as a solid. LC/MS m/e calcd for $C_{21}H_{19}NO_7$ (MH$^+$) 398 found 398.

Example 105

N-[1-(3-sec-Butoxy-benzoyl)-6,7-dimethoxy-isoquinolin-4-ylmethyl]-C,C,C-trifluoro-methane-sulfonamide

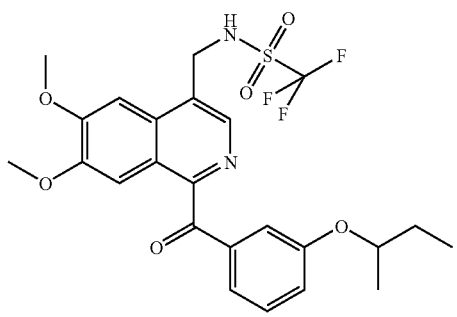

A solution of 1-(3-sec-butoxy-benzyl)-4-chloromethyl-6,7-dimethoxy-isoquinoline (1.0 g, 2.5 mmol) in dimethylsulfoxide (2 mL) was added to a solution of sodium azide (813 mg, 12.5 mmol) in dimethylsulfoxide (10 mL) prewarmed to 65° C. The solution was stirred at 65° C. for 1½ hrs. The reaction mixture was cooled and dissolved in ethyl acetate (100 mL). This ethyl acetate solution was washed with saturated aqueous sodium bicarbonate solution (2×20 mL), saturated aqueous sodium chloride solution (20 mL), dried over magnesium sulfate, filtered and concentrated in vacuo to afford 4-azidomethyl-1-(3-sec-butoxy-benzyl)-6,7-dimethoxy-isoquinoline (550 mg, 54%) as a light yellow solid which was used without further purification: APCI-MS m/e calcd for $C_{23}H_{26}N_4O_3$ (M+H$^+$) 407.5, found 406.9; $^1$H NMR (300 MHz) compatible.

A solution of 4-azidomethyl-1-(3-sec-butoxy-benzyl)-6,7-dimethoxy-isoquinoline (550 mg, 1.35 mmol), di-tert-butyl-dicarbonate (443 mg, 2.03 mmol) and glacial acetic acid (200 uL) in distilled tetrahydrofuran (15 mL) was hydrogenated with 50 mg 10% Pd/C at 40 psi for 3 hrs. The solution was filtered through a celite plug and evaporated. The residue was redissolved in ethyl acetate (40 mL) and washed with saturated aqueous ammonium chloride solution (2×10 mL), saturated aqueous sodium bicarbonate solution (10 mL), saturated aqueous sodium chloride solution (10 mL), dried over magnesium sulfate, filtered and concentrated in vacuo to afford [1-(3-sec-butoxy-benzyl)-6,7-dimethoxy-isoquinolin-4-ylmethyl]-carbamic acid tert-butyl ester (650 mg) as a light tan solid which was used without further purification: APCI-MS m/e calcd for $C_{28}H_{36}N_2O_5$ (M+H$^+$) 481.6, found 481.1; $^1$H NMR (300 MHz) compatible.

A solution of [1-(3-sec-butoxy-benzyl)-6,7-dimethoxy-isoquinolin-4-ylmethyl]-carbamic acid tert-butyl ester (645 mg, 1.35 mmol) and selenium dioxide (299 mg, 2.7 mmol) in ethyl acetate (30 mL) was refluxed for 1 hr. After cooling the slightly brown solution was filtered through a plug of silica gel. The plug was washed well with ethyl acetate and the combined filtrates were concentrated in vacuo to yield a light brown solid (670 mg). Flash chromatography (Merck Silica gel 60, 70–230 mesh, 20% ethyl acetate/hexane, 25% ethyl acetate/hexane, 30% ethyl acetate/hexane, and 35% ethyl acetate/hexane) afforded [1-(3-sec-butoxy-benzoyl)-6,7-dimethoxy-isoquinolin-4-ylmethyl]-carbamic acid tert-butyl ester (211 mg, 32%) as a light yellow solid: ES-MS m/e calcd for $C_{28}H_{36}N_2O_5$ (M+H$^+$) 495.6, found 495.3; $^1$H NMR (300 MHz) compatible.

[1-(3-sec-Butoxy-benzoyl)-6,7-dimethoxy-isoquinolin-4-ylmethyl]-carbamic acid tert-butyl ester (50.3 mg, 101 mmol) was dissolved in methylene chloride (1 mL). Trifluoroacetic acid (1 mL) was added and the solution was stirred at room temperature for 30 min. The mixture was evaporated in vacuo and twice evaporated from acetonitrile to yield a yellow oil. This oil was dissolved in acetonitrile (3 mL) and chilled in an ice bath under argon. To this solution was added triethyl amine (21 uL, 152 mmol) and trifluoromethanesulfonyl chloride (13 uL, 122 mmol). After 1 hr at ice bath temperature, additional portions of triethyl amine (41 uL, 300 mmol) and trifluoromethanesulfonyl chloride (26 uL, 145 mmol) were added. The solution was warmed to room temperature an stirred for 3 hrs. The reaction mixture was diluted with ether (25 mL) and washed with saturated aqueous sodium bicarbonate solution (3×7 mL), saturated aqueous ammonium chloride solution (3×7 mL), saturated aqueous sodium chloride solution (7 mL), dried over magnesium sulfate, filtered and concentrated in vacuo to afford 46.8 mg of a brown solid. Flash chromatography (Merck Silica gel 60, 70–230 mesh, 20% ethyl acetate/hexane, 30% ethyl acetate/hexane, and 40% ethyl acetate/hexane) afforded N-[1-(3-sec-butoxy-benzoyl)-6,7-dimethoxy-isoquinolin-4-ylmethyl]-C,C,C-trifluoro-methanesulfonamide (14.7 mg, 28%) as a light yellow solid: APCI-MS m/e calcd for $C_{24}H_{25}F_3N_2O_6S$ (M–H$^+$) 525.5, found 525.2; $^1$H NMR (300 MHz) compatible.

Example 106

6,7-Dimethoxy-1-(3-methoxy-benzoyl)-isoquinoline-4-carboxylic acid (2-morpholin-4-yl-ethyl)-amide; trifluoroacetate salt

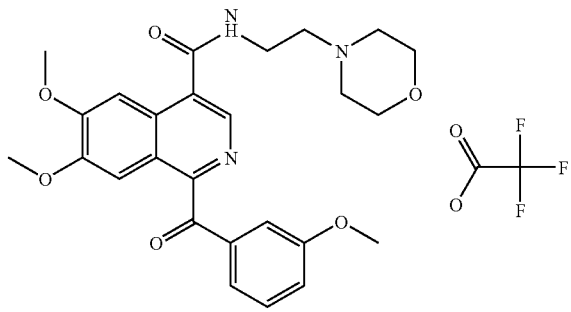

A solution of 6,7-dimethoxy-1-(3-methoxy-benzoyl)-isoquinoline-4-carboxylic acid (26.0 mg, 70.7 mmol) in dry, N,N-dimethylformamide (2 mL) was chilled in an ice bath under argon. With stirring, triethylamine (12 uL, 84.9 mmol) and isobutylchloroformate (11 uL, 84.9 uL) were added. The solution was stirred for 30 min and then 4-(2-aminoethyl)morpholine (46 uL, 353 mmol) was added. The solution was allowed to warmed to room temperature with stirring for 1 hr. and then diluted with ethyl acetate (30 mL). The ethyl acetate solution was washed sequentially with saturated aqueous sodium bicarbonate solution (2×5 mL), water (5 mL), and saturated aqueous sodium chloride solution (5 mL), dried over magnesium sulfate, filtered and concentrated in vacuo to afford 75 mg of an off white solid. This crude material was purified by preparative HPLC on a YMS Basic 10μ column (2×25 cm) and eluted with a linear gradient of 0–50% B (buffer A: 0.1% TFA/H$_2$O, buffer B: 0.1% TFA/CH3CN) in 30 min. The main peak was cut by analytical HPLC analysis of collected fractions, pooled and lyophilized to yield 18.2 mg (36%) of an off-white, amorphous powder as a 1:2 trifluoroacetate salt: APCI-MS m/e calcd for C$_{26}$H$_{29}$N$_3$O$_6$ (M+H$^+$) 480.5, found 480.1; $^1$H NMR (300 MHz) compatible.

Example 107

6,7-Dimethoxy-1-(3-methoxy-benzoyl)-isoquinoline-4-carboxylic acid (2-cyanoethyl)-amide

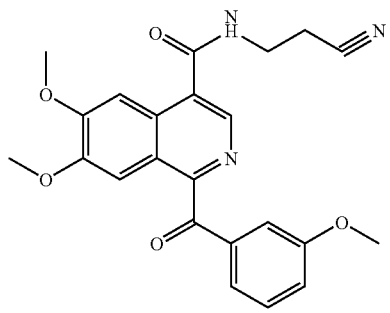

A solution of 6,7-dimethoxy-1-(3-methoxy-benzoyl)-isoquinoline-4-carboxylic acid (170 mg, 0.46 mmol) in dry, N,N-dimethylformamide (5 mL) was chilled in an ice bath under argon. With stirring, triethylamine (97 uL, 0.69 mmol) and isobutylchloroformate (72 uL, 0.56 uL) were added. The solution was stirred for 30 min and then 3-aminopropionitrile fumarate (118 mg, 0.92 mmol) and triethylamine (250 uL, 1.79 mmol) were added. The solution was allowed to warmed to room temperature with stirring overnight. The reaction mixture was poured into a 2% aqueous sodium bicarbonate solution (50 mL) and extracted with ethyl acetate (3×25 mL). The combined ethyl acetate layers were dried over magnesium sulfate, filtered and concentrated in vacuo to afford 107 mg (55%) of an off white solid and used without further purification: APCI-MS m/e calcd for C$_{23}$H$_{21}$N$_3$O$_5$[](M−H$^+$) 420.4, found 420.0; $^1$H NMR (300 MHz) compatible.

Example 108

6,7-Dimethoxy-1-(3-methoxy-benzoyl)-isoquinoline-4-carboxylic acid hydroxyamide; trifluoroacetate salt

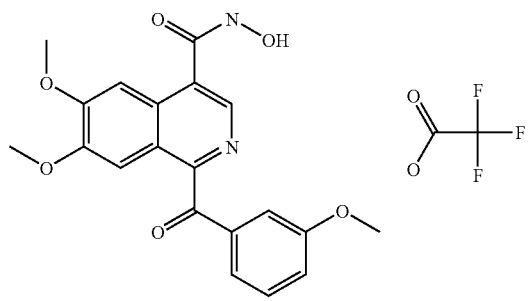

A solution of 6,7-dimethoxy-1-(3-methoxy-benzoyl)-isoquinoline-4-carboxylic acid (26.0 mg, 70.7 mmol) in dry, N,N-dimethylformamide (2 mL) was chilled in an ice bath under argon. With stirring, triethylamine (12 uL, 84.9 mmol) and isobutylchloroformate (11 uL, 84.9 mmol) were added. The solution was stirred for 30 min and then 4-(2-aminoethyl)morpholine (46 uL, 353 mmol) was added. The solution was allowed to warmed to room temperature with stirring for 1 hr. and then diluted with ethyl acetate (30 mL). The ethyl acetate solution was washed sequentially with saturated aqueous sodium bicarbonate solution (2×5 mL), water (5 mL), and saturated aqueous sodium chloride solution (5 mL), dried over magnesium sulfate, filtered and concentrated in vacuo to afford 75 mg of an off white solid. This crude material was purified by preparative HPLC on a YMS Basic 10μ column (2×25 cm) and eluted with a linear gradient of 0–50% B (buffer A: 0.1% TFA/H$_2$O, buffer B: 0.1% TFA/CH3CN) in 30 min. The main peak was cut by analytical HPLC analysis of collected fractions, pooled and lyophilized to yield 20 mg of an off-white, amorphous powder as a 1:1 trifluoroacetate salt: APCI-MS m/e calcd for C$_{20}$H$_{18}$N$_2$O$_6$ (M+H$^+$) 383.4, found 383.1; $^1$H NMR (300 MHz) compatible.

Example 109

6,7-Dimethoxy-1-(3-methoxy-benzoyl)-isoquinoline-4-carboxylic acid methoxy-amide

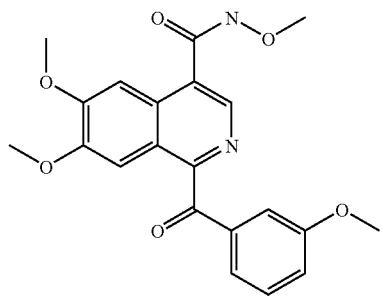

A solution of 6,7-dimethoxy-1-(3-methoxy-benzoyl)-isoquinoline-4-carboxylic acid (34.1 mg, 0.092 mmol) in dry, N,N-dimethylformamide (1 mL) was chilled in an ice bath under argon. With stirring, triethylamine (84 uL, 0.603 mmol) and isobutylchloroformate (18 uL, 0.139 mmol) were added. The solution was stirred for 30 min and then methoxyamine hydrochloride (39 mg, 0.464 mmol) was added. The solution was allowed to warmed to room temperature with stirring for 2 hrs. and then evaporated to dryness in vacuo. This crude material was purified by preparative HPLC on a YMS Basic 10µ column (2×25 cm) and eluted with a linear gradient of 10–60% B (buffer A: 0.1% TFA/H$_2$O, buffer B: 0.1% TFA/CH3CN) in 30 min. The main peak was cut by analytical HPLC analysis of collected fractions, pooled and lyophilized to yield 15 mg (40%) of a light yellow, amorphous powder as a 1:1 trifluoroacetate salt: APCI-MS m/e calcd for C$_{21}$H$_{20}$N$_2$O$_6$ (M+H$^+$) 397.4, found 397.3; $^1$H NMR (300 MHz) compatible.

Example 110

6,7-Dimethoxy-1-(3-methoxy-benzoyl)-isoquinoline-4-carboxylic acid methoxy-methyl-amide

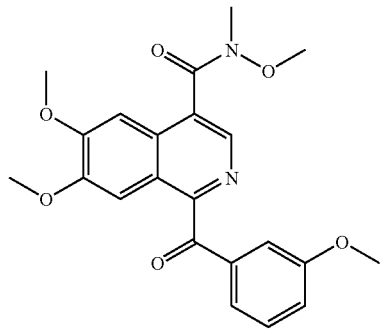

A solution of 6,7-dimethoxy-1-(3-methoxy-benzoyl)-isoquinoline-4-carboxylic acid (36.8 mg, 0.100 mmol) in dry, N,N-dimethylformamide (1 mL) was chilled in an ice bath under argon. With stirring, triethylamine (160 uL, 1.15 mmol) and isobutylchloroformate (19.5 uL, 0.150 mmol) were added. The solution was stirred for 30 min and then N,O-dimethylhydroxylamine hydrochloride (98 mg, 1.00 mmol) was added. The solution was allowed to warmed to room temperature with stirring for 2 hrs. and then evaporated to dryness in vacuo. This crude material was purified by preparative HPLC on a YMS Basic 10µ column (2×25 cm) and eluted with a linear gradient of 10–60% B (buffer A: 0.1% TFA/H$_2$O, buffer B: 0.1% TFA/CH3CN) in 30 min. The main peak was cut by analytical HPLC analysis of collected fractions, pooled and lyophilized to yield 21.7 mg (48%) of a light yellow, amorphous powder as a 1:1 trifluoroacetate salt: APCI-MS m/e calcd for C$_{22}$H$_{22}$N$_2$O$_6$ (M–H$^+$) 411.4, found 411.4; $^1$H NMR (300 MHz) compatible.

Example 111

(4-Hydroxymethyl-6,7-dimethoxy-isoquinolin-1-yl)-(3-isopropoxy-phenyl)-methanone

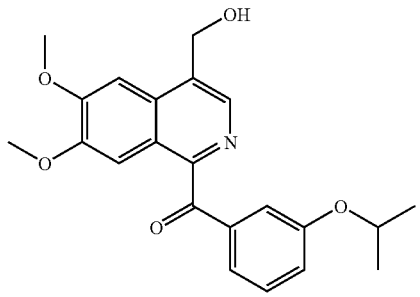

A solution of 1-(3-isopropoxy-benzyl)-6,7-dimethoxy-isoquinoline-4-carbaldehyde (200 mg, 0.547 mmol) and selenium dioxide (121 mg, 1.09 mmol) in ethyl acetate was refluxed for 45 min. The mixture was cooled and filtered through celite. The celite was washed well with ethyl acetate and the combined filtrates were concentrated in vacuo to afford 1-(3-isopropoxy-benzoyl)-6,7-dimethoxy-isoquinoline-4-carbaldehyde (160 mg, 77%) as a light yellow solid that was used without further purification: APCI-MS (M+H$^+$) m/e 380; $^1$H NMR (300 MHz) compatible.

A solution of sodium borohydride (32 mg, 0.84 mmol) in ethanol (1.5 mL) was warmed slightly and filtered. This solution was diluted with methylene chloride (3.5 mL), placed under argon and chilled to –78° C. A solution of (1-(3-isopropoxy-benzoyl)-6,7-dimethoxy-isoquinoline-4-carbaldehyde (160 mg, 0.42 mmol) in a 30% ethanol in methylene chloride solution (5 mL) was added dropwise to the above sodium borohydride solution over 10 min. The reaction mixture was stirred at –78° C. for 1.25 hr at which time freshly distilled acetaldehyde (236 uL, 4.2 mmol) was added dropwise. Stirring was continued at –78° C. for an additional 1 hr and then the temperature was allowed to slowly rise to ambient temperature for 30 min. The reaction mixture was treated with saturated aqueous ammonium chloride solution (3 mL), diluted with methylene chloride (30 mL), washed with saturated aqueous ammonium chloride solution (20 mL), saturated aqueous sodium bicarbonate solution (2×20 mL), and saturated sodium chloride solution (20 mL). The organic layer was dried over magnesium sulfate, filtered and concentrated in vacuo to afford 190 mg of a light yellow solid. Biotage chromatography (FLASH 40M, Silica, 25% ethyl acetate/hexane, 35% ethyl acetate/hexane, 45% ethyl acetate/hexane, 55% ethyl acetate/hexane, 65% ethyl acetate/hexane, 75% ethyl acetate/hexane) afforded (4-hydroxymethyl-6,7-dimethoxy-isoquinolin-1-yl)-(3-isopropoxy-phenyl)-methanone (163 mg, 99%) as a white solid: ES-MS (M+H+) m/e calcd for $C_{22}H_{23}NO_5$ 382.4, found 382; $^1H$ NMR (300 MHz) compatible.

Example 112

6,7-Dimethoxy-1-(3-methoxy-5-methyl-benzoyl)-isoquinoline-4-carboxylic acid; hydrochloride salt

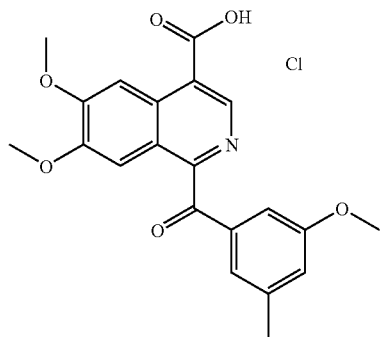

A solution of 3,5-dimethylanisole (1.11 g, 8.15 mmol), N-bromosuccinimide (1.52 g, 8.55 mmol), and 2,2'-bisisobutyronitrile (27 mg, 0.16 mmol) in carbontetrachloride (10 mL) was refluxed for 2 hrs. The reaction mixture was cooled, filtered and concentrated in vacuo to afford 1-bromomethyl-3-methoxy-5-methyl-benzene as a slightly yellow oil (1.66 g). This material was used without further purification: $^1H$ NMR (300 MHz) compatible.

A solution of 1-bromomethyl-3-methoxy-5-methyl-benzene (1.66 g, 7.7 mmol) and sodium cyanide (1.89 g, 38.5 mmol) in ethanol (15 mL) and water (5 mL) was warmed to 60° C. for 2 hrs. The reaction mixture was cooled, concentrated in vacuo, diluted with water (100 mL), and extracted with methylene chloride (3×20 mL). The combined organic layers were dried over magnesium sulfate, filtered and concentrated in vacuo to afford 1.16 g of a light yellow oil. The crude 1-cyanomethyl-3-methoxy-5-methyl-benzene (1.16 g, 7.1 mmol) and sodium hydroxide (1.44 g, 35.9 mmol) in ethanol (20 mL) and water (10 mL) was refluxed overnight. The reaction mixture was cooled, concentrated in vacuo, diluted with water, and extracted with methylene chloride (3×10 mL). The aqueous layer was acidified to pH 2 with 6N hydrochloric acid and extracted with methylene chloride (3×20 mL). The combined organic layers were dried over magnesium sulfate, filtered and concentrated in vacuo to afford 0.86 g (62% for 2 steps) of (3-methoxy-5-methyl-phenyl)-acetic acid as an off white solid. This material was used without further purification: $^1H$ NMR (300 MHz) compatible.

A solution of (3-methoxy-5-methyl-phenyl)-acetic acid (512.8 mg, 2.84 mmol), 3-amino-2-(3,4-dimethoxy-phenyl)-propionic acid ethyl ester (825 mg, 2.84 mmol), and triethylamine (912 uL, 6.54 mmol) in dry methylene chloride (25 mL) was chilled in an ice bath under argon. 1-(3-Dimethylaminopropyl)-3-ethylcarbodiimide hydrochloride (573 mg, 2.98 mmol) was added in one portion and the mixture stirred at room temperature for 72 hrs. The reaction mixture was poured into ethyl acetate (100 mL) and extracted with 2.5% aqueous potassium bisulfate (3×20 mL), 5% aqueous sodium bicarbonate (3×20 mL), and saturated aqueous sodium chloride (20 mL). The organic layer was dried over magnesium sulfate, filtered and concentrated in vacuo to afford 2-(3,4-dimethoxy-phenyl)-3-[2-(3-methoxy-5-methyl-phenyl)-acetylamino]-propionic acid ethyl ester as a light tan foam (0.79 g, 67%). This material was used without further purification: $^1H$ NMR (300 MHz) compatible.

A solution of 2-(3,4-dimethoxy-phenyl)-3-[2-(3-methoxy-5-methyl-phenyl)-acetylamino]-propionic acid ethyl ester (0.79 g, 1.9 mmol) and phosphorus pentachloride (0.59 g, 2.85 mmol) in dry methylene chloride (25 mL) was stirred at room temperature overnight. A cold, saturated aqueous sodium bicarbonate solution (75 mL) was added to the reaction mixture and stirred for 1 hr. The layers were separated and the aqueous layer extracted with methylene chloride (2×25 mL). The combined organic layers were dried over magnesium sulfate, filtered and concentrated in vacuo to afford 6,7-dimethoxy-1-(3-methoxy-5-methyl-benzyl)-3,4-dihydro-isoquinoline-4-carboxylic acid ethyl ester as a light green oil (0.73 g, 97%). This material was used without further purification: $^1H$ NMR (300 MHz) compatible.

A solution of 6,7-dimethoxy-1-(3-methoxy-5-methyl-benzyl)-3,4-dihydro-isoquinoline-4-carboxylic acid ethyl ester (0.73 g, 1.8 mmol) and 10% palladium on carbon (230 mg) in xylene (15 mL) was refluxed overnight. The reaction mixture was cooled, filtered through celite, and concentrated in vacuo to afford 6,7-dimethoxy-1-(3-methoxy-5-methyl-benzyl)-isoquinoline-4-carboxylic acid ethyl ester as a light brown oil (0.63 g, 89%). This material was used without further purification: $^1H$ NMR (300 MHz) compatible.

A solution of 6,7-dimethoxy-1-(3-methoxy-5-methyl-benzyl)-isoquinoline-4-carboxylic acid ethyl ester (0.63 g, 1.59 mmol) and selenium dioxide (0.35 g, 3.28 mmol) in ethyl acetate was refluxed for 2 hrs. The mixture was cooled and filtered through celite. The celite was washed well with ethyl acetate and methylene chloride (5 mL) and the combined filtrates were concentrated in vacuo to afford 0.55 g of a brown solid. Biotage chromatography (FLASH 40M, Silica, chloroform, 0.5% methanol/chloroform) afforded 6,7-dimethoxy-1-(3-methoxy-5-methyl-benzoyl)-isoquinoline-4-carboxylic acid ethyl ester (0.55 g, 77%): $^1H$ NMR (300 MHz) compatible.

A solution of 6,7-dimethoxy-1-(3-methoxy-5-methyl-benzoyl)-isoquinoline-4-carboxylic acid ethyl ester (65.5 mg, 0.159 mmol) and 10M aqueous sodium hydroxide solution (64 uL, 0.639 mmol) in ethanol (4 mL) and water (2 mL) was refluxed for 1 hr. The reaction mixture was cooled, acidified to pH 4–5 with glacial acetic acid and diluted with water (100 mL). The aqueous mixture was extracted with methylene chloride (3×20 mL). The combined organic layers were The combined organic layers were dried over magnesium sulfate, filtered and concentrated in vacuo to afford 72 mg of a yellow solid. This crude material was purified by preparative HPLC on a Delta Pak C18-100 Å column (3×30 cm) and eluted with a linear gradient of 40–95% B (buffer A: 0.1% TFA/H2O, buffer B: 0.1% TFA/CH3CN) in 30 min. The main peak was cut by analytical HPLC analysis of collected fractions, pooled, evaporated, redissolved in acetonitrile/water containing 2 drops concentrated hydrochloric acid and lyophilized to yield 53.3 mg (80%) of a light yellow, amorphous powder as a 1:1 hydrochloride salt: ES-MS m/e calcd for $C_{21}H_{19}NO_6$ (M–H+) 382.4, found 382.1; $^1H$ NMR (300 MHz) compatible.

Example 113

[4-(4-Hydroxy-4-phenyl-piperidine-1-carbonyl)-6,7-dimethoxy-isoquinolin-1-yl]-(3-methoxy-phenyl)-methanone

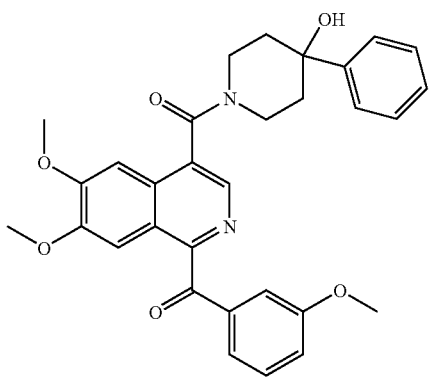

A solution of 6,7-dimethoxy-1-(3-methoxy-benzoyl)-isoquinoline-4-carboxylic acid (30.0 mg, 81.65 mmol) in dry, N,N-dimethylformamide (2 mL) was chilled in an ice bath under argon. With stirring, triethylamine (14.4 uL, 102 mmol) and isobutylchloroformate (13.4 uL, 102 mmol) were added. The solution was stirred for 30 min and then 4-hydroxy, 4-phenylpiperidine (28.9 mg 1.633 mM) was added. The solution was allowed to warm to room temperature with stirring for 1 hr. and then diluted with ethyl acetate (30 mL), The ethyl acetate solution was washed sequentially with saturated sodium bicarbonate solution (2×5 mL), water (5 mL), and saturated sodium chloride solution (5 mL), dried over magnesium sulfate, filtered and concentrated in vacuo to afford 50 mg of solid. This crude material was purified by flash chromatography, eluting with 50% ethyl acetate in hexanes (containing 1% acetic acid) and then increasing gradually to 80% ethyl acetate in hexanes After tic analysis, fractions were pooled and evaporated to yield 24 mg (55.8%) of an off-white, powder as an acetate salt: APCI-MS m/e calcd for $C_{31}H_{30}N_2O_6$ (M+H) 527.6, found 527; H NMR (300 MHz) compatible.

Example 114

{[6,7-Dimethoxy-1-(3-methoxy-benzoyl)-isoquinoline-4-carbonyl]-amino}-acetic acid ethyl ester

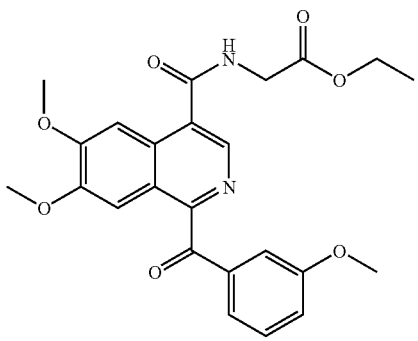

A solution of 6,7-dimethoxy-1-(3-methoxy-benzoyl)-isoquinoline-4-carboxylic acid (30.0 mg, 81.65 mmol) in dry, N,N-dimethylformamide (2 mL) chilled in an ice-bath under argon. With stirring, triethylamine (14.4 uL, 102 mmol) and isobutylchloroformate (13.4 uL, 102 mmol) were added. The solution was stirred for 30 min and then solution of glycine ethyl ester hydrochloride (227 mg, 1,633 mM) in 4 mL of dimethylformamide and triethylamine (0.229 mL, 1.633 mM) were added and the reaction was allowed to warm to room temperature with stirring for 1 hr. and then diluted with ethyl acetate (30 mL), The ethyl acetate solution was washed sequentially with saturated sodium bicarbonate solution (2×5 mL), water (5 mL), and saturated sodium chloride solution (5 mL), dried over magnesium sulfate, filtered and concentrated in vacuo to afford 46 mg solid. This crude material was purified by flash chromatography, eluting with 50% ethyl acetate in hexanes (containing 1% acetic acid) and then increasing gradually to 80% ethyl acetate in hexanes After tlc analysis, fractions were pooled and evaporated to yield 36 mg (79.4%) of white, powder as an acetate salt: APCI-MS m/e calcd for $C_{24}H_{24}N_2O_7$ (M+H) 453.5, found 453; H NMR (300 MHz) compatible

Example 115

[4-(4-Hydroxy-piperidine-1-carbonyl)-6,7-dimethoxy-isoquinolin-1-yl]-(3-methoxy-phenyl)-methanone

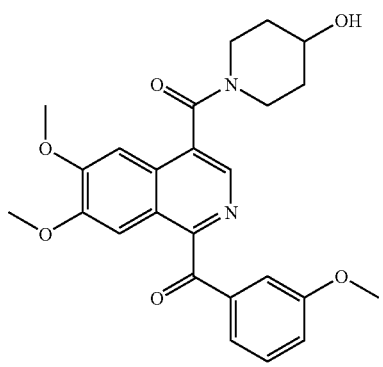

A solution of 6,7-dimethoxy-1-(3-methoxy-benzoyl)-isoquinoline-4-carboxylic acid (30.0 mg, 61.75 mmol) in dry, N,N-dimethylformamide (2 mL) was chilled in an ice bath under argon. With stirring, triethylamine (14.4 uL, 102 mmol) and isobutylchloroformate (13.4 uL, 102 mmol) were added. The solution was stirred for 30 min and then 4-hydroxypiperidine (165 mg, 1.633 mmol) was added. The solution was allowed to warm to room temperature with stirring for 1 hr. and then diluted with ethyl acetate (30 mL). The ethyl acetate solution was washed sequentially with saturated aqueous sodium bicarbonate solution (2×5 mL), water (5 mL), and saturated aqueous sodium chloride solution (5 mL), dried over magnesium sulfate, filtered and concentrated in vacuo to afford 35 mg of an off white solid. This crude material was purified by flash chromatography eluting with 50% ethyl acetate in hexanes (containing 1% acetic acid) and then increasing gradually to 80% ethyl acetate in hexanes. After tlc analysis, fractions were pooled and evaporated to yield 25 mg (68%) of product as an acetic acid salt: APCI-MS m/e calcd for $C_{25}H_{26}N_2O_6$ (M+H) 451.5, found 451, H NMR (300 MHz) compatible.

Example 116

(6,7-Dimethoxy-4-pyrrolidin-1-ylmethyl-isoquinolin-1-yl)-(3-methoxy-phenyl)-methanone

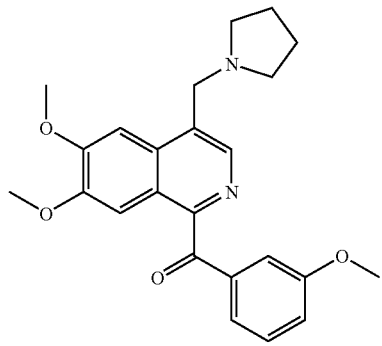

A solution of 6,7-dimethoxy-1-(3-methoxy-benzoyl)-isoquinoline-4-methylene alcohol (30.0 mg, 84.98 mmol) in dry, tetrahydrofuran was chilled in an ice-bath under argon. With stirring, triethylamine (17.9 uL, 127 mmol) and methanesulfonyl chloride (8.8 uL, 127 mmol) were added. The reaction was stirred for 1 hour. Pyrrolidine (200 uL, 2.4 mmol) was added and the reaction was stirred at room temperature overnight. Biotage chromatography (FLASH 40M, Silica, 30% ethyl acetate/hexane) afforded (6,7-Dimethoxy-4-pyrrolidin-1-ylmethyl-isoquinolin-1-yl)-(3-methoxy-phenyl)-methanone (27 mg) as an off-white solid: APCI-MS (M+H$^+$) m/e calcd for $C_{24}H_{26}N_2O_4$ 407.5, found 407; $^1$H NMR (300 MHz) compatible.

Example 117

6,7-Dimethoxy-1-(3-methoxy-benzoyl)-isoquinoline-4-carboxylic acid amide

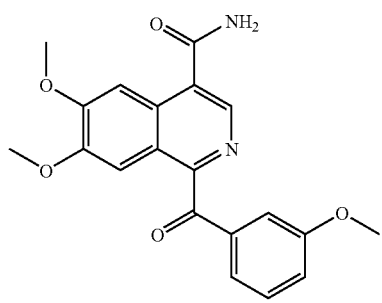

A solution of 6,7-dimethoxy-1-(3-methoxy-benzoyl)-isoquinoline-4-carboxylic acid (30 mg, 81.7 mmol), ammonium chloride (43.5 mg. 0.817 mM) and triethylamine (0.115 mL, 0.817 mM) in 2 mL of dimethylformamide was stirred with O-benzotriazol-1-yl-N,N,N,N-tetramethyluronium hexafluorophosphate (61.9 mg. 0.163 mM) at room temperature for 20 hours. Poured into 20 mL of water and 20 mL of ethyl acetate, extracted ethyl acetate layer with saturated sodium bicarbonate, dried ethyl acetate solution. over anhydrous magnesium sulfate and evaporated to give 5.4 mg of an off-white solid pure product: APCI-MS m/e calcd for $C_{20}H_{18}N_2O_6$ (M+H.) 367.4, found 367; H NMR (300 MHz) compatible.

Example 118

(4-Hydroxymethyl-6,7-dimethoxy-isoquinolin-1-yl)-(3-methoxy-phenyl)-methanone

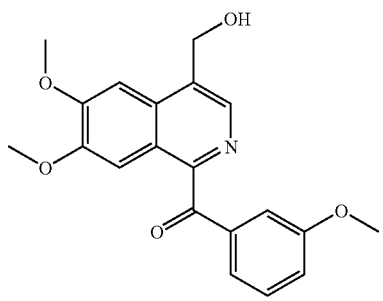

A solution of 6,7-dimethoxy-1-(3-methoxy-benzyl)-isoquinoline-4-carboxylic acid ethyl ester (50 mg, 0.13 mmol) in 2 ml dry tetrahydrofuran at room temperature was treated with lithium aluminum hydride (1M in THF, 0.26 mL, 0.26 mmol) for 30 minutes. The reaction mixture was poured into ice-cold 10% sodium sulfate and extracted with methylene chloride. The organic layers were dried over magnesium sulfate, filtered and concentrated in vacuo to afford crude alcohol. This material was dissolved in pyridine (1 mL) and treated with acetic anhydride (0.5 mL) and stirred at room temperature overnight. Evaporation of this reaction mixture afforded crude 6,7-dimethoxy-1-(3-methoxy-benzyl)-isoquinoline-4-hydroxymethyl acetate: APCI-MS (M+H$^+$) m/e calcd for $C_{22}H_{23}NO_5$ 381.4, found 382; $^1$H NMR (300 MHz) compatible.

The above acetate was refluxed with selenium dioxide (24.5 mg, 0.221 mmol) in ethylacetate (2 mL) for 75 minutes. The mixture was cooled and filtered through celite. The celite was washed well with ethyl acetate and methylene chloride (5 mL) and the combined filtrates were concentrated in vacuo to afford crude ketone. This crude material was dissolved in tetrahydrofuran (1 mL) and water (0.5 mL) and treated with lithium hydroxide hydrate (8 mg, 0.143 mmol) for 3 hours. The reaction mixture was diluted with water (20 mL) and extracted twice with ethyl acetate. The combined organic layers were dried over magnesium sulfate, filtered and concentrated in vacuo to afford crude product. Biotage chromatography (FLASH 40M, Silica, 30% ethyl acetate/hexane) afforded (4-hydroxymethyl-6,7-dimethoxy-isoquinolin-1-yl)-(3-methoxy-phenyl)-methanone (39 mg) as an off-white solid: ES-MS (M+H$^+$) m/e calcd for $C_{20}H_{19}NO_5$ 354.4, found 354; $^1$H NMR (300 MHz) compatible.

Example 119

(6,7-Dimethoxy-4-methoxymethyl-isoquinolin-1-yl)-(3-methoxy-phenyl)-methanone

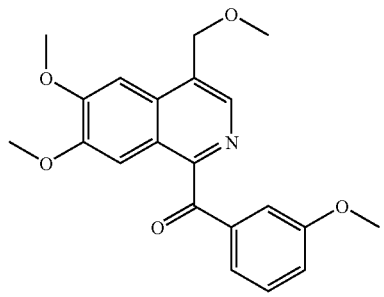

A solution of 6,7-dimethoxy-1-[3-methoxy-benzoyl]-isoquinoline-4-carboxylic acid ethyl ester (100 mg, 0.253 mmol) in THF (10 mL) was treated with lithium aluminum hydride (1M in THF, 3.03 mL, 3.03 mmol) in an ice bath under argon for 60 minutes. The reaction mixture was treated with a 15% solution of sodium sulfate, stirred for 15 minutes, and extracted twice with ethyl acetate. The combined organic layers were dried over magnesium sulfate, filtered and concentrated in vacuo to afford crude product. Biotage chromatography (FLASH 40M, Silica, ethyl acetate/hexane) afforded the bis-alcohol (48 mg) as an off-white solid: $^1$H NMR (300 MHz) compatible.

The above alcohol was dissolved in dry toluene with imidazole (17.2 mg, 0.253 mmol) and evaporated three times to dryness. The residue was dissolved in anhydrous DMF (3 mL) and treated with t-butyl-dimethylsilyl chloride (22.8 mg, 0.157 mmol) under argon for 5 hours and room temperature. Dimethylamino-pyridine (5 mg) was added to the reaction mixture and stirring continued overnight. The crude reaction mixture was taken into ethyl acetate (10 mL) and saturated sodium bicarbonate (10 mL), separated and washed with saturated sodium chloride. The organic layer was evaporated and treated with 1N HCL in methanol and evaporated to afford crude mono-silylated, mono-alcohol material.

The above alcohol (45 mg) was dissolved in DMF and treated with sodium hydride (16 mg, 0.2 mmol) and methyl iodide (15 uL) at room temperature for 1 hour. Water was added to the reaction mixture and extracted with ethyl acetate. The combined organic layers with dried over magnesium sulfate, filtered and evaporated to yield crude methylated product. This material was dissolved in THF (1.5 mL) and treated with tetrabutylammonium fluoride (1M in THF, 0.5 mL, 0.5 mmol) at room temperature overnight. The reaction mixture was diluted with water and extracted with ethyl acetate. The combined organic layers were dried over magnesium sulfate, filtered, and evaporated to dryness. This crude alcohol was refluxed with selenium dioxide (25 mg, 0.21 mmol) in ethyl acetate for 1 hour. The mixture was cooled and filtered through celite. The celite was washed well with ethyl acetate and methylene chloride (5 mL) and the combined filtrates were concentrated in vacuo to afford crude ketone. Biotage chromatography (FLASH 40M, Silica, ethyl acetate/hexane) afforded the (6,7-Dimethoxy-4-methoxymethyl-isoquinolin-1-yl)-(3-methoxy-phenyl)-methanone (4 mg) as an off-white solid: APCI-MS (M+H$^+$) m/e calcd for $C_{21}H_{21}NO_5$ 368.4, found 368; $^1$H NMR (300 MHz) compatible.

Example 120

6,7-Dimethoxy-1-[3-(2-morpholin-4-yl-acetylamino)-benzoyl]-isoquinoline-4-carboxylic acid; compound with trifluoro-acetic acid

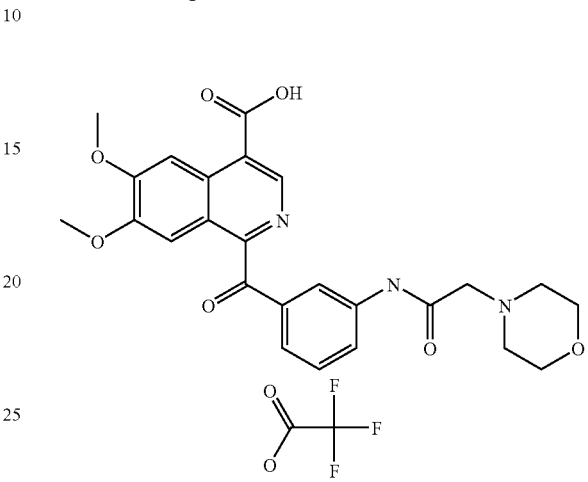

A solution of 3,4-dimethoxy-phenyl amine hydrochloride salt (2.375 g, 8.197 mmol), m-nitrophenylacetic acid (1.485 g, 8.197 mmol), diisopropylethylamine (4.998 mL, 28.6 mmol) in anhydrous DMF (60 mL) was treated with O-benzotriazol-1-yl-N,N,N,N-tetramethyluronium hexafluorophosphate (3.429 g, 9.016 mmol) at room temperature overnight. The reaction mixture was concentrated, dissolved in ethyl acetate (120 mL) and washed with saturated sodium bicarbonate, 0.1N HCL, and saturated sodium chloride. The organic layer was dried over magnesium sulfate, filtered and evaporated to yield 3.4 g of a yellow-brown oily solid: APCI-MS (M+H$^+$) m/e calcd for $C_{21}H_{24}N_2O_7$ 417.4, found 417.3; $^1$H NMR (300 MHz) compatible.

The above material was dissolved in methylene chloride (60 mL) and stirred with phosphorous pentachloride (2.56 g, 12.29 mmol) at room temperature overnight. A cold, saturated solution of sodium bicarbonate was poured into the reaction mixture slowly. After stirring, the layers were separated and the aqueous layer extracted once with methylene chloride. The combined organic layers were dried over magnesium sulfate, filtered and evaporated to yield 2.67 g of crude material. Biotage chromatography (FLASH 40M, Silica, 20% ethyl acetate/hexane) afforded 1.25 g of an off-white solid: APCI-MS (M+H$^+$) m/e calcd for $C_{21}H_{22}N_2O_6$ 399.4, found 399.3; $^1$H NMR (300 MHz) compatible. This material and sulfur powder (0.17 g, 5.339 mmol) were dissolved in methylene chloride and evaporated. The residue was heated at 160–165° C. for 1 hour. The reaction mixture was cooled, dissolved in ethyl acetate containing some methylene chloride and filtered through celite. The effluent was evaporated to crude product. Biotage chromatography (FLASH 40M, Silica, ethyl acetate/hexane) afforded 0.96 g of 6,7-dimethoxy-1-(3-nitro-benzyl)-isoquinoline-4-carboxylic acid ethyl ester a yellow solid: APCI-MS (M+H$^+$) m/e calcd for $C_{21}H_{20}N_2O_6$ 397.4, found 397.2; $^1$H NMR (300 MHz) compatible.

The above nitro compound (50 mg, 0.126 mmol) was treated with tin chloride (73 mg, 0.325 mmol) in THF (7 mL) and 6N HCl (3 mL) at room temperature overnight. The reaction mixture was treated with ice-cold saturated sodium bicarbonate and extracted with ethyl acetate. The combined organic layers were dried over magnesium sulfate, filtered and dried to a crude solid. The material was immediately treated with bromoacetyl bromide (13.1 uL, 0.151 mmol) and pyridine (41.26 uL, 0.63 mmol) in dry THF (5 mL) at 0° C. under argon for 1 hour. The reaction mixture was treated with morpholine (110 uL, 1.26 mmol), warmed to room temperature and stirred overnight. The reaction mixture was diluted with water (30 mL) and extracted with ethyl acetate (2×30 mL). The combined organic layers were dried over magnesium sulfate, filtered and evaporated to dryness.

The above crude material was refluxed with selenium dioxide (30 mg, 0.27 mmol) in ethyl acetate for 1 hour. The mixture was cooled and filtered through celite. The celite was washed well with ethyl acetate and the combined filtrates were concentrated in vacuo to afford 77 mg of crude ketone. Biotage chromatography (FLASH 40M, Silica, ethyl acetate) afforded pure material (25 mg) as an off-white solid: $^1$H NMR (300 MHz) compatible.

The above ketone ester was dissolved in THF/ethanol (1:1, 4.5 mL) and treated with 4N sodium hydroxide (47.25 uL, 0.189 mmol) at room temperature for 6.5 hours. The reaction mixture was diluted with water, and extracted with ethyl acetate. The pH of the aqueous layer was adjusted to 6.6 and evaporated to a small volume. Preparative HPLC purification yielded 25.5 mg of 6,7-dimethoxy-1-[3-(2-morpholin-4-yl-acetylamino)-benzoyl]-isoquinoline-4-carboxylic acid; compound with trifluoro-acetic acid as an off-white solid: ES-MS (M+H$^+$) m/e calcd for $C_{25}H_{25}N_3O_7$ 481.5, found 481.4; $^1$H NMR (300 MHz) compatible.

Example 121

6,7-Dimethoxy-1-[3-(2-pyrrolidin-1-yl-acetylamino)-benzoyl]-isoquinoline-4-carboxylic acid; compound with trifluoro-acetic acid

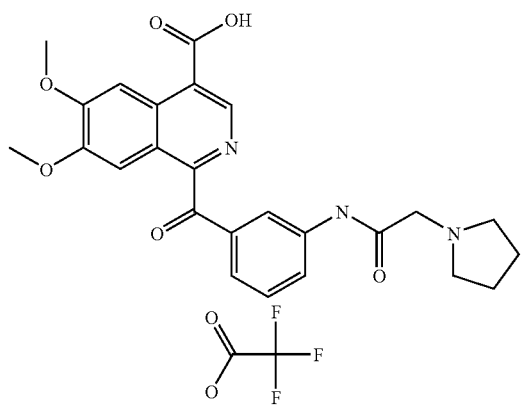

The above 6,7-dimethoxy-1-(3-nitro-benzyl)-isoquinoline-4-carboxylic acid ethyl ester (50 mg, 0.126 mmol) was treated with tin chloride (73 mg, 0.325 mmol) in THF (7 mL) and 6N HCl (3 mL) at room temperature overnight. The reaction mixture was treated with ice-cold saturated sodium bicarbonate and extracted with ethyl acetate. The combined organic layers were dried over magnesium sulfate, filtered and dried to a crude solid. The material was immediately treated with bromoacetyl bromide (15 uL, 0.163 mmol) and pyridine (51 uL, 0.63 mmol) in dry THF (5 mL) at 0° C. under argon for 1 hour. The reaction mixture was treated with pyrrolidine (105 uL, 1.26 mmol), warmed to room temperature and stirred overnight. The reaction mixture was diluted with water (30 mL) and extracted with ethyl acetate (2×30 mL). The combined organic layers were dried over magnesium sulfate, filtered and evaporated to dryness.

The above crude material was refluxed with selenium dioxide (30 mg, 0.27 mmol) in ethyl acetate (5 mL) for 1 hour. The mixture was cooled and filtered through celite. The celite was washed well with ethyl acetate and the combined filtrates were concentrated in vacuo to afford 35 mg of crude ketone.

The above ketone ester was dissolved in THF (3 mL) and ethanol (1 mL) and treated with 4N sodium hydroxide (71.25 uL, 0.285 mmol) at room temperature for 6.5 hours. The reaction mixture was diluted with water, and extracted with ethyl acetate. The pH of the aqueous layer was adjusted to 6.5 and evaporated to a small volume. Preparative HPLC purification yielded 3.6 mg of 6,7-imethoxy-1-[3-(2-pyrrolidin-1-yl-acetylamino)-benzoyl]-isoquinoline-4-carboxylic acid; compound with trifluoro-acetic acid as an off-white solid: ES-MS (M+H$^+$) m/e calcd for $C_{25}H_{25}N_3O_6$ 464.5, found 464.2; $^1$H NMR (300 MHz) compatible.

Example 122

1-(3-Butyrylamino-benzoyl)-6,7-dimethoxy-isoquinoline-4-carboxylic acid

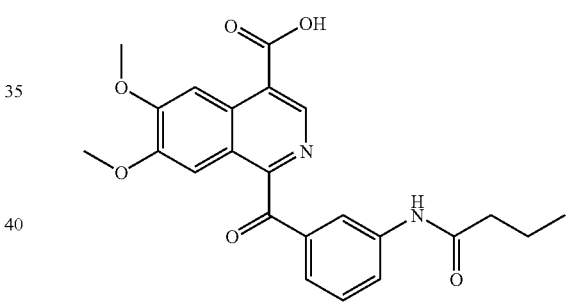

The above 6,7-dimethoxy-1-(3-nitro-benzyl)-isoquinoline-4-carboxylic acid ethyl ester (50 mg, 0.126 mmol) was treated with tin chloride (73 mg, 0.325 mmol) in THF (7 mL) and 6N HCl (3 mL) at room temperature overnight. The reaction mixture was treated with ice-cold saturated sodium bicarbonate and extracted with ethyl acetate. The combined organic layers were dried over magnesium sulfate, filtered and dried to a crude solid. The material was immediately treated with butyric anhydride (412 uL, 2.52 mmol) and pyridine (305 uL, 3.783 mmol) in dry THF (5 mL) at room temperature under argon overnight. The reaction mixture was evaporated diluted with ethyl acetate and extracted with saturated sodium bicarbonate and water. The organic layer was dried over magnesium sulfate, filtered and evaporated to dryness.

The above crude material was refluxed with selenium dioxide (60 mg, 0.54 mmol) in ethyl acetate (5 mL) for 1 hour. The mixture was cooled and filtered through celite. The celite was washed well with ethyl acetate and the combined filtrates were concentrated in vacuo to afford crude ketone. Biotage chromatography (FLASH 40M, Silica, 50% ethyl acetate/hexane) afforded pure material (18 mg) as an off-white solid: $^1$H NMR (300 MHz) compatible.

The above ketone ester was dissolved in ethanol (6 mL) and THF (2 mL) and treated with 4N sodium hydroxide (35.5 uL, 0.14 mmol) at room temperature for 4 hours and 4° C. over the weekend. The reaction mixture was diluted with water, and extracted with ethyl acetate. The pH of the aqueous layer was adjusted to 2.5, extracted with ethyl acetate. The combined organic layers were dried over magnesium sulfate, filtered and evaporated dryness to yield 15.8 mg of 1-(3-butyrylamino-benzoyl)-6,7-dimethoxy-isoquinoline-4-carboxylic acid as an off-white solid: APCI-MS (M+H$^+$) m/e calcd for $C_{23}H_{22}N_2O_6$ 423.4, found 423.3; $^1$H NMR (300 MHz) compatible.

Example 123

N-[6,7-Dimethoxy-1-(3-methoxy-benzoyl)-isoquinolin-4-yl]-acetamide, hydrochloride salt

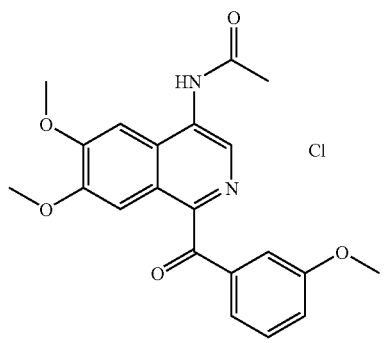

6,7-Dimethyoxy-isocarbostyryl (410 mg, 2 mmol) in acetic acid (10 mL) was treated with a solution of 70% nitric acid in acetic acid (3 mL) in an ice bath. The reaction was stirred and warmed to room temperature over 45 minutes. The orange-yellow reaction was stirred at room temperature overnight. The mixture was poured into water and extracted with methylene chloride (4×50 mL). The combined organic layers were dried over magnesium sulfate, filtered and evaporated to a crude solid. Biotage chromatography (FLASH 40M, Silica, ethyl acetate/hexane/acetic acid) afforded pure material (62 mg) as a yellow solid: ES-MS (M+H$^+$) m/e calcd for $C_{11}H_{10}N_2O_5$ 251.2, found 251.0; $^1$H NMR (300 MHz) compatible.

The above nitro compound was refluxed with phosphorous oxychloride (6 mL) for 11 hours. The reaction mixture was evaporated, dissolved in ethyl acetate (25 mL) and extracted with saturated sodium bicarbonate. The aqueous layer was back extracted with ethyl acetate and the combined organic layers were dried over magnesium sulfate, filtered and evaporated to dryness to yield 62 mg of a yellow solid.

The above chloro-nitro compound, m-anisaldehyde (30.45 uL, 0.25 mmol), and dimethyl-imidazolium iodide (23.3 mg, 0.25 mmol) were dissolved in dry DMF (3 mL) and treated with sodium hydride (60% in oil, 10 mg, 0.25 mmol) at room temperature for 15 min and 80–85° C. for 2 hours. The reaction mixture was poured into water (50 mL) and extracted with methylene chloride (3×50 mL). The combined organic layers were dried over magnesium sulfate, filtered and evaporated to dryness. Biotage chromatography (FLASH 40M, Silica, ethyl acetate/hexane/acetic acid) afforded product (49 mg) as a yellow solid: ES-MS (M+H$^+$) m/e calcd for $C_{19}H_{16}N_2O_6$ 369, found 369; $^1$H NMR (300 MHz) compatible.

The above nitro compound (30 mg, 0.081 mmol) was treated with tin chloride (73 mg, 0.325 mmol) in THF (7 mL) and 6N HCl (3 mL) at room temperature overnight. The reaction mixture was treated with ice-cold saturated sodium bicarbonate and extracted with ethyl acetate. The combined organic layers were dried over magnesium sulfate, filtered and dried to a crude solid. Preparative HPLC purification yielded 8 mg of amine as a solid. This material was treated with pyridine/acetic anhydride (1:1, 4 mL) at room temperature for 2 hours. The reaction mixture was evaporated, redissolved in ethyl acetate and washed with saturated sodium bicarbonate. The organic layer was dried over magnesium sulfate, filtered, and evaporated to yield 7 mg of a crude product. Preparative HPLC purification yielded 3.6 mg of N-[6,7-dimethoxy-1-(3-methoxy-benzoyl)-isoquinolin-4-yl]-acetamide. HCl as an off-white solid: APCI-MS (M+H$^+$) m/e calcd for $C_{21}H_{20}N_2O_5$ 381.4, found 381.3; $^1$H NMR (300 MHz) compatible.

Example 124

[6,7-Dimethoxy-1-(3-methoxy-benzoyl)-isoquinolin-4-yl]-carbamic acid methyl ester; compound with trifluoro-acetic acid

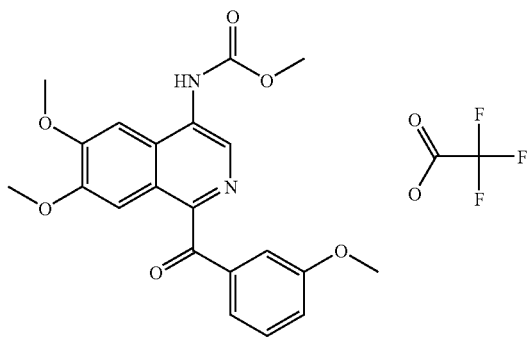

The above [4-nitro-6,7-dimethoxy-isoquinolin-1-yl]-(3-methoxy-phenyl)-methanone (150 mg, 0.407 mmol) was treated with tin chloride (459 mg, 2.03 mmol) in THF (30 mL) and 6N HCl (19 mL) at room temperature overnight. The reaction mixture was treated with ice-cold saturated sodium bicarbonate and extracted with ethyl acetate. The combined organic layers were dried over magnesium sulfate, filtered and dried to a crude solid. 75 mg (0.203 mmol) of this crude solid was dissolved in dry THF (5 mL) and treated with pyridine (24.6 uL, 0.364 mmol) and methylchloroformate (18.7 uL, 0.243 mmol) under argon at 0° C. The reaction was stirred at room temperature overnight. The reaction mixture was poured into ice water and extracted with ethyl acetate. The combined ethyl acetate layers were dried over magnesium sulfate, filtered, and evaporated to crude product. Preparative HPLC purification yielded 23 mg of [6,7-dimethoxy-1-(3-methoxy-benzoyl)-isoquinolin-4-yl]-carbamic acid methyl ester; trifluoro-acetic acid salt as an off-white solid: APCI-MS (M+H$^+$) m/e calcd for $C_{21}H_{20}N_2O_6$ 397.4, found 397.4; $^1$H NMR (300 MHz) compatible.

Example 125

C-Chloro-N-[1-(3-isopropoxy-benzoyl)-6,7-dimethoxy-isoquinolin-4-ylmethyl]-methanesulfonamide, hydrochloride salt

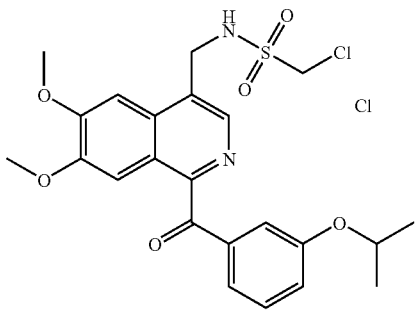

The above 1-(3-isopropoxy)-benzyl-4-chloromethyl-6,7-di-methoxyisoquinoline (1.014 g, 2.62 mmol) was dissolved in DMSO (5 mL) and added to a solution of sodium azide (851 mg, 13.1 mmol) suspended in 10 ml of DMSO. The mixture was stirred at 65° C. for 1 hr. The mixture was dissolved in ethyl acetate (200 mL) and water (200 mL). The organic layer was separated, washed with saturated sodium chloride, dried over magnesium sulfate, filtered and evaporated. Biotage chromatography (FLASH 40M, Silica, ethyl acetate/hexane) afforded the azide (512 mg) as an off-white solid: $^1$H NMR (300 MHz) compatible.

The above azide (112 mg, 0.285 mmol) was dissolved in THF (10 mL) and treated with di-tert-butyl dicarbonate (68 mg, 0.314 mmol) and 10% palladium on activated carbon (25 mg). The mixture was hydrogenated at 40 psi for 1 hr. The mixture was filtered through Celite, evaporated and the residue was washed with hexane to give [1-(3-isopropoxy-benzyl)-6,7-dimethoxy-isoquinolin-4-ylmethyl]-carbamic acid tert-butyl ester (62 mg): APCI-MS (M+H$^+$) m/e calcd for $C_{27}H_{34}N_2O_5$ 467.6, found 467.

The above solid (1.75 g, 3.76 mmol) was refluxed with selenium dioxide (150 mg, 1.356 mmol) in ethyl acetate (20 mL) for 1 hr. The mixture was cooled and filtered through a layer of silica gel and washed with ethyl acetate. The filtrates were evaporated to obtain 337 mg of [1-(3-isopropoxy-benzoyl)-6,7-dimethoxy-isoquinolin-4-ylmethyl]-carbamic acid tert-butyl ester.

The above compound (313 mg, 0.652 mmol) was dissolved in 5 ml of methylene chloride and treated with trifluoroacetic acid (10 ml). The mixture was stirred at room temperature for 75 minutes. Solvents were evaporated and the residue was dissolved in 20 ml of methylene chloride. Then gaseous hydrogen chloride was bubbled through for 10 minutes. The mixture was evaporated and the residue was triturated with dry ether. The solid was dried to give a crude product (276 mg) as a hydrochloride salt.

The above amine (50 mg, 0.113 mmol) was dissolved in DMF (2.5 mL) and treated with triethyl amine (159 uL, 1.13 mmol) and chloromethylsulfonyl chloride (20 uL, 0.226 mmol) in an ice-bath under argon for 1 hour. An additional equivalent of chloromethylsulfonyl chloride (10 uL, 0.113 mmol) was added and stirring continued at room temperature overnight. The reaction mixture was evaporated to yield a crude residue. Preparative HPLC purification yielded 11 mg of C-chloro-N-[1-(3-isopropoxy-benzoyl)-6,7-dimethoxy-isoquinolin-4-ylmethyl]-methanesulfonamide hydrochloride salt as an off-white solid: ES-MS (M+H$^+$) m/e calcd for $C_{23}H_{25}ClN_2O_6S$ 493.9, found 493.9; $^1$H NMR (300 MHz) compatible.

Example 126

Thiophene-2-sulfonic acid [1-(3-isopropoxy-benzoyl)-6,7-dimethoxy-isoquinolin-4-ylmethyl]-amide

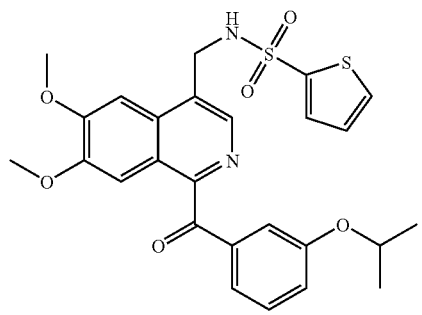

The above [4-aminomethyl-6,7-dimethoxy-isoquinolin-1-yl]-(3-methoxy-phenyl)-methanone hydrochloride salt (50 mg, 0.055 mmol) in DMF (5 mL) was treated with triethylamine (46.5 uL, 0.33 mmol) and 2-thiophenesulfonyl chloride (15 mg, 0.0825 mmol) under argon at room temperature overnight. The reaction mixture was diluted with saturated sodium bicarbonate and extracted twice with ethyl acetate. The combined organic layers were washed with saturated sodium chloride, dried over magnesium sulfate, filtered and evaporated to dryness. Biotage chromatography (FLASH 40M, Silica, ethyl acetate/hexane) afforded thiophene-2-sulfonic acid [1-(3-isopropoxy-benzoyl)-6,7-dimethoxy-isoquinolin-4-ylmethyl]-amide (52 mg) as an off-white solid: APCI-MS (M+H$^+$) m/e calcd for $C_{26}H_{26}N_2O_6S_2$ 527.6, found 526.9; $^1$H NMR (300 MHz) compatible.

Example 127

2,2,2-Trifluoro-ethanesulfonic acid [1-(3-isopropoxy-benzoyl)-6,7-dimethoxy-isoquinolin-4-ylmethyl]-amide

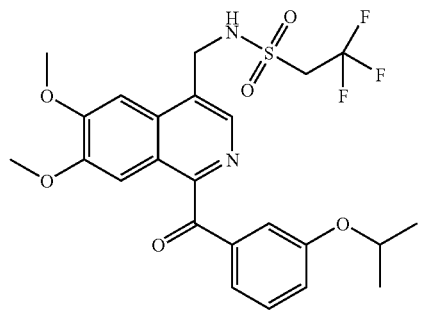

The above [4-aminomethyl-6,7-dimethoxy-isoquinolin-1-yl]-(3-methoxy-phenyl)-methanone hydrochloride salt (55 mg, 0.121 mmol) and triethylamine (59.5 uL, 0.423 mmol) in methylene chloride (10 mL) was cooled to −78° C. Trifluoroethanesulfonyl chloride (16 uL, 0.145 mmol) was added dropwise and the reaction mixture stirred for 1 hour. The reaction mixture was diluted with saturated sodium bicarbonate warmed to room temperature and extracted with ethyl acetate (2×50 mL). The combined organic layers were dried over magnesium sulfate, filtered and evaporated to dryness. Biotage chromatography (FLASH 40M, Silica, ethyl acetate/hexane) afforded 2,2,2-trifluoro-ethanesulfonic acid [1-(3-isopropoxy-benzoyl)-6,7-dimethoxy-isoquinolin-4-ylmethyl]-amide (50 mg) as an off-white solid: APCI-MS (M+H$^+$) m/e calcd for $C_{24}H_{25}F_3N_2O_6S$ 527.6, found 526.9; $^1$H NMR (300 MHz) compatible.

Example 128

6,7-Dimethoxy-1-benzoylisoquinolin-4-carboxylic acid

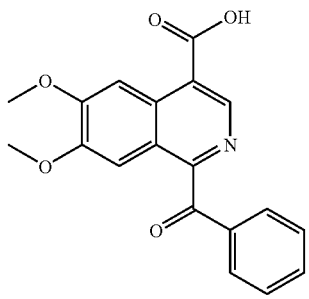

α-Aminomethyl-3,4-dimethoxybenzene-acetic acid ethyl ester hydrochloride (intermediate in the preparation of Example 30) (510 mg, 1.76 mmol) was mixed with 3-phenylacetic acid (240 mg, 1.76 mmol), EDCI (374 mg, 1.94 mmol), and HOBT (238 mg, 1.76 mmol) in 25 ml of methylene chloride containing triethylamine (0.50 ml, 3.62 mmol). The mixture was stirred overnight and then extracted with methylene chloride and 1N hydrochloric acid. The organic layer was washed first with 1N hydrochloric acid, then with brine and finally with saturated sodium bicarbonate solution. After the evaporation of solvents, an oil was obtained (560 mg, 86%).

The above oil (560 mg, 1.51 mmol) was dissolved into 10 ml of methylene chloride. Then phosphorus pentachloride (625 mg, 3.0 eq) was added. The mixture was stirred at room temperature overnight. The mixture was then poured into ice and the resulted solution was extracted with methylene chloride. The organic layer was washed with brine followed by saturated sodium bicarbonate solution. After the evaporation of solvents, an oil was obtained (498 mg). ES-MS showed molecular weight (M+H) 354 which is consistent with the desired dihydroisoquinoline structure.

The above dihydroisoquinoline derivative (498 mg, 1.41 mmol) was mixed with sulfur (67.7 mg, 1.5 eq) and the mixture was heated at 165° C. for 25 minutes until no further gas was observed. Then ethanol (15 ml) was added to the hot mixture with stirring. The solid was removed by filtering. The filtrate was evaporated and the residue was purified through a flash column chromatography using ethyl acetate and hexane (1/2 ratio) to give a solid product 1-benzyl-6,7-dimethoxyisoquinoline-4-carboxylic acid ethyl ester (78 mg).

The above 1-benzyl-6,7-dimethoxyisoquinoline-4-carboxylic acid ethyl ester (77.1 mg, 0.22 mmol) was dissolved in 5 ml of acetic acid. Then selenium dioxide (36.6 mg, 1.50 eq) was added and the mixture was refluxed for 1 hr until no more starting material was left. The mixture was evaporated to dryness and the residue was extracted with ethyl acetate and sodium bicarbonate solution. The organic layer was dried over sodium sulfate and then concentrated. The residue was dissolved in 5 ml of ethyl acetate and the solution was passed through a layer of silica gel. The solution was concentrated go give a pure 1-benzoyl-6,7-dimethoxyisoquinoline-4-carboxylic acid ethyl ester (70 mg, 87%).

The above ester (36 mg) was dissolved into 4 ml of methanol. Then 0.2 ml of 1N sodium hydroxide solution was added. The mixture was refluxed for 1 hr. The solution was evaporated to dryness. The residue was dissolved in 4 ml of water and acidified with 1N hydrochloric acid. The precipitate was filtered and dried to give the title compound as a solid. ES-MS (M+H) 338.

Example 129

In Vitro GFAT Assay

Enzyme Preparation:

COS cells transfected with GFAT-alpha or GFAT-beta, grown to 90% confluency were scrapped into buffer containing PBS 100 mM, KCl 50 mM, EDTA 10 mM and protease inhibitors leupeptin, A-protinin, PMSF & pepstatin. The final concentration is 4×10−7 cells/ml. This was sonicated with a microtip probe at setting 4 for 15 seconds on ice in a volume of 3–4 ml.

Incubation Buffer:

The buffer was prepared to contain: glutamine (8 mM, 0.01 ml), fructose 6-phosphate (100 mM, 0.01 ml), PBS 10× (0.01 ml), EDTA (50 mM, 0.01 ml), ±inhibitor (0.01 ml), enzyme (0.005 ml), and water (dilute to 0.10 ml).

Procedure:

The inhibitors were made up in 100% DMSO and diluted in a microtiter plate. The inhibitors were then added to the assay plate along with DMSO as a control. A reaction mixture was made, including enough for the standard curve samples, and kept on ice. The reaction was started by adding 90 ul of the mixture to the 96 well plate. The plate was covered with an adhesive plate sealer and placed in a 37° C. water bath for 60 minutes. Care should be take to ensure that no air bubbles form under the plate. After incubation, 10 ul of the glucosamine 6-phosphate standards made up in DMSO were added to the standard curve wells. A concentration range of 2.5 to 30 nmoles was in the linear part of the curve and covers the quantity of glucosamine 6-phosphate produced. The cold incubation mixture containing the enzyme is added to the control and standard curve wells. The glucosamine 6-phosphate was then acetylated by adding 10 ul of acetic anhydride 1.5% in acetone followed by 50 ul of potassium tetraborate (200 mM). The plate was sealed with a new cover and shaken for 2 minutes on a microshaker. The plate was placed in an 80° C. water bath for 25 minutes. The plate was then placed on ice for 5 minutes. 130 ul of Ehrlich's reagent was added to the wells and the plate placed in a 37° C. water bath for 20 minutes. The plate was the read at 585 nm. A softmax program interpolated the ODs from the standard curve to give the nmoles produced.

The compounds of the present invention have GFAT inhibitory activity with IC$_{50}$ below 100 μM.

What is claimed is:

1. A compound of formula (I):

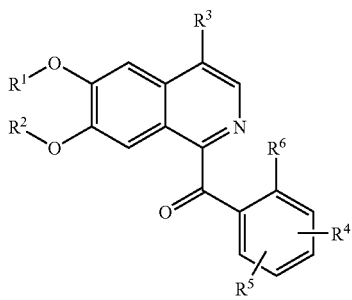

wherein
- $R^1$ is -lower alkyl, —$CH_2$-aryl, -cycloalkyl, —$(CH_2)_3$—$OC(=O)CH_3$, -lower alcohol, -lower alkyl-$R^{10}$, —$CH_2COOH$, or —$CH_2CH_2OCH_2CH_3$;
- $R^2$ is -lower alkyl, —$CH_2$-aryl, -lower alcohol, —$CH_2C(=O)NH_2$, or -lower alkyl-$R^{10}$, wherein at least one of $R^1$ or $R^2$ is —$CH_3$;
- $R^3$ is —COOH, -lower alkyl-COOH, -lower alcohol, —$CH_2OCH_3$, —$CH_2NH_2$, —$CH_2NHSO_2R^{11}$, —$C(=O)R^{12}$, —$CNHCH_2CH_2$—$R^{12}$, —$C(=NH)$—$R^{12}$, —$(CH_2)_nNHC(=O)R^{13}$, —$(CH_2)_mC(=O)N(R^{15})(R^{16})$, —$C(=NH)$—$R^{17}$, or —$(CH_2)_n$—$R^{18}$;
- $R^4$ is —H, -lower alkoxy, —O—$C(R^7R^8)C(=O)R^{19}$, -halo, —$SCH_3$, —$C=CHC(=O)$—$R^{10}$, —$CH_2CH_2C(=O)$—$R^{10}$, —O-lower alcohol, —$OCH_2CH(OH)CH_2N=N^{\pm}N^-$, —$OCH_2CH_2OCH_2CH_2Cl$, —$NHC(=O)CH_2$—$R^{10}$, —$NHC(=O)CH_2$-lower alkyl, —$O(CH_2)_n$-cycloalkyl, —O-lower alkene, or a 5 membered unsaturated heterocyclic ring containing one hetero atom which is S or O;
- $R^5$ and $R^6$ are each independently —H, -halo or -lower alkoxy;
- $R^7$ and $R^8$ are each independently —H or —$CH_3$,
- $R^{10}$ is a 5 or 6 membered saturated heterocyclyl containing 1 or 2 heteroatoms, wherein each hetero atom is selected from N and O, and the group is bound to the remainder of the molecule at a ring N;
- $R^{11}$ is —$CF_3$, -lower alkyl, —$CH_2Cl$, —$CH_2CF_3$, or —$R^{12}$;
- $R^{12}$ is a 5 or 6 membered saturated substituted or unsubstituted heterocyclic ring containing one hetero atom which is selected from N, O, and S wherein the substituted ring is the heterocyclic ring substituted with —OH or -phenyl;
- $R^{13}$ is -lower alkyl, -lower alkoxy, or —$(CH_2)_nR^{14}$;
- $R^{14}$ is a 5 or 6 membered saturated or unsaturated heterocyclic ring containing one or two hetero atoms which are selected from N and O;
- $R^{15}$ is —H or —$CH_3$;
- $R^{16}$ is —H, -lower alkyl, —$C\equiv N$, —OH, -lower alkoxy, or —$CH_2COOCH_2CH_3$;
- $R^{17}$ is -lower alkoxy —$NH_2$ or —N-lower alkyl;
- $R^{18}$ is a saturated or unsaturated 5 membered substituted or unsubstituted heterocyclic ring containing from 1 to 4 hetero atoms wherein the hetero atoms are selected from N, O and S, wherein the substituted ring is the heterocyclic ring which is substituted at one or two ring carbons with =O, or substituted at a ring N with -lower alcohol or -lower alkyl;
- $R^{19}$ is —OH, —$NHCH(CH_3)_2$, —$N(CH_3)CH_2$-aryl, —$N(CH_3)$-lower alkyl,

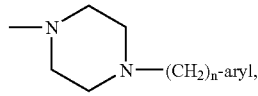

or 5 or 6 membered saturated substituted or an unsubstituted heterocyclyl containing 1 or 2 heteroatoms wherein each heteroatom is independently selected from N, O and S, wherein said substituted heterocyclyl is the heterocyclyl substituted with lower alkyl;
- m is 0, 1 or 2;
- n is 0 or 1;

and pharmaceutically acceptable salts and esters thereof.

2. The compound according to claim 1, wherein $R^4$ is —O-lower alkyl, —O—$C(R^7R^8)C(=O)R^{19}$, -halo, —$SCH_3$, —$C=CHC(=O)$—$R^{10}$, —$CH_2CH_2C(=O)$—$R^{10}$, —O-lower alcohol, —$OCH_2CH(OH)CH_2N=N^{\pm}N^-$, —$OCH_2CH_2OCH_2CH_2Cl$, —$NHC(=O)CH_2$—$R^{10}$, —$NHC(=O)CH_2$-lower alkyl, —$O(CH_2)_n$-cycloalkyl, —O-lower alkene, or a 5 membered unsaturated heterocyclic ring containing one hetero atom which is S or O.

3. The compound according to claim 1, wherein $R^4$, $R^5$ and $R^6$ are each —H, and $R^1$ and $R^2$ are each —$CH_3$.

4. The compound according to claim 1, wherein $R^4$, $R^5$ and $R^6$ are each —H, and $R^3$ is —COOH.

5. The compound according to claim 1, wherein the compound is selected from:
- 2-[6,7-Dimethoxy-1-(3-methoxy-benzoyl)-isoquinolin-4-yl]-acetamide (Example 8);
- 3-[1-(3-Isopropoxy-benzoyl)-6,7-dimethoxy-isoquinolin-4-yl]-propionamid (Example 11);
- (4-Aminomethyl-6,7-dimethoxy-isoquinolin-1-yl)-(3-isopropoxy-phenyl)-methanone (Example 13);
- 2-[1-(3-Isopropoxy-benzoyl)-6,7-dimethoxy-isoquinolin-4-yl]-acetamide (Example 25);
- (4-Aminomethyl-6,7-dimethoxy-isoquinolin-1-yl)-(2-fluoro-5-methoxy-phenyl)-methanone (Example 27);
- 1-(2,6-Difluoro-benzoyl)-6,7-dimethoxy-isoquinoline-4-carboxylic acid (Example 33);
- N-[1-(2,6-Difluoro-benzoyl)-6,7-dimethoxy-isoquinolin-4-ylmethyl]-C,C,C-trifluoro-methanesulfonamide (Example 34);
- 6,7-Dimethoxy-1-[3-(3-oxo-3-pyrrolidin-1-yl-propenyl)-benzoyl]-isoquinoline-4-carboxylic acid (Example 35);
- 6,7-Dimethoxy-1-{3-[(1-phenyl-ethylcarbamoyl)-methoxy]-benzoyl}-isoquinoline-4-carboxylic acid; compound with trifluoro-acetic acid (Example 39);
- 6,7-Dimethoxy-1-{3-[(1-phenyl-ethylcarbamoyl)-methoxy]-benzoyl}-isoquinoline-4-carboxylic acid; compound with trifluoro-acetic acid (Example 42);
- 1-[3-(1-Isopropylcarbamoyl-1-methyl-ethoxy)-benzoyl]-6,7-dimethoxy-isoquinoline-4-carboxylic acid; compound with trifluoro-acetic acid (Example 47);
- 1-(3-Furan-2-yl-benzoyl)-6,7-dimethoxy-isoquinoline-4-carboxylic acid; compound with trifluoro-acetic acid (Example 49);
- 6,7-Dimethoxy-1-(3-thiophen-3-yl-benzoyl)-isoquinoline-4-carboxylic acid; compound with trifluoro-acetic acid (Example 50);
- (2-Fluoro-5-isopropoxy-phenyl)-[4-(2-hydroxy-ethyl)-6,7-dimethoxy-isoquinolin-1-yl]-methanone (Example 53);

7-Benzyloxy-6-methoxy-1-(3-methoxy-benzoyl)-isoquinoline-4-carboxylic acid (Example 62);
7-(2-Hydroxy-ethoxy)-6-methoxy-1-(3-methoxy-benzoyl)-isoquinoline-4-carboxylic acid (Example 64);
7-Carbamoylmethoxy-6-methoxy-1-(3-methoxy-benzoyl)-isoquinoline-4-carboxylic acid (Example 65);
6-Methoxy-1-(3-methoxy-benzoyl)-7-(2-pyrrolidin-1-yl-ethoxy)-isoquinoline-4-carboxylic acid hydrochloride (Example 66);
6-Benzyloxy-7-methoxy-1-(3-methoxy-benzoyl)-isoquinoline-4-carboxylic acid (Example 67);
6-Cyclopentyloxy-7-methoxy-1-(3-methoxy-benzoyl)-isoquinoline-4-carboxylic acid (Example 69);
6-(3-Acetoxy-propoxy)-7-methoxy-1-(3-methoxy-benzoyl)-isoquinoline-4-carboxylic acid (Example 70);
6-(3-Hydroxy-propoxy)-1-(3-isopropoxy-benzoyl)-7-methoxy-isoquinoline-4-carboxylic acid; compound with trifluoroacetic acid (Example 71);
6-Carboxymethoxy-1-(3-isopropoxy-benzoyl)-7-methoxy-isoquinoline-4-carboxylic acid (Example 73);
6-(3-Acetoxy-propoxy)-1-(3-ethoxy-benzoyl)-7-methoxy-isoquinoline-4-carboxylic acid (Example 74);
1-(3-Ethoxy-benzoyl)-6-(2-ethoxy-ethoxy)-7-methoxy-isoquinoline-4-carboxylic acid (Example 76);
1-(3-Ethoxy-benzoyl)-6-(2-hydroxy-ethoxy)-7-methoxy-isoquinoline-4-carboxylic acid (Example 77);
6,7-Dimethoxy-1-(3-methylsulfanyl-benzoyl)-isoquinoline-4-carboxylic acid; compound with trifluoroacetic acid (Example 80);
1-(3-Ethoxy-benzoyl)-6,7-dimethoxy-isoquinoline-4-carboximidic acid ethyl ester, hydrochloride salt (Example 87A);
1-(3-Ethoxy-benzoyl)-6,7-dimethoxy-isoquinoline-4-carboxylic acid amide, hydrochloride salt (Example 87B);
1-(3-Ethoxy-benzoyl)-6,7-dimethoxy-isoquinoline-4-carboxamidine, trifluoroacetic acid salt (Example 88);
(3-Ethoxy-phenyl)-[4-(imino-morpholin-4-yl-methyl)-6,7-dimethoxy-isoquinolin-1-yl]-methanone, trifluoroacetic acid salt (Example 90);
1-(3-Ethoxy-benzoyl)-6,7-dimethoxy-N,N-dimethyl-isoquinoline-4-carboxamidine, trifluoroacetic acid salt (Example 91);
1-(3-Ethoxy-benzoyl)-6,7-dimethoxy-N,N-dimethyl-isoquinoline-4-carboxamidine, trifluoroacetic acid salt (Example 92);
rac-[3-(3-Azido-2-hydroxy-propoxy)-phenyl]-[6,7-dimethoxy-4-(1H-tetrazol-5-yl)-isoquinolin-1-yl]-methanone, trifluoroacetic acid salt (Example 94);
(3-Cyclopentyloxy-4-methoxy-phenyl)-[6,7-dimethoxy-4-(1H-tetrazol-5-yl)-isoquinolin-1-yl]-methanone, trifluoroacetic acid salt (Example 95);
(3-Allyloxy-phenyl)-[6,7-dimethoxy-4-(1H-tetrazol-5-yl)-isoquinolin-1-yl]-methanone, trifluoroacetic acid salt (Example 97);
(3-But-2-enyloxy-phenyl)-[6,7-dimethoxy-4-(1H-tetrazol-5-yl)-isoquinolin-1-yl]-methanone, trifluoroacetic acid salt (Example 98);
(3-Cyclopentyloxy-phenyl)-[6,7-dimethoxy-4-(1H-tetrazol-5-yl)-isoquinolin-1-yl]-methanone, trifluoroacetic acid salt (Example 99);
(3-Cyclopropylmethoxy-phenyl)-[6,7-dimethoxy-4-(1H-tetrazol-5-yl)-isoquinolin-1-yl]-methanone, trifluoroacetic acid salt (Example 100);
(3-Cycloheptyloxy-phenyl)-[6,7-dimethoxy-4-(1H-tetrazol-5-yl)-isoquinolin-1-yl]-methanone, trifluoroacetic acid salt (Example 101);
1-(3-hydroxyethoxy-benzoyl)-6,7-dimethoxy-isoquinoline-4-carboxylic acid (Example 102);
1-{3-[2-(2-Chloro-ethoxy)-ethoxy]-benzoyl}-6,7-dimethoxy-isoquinoline-4-carboxylic acid, trifluoroacetic acid salt (Example 103);
1-(3,5-Dimethoxy-benzoyl)-6,7-dimethoxy-isoquinoline-4-carboxylic acid, trifluoroacetic acid salt (Example 104);
6,7-Dimethoxy-1-(3-methoxy-benzoyl)-isoquinoline-4-carboxylic acid (2-morpholin-4-yl-ethyl)-amide (Example 106);
6,7-Dimethoxy-1-(3-methoxy-benzoyl)-isoquinoline-4-carboxylic acid (2-cyano-ethyl)-amide (Example 107);
6,7-Dimethoxy-1-(3-methoxy-benzoyl)-isoquinoline-4-carboxylic acid hydroxyamide (Example 108);
6,7-Dimethoxy-1-(3-methoxy-benzoyl)-isoquinoline-4-carboxylic acid methoxy-amide (Example 109);
6,7-Dimethoxy-1-(3-methoxy-benzoyl)-isoquinoline-4-carboxylic acid methoxy-methyl-amide (Example 110);
(4-Hydroxymethyl-6,7-dimethoxy-isoquinolin-1-yl)-(3-isopropoxy-phenyl)-methanone (Example 111);
6,7-Dimethoxy-1-(3-methoxy-5-methyl-benzoyl)-isoquinoline-4-carboxylic acid (Example 112);
[4-(4-Hydroxy-4-phenyl-piperidine-1-carbonyl)-6,7-dimethoxy-isoquinolin-1-yl]-(3-methoxy-phenyl)-methanone (Example 113);
{[6,7-Dimethoxy-1-(3-methoxy-benzoyl)-isoquinoline-4-carbonyl]-amino}-acetic acid ethyl ester (Example 114);
[4-(4-Hydroxy-piperidine-1-carbonyl)-6,7-dimethoxy-isoquinolin-1-yl]-(3-methoxy-phenyl)-methanone (Example 115);
6,7-Dimethoxy-1-(3-methoxy-benzoyl)-isoquinoline-4-carboxylic acid amide (Example 117);
(4-Hydroxymethyl-6,7-dimethoxy-isoquinolin-1-yl)-(3-methoxy-phenyl)-methanone (Example 118);
(6,7-Dimethoxy-4-methoxymethyl-isoquinolin-1-yl)-(3-methoxy-phenyl)-methanone (Example 119);
6,7-Dimethoxy-1-[3-(2-morpholin-4-yl-acetylamino)-benzoyl]-isoquinoline-4-carboxylic acid; compound with trifluoro-acetic acid (Example 120);
6,7-Dimethoxy-1-[3-(2-pyrrolidin-1-yl-acetylamino)-benzoyl]-isoquinoline-4-carboxylic acid; compound with trifluoro-acetic acid (Example 121); and
1-(3-Butyrylamino-benzoyl)-6,7-dimethoxy-isoquinoline-4-carboxylic acid (Example 122).

6. A compound of formula (1),

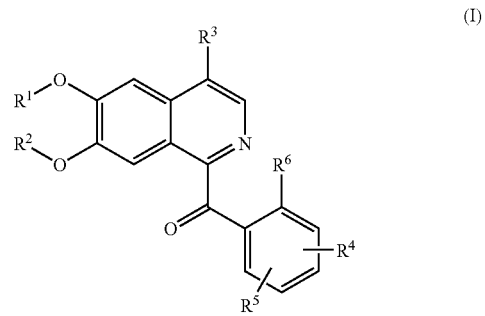

wherein
$R^1$ and $R^2$ are each independently -lower alkyl or -lower alkyl-$R^{10}$, wherein at least one of $R^1$ or $R^2$ is —$CH_3$;

R³ is —COOH, -lower alkyl-COOH, —(CH₂)ₙNHC(=O)R¹³, —H₂NHSO₂R¹¹, or —CH₂)ₙ—R¹⁸;

R⁴ is -lower alkoxy or —OC(R⁷R⁸)C(=O)R¹⁹;

R⁵ and R⁶ are each independently —H or -halo;

R⁷ and R⁸ are each independently —H or —CH₃,

R¹⁰ is a 5 or 6 membered saturated heterocyclyl containing 1 or 2 heteroatoms, wherein each hetero atom is selected from N and O, and the group is bound to the remainder of the molecule at a ring N;

R¹¹ is —CF₃, -lower alkyl, —CH₂Cl, —CH₂CF₃, or —R¹²;

R¹² is a 5 or 6 membered saturated substituted or unsubstituted heterocyclic ring containing one hetero atom which is selected from N, O, and S wherein the substituted ring is the heterocyclic ring substituted with —OH or -phenyl;

R¹³ is -lower alkyl, -lower alkoxy, or —(CH₂)ₙR¹⁴;

R¹⁴ is a 5 or 6 membered saturated or unsaturated heterocyclic ring containing one or two hetero atoms which are selected from N and O;

R¹⁸ is a saturated or unsaturated 5 membered substituted or unsubstituted heterocyclic ring containing from 1 to 4 hetero atoms wherein the hetero atoms are selected from N, O and S, wherein the substituted ring is the heterocyclic ring which is substituted at one or two ring carbons with =O, or substituted at a ring N with -lower alcohol or -lower alkyl;

R¹⁹ is —OH, —NHCH(CH₃)₂, —N(CH₃)CH₂-aryl, —N(CH₃)-lower alkyl,

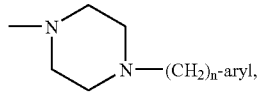

or 5 or 6 membered saturated substituted or an unsubstituted heterocyclyl containing 1 or 2 heteroatoms wherein each heteroatom is independently selected from N, O and S, wherein said substituted heterocyclyl is the heterocyclyl substituted with lower alkyl;

m is 0, 1 or 2;

n is 0 or 1;

and pharmaceutically acceptable salts and esters thereof.

7. The compound according to claim 6, wherein R⁷ and R⁸ are each —CH₃.

8. The compound according to claim 6, wherein R¹⁰ is —CH₂CH₂— morpholinyl and the morpholinyl is bound at a ring N.

9. The compound according to claim 6, wherein R¹¹ is —CF₃.

10. The compound according to claim 6, wherein R¹⁹ is —NHCH(CH₃)₂.

11. The compound according to claim 6, wherein R³ is —CH₂)ₙNHC(=O)R¹³, and n is 1.

12. The compound according to claim 6, wherein R³ is —(CH₂)ₙNHC(=O)R¹³, and R¹³ is —CH₃.

13. The compound according to claim 6, wherein R³ is —(CH²)ₙ—R¹⁸ and R¹⁸ is an unsaturated 5 membered substituted or unsubstituted heterocyclic ring containing from 2 to 4 hetero atoms which are each N, wherein the substituted ring is the heterocyclic ring which is substituted at a ring N with -lower alkyl or -lower alcohol, and n is 0.

14. The compound according to claim 13, wherein R¹⁸ is tetrazole or substituted tetrazole.

15. The compound according to claim 6, wherein the compound is selected from 1-(2,6-Difluoro-3-isopropoxy-benzoyl)-6,7-dimethoxy-isoquinoline-4-carboxylic acid; compound with trifluoro-acetic acid;

1-(3-sec-Butoxy-benzoyl)-6,7-dimethoxy-isoquinoline-4-carboxylic acid; compound with trifluoro-acetic acid;

1-(3-Isopropoxy-benzoyl)-6,7-dimethoxy-isoquinoline-4-carboxylic acid;

N-[1-(3-Isopropoxy-benzoyl)-6,7-dimethoxy-isoquinolin-4-ylmethyl]-acetamide;

1-[3-(1-Isopropylcarbamoyl-1-methyl-ethoxy)-benzoyl]-6,7-dimethoxy-isoquinoline-4-carboxylic acid; compound with trifluoro-acetic acid;

C,C,C-Trifluoro-N-[1-(2-fluoro-5-methoxy-benzoyl)-6,7-dimethoxy-isoquinolin-4-ylmethyl]-methanesulfonamide;

6,7-Dimethoxy-1-(3-methoxy-benzoyl)-isoquinoline-4-carboxylic acid;

[6,7-Dimethoxy-4-(1H-tetrazol-5-yl)-isoquinolin-1-yl]-(3-ethoxy-phenyl)-methanone; compound, trifluoro-acetic acid salt;

2-[1-(2-Fluoro-5-isopropoxy-benzoyl)-6,7-dimethoxy-isoquinolin-4-yl]-4-methyl-pentanoic acid; compound with trifluoro-acetic acid;

N-[1-(3-Isopropoxy-benzoyl)-6,7-dimethoxy-isoquinolin-4-ylmethyl]-nicotinamide;

[6,7-Dimethoxy-1-(3-methoxy-benzoyl)-isoquinolin-4-yl]-acetic acid;

1-(3-Butoxy-benzoyl)-6,7-dimethoxy-isoquinoline-4-carboxylic acid;

1-(3-Ethoxy-benzoyl)-7-methoxy-6-(2-morpholin-4-yl-ethoxy)-isoquinoline-4-carboxylic acid hydrochloride (Example 79);

C,C,C-Trifluoro-N-[1-(3-isopropoxy-benzoyl)-6,7-dimethoxy-isoquinolin-4-ylmethyl]-methanesulfonamide (Example 23);

6,7-Dimethoxy-1-[3-(2-oxo-2-pyrrolidin-1-yl-ethoxy)-benzoyl]-isoquinoline-4-carboxylic acid (Example 1);

6,7-Dimethoxy-1-{3-[2-(4-methyl-piperazin-1-yl)-2-oxo-ethoxy]-benzoyl}-isoquinoline-4-carboxylic acid (Example 2);

6,7-Dimethoxy-1-[3-(2-morpholin-4-yl-2-oxo-ethoxy)-benzoyl]-isoquinoline-4-carboxylic acid (Example 3);

1-{3-[(Benzyl-methyl-carbamoyl)-methoxy]-benzoyl}-6,7-dimethoxy-isoquinoline-4-carboxylic acid (Example 4);

1-{3-[2-(4-Benzyl-piperazin-1-yl)-2-oxo-ethoxy]-benzoyl}-6,7-dimethoxy-isoquinoline-4-carboxylic acid (Example 5);

1-(3-Carboxymethoxy-benzoyl)-6,7-dimethoxy-isoquinoline-4-carboxylic acid (Example 6);

N-[1-(3-Isopropoxy-benzoyl)-6,7-dimethoxy-isoquinolin-4-yl]-acetamide (Example 12);

Pyrazine-2-carboxylic acid [1-(3-isopropoxy-benzoyl)-6,7-dimethoxy-isoquinolin-4-ylmethyl]-amide (Example 16);

N-[1-(3-Isopropoxy-benzoyl)-6,7-dimethoxy-isoquinolin-4-ylmethyl]-2-pyridin-3-yl-acetamide (Example 17);

3H-Imidazole-4-carboxylic acid [1-(3-isopropoxy-benzoyl)-6,7-dimethoxy-isoquinolin-4-ylmethyl]-amide (Example 18);

N-[1-(3-Isopropoxy-benzoyl)-6,7-dimethoxy-isoquinolin-4-ylmethyl]-isonicotinamide (Example 19);

Morpholine-4-carboxylic acid [1-(3-isopropoxy-benzoyl)-6,7-dimethoxy-isoquinolin-4-ylmethyl]-amide (Example 20);
N-[1-(3-Isopropoxy-benzoyl)-6,7-dimethoxy-isoquinolin-4-ylmethyl]-methanesulfonamide (Example 21);
Ethanesulfonic acid [1-(3-isopropoxy-benzoyl)-6,7-dimethoxy-isoquinolin-4-ylmethyl]-amide (Example 22);
[1-(3-Isopropoxy-benzoyl)-6,7-dimethoxy-isoquinolin-4-yl]-acetic acid (Example 24);
1-(2-Fluoro-5-methoxy-benzoyl)-6,7-dimethoxy-isoquinoline-4-carboxylic acid (Example 26);
N-[1-(2-Fluoro-5-methoxy-benzoyl)-6,7-dimethoxy-isoquinolin-4-ylmethyl]-methanesulfonamide (Example 28);
1-(2-Fluoro-5-isopropoxy-benzoyl)-6,7-dimethoxy-isoquinoline-4-carboxylic acid (Example 30);
[1-(2-Fluoro-5-isopropoxy-benzoyl)-6,7-dimethoxy-isoquinolin-4-yl]-acetic acid (Example 31);
2-[1-(2-Fluoro-5-isopropoxy-benzoyl)-6,7-dimethoxy-isoquinolin-4-yl]-propionic acid (Example 32);
6,7-Dimethoxy-1-[3-(3-oxo-3-pyrrolidin-1-yl-propyl)-benzoyl]-isoquinoline-4-carboxylic acid (Example 36);
1-[3-(Isopropylcarbamoyl-methoxy)-benzoyl]-6,7-dimethoxy-isoquinoline-4-carboxylic acid; compound with trifluoro-acetic acid (Example 37);
6,7-Dimethoxy-1-[3-(2-oxo-2-thiomorpholin-4-yl-ethoxy)-benzoyl]-isoquinoline-4-carboxylic acid; compound with trifluoro-acetic acid (Example 38);
1-{3-[(Ethyl-methyl-carbamoyl)-methoxy]-benzoyl}-6,7-dimethoxy-isoquinoline-4-carboxylic acid; compound with trifluoro-acetic acid (Example 40);
6,7-Dimethoxy-1-{3-[2-oxo-2-(4-phenyl-piperazin-1-yl)-ethoxy]-benzoyl}-isoquinoline-4-carboxylic acid; compound with trifluoro-acetic acid (Example 41);
1-(3-Isobutoxy-benzoyl)-6,7-dimethoxy-isoquinoline-4-carboxylic acid; compound with trifluoro-acetic acid (Example 43);
1-[3-(1,1-Dimethyl-2-oxo-2-pyrrolidin-1-yl-ethoxy)-benzoyl]-6,7-dimethoxy-isoquinoline-4-carboxylic acid; compound with trifluoro-acetic acid (Example 45);
1-(3-Butoxy-benzoyl)-6,7-dimethoxy-isoquinoline-4-carboxylic acid (Example 48);
2-[1-(3-Isopropoxy-benzoyl)-6,7-dimethoxy-isoquinolin-4-ylmethyl]-[1,2,4]oxadiazolidine-3,5-dione; compound with trifluoro-acetic acid (Example 51);
3-[1-(3-Isopropoxy-benzoyl)-6,7-dimethoxy-isoquinolin-4-ylmethyl]-thiazolidine-2,4-dione; compound with trifluoro-acetic acid (Example 52);
2-[1-(2-Fluoro-5-isopropoxy-benzoyl)-6,7-dimethoxy-isoquinolin-4-yl]-4-methyl-pentanoic acid; compound with trifluoro-acetic acid (Example 54);
1-(2,6-Difluoro-3-methoxy-benzoyl)-6,7-dimethoxy-isoquinoline-4-carboxylic acid; compound with trifluoro-acetic acid (Example 55);
[6,7-Dimethoxy-4-(1H-tetrazol-5-ylmethyl)-isoquinolin-1-yl]-(2-fluoro-5-methoxy-phenyl)-methanone (Example 57);
7-Butoxy-6-methoxy-1-(3-methoxy-benzoyl)-isoquinoline-4-carboxylic acid (Example 63);
6-Butoxy-7-methoxy-1-(3-methoxy-benzoyl)-isoquinoline-4-carboxylic acid (Example 68);
1-(3-Isopropoxy-benzoyl)-7-methoxy-6-(2-pyrrolidin-1-yl-ethoxy)-isoquinoline-4-carboxylic acid hydrochloride (Example 72);
6-(3-Acetoxy-propoxy)-1-(3-ethoxy-benzoyl)-7-methoxy-isoquinoline-4-carboxylic acid hydrochloride (Example 75);
1-(3-Ethoxy-benzoyl)-6-isopropoxy-7-methoxy-isoquinoline-4-carboxylic acid (Example 78);
1-(3-Ethoxy-benzoyl)-7-methoxy-6-(2-morpholin-4-yl-ethoxy)-isoquinoline-4-carboxylic acid hydrochloride (Example 79);
[1-(3-sec-Butoxy-benzoyl)-6,7-dimethoxy-isoquinolin-4-yl]-acetic acid; 1:1 trifluoro-acetic acid (Example 81);
1-(3-Ethoxy-benzoyl)-6,7-dimethoxy-isoquinoline-4-carboxylic acid (Example 84);
(3-Ethoxy-phenyl)-{4-[1-(2-hydroxy-ethyl)-1H-tetrazol-5-yl]-6,7-dimethoxy-isoquinolin-1-yl}-methanone, trifluoroacetic acid salt (Example 85A);
(3-Ethoxy-phenyl)-{4-[2-(2-hydroxy-ethyl)-1H-tetrazol-5-yl]-6,7-dimethoxy-isoquinolin-1-yl}-methanone, trifluoroacetic acid salt (Example 85B);
[6,7-Dimethoxy-4-(1-methyl-1H-tetrazol-5-yl)-isoquinolin-1-yl]-(3-ethoxy-phenyl)-methanone, trifluoroacetic acid salt (Example 86);
[4-(4,5-Dihydro-1H-imidazol-2-yl)-6,7-dimethoxy-isoquinolin-1-yl]-(3-ethoxy-phenyl)-methanone, trifluoroacetic acid salt (Example 89);
[6,7-Dimethoxy-4-(1H-tetrazol-5-yl)-isoquinolin-1-yl]-[3-(2-hydroxy-ethoxy)-phenyl]-methanone, trifluoroacetic acid salt (Example 93);
[6,7-Dimethoxy-4-(1H-tetrazol-5-yl)-isoquinolin-1-yl]-(3-isopropoxy-phenyl)-methanone, trifluoroacetic acid salt (Example 96);
N-[1-(3-sec-Butoxy-benzoyl)-6,7-dimethoxy-isoquinolin-4-ylmethyl]-C,C,C-trifluoro-methanesulfonamide (Example 105);
(6,7-Dimethoxy-4-pyrrolidin-1-ylmethyl-isoquinolin-1-yl)-(3-methoxy-phenyl)-methanone (Example 116);
N-[6,7-Dimethoxy-1-(3-methoxy-benzoyl)-isoquinolin-4-yl]-acetamide, hydrochloride salt (Example 123);
[6,7-Dimethoxy-1-(3-methoxy-benzoyl)-isoquinolin-4-yl]-carbamic acid methyl ester; compound with trifluoro-acetic acid (Example 124);
C-Chloro-N-[1-(3-isopropoxy-benzoyl)-6,7-dimethoxy-isoquinolin-4-ylmethyl]-methanesulfonamide, hydrochloride salt (Example 125);
Thiophene-2-sulfonic acid [1-(3-isopropoxy-benzoyl)-6,7-dimethoxy-isoquinolin-4-ylmethyl]-amide (Example 126); and
2,2,2-Trifluoro-ethanesulfonic acid [1-(3-isopropoxy-benzoyl)-6,7-dimethoxy-isoquinolin-4-ylmethyl]-amide (Example 127).

16. The compound according to claim 15, wherein the compound is selected from 1-(2,6-Difluoro-3-isopropoxy-benzoyl)-6,7-dimethoxy-isoquinoline-4-carboxylic acid; compound with trifluoro-acetic acid;
1-(3-sec-Butoxy-benzoyl)-6,7-dimethoxy-isoquinoline-4-carboxylic acid; compound with trifluoro-acetic acid;
1-(3-Isopropoxy-benzoyl)-6,7-dimethoxy-isoquinoline-4-carboxylic acid;
N-[1-(3-Isopropoxy-benzoyl)-6,7-dimethoxy-isoquinolin-4-ylmethyl]-acetamide;
1-[3-(1-Isopropylcarbamoyl-1-methyl-ethoxy)-benzoyl]-6,7-dimethoxy-isoquinoline-4-carboxylic acid; compound with trifluoro-acetic acid;

C,C,C-Trifluoro-N-[1-(2-fluoro-5-methoxy-benzoyl)-6,7-dimethoxy-isoquinolin-4-ylmethyl]-methanesulfonamide;

6,7-Dimethoxy-1-(3-methoxy-benzoyl)-isoquinoline-4-carboxylic acid;

[6,7-Dimethoxy-4-(1H-tetrazol-5-yl)-isoquinolin-1-yl]-(3-ethoxy-phenyl)-methanone; compound, trifluoro-acetic acid salt;

2-[-(2-Fluoro-5-isopropoxy-benzoyl)-6,7-dimethoxy-isoquinolin-4-yl]-4-methyl-pentanoic acid; compound with trifluoro-acetic acid;

N-[1-(3-Isopropoxy-benzoyl)-6,7-dimethoxy-isoquinolin-4-ylmethyl]-nicotinamide;

[6,7-Dimethoxy-1-(3-methoxy-benzoyl)-isoquinolin-4-yl]-acetic acid; and 1-(3-Butoxy-benzoyl)-6,7-dimethoxy-isoquinoline-4-carboxylic acid.

17. The compound according to claim 15, wherein the compound is 1-(3-Ethoxy-benzoyl)-7-methoxy-6-(2-morpholin-4-yl-ethoxy)-isoquinoline-4-carboxylic acid hydrochloride.

18. The compound according to claim 15, wherein the compound is

C,C,C-Trifluoro-N-[1-(3-isopropoxy-benzoyl)-6,7-dimethoxy-isoquinolin-4-ylmethyl]-methanesulfonamide.

19. A pharmaceutical composition comprising a compound or a pharmaceutically acceptable salt or ester thereof according to claim 1, and a pharmaceutically acceptable carrier.

20. A pharmaceutical composition comprising a compound or a pharmaceutically acceptable salt or ester thereof according to claim 6, and a pharmaceutically acceptable carrier.

21. A method for the treatment of type II diabetes in a patient in need of such treatment, comprising administering to the patient a compound according to claim 1 in an amount of from about 10 mg to about 1,000 mg per day.

22. A method for the treatment of type II diabetes in a patient in need of such treatment, comprising administering to the patient a compound according to claim 6 in an amount of from about 10 mg to about 1,000 mg per day.

* * * * *

UNITED STATES PATENT AND TRADEMARK OFFICE
CERTIFICATE OF CORRECTION

PATENT NO. : 7,067,529 B2  Page 1 of 1
APPLICATION NO. : 10/827514
DATED : June 27, 2006
INVENTOR(S) : David Robert Bolin et al.

It is certified that error appears in the above-identified patent and that said Letters Patent is hereby corrected as shown below:

TITLE Pg. ITEM (75)
Inventors:
 David Robert Bolin, Montclair, NJ
 Shaoqing Chen, Bridgewater, NJ
 Steven Gregory Mischke, Florham Park, NJ
 Yimin Qian, Wayne, NJ Signed and Sealed this Seventeenth Day of October, 2006

JON W. DUDAS
*Director of the United States Patent and Trademark Office*